(12) United States Patent
Brown et al.

(10) Patent No.: US 7,615,642 B2
(45) Date of Patent: Nov. 10, 2009

(54) THERAPEUTIC COMPOUNDS

(75) Inventors: William Brown, Montreal (CA); Ziping Liu, Montreal (CA); Daniel Page, Montreal (CA); Zena Qadoumi, Burnaby (CA); Sanjay Srivastava, Montreal (CA); Maxime Tremblay, Montreal (CA); Christopher Walpole, Montreal (CA); Zhong-yong Wei, Montreal (CA); Hua Yang, Montreal (CA)

(73) Assignee: AstraZeneca AB, Sodertalje (SE)

( * ) Notice: Subject to any disclaimer, the term of this patent is extended or adjusted under 35 U.S.C. 154(b) by 106 days.

(21) Appl. No.: 11/735,528

(22) Filed: Apr. 16, 2007

(65) Prior Publication Data

US 2007/0244092 A1   Oct. 18, 2007

Related U.S. Application Data

(60) Provisional application No. 60/745,011, filed on Apr. 18, 2006.

(51) Int. Cl.
*A61K 31/4184* (2006.01)
*C07D 403/14* (2006.01)

(52) U.S. Cl. .................... 548/304.7; 514/394

(58) Field of Classification Search .............. 548/304.7
See application file for complete search history.

(56) References Cited

U.S. PATENT DOCUMENTS

| 5,482,956 | A | 1/1996 | Lunkenheimer et al. |
| 6,166,219 | A | 12/2000 | Yamasaki et al. |
| 6,348,032 | B1 | 2/2002 | Sperl et al. |
| 6,352,985 | B1 | 3/2002 | Yamasaki et al. |
| 6,376,515 | B2 | 4/2002 | Zhu et al. |
| 6,534,535 | B1 | 3/2003 | Zhu et al. |
| 6,632,815 | B2 | 10/2003 | Zhu et al. |
| 6,686,368 | B1 | 2/2004 | Zhu et al. |
| 6,720,317 | B1 | 4/2004 | Zhu et al. |
| 6,835,739 | B2 | 12/2004 | Zhu et al. |
| 6,844,367 | B1 | 1/2005 | Zhu et al. |
| 7,030,139 | B2 | 4/2006 | Cheng et al. |
| 7,115,645 | B2 | 10/2006 | Halfbrodt et al. |
| 2002/0082280 | A1 | 6/2002 | Sperl et al. |
| 2006/0052421 | A1 | 3/2006 | Welter et al. |
| 2006/0094750 | A1 | 5/2006 | Kon-I et al. |
| 2006/0264490 | A1 | 11/2006 | Page et al. |
| 2007/0072853 | A1 | 3/2007 | Liu et al. |
| 2007/0082899 | A1 | 4/2007 | Page et al. |
| 2007/0225346 | A1 | 9/2007 | Bohlin et al. |

FOREIGN PATENT DOCUMENTS

| EP | 0597304 B1 | 1/2001 |
| EP | 0583665 B1 | 3/2003 |
| EP | 1403255 A1 | 3/2004 |
| FR | 5354 M | 9/1967 |
| FR | 1604908 | 6/1972 |
| WO | 9411349 A1 | 5/1994 |
| WO | 9411350 A | 5/1994 |
| WO | 9724334 A1 | 7/1997 |
| WO | 0112600 A1 | 2/2001 |
| WO | 0119798 A2 | 3/2001 |
| WO | 0151473 A1 | 7/2001 |
| WO | 0200651 A2 | 1/2002 |
| WO | 02046168 A1 | 6/2002 |
| WO | 02085866 A1 | 10/2002 |
| WO | 2004085385 A2 | 10/2004 |
| WO | 2004108688 A1 | 12/2004 |
| WO | 2004108712 A1 | 12/2004 |
| WO | 2005007625 A2 | 1/2005 |
| WO | 2005021547 A2 | 3/2005 |
| WO | 2005030732 A1 | 4/2005 |
| WO | 2005030733 A1 | 4/2005 |
| WO | 2005030761 A1 | 4/2005 |
| WO | 2005030762 A1 | 4/2005 |
| WO | 2005113542 A2 | 12/2005 |
| WO | 2006009876 A2 | 1/2006 |
| WO | 2006012642 A2 | 2/2006 |
| WO | 2006033627 A1 | 3/2006 |
| WO | 2006033628 A1 | 3/2006 |
| WO | WO 2006/033629 A1 | 3/2006 |
| WO | WO 2006/033630 A1 | 3/2006 |
| WO | WO 2006/033631 A1 | 3/2006 |
| WO | WO 2006/033632 A1 | 3/2006 |
| WO | WO 2006/033633 A1 | 3/2006 |
| WO | WO 2006/048754 A1 | 5/2006 |
| WO | WO 2006/078941 A2 | 7/2006 |
| WO | WO 2007/108754 A1 | 9/2007 |

OTHER PUBLICATIONS

Final Rejection issued for U.S. Appl. No. 11/419,603, filed Dec. 24, 2008.
Final Rejection issued for U.S. Appl. No. 11/689,864 filed Jan. 8, 2009.

(Continued)

*Primary Examiner*—Laura L. Stockton
(74) *Attorney, Agent, or Firm*—Kenneth F. Mitchell

(57) ABSTRACT

Compounds of formula I or pharmaceutically acceptable salts thereof:

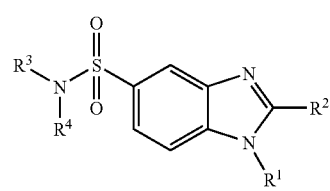

wherein $R^1$, $R^2$, $R^3$ and $R^4$ are as defined in the specification as well as salts and pharmaceutical compositions including the compounds are prepared. They are useful in therapy, in particular in the management of pain.

2 Claims, No Drawings

OTHER PUBLICATIONS

Chawla et al "Challenges in Polymorphism of Pharmaceuticals," CRIPS, vol. 5(1), Jan.-Mar. 2004, pp. 9-12.

Newman et al., "Solid-state analysis of the active pharmaceutical ingredient in drug products," Drug Discovery Today, vol. 8(19), Oct. 2003, pp. 898-905.

Non-Final Office Action issued for U.S. Appl. No. 11/419,603 filed Jun. 23, 2008.

Non-Final Office Action issued for U.S. Appl. No. 11/689,864 filed Jul. 9, 2008.

Brittain et al., "Effects of Pharmaceutical Processing on Drug Polymorphs and Solvates," Polymorphism in Pharmaceutical Solids, vol. 95, pp. 331-361, Drug and the Pharmaceutical Science, 1999.

Express-Pharma-Online (http://www.expresspharmaonline.com/20031023/edit02.shtml) Express Pharma Pulse, issued Oct. 23, 2003.

Evans et al., "Synthesis of a group of 1H-benzimidazoles and their screening for antiinflammatory activity," Eur J Med Chem, 1996, vol. 31, pp. 635-642, example 27.

Holenz et al., "Medicinal chemistry driven approaches toward novel and selective serotonin 5-HT6 receptor ligands," J. Med. Chem., 2005, vol. 48, pp. 1781-1795, table 1, compound 16, abstract.

Li et al., "Benzimidazole derivatives as novel nonpeptide luteinizing hormone-releasing hormone (LHRH) antagonists. Part 2: Benzimidazole-5-sulfonamides," Bioorganic & Medicinal Chemistry Letters, 2005, 15(3), pp. 805-807.

STN International, File Caplus, accession No. 1972:419030, doc. No. 77:19030, Koshienko et al., "Benzo(1,2-d:3,4-d')diimidazole derivatives. II. Behavior of 3,6-dimethyl-and 3,6,7-trimethylbenzo(1,2-d:3,4-d')diimidazole toward nucleophilic agents," Khimiya Geterotsiklicheskikh Soedinenii, 1971, 7(8), pp. 1132-5; XP002307925.

STN Intnl, File Chemcats, access No. 2003:1839419, Benzenesulfonamide, N-(1,2-dimethyl-1H-benzimidazol-5-yl)-, CAS Reg No. 488708-12-9; & STN Intnl, File Chemcats, access No. 2003:2399372, "Benzenesulfonamide, N-(2-methyl-1-(phenylmethyl)-1H-benzimidazol-5-yl-", CAS Registry No. 488841-64-1; & STN Intnl, File Chemcats, access No. 2003:2595844, "Benzenesulfonamide, 4-methyl-N-(2-methyl-1-(phenylmethyl)-1H-benzimidazole-5-yl)-", CAS Reg No. 312617-94-0.

STN Intnl, File Chemcats, accession No. 2003:1839419, "Benzenesulfonamide, N-(1,2-dimethyl-1H-benzimidazol-5-yl)-" CAS Registry No. 488708-12-9; & STN Intnl, File Chemcats, accession No. 2003:1845322, "Benzenesulfonamide, 4-bromo-N-(1,2-dimethyl-1H-benzimidazol-5-yl)-", CAS Registry No. 489397-82-2; & STN Intnl. File Chemcats, accession No. 2003:2305521, "Benzenesulfonamide, N-(1,2-dimethyl-1H-benzinnidazol-5-yl)-1-fluoro-", CAS Registry No. 503429-33-2.

STN Intnl, file Registry, see RN: 848855-83-4, Apr. 20, 2005.

STN Intnl, File Caplus, accession No. 1975:408737, doc No. 83:8737, Bieksa, V. et al., "Relation of the reactivity of chloroethyl derivatives of 3,4-diaminobenzenesulfopiperidides to the structure of alkylating group", Lietuvos TSR Mokslu Akademijos Darbai, Serija B: Chemija, Technika, Fizine Geografija, (1974), (3) 91-8.

STN Intnl, File Caplus, accession No. 1973:515496, doc No. 79:115496, Bieksa, V. et al. "Chloroalkyl derivatives of benzimidazoles. 1. Chloroethyl derivatives of 2-methylbenzimidazole-5-sulfonamide," Lietuvos TSR Mokslu Akademijos Darbai, Serija B: Chemija, Technika, Fizine Geografija, (1973), (2), 93-103.

ISR issued for PCT/SE2007/000359 on Aug. 8, 2007.

English abstract for EP 0597304, 1994.

English abstract for EP 1604908, 1973.

English abstract for FR 5354M, 1996.

English abstract for WO 9411349, 1994.

English abstract for WO 9411350, 1994.

English abstract for WO 9724334, 1997.

English abstract for WO 0151473, 2001.

THERAPEUTIC COMPOUNDS

This application claims the benefit under 35 U.S.C. § 119 (e) to U.S. Provisional Application No. 60/745,011 filed on Apr. 18, 2006, which is incorporated herein by reference for its entirety.

BACKGROUND OF THE INVENTION

1. Field of the Invention

The invention is related to therapeutic compounds, pharmaceutical compositions containing these compounds, manufacturing processes thereof and uses thereof. Particularly, the present invention is related to compounds that may be effective in treating pain, cancer, multiple sclerosis, Parkinson's disease, Huntington's chorea, Alzheimer's disease, anxiety disorders, gastrointestinal disorders and/or cardiovascular disorders.

2. Discussion of Relevant Technology

Pain management has been an important field of study for many years. It has been well is known that cannabinoid receptor (e.g., $CB_1$ receptor, $CB_2$ receptor) ligands including agonists, antagonists and inverse agonists produce relief of pain in a variety of animal models by interacting with $CB_1$ and/or $CB_2$ receptors. Generally, $CB_1$ receptors are located predominately in the central nervous system, whereas $CB_2$ receptors are located primarily in the periphery and are primarily restricted to the cells and tissues derived from the immune system.

While $CB_1$ receptor agonists, such as $\Delta^9$-tetrahydrocannabinol ($\Delta^9$-THC) and anadamide, are useful in anti-nociception models in animals, they tend to exert undesired CNS side effects, e.g., psychoactive side effects, the abuse potential, drug dependence and tolerance, etc. These undesired side effects are known to be mediated by the $CB_1$ receptors located in CNS. There are lines of evidence, however, suggesting that CB1 agonists acting at peripheral sites or with limited CNS exposure can manage pain in humans or animals with much improved overall in vivo profile.

Therefore, there is a need for new $CB_1$ receptor ligands such as agonists that may be useful in managing pain or treating other related symptoms or diseases with reduced or minimal undesirable CNS side effects.

DESCRIPTION OF THE EMBODIMENTS

The present invention provides $CB_1$ receptor ligands which may be useful in treating pain and/or other related symptoms or diseases.

Unless specified otherwise within this specification, the nomenclature used in this specification generally follows the examples and rules stated in *Nomenclature of Organic Chemistry, Sections A, B, C, D, E, F, and H*, Pergamon Press, Oxford, 1979, which is incorporated by references herein for its exemplary chemical structure names and rules on naming chemical structures.

The term "$C_{m-n}$" or "$C_{m-n}$ group" used alone or as a prefix, refers to any group having m to n carbon atoms.

The term "hydrocarbon" used alone or as a suffix or prefix, refers to any structure comprising only carbon and hydrogen atoms up to 14 carbon atoms.

The term "hydrocarbon radical" or "hydrocarbyl" used alone or as a suffix or prefix, refers to any structure as a result of removing one or more hydrogens from a hydrocarbon.

The term "alkyl" used alone or as a suffix or prefix, refers to a saturated monovalent straight or branched chain hydrocarbon radical comprising 1 to about 12 carbon atoms. Illustrative examples of alkyls include, but are not limited to, $C_{1-6}$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl, and longer alkyl groups, such as heptyl, and octyl. An alkyl can be unsubstituted or substituted with one or two suitable substituents.

The term "alkylene" used alone or as suffix or prefix, refers to divalent straight or branched chain hydrocarbon radicals comprising 1 to about 12 carbon atoms, which serves to links two structures together.

The term "alkenyl" used alone or as suffix or prefix, refers to a monovalent straight or branched chain hydrocarbon radical having at least one carbon-carbon double bond and comprising at least 2 up to about 12 carbon atoms. The double bond of an alkenyl can be unconjugated or conjugated to another unsaturated group. Suitable alkenyl groups include, but are not limited to $C_{2-6}$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkenyl can be unsubstituted or substituted with one or two suitable substituents.

The term "alkynyl" used alone or as suffix or prefix, refers to a monovalent straight or branched chain hydrocarbon radical having at least one carbon-carbon triple bond and comprising at least 2 up to about 12 carbon atoms. The triple bond of an alkynyl group can be unconjugated or conjugated to another unsaturated group. Suitable alkynyl groups include, but are not limited to, $C_{2-6}$alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl can be unsubstituted or substituted with one or two suitable substituents.

The term "cycloalkyl," used alone or as suffix or prefix, refers to a saturated monovalent ring-containing hydrocarbon radical comprising at least 3 up to about 12 carbon atoms. Examples of cycloalkyls include, but are not limited to, $C_{3-7}$cycloalkyl groups, such as cyclopropyl, cyclobutyl, cyclopentyl, cyclohexyl, and cycloheptyl, and saturated cyclic and bicyclic terpenes. A cycloalkyl can be unsubstituted or substituted by one or two suitable substituents. Preferably, the cycloalkyl is a monocyclic ring or bicyclic ring.

The term "cycloalkenyl" used alone or as suffix or prefix, refers to a monovalent ring-containing hydrocarbon radical having at least one carbon-carbon double bond and comprising at least 3 up to about 12 carbon atoms.

The term "cycloalkynyl" used alone or as suffix or prefix, refers to a monovalent ring-containing hydrocarbon radical having at least one carbon-carbon triple bond and comprising about 7 up to about 12 carbon atoms.

The term "aryl" used alone or as suffix or prefix, refers to a monovalent hydrocarbon radical having one or more polyunsaturated carbon rings having aromatic character, (e.g., 4n+2 delocalized electrons) and comprising 5 up to about 14 carbon atoms.

The term "arylene" used alone or as suffix or prefix, refers to a divalent hydrocarbon radical having one or more polyunsaturated carbon rings having aromatic character, (e.g., 4n+2 delocalized electrons) and comprising 5 up to about 14 carbon atoms, which serves to link two structures together.

The term "heterocycle" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s). Heterocycle may be saturated or unsaturated, containing one or more double bonds, and heterocycle may contain more than one ring. When a heterocycle contains more than one ring, the rings may be fused or unfused. Fused rings generally refer to at least two rings share two atoms therebetween. Heterocycle may have aromatic character or may not have aromatic character.

The term "heteroaromatic" used alone or as a suffix or prefix, refers to a ring-containing structure or molecule having one or more multivalent heteroatoms, independently selected from N, O, P and S, as a part of the ring structure and including at least 3 and up to about 20 atoms in the ring(s), wherein the ring-containing structure or molecule has an aromatic character (e.g., 4n+2 delocalized electrons).

The term "heterocyclic group," "heterocyclic moiety," "heterocyclic," or "heterocyclo" used alone or as a suffix or prefix, refers to a radical derived from a heterocycle by removing one or more hydrogens therefrom.

The term "heterocyclyl" used alone or as a suffix or prefix, refers a monovalent radical derived from a heterocycle by removing one hydrogen therefrom.

The term "heterocyclylene" used alone or as a suffix or prefix, refers to a divalent radical derived from a heterocycle by removing two hydrogens therefrom, which serves to links two structures together.

The term "six-membered" used as prefix refers to a group having a ring that contains six ring atoms.

The term "five-membered" used as prefix refers to a group having a ring that contains five ring atoms.

A five-membered ring heteroaryl is a heteroaryl with a ring having five ring atoms wherein 1, 2 or 3 ring atoms are independently selected from N, O and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein 1, 2 or 3 ring atoms are independently selected from N, O and S.

Exemplary six-membered ring heteroaryls are pyridyl, pyrazinyl, pyrimidinyl, triazinyl and pyridazinyl.

The term "heteroaryl" used alone or as a suffix or prefix, refers to a heterocyclyl having aromatic character.

The term "heterocylcoalkyl" used alone or as a suffix or prefix, refers to a monocyclic or polycyclic ring comprising carbon and hydrogen atoms and at least one heteroatom, preferably, 1 to 3 heteroatoms selected from nitrogen, oxygen, and sulfur, and having no unsaturation. Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 3 to 6 carbon atoms and form 1 to 3 heteroatoms, referred to herein as $C_{3-6}$heterocycloalkyl.

Heterocycle includes, for example, monocyclic heterocycles such as: aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide.

In addition, heterocycle includes aromatic heterocycles, for example, pyridine, pyrazine, pyrimidine, pyridazine, thiophene, furan, furazan, pyrrole, imidazole, thiazole, oxazole, pyrazole, isothiazole, isoxazole, 1,2,3-triazole, tetrazole, 1,2,3-thiadiazole, 1,2,3-oxadiazole, 1,2,4-triazole, 1,2,4-thiadiazole, 1,2,4-oxadiazole, 1,3,4-triazole, 1,3,4-thiadiazole, and 1,3,4-oxadiazole.

Additionally, heterocycle encompass polycyclic heterocycles, for example, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine.

In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

Heterocyclyl includes, for example, monocyclic heterocyclyls, such as: aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydro-pyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In addition, heterocyclyl includes aromatic heterocyclyls or heteroaryl, for example, pyridinyl, pyrazinyl, pyrimidinyl, pyridazinyl, thienyl, furyl, furazanyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4 oxadiazolyl.

Additionally, heterocyclyl encompasses polycyclic heterocyclyls (including both aromatic or non-aromatic), for example, indolyl, indolinyl, isoindolinyl, quinolinyl, tetrahydroquinolinyl, isoquinolinyl, tetrahydroisoquinolinyl, 1,4-benzodioxanyl, coumarinyl, dihydrocoumarinyl, benzofuranyl, 2,3-dihydrobenzofuranyl, isobenzofuranyl, chromenyl, chromanyl, isochromanyl, xanthenyl, phenoxathiinyl, thianthrenyl, indolizinyl, isoindolyl, indazolyl, purinyl, phthalazinyl, naphthyridinyl, quinoxalinyl, quinazolinyl, cinnolinyl, pteridinyl, phenanthridinyl, perimidinyl, phenanthrolinyl, phenazinyl, phenothiazinyl, phenoxazinyl, 1,2-benzisoxazolyl, benzothiophenyl, benzoxazolyl, benzthiazolyl, benzimidazolyl, benztriazolyl, thioxanthinyl, carbazolyl, carbolinyl, acridinyl, pyrolizidinyl, and quinolizidinyl.

In addition to the polycyclic heterocyclyls described above, heterocyclyl includes polycyclic heterocyclyls wherein the ring fusion between two or more rings includes more than one bond common to both rings and more than two atoms common to both rings. Examples of such bridged heterocycles include quinuclidinyl, diazabicyclo[2.2.1]heptyl; and 7-oxabicyclo[2.2.1]heptyl.

The term "alkoxy" used alone or as a suffix or prefix, refers to radicals of the general is formula —O—R, wherein R is selected from a hydrocarbon radical. Exemplary alkoxy includes methoxy, ethoxy, propoxy, isopropoxy, butoxy, t-butoxy, isobutoxy, cyclopropylmethoxy, allyloxy, and propargyloxy.

The term "amine" or "amino" refers to —NH$_2$.

Halogen includes fluorine, chlorine, bromine and iodine.

"Halogenated," used as a prefix of a group, means one or more hydrogens on the group are replaced with one or more halogens.

"RT", "r.t." or "rt" means room temperature.

"DMF" refers to dimethyl formamide.

"DIPEA" refers to N,N-diisopropylethylamine.

"HATU" refers to 2-(7-Aza-1H-benzotriazole-1-yl)-1,1,3,3-tetramethyluronium hexafluorophosphate.

One aspect of the invention is a compound of formula I, a pharmaceutically acceptable salt thereof, a diastereomer, an enantiomer, or a mixture thereof:

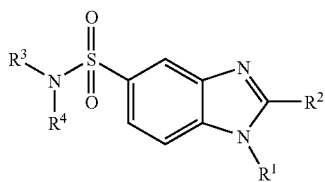

I wherein:

$R^1$ is selected from $C_{1-10}$alkyl, $C_{2-10}$alkenyl, $C_{1-10}$alkoxy, $C_{6-10}$aryl-$C_{1-6}$alkyl, $C_{6-10}$aryl-C(=O)—$C_{1-6}$alkyl, $C_{3-10}$cycloalkyl-$C_{1-6}$alkyl, $C_{4-8}$cycloalkenyl-$C_{1-6}$alkyl, $C_{3-6}$heterocyclyl-$C_{1-6}$alkyl, $C_{3-6}$heterocyclyl-C(=O)—$C_{1-6}$alkyl, $C_{6-10}$aryl, $C_{6-10}$aryl-C(=O)—, $C_{3-10}$cycloalkyl, $C_{4-8}$cycloalkenyl, $C_{3-6}$heterocyclyl and $C_{3-6}$heterocyclyl-C(=O)—; wherein said $C_{1-10}$alkyl, $C_{2-10}$alkenyl, $C_{1-10}$alkoxy, $C_{6-10}$aryl-$C_{1-6}$alkyl, $C_{6-10}$aryl-C(=O)—$C_{1-6}$alkyl, $C_{3-10}$cycloalkyl-$C_{1-6}$alkyl, $C_{4-8}$cycloalkenyl-$C_{1-6}$alkyl, $C_{3-6}$heterocyclyl-$C_{1-6}$alkyl, $C_{3-6}$heterocyclyl-C(=O)—$C_{1-6}$alkyl, $C_{6-10}$aryl, $C_{6-10}$aryl-C(=O)—, $C_{3-10}$cycloalkyl, $C_{4-8}$cycloalkenyl, $C_{3-6}$heterocyclyl or $C_{3-6}$heterocyclyl -C(=O)— is optionally substituted by one or more groups selected from carboxy, —(C=O)—NH$_2$, halogen, cyano, nitro, methoxy, ethoxy, methyl, ethyl, hydroxy, —N($R^6$)—C(=O)$R^5$, —S(=O)$_2$—NR$^5$R$^6$, —C(=O)—NR$^5$R$^6$, —NH—C(=O)—NR$^5$R$^6$ and —NR$^5$R$^6$;

$R^2$ is selected from the group consisting of $C_{1-10}$alkyl, $C_{2-10}$alkenyl, $C_{2-10}$alkynyl, $C_{3-8}$cycloalkyl, $C_{3-8}$cycloalkyl-$C_{1-6}$alkyl, $C_{4-8}$cycloalkenyl-$C_{1-6}$alkyl, $C_{3-6}$heterocycloalkyl-$C_{1-6}$alkyl, $C_{4-8}$cycloalkenyl and $C_{3-6}$heterocycloalkyl, wherein said $C_{1-10}$alkyl, $C_{2-10}$alkenyl, $C_{2-10}$alkynyl, $C_{3-8}$cycloalkyl, $C_{3-8}$cycloalkyl-$C_{1-6}$alkyl, $C_{4-8}$cycloalkenyl-$C_{1-6}$alkyl, $C_{3-6}$heterocycloalkyl-$C_{1-6}$alkyl, $C_{4-8}$cycloalkenyl or $C_{3-6}$heterocycloalkyl used in defining $R^2$ is optionally substituted by one or more groups selected from carboxy, —(C=O)—NH$_2$, halogen, cyano, nitro, methoxy, ethoxy, methyl, ethyl, hydroxy, and —NR$^5$R$^6$;

$R^3$ and $R^4$ are independently selected from —H, —OH, amino, $R^7$ and —O—$R^7$, wherein $R^7$ is independently selected from $C_{1-6}$alkyl, $C_{2-6}$alkenyl, $C_{2-6}$alkynyl, $C_{3-6}$cycloalkyl, $C_{3-6}$cycloalkyl-$C_{1-4}$alkyl, phenyl and benzyl, wherein $R^3$ and $R^4$ are not —H at the same time, and wherein said $C_{1-6}$alkyl, $C_{2-6}$alkenyl, $C_{2-6}$alkynyl, $C_{3-6}$cycloalkyl, $C_{3-6}$cycloalkyl-$C_{1-4}$alkyl, phenyl or benzyl in defining $R^7$ is optionally substituted by one or more groups selected from carboxy, halogen, cyano, nitro, methoxy, ethoxy, hydroxy, and —NR$^5$R$^6$; or $R^3$ and $R^4$ together with the nitrogen connected thereto form a 5- or 6-membered heterocycle ring, wherein said ring is optionally substituted by one or more groups selected from carboxy, halogen, cyano, nitro, methoxy, ethoxy, hydroxy, —(CH$_2$)$_m$—C(=O)NR$^5$R$^6$, —(CH$_2$)$_m$NH—C(=O)NR$^5$R$^6$, —(CH$_2$)$_m$—N(R$^5$)C(=O)R$^6$, —(CH$_2$)$_m$—N(R$^5$)C(=O)—OR$^6$, —(CH$_2$)$_m$—C(=O)—OR$^6$, —(CH$_2$)$_m$—O—C(=O)—R$^6$, —(CH$_2$)$_m$—OR$^6$, and —NR$^5$R$^6$; and wherein $R^5$ and $R^6$ are independently selected from —H, $C_{1-6}$alkyl optionally substituted with —OH, methoxy, ethoxy or halogen, $C_{3-6}$cycloalkyl-$C_{0-m}$alkyl optionally substituted with —OH, methoxy, ethoxy or halogen, $C_{2-6}$alkenyl optionally substituted with —OH, methoxy, ethoxy or halogen, and a divalent $C_{1-6}$alkylene optionally substituted with —OH, methoxy, ethoxy or halogen that together with another divalent $R^5$ or $R^6$ form a portion of a ring; and m is 0, 1, 2 or 3.

In a particular embodiment, $R^1$ is selected from $C_{3-7}$cycloalkyl-$C_{1-2}$alkyl and $C_{2-6}$heterocycloalkyl-$C_{1-2}$alkyl, wherein said $C_{3-7}$cycloalkyl or $C_{2-6}$heterocycloalkyl is optionally substituted with one or more groups selected from carboxy, —C(=O)—NH$_2$, halogen, cyano, nitro, methoxy, ethoxy, methyl, ethyl, hydroxy, and amino.

In another particular embodiment, $R^1$ is selected from cyclohexylmethyl and tetrahydropyranylmethyl wherein said cyclohexylmethyl or tetrahydropyranylmethyl is optionally substituted with one or more groups selected from carboxy, —C(=O)—NH$_2$, halogen, cyano, nitro, methoxy, ethoxy, methyl, ethyl, hydroxy, and amino.

In a further embodiment, $R^1$ is selected from cyclohexylmethyl and tetrahydropyranylmethyl wherein said cyclohexylmethyl or tetrahydropyranylmethyl is optionally substituted with one or more groups selected from methyl, hydroxy, chloro, fluoro and bromo.

In an even further embodiment, $R^1$ is selected from cyclohexylmethyl and tetrahydropyran-4-ylmethyl wherein said cyclohexylmethyl or tetrahydropyran-4-ylmethyl is optionally substituted with one or more groups selected from chloro and fluoro.

In a yet further embodiment, $R^1$ is selected from cyclohexylmethyl, (4,4-difluorocyclohexyl)methyl, (4-fluorocyclohexyl)methyl and tetrahydro-2H-pyran-4-ylmethyl.

In another particular embodiment, $R^2$ is selected from $C_{1-6}$alkyl, $C_{2-6}$alkenyl, $C_{3-6}$cycloalkyl, and $C_{3-6}$cycloalkyl-$C_{1-2}$alkyl, wherein said $C_{1-6}$alkyl, $C_{2-6}$alkenyl, $C_{3-6}$cycloalkyl, or $C_{3-6}$cycloalkyl-$C_{1-2}$alkyl is optionally substituted by one or more groups selected from halogen, methoxy, ethoxy, methyl, ethyl, and hydroxy.

In a further embodiment, $R^2$ is selected from ethyl, propyl, isopropyl, n-butyl, isobutyl, t-butyl, 1-pentyl, 2-pentyl, 3-pentyl, 1,1-dimethyl-1-propyl, 3-methyl-1-butyl, and 2,2dimethyl-1-propyl, wherein said propyl, isopropyl, n-butyl, isobutyl, t-butyl, 1-pentyl, 2-pentyl, 3-pentyl, 1,1-dimethyl-1-propyl, 3-methyl-1-butyl, or 2,2dimethyl-1-propyl is optionally substituted by one or more groups selected from halogen, methoxy and ethoxy.

In an even further embodiment, $R^2$ is selected from 1,1-difluoroethyl, propyl, isopropyl, n-butyl, isobutyl, t-butyl, 1-pentyl, 2-pentyl, 3-pentyl, 1,1-dimethyl-1-propyl, 3-methyl-1-butyl, and 2,2dimethyl-1-propyl.

In an even further embodiment, $R^2$ is selected from t-butyl, 1,1-difluoroethyl and 1,1-dimethyl-1-propyl.

In another particular embodiment, $R^3$ and $R^4$ together with the nitrogen connected thereto form a 5- or 6-membered heterocycle ring, wherein said ring is optionally substituted by is one or more groups selected from carboxy, halogen, cyano, nitro, methoxy, ethoxy, hydroxy, carboxy, —$(CH_2)_m$—C(=O)$NR^5R^6$ and —$NR^5R^6$, wherein $R^5$ and $R^6$ are independently selected from —H, $C_{1-6}$alkyl optionally substituted with —OH, methoxy, ethoxy or halogen, $C_{3-6}$cycloalkyl-$C_{0-m}$alkyl optionally substituted with —OH, methoxy, ethoxy or halogen, $C_{2-6}$alkenyl optionally substituted with —OH, methoxy, ethoxy or halogen, and a divalent $C_{1-6}$alkylene optionally substituted with —OH, methoxy, ethoxy or halogen that together with another divalent $R^5$, $R^6$ or $R^7$ form a portion of a ring; and m is 0, 1, 2 or 3.

In a further embodiment,

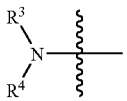

of formula I is represented by

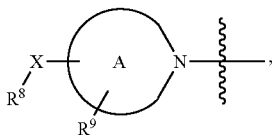

wherein $R^8$ is selected from hydrogen, $C_{1-4}$alkyl, halogenated $C_{1-4}$alkyl, hydroxy-$C_{1-4}$alkyl, $C_{3-6}$cycloalkyl, $C_{3-6}$cycloalkyl-$C_{1-2}$alkyl, methoxy-$C_{1-4}$alkyl, ethoxy-$C_{1-4}$alkyl, and $C_{2-4}$alkenyl; $R^9$ is selected from hydrogen, hydroxy, halogen, isocyanato, methoxy, ethoxy, $C_{1-4}$alkyl, halogenated $C_{1-4}$alkyl, phenyl, benzyl, amino, $C_{3-6}$cycloalkyl, $C_{3-6}$cycloalkyl-$C_{1-2}$alkyl, and $C_{1-4}$alkoxymethyl; X is selected from —O—C(=O)—, —C(=O)—NH—, —NH—C(=O)—, —C(=O)—NHCH_2—, —NH—C(=O)CH_2—, —NH—C(=O)—NH—, —O—C(=O)—NH—, —C(=O)—O—, and —NH—C(=O)—O—;

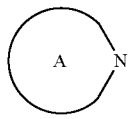

is a 5 or 6-membered heterocycle which optionally contains one additional heteroatom selected from O and N on its ring in addition to the nitrogen shown. Particularly,

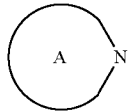

is selected from piperidinyl, isoxazolindinyl, azetidinyl, morpholinyl, pyrazolyl, pyrrolyl and pyrrolidinyl.

In a further embodiment, $R^3$ and $R^4$ together with the nitrogen connected thereto form a 5- or 6-membered heterocycle ring selected from piperidinyl, isoxazolindinyl, azetidinyl, morpholinyl, pyrazolyl, pyrrolyl and pyrrolidinyl, wherein said piperidinyl, isoxazolindinyl, azetidinyl, morpholinyl, pyrazolyl, pyrrolyl or pyrrolidinyl is optionally substituted by one or more groups selected from methyl, cyclopropyl, amino, cyclobutanylcarbonylamino, hydrocarbonyl, 2-hydroxyethylaminocarbonyl, isopropylaminocarbonyl, cyclobutanylaminocarbonyl, ethylaminocarbonyl, cyclopropylaminocarbonyl, methoxycarbonyl, ethoxycarbonyl, hydroxycarbonyl, t-butoxycarbonyl, t-butoxycarbonylamino, allylaminocarbonyl, methylaminocarbonyl, fluoro, aminocarbonyl, 2-fluoroethylaminocarbonyl, propylaminocarbonyl, cyclopropylmethylaminocarbonyl, cyclobutylmethylaminocarbonyl, phenyl, trifluoromethyl, methoxy, ethyl, methoxymethyl, benzyl, t-butoxycarbonylamino, ethylaminocarbonylamino, isocyanato, cyclopropylaminocarbonylamino, 2-hydroxyethylaminocarbonylamino, hydroxy, ethylaminocarboxy, acetylamino, propionylamino, ethylaminocarbonylmethyl, 2-fluoroethylaminocarbonylmethyl, 2,2-difluoroethylaminocarbonyl, 2,2-difluoroethylaminocarbonylmethyl, acetylaminomethyl, cyclopropylcarbonylaminomethyl, propionylaminomethyl, and methylaminocarbonylmethyl.

In another embodiment, $R^3$ and $R^4$ are independently selected from $C_{1-6}$alkyl, $C_{3-6}$cycloalkyl, phenyl, benzyl, $C_{3-6}$cycloalkyl-$C_{1-4}$alkyl, $C_{2-6}$alkenyl and $C_{1-6}$alkoxy.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be appreciated that certain compounds of the present invention may exist as geometrical isomers, for example E and Z isomers of alkenes. The present invention includes any geometrical isomer of a compound of Formula I. It will further be understood that the present invention encompasses tautomers of the compounds of the formula I.

It will also be understood that certain compounds of the present invention may exist in solvated, for example hydrated, as well as unsolvated forms. It will further be understood that the present invention encompasses all such solvated forms of the compounds of the formula I.

Within the scope of the invention are also salts of the compounds of the formula I. Generally, pharmaceutically acceptable salts of compounds of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound of formula I above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

We have now found that the compounds of the invention have activity as pharmaceuticals, in particular as modulators or ligands such as agonists, partial agonists, inverse agonist or antagonists of $CB_1$ receptors. More particularly, the compounds of the invention exhibit activity as agonist of the $CB_1$ receptors and are useful in therapy, especially for relief of various pain conditions such as chronic pain, neuropathic pain, acute pain, cancer pain, pain caused by rheumatoid arthritis, migraine, visceral pain etc. This list should however not be interpreted as exhaustive. Additionally, compounds of the present invention are useful in other disease states in which dysfunction of $CB_1$ receptors is present or implicated. Furthermore, the compounds of the invention may be used to treat cancer, multiple sclerosis, Parkinson's disease, Huntington's chorea, Alzheimer's disease, anxiety disorders, gastrointestinal disorders and cardiovascular disorders.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of cannabinoid receptors is present or implicated in that paradigm. This may involve the use of isotopically labeled versions of the compounds of the invention in diagnostic techniques and imaging applications such as positron emission tomography (PET).

Compounds of the invention are useful for the treatment of diarrhea, depression, anxiety and stress-related disorders such as post-traumatic stress disorders, panic disorder, generalized anxiety disorder, social phobia, and obsessive compulsive disorder, urinary incontinence, premature ejaculation, various mental illnesses, cough, lung edema, various gastro-intestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following myocardial infarction, spinal injury and drug addiction, including the treatment of alcohol, nicotine, pied and other drug abuse and for disorders of the sympathetic nervous system for example hypertension.

Compounds of the invention are useful as an analgesic agent for use during general anaesthesia and monitored anaesthesia care. Combinations of agents with different properties are often used to achieve a balance of effects needed to maintain the anesthetic state (e.g. amnesia, analgesia, muscle relaxation and sedation). Included in this combination are inhaled anesthetics, hypnotics, anxiolytics, neuromuscular blockers and opioids.

Another aspect of the present invention is the use of a compound according to Formula I, for the inhibition of transient lower esophageal sphincter relaxations (TLESRs) and thus for treatment or prevention of gastroesophageal reflux disorder (GERD). The major mechanism behind reflux has been considered to depend on a hypotonic lower esophageal sphincter. However, e.g. Holloway & Dent (1990) *Gastroenterol. Clin. N. Amer.* 19, pp. 517-535, has shown that most reflux episodes occur during transient lower esophageal sphincter relaxations (TLESRs), i.e. relaxations not triggered by swallows. In yet further embodiments of the present invention, the compound according to Formula I are useful for the prevention of reflux, treatment or prevention of regurgitation, treatment or prevention of asthma, treatment or prevention of laryngitis, treatment or prevention of lung disease and for the management of failure to thrive.

A further aspect of the present invention is the use of a compound according to Formula I, for the manufacture of a medicament for the inhibition of transient lower esophageal sphincter relaxations, for the treatment or prevention of GERD, for the prevention of reflux, for the treatment or prevention of regurgitation, treatment or prevention of asthma, treatment or prevention of laryngitis, treatment or prevention of lung disease and for the management of failure to thrive.

Still another aspect of the present invention is the use of a compound according to Formula I for the manufacture of a medicament for the treatment or prevention of functional gastrointestinal disorders, such as functional dyspepsia (FD). Yet another aspect of the present invention is the use of a compound according to Formula I for the manufacture of a medicament for the treatment or prevention of irritable bowel syndrome (IBS), such as constipation predominant IBS, diarrhea predominant IBS or alternating bowel movement predominant IBS. Exemplary irritable bowel syndrome (IBS) and functional gastrointestinal disorders (FGD), such as functional dyspepsia (FD), are illustrated in Thompson W G, Longstreth G F, Drossman D A, Heaton K W, Irvine E J, Mueller-Lissner S A. C. *Functional Bowel Disorders and Functional Abdominal Pain*. In: Drossman D A, Talley N J, Thompson W G, Whitehead W E, Coraziarri E, eds. *Rome II: Functional Gastrointestinal Disorders: Diagnosis, Pathophysiology and Treatment*. 2 ed. McLean, V A: Degnon Associates, Inc.; 2000:351-432 and Drossman D A, Corazziari E, Talley N J, Thompson W G and Whitehead W E. *Rome II: A multinational consensus document on Functional Gastrointestinal Disorders*. Gut 45(Suppl. 2), II1-II81.9-1-1999.

Also within the scope of the present invention is the use of any of the compounds according to the Formula I above, for the manufacture of a medicament for the treatment of any of the conditions discussed above.

A further aspect of the invention is a method for the treatment of a subject suffering from any of the conditions discussed above, whereby an effective amount of a compound according to the formula I above, is administered to a patient in need of such treatment.

Thus, the invention provides a compound of formula I, or pharmaceutically acceptable salt or solvate thereof, as hereinbefore defined for use in therapy.

In a further aspect, the present invention provides the use of a compound of formula I, or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

The compounds of the present invention are useful in therapy, especially for the therapy of various pain conditions including, but not limited to: acute pain, chronic pain, neuropathic pain, back pain, cancer pain, and visceral pain.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the invention, the route of administration may be oral, intravenous or intramuscular.

The dosage will depend on the route of administration, the severity of the disease, age and weight of the patient and other factors normally considered by the attending physician, when determining the individual regimen and dosage level at the most appropriate for a particular patient.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substance, which may also act as diluents, flavoring agents, solubilizers, lubricants, suspending agents, binders, or tablet-disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized molds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (percent by weight), more preferably from 0.10 to 50% w, of the compound of the invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

Within the scope of the invention is the use of any compound of formula I as defined above for the manufacture of a medicament.

Also within the scope of the invention is the use of any compound of formula I for the manufacture of a medicament for the therapy of pain.

Additionally provided is the use of any compound according to Formula I for the manufacture of a medicament for the therapy of various pain conditions including, but not limited to: acute pain, chronic pain, neuropathic pain, back pain, cancer pain, and visceral pain.

A further aspect of the invention is a method for therapy of a subject suffering from any of the conditions discussed above, whereby an effective amount of a compound according to the formula I above, is administered to a patient in need of such therapy.

Additionally, there is provided a pharmaceutical composition comprising a compound of Formula I, or a pharmaceutically acceptable salt thereof, in association with a pharmaceutically acceptable carrier.

Particularly, there is provided a pharmaceutical composition comprising a compound of Formula I, or a pharmaceutically acceptable salt thereof, in association with a pharmaceutically acceptable carrier for therapy, more particularly for therapy of pain.

Further, there is provided a pharmaceutical composition comprising a compound of Formula I, or a pharmaceutically acceptable salt thereof, in association with a pharmaceutically acceptable carrier use in any of the conditions discussed above.

In a further embodiment, a compound of formula I or a pharmaceutically acceptable salt, solvate or in vivo hydrolysable ester thereof, or a pharmaceutical composition or formulation comprising a compound of formula I may be administered concurrently, simultaneously, sequentially or separately with one or more pharmaceutically active compound(s) selected from the following:

(i) antidepressants such as amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, reboxetine, robalzotan, sertraline, sibutramine, thionisoxetine, tranylcypromaine, trazodone, trimipramine, venlafaxine and equivalents and pharmaceutically active isomer(s) and metabolite(s) thereof;

(ii) atypical antipsychotics including for example quetiapine and pharmaceutically active isomer(s) and metabolite(s) thereof, amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, lithium, loxapine, mesoridazine, olanzapine, paliperidone, perlapine, perphenazine, phenothiazine, phenylbutlypiperidine, pimozide, prochlorperazine, risperidone, quetiapine, sertindole, sulpiride, suproclone, suriclone, thioridazine, trifluoperazine, trimetozine, valproate, valproic acid, zopiclone, zotepine, ziprasidone and equivalents thereof;

(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutlypiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof;

(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof;

(v) anticonvulsants including, for example, carbamazepine, valproate, lamotrogine, gabapentin and equivalents and pharmaceutically active isomer(s) and metabolite(s) thereof;

(vi) Alzheimer's therapies including, for example, donepezil, memantine, tacrine and equivalents and pharmaceutically active isomer(s) and metabolite(s) thereof;

(vii) Parkinson's therapies including, for example, defray, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase and equivalents and pharmaceutically active isomer(s) and metabolite(s) thereof;

(viii) migraine therapies including, for example, almotriptan, amantadine, bromocriptine, butalbital, cabergoline, dichloralphenazone, eletriptan, frovatriptan, lisuride, naratriptan, pergolide, pramipexole, rizatriptan, ropinirole, sumatriptan, zolmitriptan, zomitriptan, and equivalents and pharmaceutically active isomer(s) and metabolite(s) thereof;

(ix) stroke therapies including, for example, abciximab, activase, NXY-059, citicoline, crobenetine, desmoteplase, repinotan, traxoprodil and equivalents and pharmaceutically active isomer(s) and metabolite(s) thereof;

(x) over active bladder urinary incontinence therapies including, for example, darafenacin, falvoxate, oxybutynin, propiverine, robalzotan, solifenacin, tolterodine and equivalents and pharmaceutically active isomer(s) and metabolite(s) thereof;

(xi) neuropathic pain therapies including, for example, gabapentin, lidoderm, pregablin and equivalents and pharmaceutically active isomer(s) and metabolite(s) thereof;

(xii) nociceptive pain therapies such as celecoxib, etoricoxib, lumiracoxib, rofecoxib, valdecoxib, diclofenac, loxoprofen, naproxen, paracetamol and equivalents and pharmaceutically active isomer(s) and metabolite(s) thereof;

(xiii) insomnia therapies including, for example, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, roletamide, triclofos, secobarbital, zaleplon, zolpidem and equivalents and pharmaceutically active isomer(s) and metabolite(s) thereof; and (xiv) mood stabilizers including, for example, carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combinations employ the compounds of this invention within the dosage range described herein and the other pharmaceutically active compound or compounds within approved dosage ranges and/or the dosage described in the publication reference.

Another aspect of the invention is a method of preparing the compounds of the present invention.

In one embodiment, the method of the invention is a method for preparing a compound of formula I,

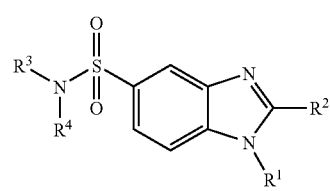

comprising the step of reacting a compound of formula II,

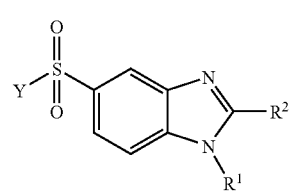

with a compound of $R^3R^4NH$, optionally in the presence of a base, such as Nag or DMAP, a solvent such as THF or MeCN, wherein Y is selected from Cl, Br, F, methoxy and OH; and $R^1$, $R^2$, $R^3$ and $R^4$ are defined as above.

Compounds of the present invention may be prepared according to the synthetic routes as depicted in Schemes 1-5.

Scheme 1

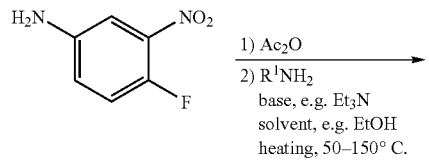

1) Ac$_2$O
2) R$^1$NH$_2$
   base, e.g. Et$_3$N
   solvent, e.g. EtOH
   heating, 50–150° C.

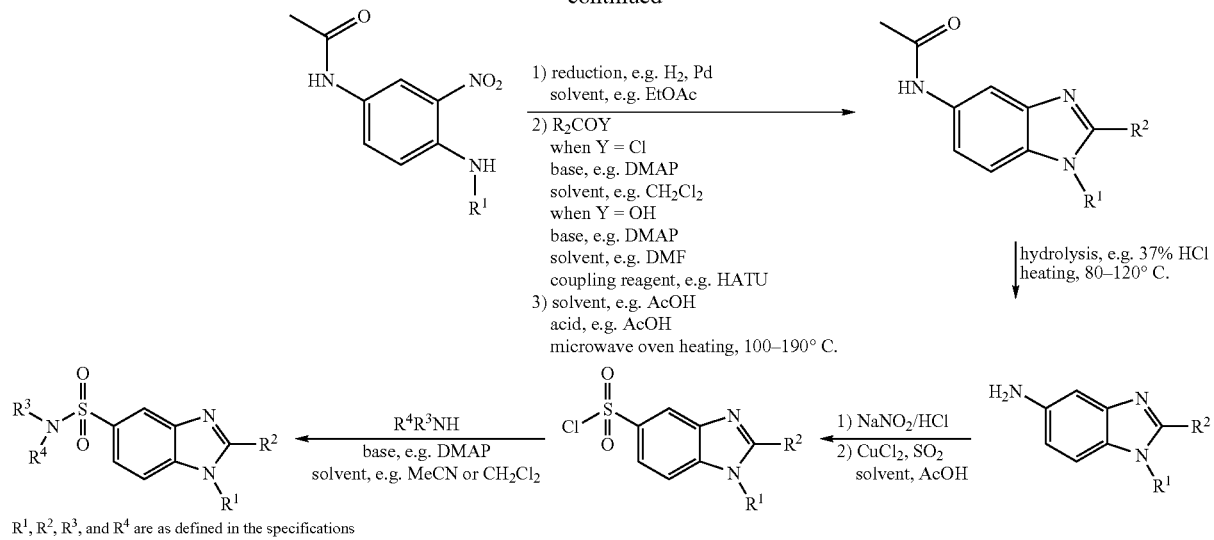
$R^1$, $R^2$, $R^3$, and $R^4$ are as defined in the specifications
Scheme 2
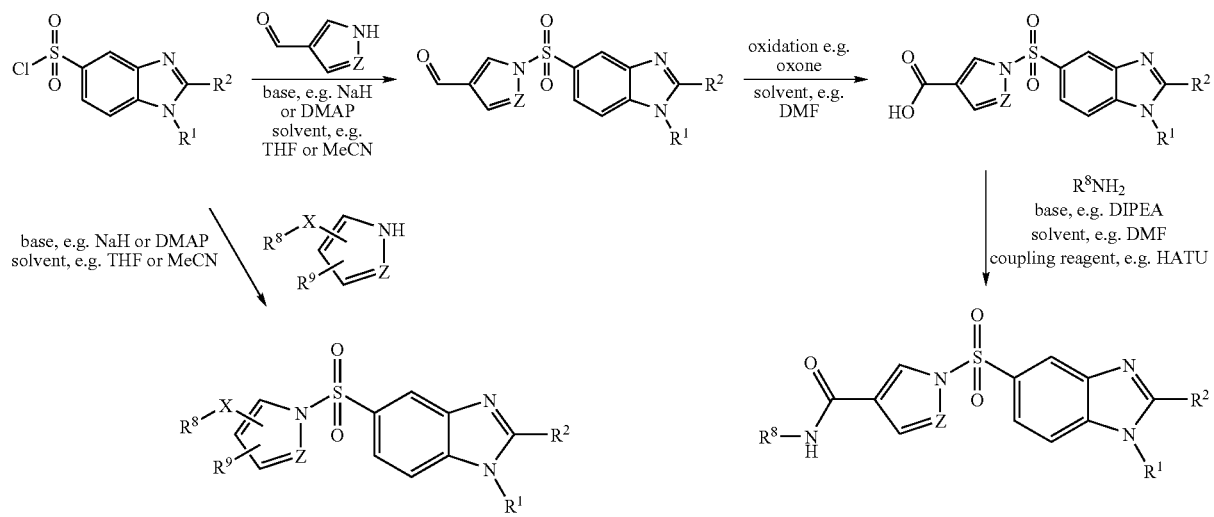
$R^1$, $R^2$, $R^8$, and $R^9$ are as defined in the specifications.
Z is C or N
Scheme 3
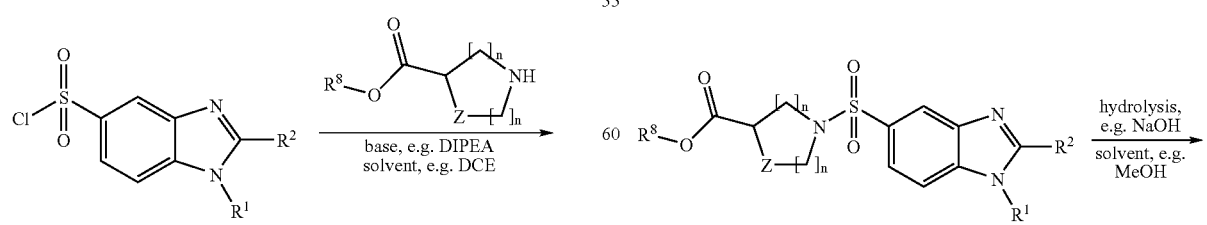

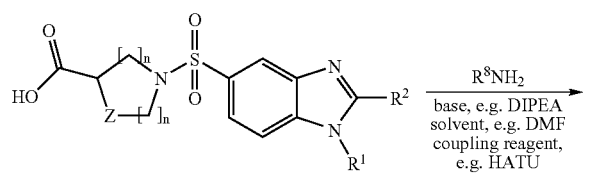
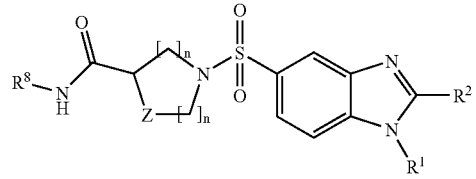
R[1], R[2], and R[8] are independently as defined above.
Z is C or N, n is 1 or 2.
Scheme 4
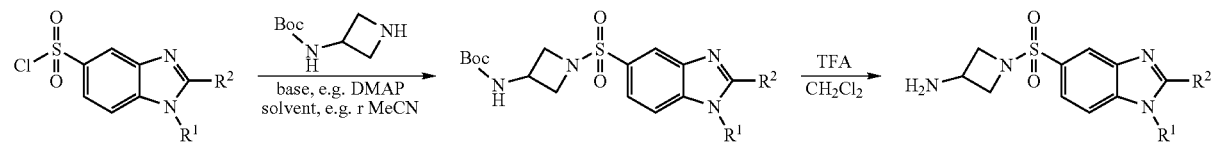
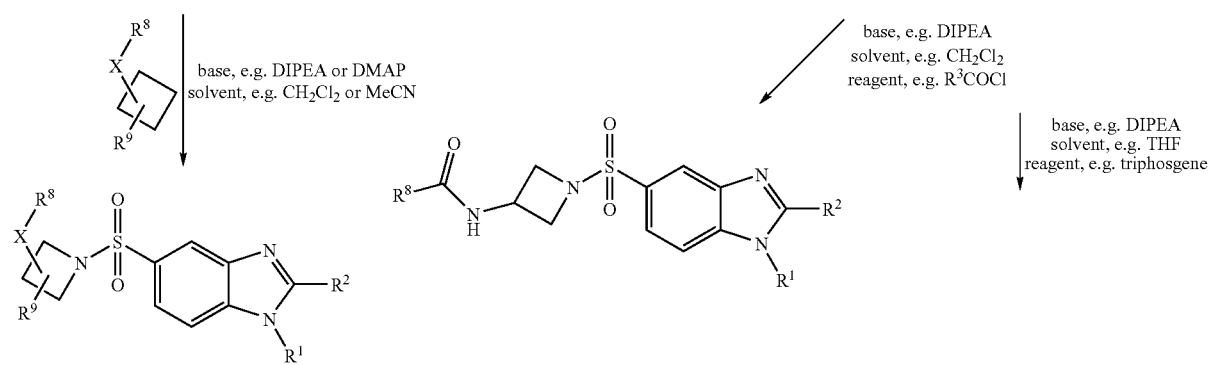
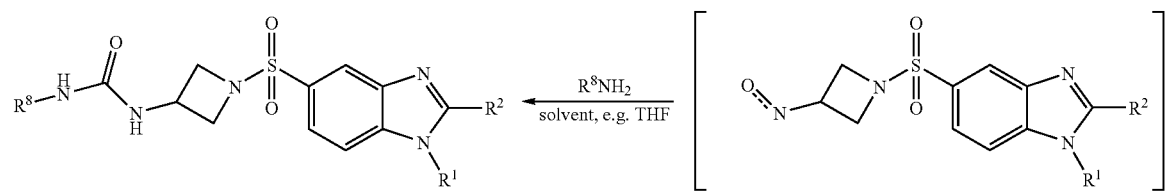
X, R[1], R[2], R[8], and R[9] are as defined above.

Scheme 5

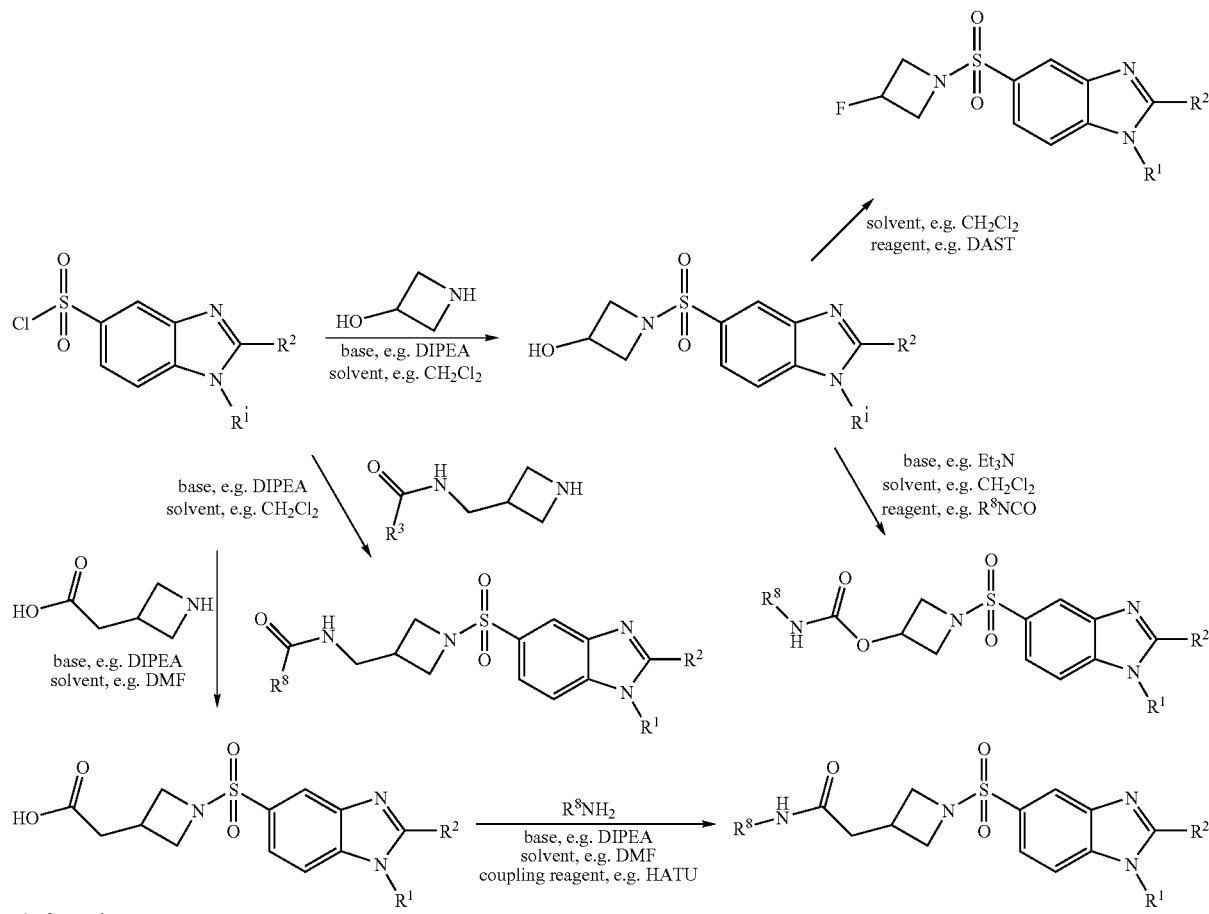

$R^1$, $R^2$, and $R^8$ are as defined above.

Biological Evaluation $hCB_1$ and $hCB_2$ Receptor Binding

Human $CB_1$ receptor from Receptor Biology ($hCB_1$) or human $CB_2$ receptor from BioSignal ($hCB_2$) membranes are thawed at 37° C., passed 3 times through a 25-gauge blunt-end needle, diluted in the cannabinoid binding buffer (50 mM Tris, 2.5 mM EDTA, 5 mM $MgCl_2$, and 0.5 mg/mL BSA fatty acid free, pH 7.4) and aliquots containing the appropriate amount of protein are distributed into 96-well plates. The $IC_{50}$ of the compounds of the invention at $hCB_1$ and $hCB_2$ are evaluated from 10-point dose-response curves done with $^3$H-CP55,940 at 20000 to 25000 dpm per well (0.17-0.21 nM) in a final volume of 300 μl. The total and non-specific binding are determined in the absence and presence of 0.2 μM of HU210 respectively. The plates are vortexed and incubated for 60 minutes at room temperature, filtered through Unifilters GF/B (presoaked in 0.1% polyethyleneimine) with the Tomtec or Packard harvester using 3 mL of wash buffer (50 mM Tris, 5 mM $MgCl_2$, 0.5 mg BSA pH 7.0). The filters are dried for 1 hour at 55° C. The radioactivity (cpm) is counted in a TopCount (Packard) after adding 65 μl/well of MS-20 scintillation liquid.

$hCB_1$ and $hCB_2$ GTPγS binding

Human $CB_1$ receptor from Receptor Biology ($hCB_1$) or human $CB_2$ receptor membranes (BioSignal) are thawed at 37° C., passed 3 times through a 25-gauge blunt-end needle and diluted in the GTPγS binding buffer (50 mM Hepes, 20 mM NaOH, 100 mM Nick, 1 mM EDTA, 5 mM $MgCl_2$, pH 7.4, 0.1% BSA). The $EC_{50}$ and $E_{max}$ of the compounds of the invention are evaluated from 10-point dose-response curves done in 300 μ with the appropriate amount of membrane protein and 100000-130000 dpm of GTPg$^{35}$S per well (0.11-0.14 nM). The basal and maximal stimulated binding is determined in absence and presence of 1 μM ($hCB_2$) or 10 μM ($hCB_1$) Win 55,212-2 respectively. The membranes are preincubated for 5 minutes with 56.25 μM (hCB2) or 112.5 μM ($hCB_1$) GDP prior to distribution in plates (15 μM ($hCB_2$) or 30 μM ($hCB_1$) GDP final). The plates are vortexed and incubated for 60 minutes at room temperature, filtered on Unifilters GF/B (presoaked in water) with the Tomtec or Packard harvester using 3 ml of wash buffer (50 mM Tris, 5 mM $MgCl_2$, 50 mM NaCl, pH 7.0). The filters are dried for 1 hour at 55° C. The radioactivity (cpm) is counted in a TopCount (Packard) after adding 65 μl/well of MS-20 scintillation liquid. Antagonist reversal studies are done in the same way except that (a) an agonist dose-response curve is done in the presence of a constant concentration of antagonist, or (b) an antagonist dose-response curve is done in the presence of a constant concentration of agonist.

Based on the above assays, the dissociation constant (Ki) for a particular compound of the invention towards a particular receptor is determined using the following equation:

$$Ki = IC_{50}/(1+[rad]/Kd),$$

Wherein $IC_{50}$ is the concentration of the compound of the invention at which 50% displacement has been observed;

[rad] is a standard or reference radioactive ligand concentration at that moment; and Kd is the dissociation constant of the radioactive ligand towards the particular receptor.

Using the above-mentioned assays, the Ki towards human $CB_1$ receptors for certain exemplified compounds of the invention is measured to be in the range of 0.88-8710 nM. The $EC_{50}$ towards human $CB_1$ receptors for certain exemplified compounds of the invention is measured to be in the range of about 0.58-1768 nM. The $E_{max}$ towards human $CB_1$ receptors for certain exemplified compounds of the invention is measured to be in the range of about 106-149%.

The following table shows certain biological activities for some of the exemplified compounds.

| Name | hCB1 KI (nM) | hCB1 EC50 (nM) | hCB1 Emax (%) | Solubility (μM) |
|---|---|---|---|---|
| 1-({2-tert-Butyl-1-[(4,4-difluorocyclohexyl)methyl]-1H-benzimidazol-5-yl}sulfonyl)-N-cyclopropyl-1H-pyrazole-4-carboxamide | 0.88 | 0.58 | 121.91 | 6.16 |
| 1-({2-tert-Butyl-1-[(4,4-difluorocyclohexyl)methyl]-1H-benzimidazol-5-yl}sulfonyl)-N-methyl-1H-pyrazole-4-carboxamide | 1.61 | 1.21 | 118.38 | 2.52 |
| 1-({2-tert-Butyl-1-[(4,4-difluorocyclohexyl)methyl]-1H-benzimidazol-5-yl}sulfonyl)-N-isopropyl-1H-pyrazole-4-carboxamide | 1.82 | 3.41 | 125.04 | 0.26 |
| (3S)-1-({2-tert-Butyl-1-[(4,4-difluorocyclohexyl)methyl]-1H-benzimidazol-5-yl}sulfonyl)-N-propylpiperidine-3-carboxamide | 2.03 | 1.69 | 133.75 | 16.78 |
| (3S)-1-({2-tert-Butyl-1-[(4,4-difluorocyclohexyl)methyl]-1H-benzimidazol-5-yl}sulfonyl)-N-cyclopropylpiperidine-3-carboxamide | 2.05 | 1.71 | 135.85 | 29.42 |
| 1-{[2-tert-Butyl-1-(tetrahydro-2H-pyran-4-ylmethyl)-1H-benzimidazol-5-yl]sulfonyl}-N-cyclopropyl-1H-pyrrole-3-carboxamide | 5.68 | 10.49 | 141.84 | 5.64 |
| 4-({2-tert-Butyl-1-[(4,4-difluorocyclohexyl)methyl]-1H-benzimidazol-5-yl}sulfonyl)-N-cyclopropylmorpholine-2-carboxamide | 11.35 | 10.44 | 119.59 | 42.45 |
| 1-{[2-tert-Butyl-1-(tetrahydro-2H-pyran-4-ylmethyl)-1H-benzimidazol-5-yl]sulfonyl}-N-ethyl-1H-pyrazole-4-carboxamide | 14.57 | 57.18 | 127.40 | 337.31 |
| (2S)-4-({2-tert-butyl-1-[(4,4-difluorocyclohexyl)methyl]-1H-benzimidazol-5-yl}sulfonyl)-N-ethylmorpholine-2-carboxamide | 18.04 | 43.77 | 155.57 | 43.36 |
| N-Cyclopropyl-1-{[2-(1,1-difluoroethyl)-1-(tetrahydro-2H-pyran-4-ylmethyl)-1H-benzimidazol-5-yl]sulfonyl}-1H-pyrrole-3-carboxamide | 19.06 | 17.76 | 118.77 | 6.20 |
| 1-{[2-tert-butyl-1-(tetrahydro-2H-pyran-4-ylmethyl)-1H-benzimidazol-5-yl]sulfonyl}-N-ethyl-1H-pyrrole-3-carboxamide | 24.16 | 84.25 | 138.14 | 27.99 |
| 1-{[2-(1,1-Difluoroethyl)-1-(tetrahydro-2H-pyran-4-ylmethyl)-1H-benzimidazol-5-yl]sulfonyl}-N-ethyl-1H-pyrrole-3-carboxamide | 87.99 | N/A | N/A | 7.45 |
| 2-tert-Butyl-5-[(3-phenylpyrrolidin-1-yl)sulfonyl]-1-(tetrahydro-2H-pyran-4-ylmethyl)-1H-benzimidazole | 110.09 | N/A | N/A | 7.29 |
| 1-{[2-tert-Butyl-1-(tetrahydro-2H-pyran-4-ylmethyl)-1H-benzimidazol-5-yl]sulfonyl}-1H-pyrazol-3-amine | 252.02 | N/A | N/A | 43.03 |
| 2-tert-Butyl-5-[(3-phenylpiperidin-1-yl)sulfonyl]-1-(tetrahydro-2H-pyran-4-ylmethyl)-1H-benzimidazole | 277.95 | N/A | N/A | 0.79 |
| 1-{[2-tert-Butyl-1-(tetrahydro-2H-pyran-4-ylmethyl)-1H-benzimidazol-5-yl]sulfonyl}-N-methylpyrrolidine-3-carboxamide | 833.36 | N/A | N/A | 2600.00 |
| 2-tert-Butyl-5-(morpholin-4-ylsulfonyl)-1-(tetrahydro-2H-pyran-4-ylmethyl)-1H-benzimidazole | 1531.76 | N/A | N/A | 128.35 |

EXAMPLES

The invention will further be described in more detail by the following Examples which describe methods whereby compounds of the present invention may be prepared, purified, analyzed and biologically tested, and which are not to be construed as limiting the invention.

Example 1

2-tert-Butyl-N,N-diethyl-1-(tetrahydro-2H-pyran-4-ylmethyl)-1H-benzimidazole-5-sulfonamide

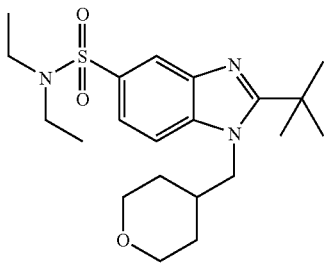

Step A: 2-tert-butyl-N,N-diethyl-1-(tetrahydro-2H-pyran-4-ylmethyl)-1H-benzimidazole-5-sulfonamide

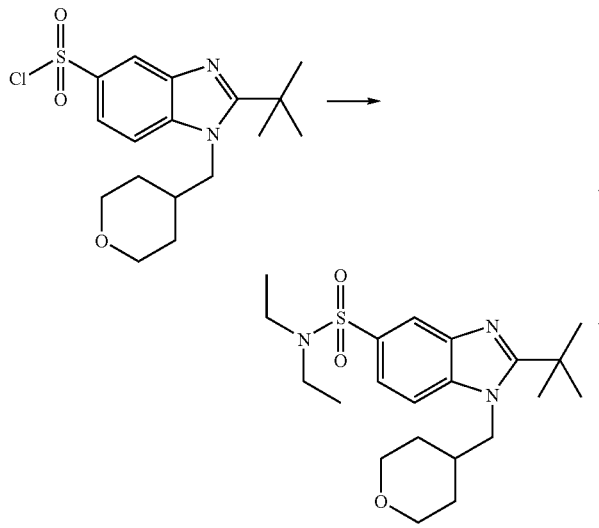

2-tert-Butyl-1-(tetrahydro-2H-pyran-4-ylmethyl)-1H-benzimidazole-5-sulfonyl chloride (61.2 mg, 0.165 mmol) (see following Steps B, C, D, E, F, G and H for preparation), was added to a solution of diethylamine (0.2 mL, 1.93 mmol) and DMAP (50 mg, 0.41 mmol) in MeCN (5 mL). The reaction mixture was stirred overnight at room temperature, diluted with EtOAc (60 mL), washed with NH$_4$Cl (2×5 mL), NaCl (2×5 mL) and dried over Na$_2$SO$_4$. The crude product was purified by MPLC using Hex/EtOAc (1:1) on silica gel to give 20.5 mg (30%) of a white solid as the title compound. $^1$H NMR (400 MHz, METHANOL-D$_4$) δ 1.13 (t, J=7.13 Hz, 6 H), 1.46-1.63 (m, 4 H), 1.66 (s, 9 H), 2.25-2.48 (m, 1 H), 3.22-3.29 (m, 4 H), 3.31-3.41 (m, 2 H), 3.94 (m, 2 H), 4.50 (d, J=7.42 Hz, 2 H), 7.89 (dd, J=8.79, 1.76 Hz, 1 H), 7.96-8.04 (m, 1 H), 8.14 (d, J=1.17 Hz, 1 H); MS (ESI) (M+H)$^+$=408.0; Anal. Calcd for C$_{21}$H$_{33}$N$_3$O$_3$S+1.00 TFA+0.1H$_2$O+0.30 EtOAc (549.84): C, 52.86; H, 6.71; N, 7.64. Found: C, 52.91; H, 6.52; N, 7.61.

Step B: N-(4-Fluoro-3-nitrophenyl)acetamide

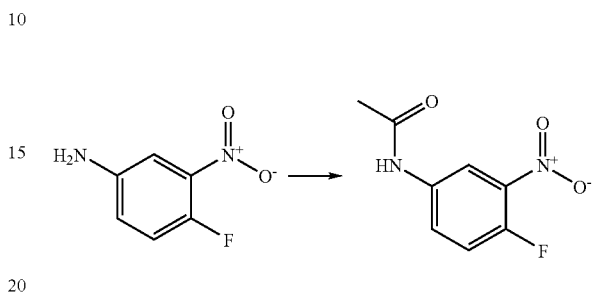

4-Fluoro-3-nitro-aniline (54.2 g, 0.347 mol) was added in portions to acetic anhydride (200 mL) at room temperature. The reaction mixture was stirred overnight at room temperature. The brown solid was collected and dried in vacuo to give the title compound. Yield: 67.5 g (98%). $^1$H NMR (400 MHz, CHLOROFORM-D) δ 2.04 (s, 3 H), 7.51 (dd, J=11.23, 9.08 Hz, 1 H), 7.80 (ddd, J=9.08, 4.00, 2.93 Hz, 1 H), 8.47 (dd, J=7.03, 2.73 Hz, 1 H), 10.38 (s, 1 H).

Step C: N-{3-Nitro-4-[(tetrahydro-2H-pyran-4-ylmethyl)amino]phenyl}acetamide

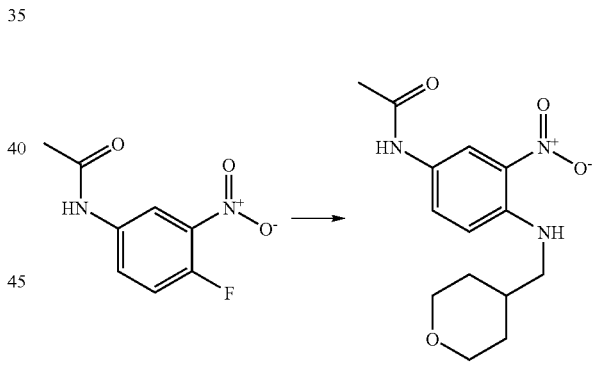

4-Aminomethyl tetrahydropyran (13.7 g, 0.119 mol) was added to a solution of N-(4-Fluoro-3-nitrophenyl)acetamide (20.2 g, 0.102 mol) and TEA (20.9 mL, 15.2 g, 0.15 mol) in EtOH (350 mL). The reaction mixture was stirred overnight at reflux. The orange-red solid was collected by filtration, washed with water and dried in vacuo. The filtrate was concentrated. The residue was dissolved in EtOAc, washed with H$_2$O, brine and dried over anhydrous Na$_2$SO$_4$. The crude product was purified by silica gel flash chromatography using EtOAc as eluent. Total yield: 28.9 g (97%). $^1$H NMR (400 MHz, CHLOROFORM-D) δ 1.4 (m, 2 H), 1.7 (m, 2 H), 1.89-2.00 (m, 1 H), 2.18 (s, 3 H), 3.22 (dd, J=6.44, 5.66 Hz, 2 H), 3.42 (dt, J=11.86, 2.05 Hz, 2 H), 4.02 (dd, J=10.94, 3.71 Hz, 2 H), 6.84 (d, J=9.37 Hz, 1 H), 7.20 (br.s, 1 H), 7.81 (dd, J=9.37, 2.54 Hz, 1 H), 8.09 (d, J=2.54 Hz, 1 H), 8.10-8.12 (m, 1 H).

Step D: N-{3-Amino-4-[(tetrahydro-2H-pyran-4-ylmethyl)amino]phenyl}acetamide

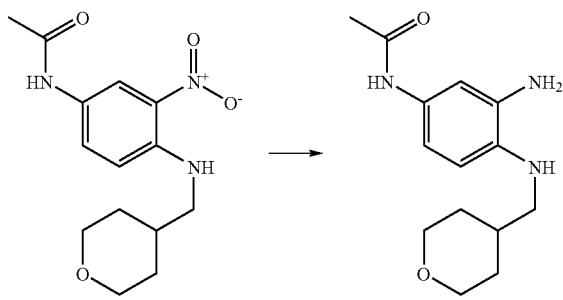

N-{3-Nitro-4-[(tetrahydro-2H-pyran-4-ylmethyl)amino]phenyl}acetamide (28.9 g, 98.5 mmol) was dissolved in 1.0 L of EtOAc containing a catalytic amount of 10% Pd/C. The solution was shaken under $H_2$ atmosphere (40 psi) using a Parr hydrogenation apparatus overnight at room temperature. The solution was filtered through celite and the solvent was evaporated. Yield: 25.9 g (99%). $^1$H NMR (400 MHz, CHLOROFORM-D) δ 1.4 (m, 2 H), 1.7 (m, 2 H), 1.82-1.91 (m, 1 H), 2.13 (s, 3 H), 2.99 (d, J=6.64, 2 H), 3.42 (dt, J=11.86, 2.05 Hz, 2 H), 4.02 (dd, J=10.94, 3.71 Hz, 2 H), 6.84 (d, J=9.37 Hz, 1 H), 7.20 (br.s, 1 H), 7.81 (dd, J=9.37, 2.54 Hz, 1 H), 8.09 (d, J=2.54 Hz, 1 H), 8.10-8.12 (m, 1 H).

Step E: N-{5-(acetylamino)-2-[(tetrahydro-2H-pyran-4-ylmethyl)amino]phenyl}-2,2-dimethylpropanamide

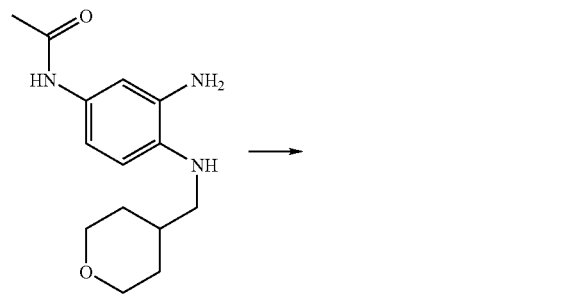

N-{3-Amino-4-[(tetrahydro-2H-pyran-4-ylmethyl)amino]phenyl}acetamide (25.9 g, 98.6 mmol) and DIPEA (20.6 mL, 15.4 g, 118 mmol) were dissolved in 500 mL of DCM. Trimethylacetyl chloride (12.7 mL, 12.5 g, 103 mmol) was added dropwise at 0° C. and the solution was stirred for 3 h at 0° C. and 1 h at room temperature. The pink solid was collected by filtration, washed with $H_2O$ and dried in vacuo. Yield: 33.1 g (97%); MS (ESI) (M+H)$^+$=348.05.

Step F: N-[2-tert-Butyl-1-(tetrahydro-2H-pyran-4-ylmethyl)-1H-benzimidazol-5-yl]acetamide

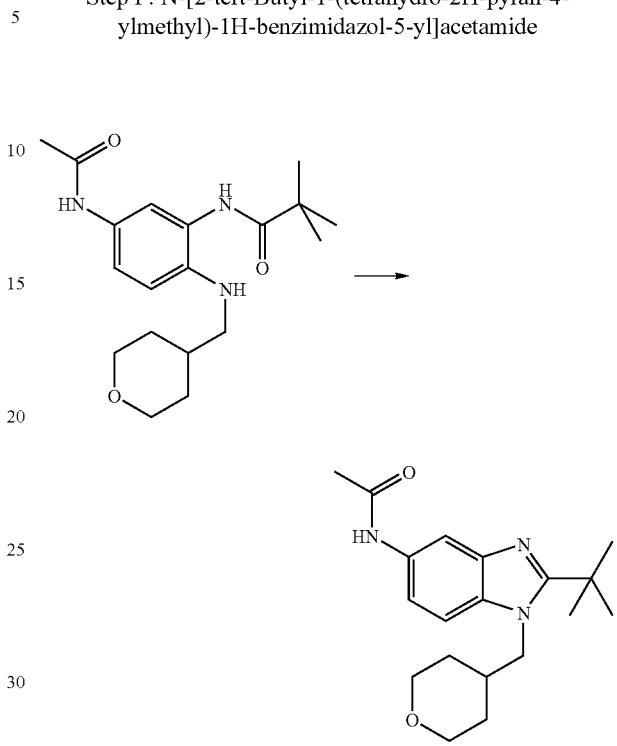

N-{5-(acetylamino)-2-[(tetrahydro-2H-pyran-4-ylmethyl)amino]phenyl}-2,2-dimethylpropanamide (33.1 g, 95.3 mmol) was dissolved in AcOH (250 mL). The solution was heated at 120° C. for 8 h. Upon evaporation of the solvent, the residue was dissolved in EtOAc (500 mL), washed with 2N NaOH (3×50 mL), brine (50 mL) and dried over anhydrous $Na_2SO_4$. The crude product was recrystallized from EtOAc. Yield: 29.0 g (92%). $^1$H NMR (400 MHz, CHLOROFORM-D): δ 1.48-1.54 (m, 4 H), 1.56 (s, 9 H), 2.20 (s, 3 H), 2.24-2.35 (m, 1 H), 3.28-3.35 (m, 2 H), 3.96 (t, J=2.83 Hz, 1 H), 3.99 (t, J=3.03 Hz, 1 H), 4.19 (d, J=7.42 Hz, 2H), 7.27 (d, J=8.59 Hz, 1 H), 7.34 (br.s, 1 H), 7.57 (dd, J=8.79, 1.95 Hz, 1 H), 7.67 (d, J=1.95 Hz, 1 H); MS (ESI) (M+H)$^+$=330.04.

Step G: 2-tert-Butyl-1-(tetrahydro-2H-pyran-4-ylmethyl)-1H-benzimidazol-5-amine

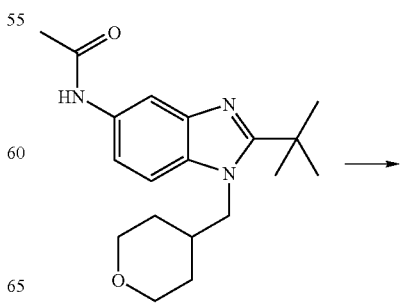

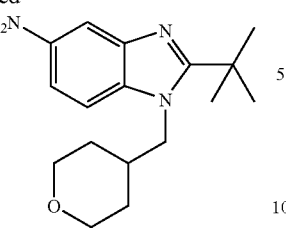

N-[2-tert-Butyl-1-(tetrahydro-2H-pyran-4-ylmethyl)-1H-benzimidazol-5-yl]acetamide (20.7 g, 62.8 mmol) was dissolved in 37% HCl (120 mL). The solution was heated at 95° C. for 20 h. After concentration, 20.4 g (100%) of a purple solid was obtained. $^1$H NMR (400 MHz, CHLOROFORM-D) δ 1.47-1.52 (m, 4 H), 1.54 (s, 9 H), 2.23-2.31 (m, 1 H), 3.28-3.36 (m, 2 H), 3.96 (t, J=3.12 Hz, 1 H), 3.97-4.00 (m, 1 H), 4.13 (d, J=7.62 Hz, 2 H), 6.66 (dd, J=8.40, 2.15 Hz, 1 H), 7.06 (d, J=2.15 Hz, 1 H), 7.10 (d, J=8.40 Hz, 1 H); MS (ESI) (M+H)$^+$=288.0.

Step H: 2-tert-butyl-1-(tetrahydro-2H-pyran-4-ylmethyl)-1H-benzimidazole-5-sulfonyl chloride

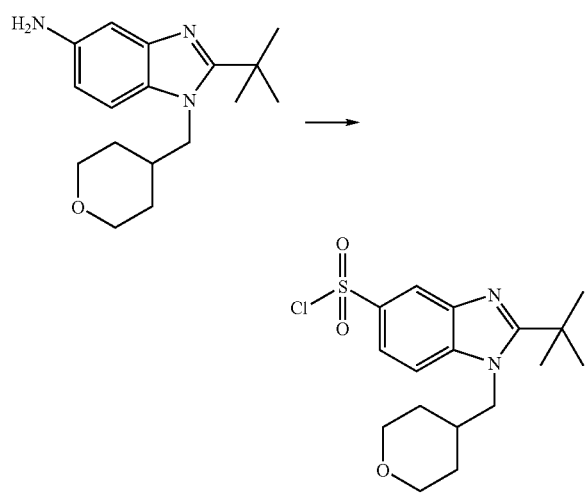

2-tert-Butyl-1-(tetrahydro-2H-pyran-4-ylmethyl)-1H-benzimidazol-5-amine hydrochloride (10.2 g, 31.4 mmol) was dissolved in concentrated hydrochloric acid (100 mL) and acetic acid (25 mL). A solution of NaNO$_2$ (2.6 g, 37.7 mmol) in H$_2$O (5 mL) was added dropwise. The temperature was kept below −2° C. After stirring for 30 min at −2° C., the diazonium solution was poured into a saturated solution of SO$_2$ in AcOH (100 mL) at 0° C. A solution of CuCl$_2$ (2.5 g, 18.8 mmol) in H$_2$O (5 mL) was added. The resulting mixture was stirred for 2 h at 0° C. and 4 h at room temperature, diluted with ice-H$_2$O (100 mL), and extracted with CH$_2$Cl$_2$ (8×200 mL). The combined organic phases were dried over MgSO$_4$. After concentration, 10.9 g (93%) of a yellow solid was obtained. $^1$H NMR (400 MHz, CHLOROFORM-D) δ 1.46-1.58 (m, 4 H), 1.59 (s, 9 H), 2.17-2.49 (m, 1 H), 3.22-3.43 (m, 2 H), 3.93-4.07 (m, 2 H), 4.27 (d, J=7.42 Hz, 2 H), 7.50 (d, J=8.79 Hz, 1 H), 7.92 (dd, J=8.69, 1.86 Hz, 1 H), 8.46 (d, J=1.76 Hz, 1 H); MS (ESI) (M+H)$^+$=370.92.

Example 2

2-tert-Butyl-5-(piperidin-1-ylsulfonyl)-1-(tetrahydro-2H-pyran-4-ylmethyl)-1H-benzimidazole

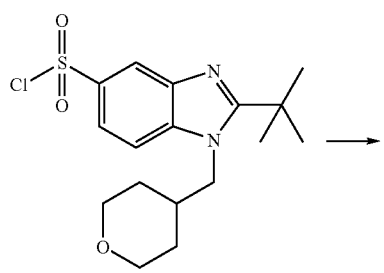

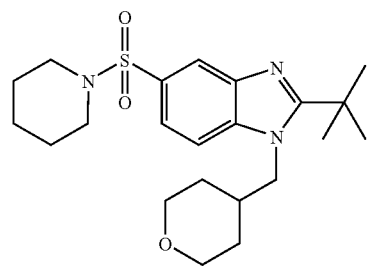

Following the same procedure in Example 1, Step A, using 2-tert-butyl-1-(tetrahydro-2H-pyran-4-ylmethyl)-1H-benzimidazole-5-sulfonyl chloride (61 mg, 0.17 mmol), piperidine (0.2 mL, 2.0 mmol) and DMAP (50 mg, 0.41 mmol) in MeCN (5 mL). The crude product was purified by MPLC using Hex/EtOAc (1:1) on silica gel to give 31 mg (45%) of a white solid as the title compound. $^1$H NMR (400 MHz, METHANOL-D$_4$) δ 1.40 (m, 2 H), 1.47-1.64 (m, 8 H), 1.65 (s, 9 H), 2.25-2.48 (m, 1 H), 2.92-3.05 (m, 4 H), 3.29-3.39 (m, 2 H), 3.88-3.98 (m, 2 H), 4.50 (d, J=7.62 Hz, 2 H), 7.82 (dd, J=8.69, 1.66 Hz, 1 H), 8.01 (d, J=8.79 Hz, 1 H), 8.06 (d, J=1.56 Hz, 1 H); MS (ESI) (M+H)$^+$=420.0; Anal. Calcd for C$_{22}$H$_{33}$N$_3$O$_3$S+1.10 TFA+0.50H$_2$O+0.10 CH$_3$OH (557.23): C, 52.38; H, 6.42; N, 7.54. Found: C, 52.38; H, 6.43; N, 7.58.

Example 3

2-tert-Butyl-5-(isoxazolidin-2-ylsulfonyl)-1-(tetrahydro-2H-pyran-4-ylmethyl)-1H-benzimidazole

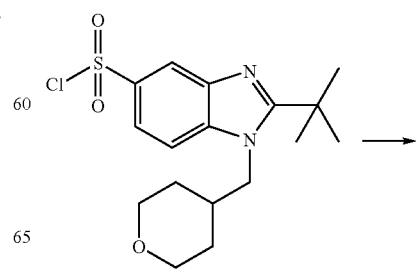

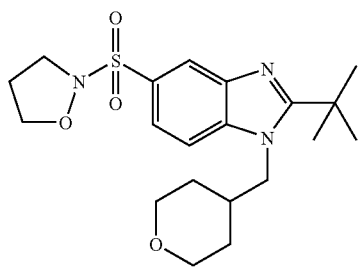

Following the same procedure in Example 1, Step A, using 2-tert-butyl-1-(tetrahydro-2H-pyran-4-ylmethyl)-1H-benzimidazole-5-sulfonyl chloride (61 mg, 0.17 mmol), isoxazolidine hydrochloride (44 mg, 0.40 mmol), DIPEA (0.2 mL, 149 mg, 1.15 mmol) and DMAP (50 mg, 0.41 mmol) in MeCN (5 mL). The crude product was purified by MPLC using Hex/EtOAc (1:1) on silica gel to give 24 mg (36%) of a white solid as the title compound. $^1$H NMR (400 MHz, METHANOL-D$_4$) δ 1.43-1.61 (m, 4 H), 1.63 (s, 9 H), 2.02-2.19 (m, 2 H), 2.25-2.42 (m, 1 H), 3.29-3.38 (m, 2 H), 3.64-3.73 (m, 2 H), 3.86 (t, J=7.13 Hz, 2 H), 3.88-3.96 (m, 2 H), 4.49 (d, J=7.42 Hz, 2 H), 7.98 (d, J=1.56 Hz, 1 H), 7.99 (s, 1 H), 8.24 (d, J=0.78 Hz, 1 H); MS (ESI) (M+H)$^+$=408.0; Anal. Calcd for C$_{20}$H$_{29}$N$_3$O$_4$S+1.20 TFA+0.20 EtOAc (561.99): C, 49.58; H, 5.70; N, 7.48. Found: C, 49.74; H, 5.53; N, 7.46.

Example 4

2-tert-Butyl-5-[(4-methylpiperidin-1-yl)sulfonyl]-1-(tetrahydro-2H-pyran-4-ylmethyl)-1H-benzimidazole

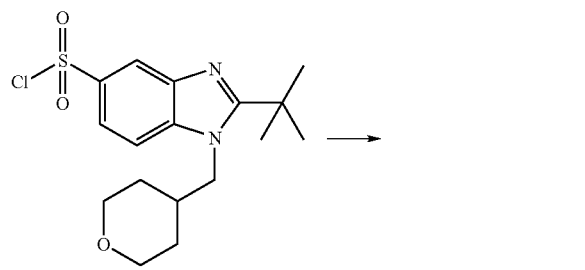

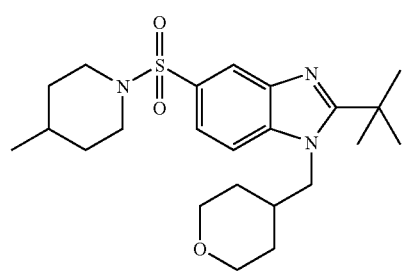

Following the same procedure in Example 1, Step A, using 2-tert-butyl-1-(tetrahydro-2H-pyran-4-ylmethyl)-1H-benzimidazole-5-sulfonyl chloride (72 mg, 0.19 mmol), 4-methylpiperidine (0.2 mL, 168 mg, 1.69 mmol) and DMAP (69 mg, 0.61 mmol) in MeCN (5 mL). The crude product was purified by MPLC using Hex/EtOAc (1:2) on silica gel to give 38 mg (45% yield) of a white solid as the title compound. $^1$H NMR (400 MHz, METHANOL-D$_4$) δ 0.90 (d, J=5.86 Hz, 3 H), 1.16-1.34 (m, 3 H), 1.49-1.64 (m, 4 H), 1.67 (s, 9 H), 1.67-1.73 (m, 2 H), 2.23-2.32 (m, 2 H), 2.33-2.44 (m, 1 H), 3.31-3.40 (m, 2 H), 3.73-3.82 (m, 2 H), 3.91-3.98 (m, 2 H), 4.52 (d, J=7.42 Hz, 2 H), 7.84 (dd, J=8.79, 1.76 Hz, 1 H), 8.03 (d, J=8.20 Hz, 1 H), 8.08 (d, J=1.17 Hz, 1 H); MS (ESI) (M+H)$^+$=434.0; Anal. Calcd for C$_{23}$H$_{35}$N$_3$O$_3$S+1.10 TFA+0.40 CH$_3$OH (571.86): C, 53.77; H, 6.65; N, 7.35. Found: C, 53.76; H, 6.69; N, 7.33.

Example 5

5-(Azetidin-1-ylsulfonyl)-2-tert-butyl-1-(tetrahydro-2H-pyran-4-ylmethyl)-1H-benzimidazole

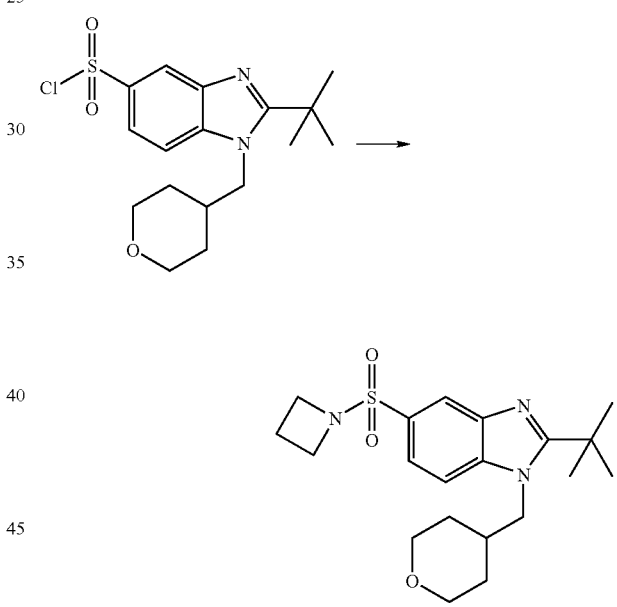

Following the same procedure in Example 1, Step A, using 2-tert-butyl-1-(tetrahydro-2H-pyran-4-ylmethyl)-1H-benzimidazole-5-sulfonyl chloride (76 mg, 0.20 mmol), azetidine (34 uL, 26 mg, 0.50 mmol) and DMAP (82 mg, 0.67 mmol) in MeCN (5 mL). The crude product was purified by MPLC using Hex/EtOAc (1:2) on silica gel to give 37 mg (46% yield) of a white solid as the title compound. $^1$H NMR (400 MHz, METHANOL-D$_4$) δ 1.52-1.65 (m, 4 H), 1.68 (s, 9 H), 1.99-2.13 (m, 2 H), 2.32-2.47 (m, 1 H), 3.32-3.43 (m, 2 H), 3.74-3.84 (m, 4 H), 3.90-4.01 (m, 2 H), 4.54 (d, J=7.42 Hz, 2 H), 7.92 (dd, J=8.79, 1.56 Hz, 1 H), 8.09 (d, J=8.79 Hz, 1 H), 8.15 (d, J=1.17 Hz, 1 H); MS (ESI) (M+H)$^+$=392.0; Anal. Calcd for C$_{20}$H$_{29}$N$_3$O$_3$S+1.20 TFA+0.40 EtOAc+0.1H$_2$O (556.60): C, 50.93; H, 5.94; N, 7.55. Found: C, 50.98; H, 5.68; N, 7.50.

Example 6

2-tert-Butyl-N-cyclobutyl-1-(tetrahydro-2H-pyran-4-ylmethyl)-1H-benzimidazole-5-sulfonamide

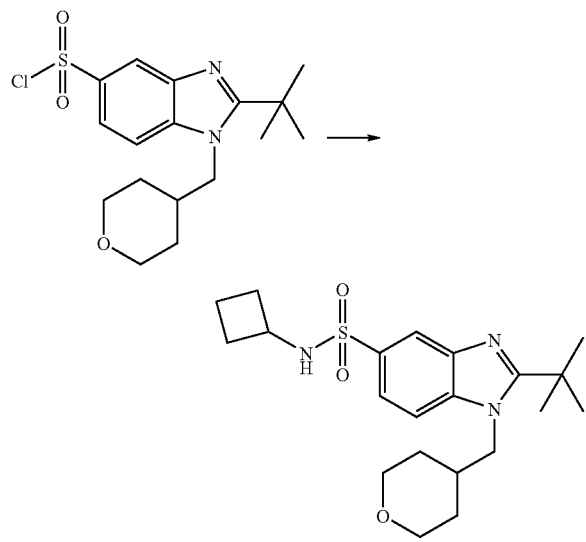

Following the same procedure in Example 1, Step A, using 2-tert-butyl-1-(tetrahydro-2H-pyran-4-ylmethyl)-1H-benzimidazole-5-sulfonyl chloride (76 mg, 0.20 mmol), cyclobutylamine (43 uL, 36 mg, 0.50 mmol) and DMAP (82 mg, 0.67 mmol) in MeCN (5 mL). The crude product was purified by MPLC using Hex/EtOAc (1:2) on silica gel to give 35 mg (42% yield) of a white solid as the title compound. $^1$H NMR (400 MHz, METHANOL-D$_4$) δ 1.48-1.66 (m, 6 H), 1.68 (s, 9 H), 1.72-1.87 (m, 2 H), 1.95-2.08 (m, 2 H), 2.28-2.50 (m, 1 H), 3.31-3.41 (m, 2 H), 3.68-3.83 (m, 1 H), 3.90-3.99 (m, 2 H), 4.53 (d, J=7.62 Hz, 2 H), 7.96 (dd, J=8.80, 1.6 Hz, 1 H), 8.04 (d, J=9.0 Hz, 1 H), 8.19 (d, J=1.17 Hz, 1 H); MS (ESI) (M+H)$^+$=406.0; Anal. Calcd for C$_{21}$H$_{31}$N$_3$O$_3$S+1.20 TFA+ 0.60 EtOAc+0.2H$_2$O (598.86): C, 51.75; H, 6.29; N, 7.02. Found: C, 51.70; H, 6.25; N, 7.03.

Example 7

2-tert-Butyl-N-cyclopropyl-1-(tetrahydro-2H-pyran-4-ylmethyl)-1H-benzimidazole-5-sulfonamide

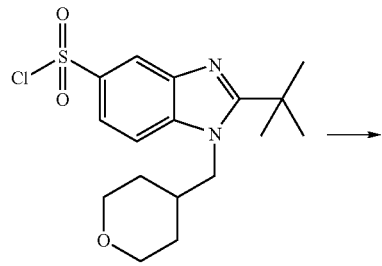

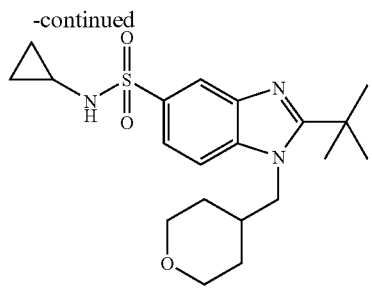

Following the same procedure in Example 1, Step A, using 2-tert-butyl-1-(tetrahydro-2H-pyran-4-ylmethyl)-1H-benzimidazole-5-sulfonyl chloride (76 mg, 0.20 mmol), cyclopropylamine (35 uL, 29 mg, 0.50 mmol) and DMAP (82 mg, 0.67 mmol) in MeCN (5 mL). The crude product was purified by MPLC using Hex/EtOAc (1:2) on silica gel to give 34 mg (43% yield) of a white solid as the title compound. $^1$H NMR (400 MHz, METHANOL-D$_4$) δ 0.45-0.51 (m, 2 H), 0.51-0.58 (m, 2 H), 1.49-1.65 (m, 4 H), 1.68 (s, 9 H), 2.10-2.22 (m, 1 H), 2.30-2.45 (m, 1 H), 3.31-3.41 (m, 2 H), 3.89-3.99 (m, 2 H), 4.54 (d, J=7.62 Hz, 2 H), 7.99 (dd, J=8.8, 1.8 Hz, 1 H), 8.07 (d, J=8.8 Hz, 1 H), 8.24 (d, J=1.17 Hz, 1 H); MS (ESI) (M+H)$^+$=392.0; Anal. Calcd for C$_{20}$H$_{29}$N$_3$O$_3$S+1.30 TFA+ 0.40 EtOAc+0.5H$_2$O (584.02): C, 49.77; H, 5.95; N, 7.20. Found: C, 49.78; H, 5.86; N, 7.20.

Example 8

2-tert-Butyl-N-cyclohexyl-1-(tetrahydro-2H-pyran-4-ylmethyl)-1H-benzimidazole-5-sulfonamide

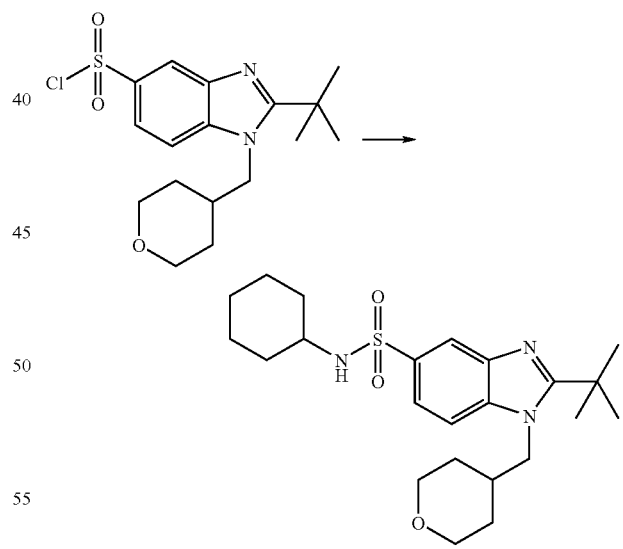

Following the same procedure in Example 1, Step A, using 2-tert-butyl-1-(tetrahydro-2H-pyran-4-ylmethyl)-1H-benzimidazole-5-sulfonyl chloride (76 mg, 0.20 mmol), cyclohexylamine (57 uL, 50 mg, 0.50 mmol) and DMAP (82 mg, 0.67 mmol) in MeCN (5 mL). The crude product was purified by MPLC using Hex/EtOAc (1:2) on silica gel to give 39 mg (44% yield) of a white solid as the title compound. $^1$H NMR (400 MHz, METHANOL-D$_4$) δ 1.09-1.23 (m, 6 H), 1.49-1.59 (m, 4 H), 1.58-1.66 (m, 4 H), 1.68 (s, 9 H), 2.31-2.46 (m, 1 H), 2.96-3.10 (m, 1 H), 3.31-3.40 (m, 2 H), 3.90-3.99 (m, 2 H), 4.53 (d, J=7.42 Hz, 2 H), 7.99 (dd, J=8.7, 1.7 Hz, 1 H), 8.05 (d, J=8.8 Hz, 1 H), 8.21 (d, J=1.17 Hz, 1 H); MS (ESI) (M+H)⁺=434.0; Anal. Calcd for $C_{23}H_{35}N_3O_3S$+1.10 TFA+ 0.40 EtOAc+0.3H$_2$O (599.69): C, 53.68; H, 6.71; N, 7.01. Found: C, 53.61; H, 6.74; N, 7.02.

Example 9

2-tert-Butyl-5-(morpholin-4-ylsulfonyl)-1-(tetrahydro-2H-pyran-4-ylmethyl)-1H-benzimidazole

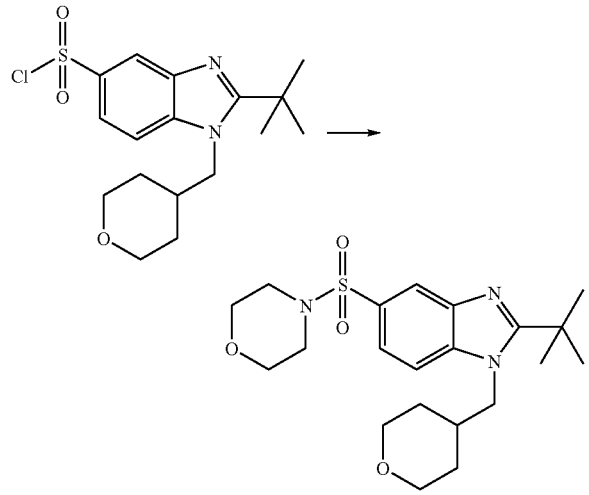

Following the same procedure in Example 1, Step A, using 2-tert-butyl-1-(tetrahydro-2H-pyran-4-ylmethyl)-1H-benzimidazole-5-sulfonyl chloride (76 mg, 0.20 mmol), morpholine (44 uL, 44 mg, 0.50 mmol) and DMAP (82 mg, 0.67 mmol) in MeCN (5 mL). The crude product was purified by MPLC using Hex/EtOAc (1:2) on silica gel to give 43 mg (50% yield) of a white solid as the title compound. ¹H NMR (400 MHz, METHANOL-D$_4$) δ 1.47-1.62 (m, 4 H), 1.65 (s, 9 H), 2.28-2.43 (m, 1 H), 2.92-3.04 (m, 4 H), 3.29-3.40 (m, 2 H), 3.64-3.74 (m, 4 H), 3.88-3.98 (m, 2 H), 4.51 (d, J=7.42 Hz, 2 H), 7.83 (dd, J=8.79, 1.76 Hz, 1 H), 8.03 (d, J=8.79 Hz, 1 H), 8.08 (d, J=1.17 Hz, 1 H); MS (ESI) (M+H)⁺=422.0; Anal. Calcd for $C_{21}H_{31}N_3O_4S$+0.90 TFA+0.20 EtOAc+ 0.80H$_2$O (556.22): C, 50.96; H, 6.36; N, 7.55. Found: C, 50.94; H, 6.46; N, 7.51.

Example 10

2-tert-Butyl-N-phenyl-1-(tetrahydro-2H-pyran-4-ylmethyl)-1H-benzimidazole-5-sulfonamide

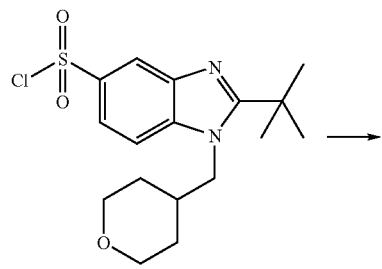

-continued

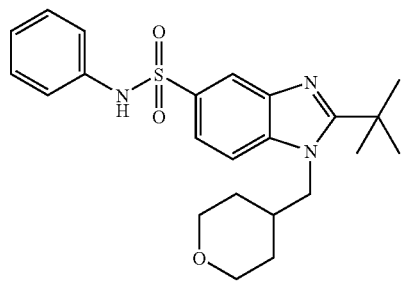

Following the same procedure in Example 1, Step A, using 2-tert-butyl-1-(tetrahydro-2H-pyran-4-ylmethyl)-1H-benzimidazole-5-sulfonyl chloride (76 mg, 0.20 mmol), aniline (46 uL, 47 mg, 0.50 mmol) and DMAP (82 mg, 0.67 mmol) in MeCN (5 mL). The crude product was purified by MPLC using Hex/EtOAc (1:1) on silica gel to give 43 mg (50% yield) of a white solid as the title compound. ¹H NMR (400 MHz, METHANOL-D$_4$) δ 1.40-1.58 (m, 4 H), 1.61 (s, 9 H), 2.21-2.38 (m, 1 H), 3.29-3.35 (m, 2 H), 3.85-3.93 (m, 2 H), 4.45 (d, J=7.62 Hz, 2 H), 6.96-7.04 (m, 1 H), 7.04-7.11 (m, 2 H), 7.11-7.21 (m, 2 H), 7.84-7.89 (m, 1 H), 7.91-7.98 (m, 1 H), 8.06 (d, J=1.17 Hz, 1 H); MS (ESI) (M+H)⁺=428.0; Anal. Calcd for $C_{23}H_{29}N_3O_3S$+1.10 TFA+0.30 EtOAc+0.2H$_2$O (583.03): C, 54.39; H, 5.69; N, 7.21. Found: C, 54.43; H, 5.68; N, 7.22.

Example 11

2-tert-Butyl-5-(1H-pyrazol-1-ylsulfonyl)-1-(tetrahydro-2H-pyran-4-ylmethyl)-1H-benzimidazole

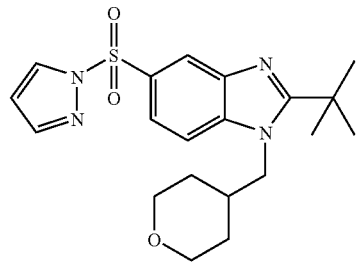

Following the same procedure in Example 1, Step A, using 2-tert-butyl-1-(tetrahydro-2H-pyran-4-ylmethyl)-1H-benzimidazole-5-sulfonyl chloride (76 mg, 0.20 mmol), pyrazole (34 mg, 0.50 mmol) and DMAP (82 mg, 0.67 mmol) in MeCN (5 mL). The crude product was purified by MPLC using Hex/EtOAc (1:1) on silica gel to give 46 mg (56% yield) of a white solid as the title compound. $^1$H NMR (400 MHz, METHANOL-D$_4$) δ 1.36-1.54 (m, 4 H), 1.56 (s, 9 H), 2.15-2.41 (m, 1 H), 3.23-3.38 (m, 2 H), 3.88 (m, 2 H), 4.37 (d, J=7.62 Hz, 2H), 6.47 (dd, J=2.73, 1.56 Hz, 1 H), 7.73 (d, J=1.37 Hz, 1 H), 7.77-7.85 (m, 1 H), 7.86-7.94 (m, 1 H), 8.26 (d, J=1.56 Hz, 1 H), 8.30 (d, J=2.73 Hz, 1 H); MS (ESI) (M+H)$^+$=403.0; Anal. Calcd for C$_{20}$H$_{26}$N$_4$O$_3$S+0.50 TFA+0.20 EtOAc (477.15): C, 54.88; H, 5.94; N, 11.74. Found: C, 54.78; H, 5.83; N, 11.69.

Example 12

2-tert-Butyl-N-methyl-N-phenyl-1-(tetrahydro-2H-pyran-4-ylmethyl)-1H-benzimidazole-5-sulfonamide

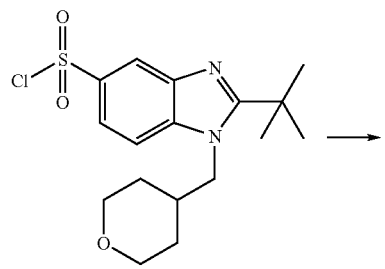

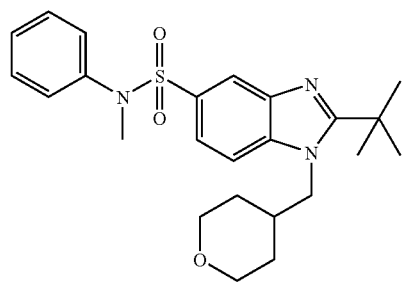

Following the same procedure in Example 1, Step A, using 2-tert-butyl-1-(tetrahydro-2H-pyran-4-ylmethyl)-1H-benzimidazole-5-sulfonyl chloride (132 mg, 0.36 mmol), N-methylaniline (0.1 mL, 99 mg, 0.92 mmol) and DMAP (120 mg, 0.98 mmol) in MeCN (5 mL). The crude product was purified by MPLC using Hex/EtOAc (4:1) on silica gel to give 59 mg (38% yield) of a white solid as the title compound. $^1$H NMR (400 MHz, METHANOL-D$_4$) δ 1.42-1.60 (m, 4 H), 1.63 (s, 9 H), 2.24-2.43 (m, 1 H), 3.19 (s, 3 H), 3.28-3.41 (m, 2 H), 3.92 (m, 2 H), 4.48 (d, J=7.42 Hz, 2 H), 7.03-7.12 (m, 2 H), 7.20-7.35 (m, 3 H), 7.60 (dd, J=8.79, 1.76 Hz, 1 H), 7.82 (d, J=1.17 Hz, 1 H), 7.94 (d, J=8.79 Hz, 1 H); MS (ESI) (M+H)$^+$=442.0; Anal. Calcd for C$_{24}$H$_{31}$N$_3$O$_3$S+1.00 TFA+0.20 EtOAc+0.10H$_2$O (575.04): C, 55.98; H, 5.92; N, 7.31. Found: C, 55.89; H, 5.87; N, 7.30.

Example 13

2-tert-Butyl-N-methyl-N-(3-methylbutyl)-1-(tetrahydro-2H-pyran-4-ylmethyl)-1H-benzimidazole-5-sulfonamide

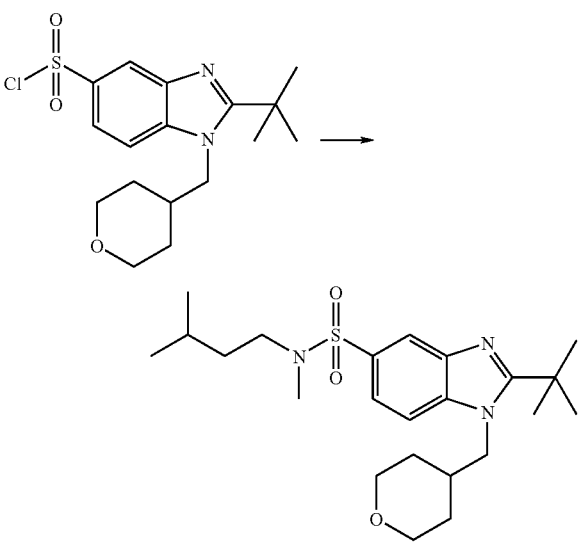

Following the same procedure in Example 1, Step A, using 2-tert-butyl-1-(tetrahydro-2H-pyran-4-ylmethyl)-1H-benzimidazole-5-sulfonyl chloride (82 mg, 0.22 mmol), methyl (3-methylbutyl)amine (45 mg, 0.44 mmol) and DMAP (54 mg, 0.44 mmol) in MeCN (4 mL). The crude product was purified by MPLC using Hex/EtOAc (1:1) on silica gel to give 57 mg (60% yield) of a white solid as the title compound. $^1$H NMR (400 MHz, METHANOL-D$_4$) δ 0.89 (d, J=6.64 Hz, 6 H), 1.39 (q, J=6.90 Hz, 2 H), 1.46-1.61 (m, 5 H), 1.64 (s, 9 H), 2.26-2.43 (m, 1 H), 2.70 (s, 3 H), 2.97-3.06 (m, 2 H), 3.29-3.38 (m, 2 H), 3.86-3.97 (m, 2 H), 4.48 (d, J=7.42 Hz, 2 H), 7.81 (dd, J=8.79, 1.76 Hz, 1 H), 7.96 (d, J=8.79 Hz, 1 H), 8.07 (d, J=1.37 Hz, 1 H); MS (ESI) (M+H)$^+$=436.0; Anal. Calcd for C$_{23}$H$_{37}$N$_3$O$_3$S+0.70 TFA+0.30 EtOAc+0.5H$_2$O (550.89): C, 55.82; H, 7.52; N, 7.63. Found: C, 55.90; H, 7.46; N, 7.63.

Example 14

2-tert-Butyl-N-isobutyl-N-methyl-1-(tetrahydro-2H-pyran-4-ylmethyl)-1H-benzimidazole-5-sulfonamide

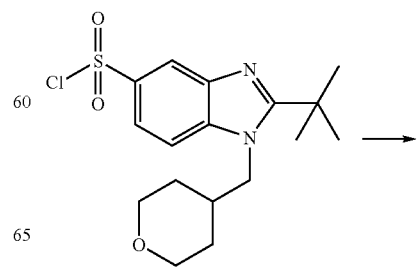

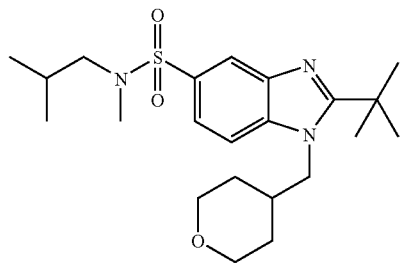

Following the same procedure in Example 1, Step A, using 2-tert-butyl-1-(tetrahydro-2H-pyran-4-ylmethyl)-1H-benzimidazole-5-sulfonyl chloride (82 mg, 0.22 mmol), isobutyl (methyl)amine (38 mg, 0.44 mmol) and DMAP (54 mg, 0.44 mmol) in MeCN (4 mL). The crude product was purified by MPLC using Hex/EtOAc (1:1) on silica gel to give 54 mg (58% yield) of a white solid as the title compound. $^1$H NMR (400 MHz, METHANOL-D$_4$) δ 0.91 (d, J=6.64 Hz, 6 H), 1.46-1.61 (m, 4 H), 1.64 (s, 9 H), 1.82-1.95 (m, 1 H), 2.25-2.45 (m, 1 H), 2.69 (s, 3 H), 2.74 (d, J=7.42 Hz, 2 H), 3.29-3.40 (m, 2 H), 3.87-4.00 (m, 2 H), 4.49 (d, J=7.42 Hz, 2 H), 7.82 (dd, J=8.69, 1.66 Hz, 1 H), 7.98 (d, J=8.79 Hz, 1 H), 8.08 (d, J=1.56 Hz, 1 H); MS (ESI) (M+H)$^+$=422.0; Anal. Calcd for C$_{22}$H$_{35}$N$_3$O$_3$S+0.90 TFA+0.20 EtOAc (541.85): C, 54.53; H, 6.98; N, 7.75. Found: C, 54.53; H, 6.99; N, 7.77.

Example 15

N,2-Di-tert-butyl-1-(tetrahydro-2H-pyran-4-ylmethyl)-1H-benzimidazole-5-sulfonamide

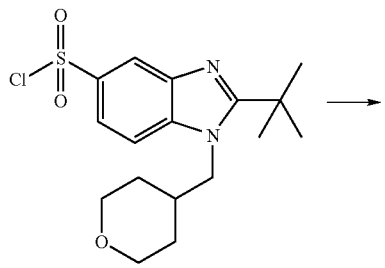

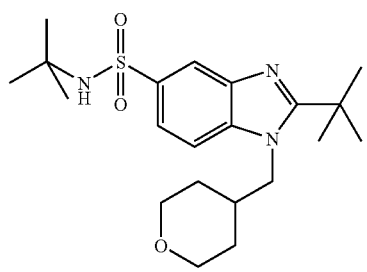

Following the same procedure in Example 1, Step A, using 2-tert-butyl-1-(tetrahydro-2H-pyran-4-ylmethyl)-1H-benzimidazole-5-sulfonyl chloride (82 mg, 0.22 mmol), tert-butylamine (32 mg, 0.44 mmol) and DMAP (54 mg, 0.44 mmol) in MeCN (4 mL). The crude product was purified by MPLC using Hex/EtOAc (1:1) on silica gel to give 40 mg (41% yield) of a white solid as the title compound. $^1$H NMR (400 MHz, METHANOL-D$_4$) δ 1.17 (s, 9 H), 1.49-1.64 (m, 4 H), 1.66 (s, 9 H), 2.29-2.44 (m, 1 H), 3.29-3.38 (m, 2 H), 3.87-3.97 (m, 2 H), 4.52 (d, J=7.62 Hz, 2 H), 7.97-8.05 (m, 2 H), 8.21 (dd, J=1.46, 0.68 Hz, 1 H); MS (ESI) (M+H)$^+$=408.0; Anal. Calcd for C$_{21}$H$_{33}$N$_3$O$_3$S+1.200 TFA+0.20 EtOAc+0.1H$_2$O (563.83): C, 51.55; H, 6.44; N, 7.45. Found: C, 51.59; H, 6.28; N, 7.41.

Example 16

2-tert-Butyl-N-cyclohexyl-N-methyl-1-(tetrahydro-2H-pyran-4-ylmethyl)-1H-benzimidazole-5-sulfonamide

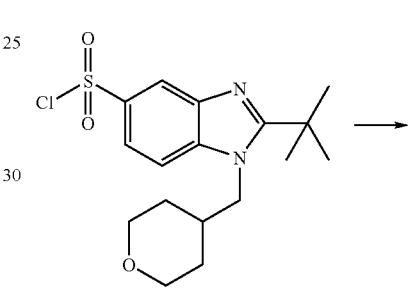

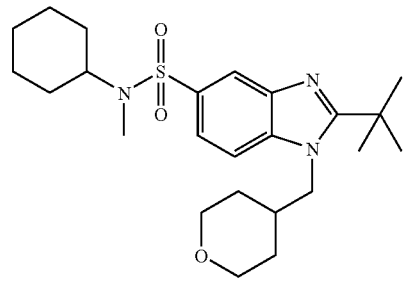

Following the same procedure in Example 1, Step A, using 2-tert-butyl-1-(tetrahydro-2H-pyran-4-ylmethyl)-1H-benzimidazole-5-sulfonyl chloride (82 mg, 0.22 mmol), cyclohexyl(methyl)amine (50 mg, 0.44 mmol) and DMAP (54 mg, 0.44 mmol) in MeCN (4 mL). The crude product was purified by MPLC using Hex/EtOAc (1:1) on silica gel to give 58 mg (59% yield) of a white solid as the title compound. $^1$H NMR (400 MHz, METHANOL-D$_4$) δ 1.22-1.32 (m, 2 H), 1.33-1.44 (m, 4 H), 1.47-1.62 (m, 6 H), 1.65 (s, 9 H), 1.66-1.74 (m, 2 H), 2.27-2.44 (m, 1 H), 2.76 (s, 3 H), 3.29-3.38 (m, 2 H), 3.68-3.81 (m, 1 H), 3.87-3.97 (m, 2 H), 4.50 (d, J=7.42 Hz, 2 H), 7.89 (dd, J=8.79, 1.76 Hz, 1 H), 8.00 (d, J=8.79 Hz, 1 H), 8.12 (d, J=1.17 Hz, 1 H); MS (ESI) (M+H)$^+$=448.0; Anal. Calcd for C$_{24}$H$_{37}$N$_3$O$_3$S+1.00 TFA+0.30 EtOAc+0.2H$_2$O (591.70): C, 55.21; H, 6.95; N, 7.10. Found: C, 55.22; H, 6.85; N, 7.08.

Example 17

2-tert-Butyl-N-methoxy-N-methyl-1-(tetrahydro-2H-pyran-4-ylmethyl)-1H-benzimidazole-5-sulfonamide

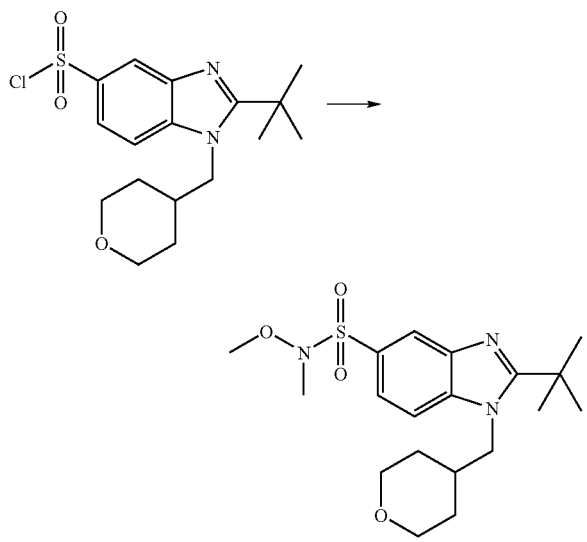

Following the same procedure in Example 1, Step A, using 2-tert-butyl-1-(tetrahydro-2H-pyran-4-ylmethyl)-1H-benzimidazole-5-sulfonyl chloride (82 mg, 0.22 mmol), N,O-dimethylhydroxylamine hydrochloride (43 mg, 0.44 mmol) and DMAP (54 mg, 0.44 mmol) in MeCN (4 mL). The crude product was purified by MPLC using Hex/EtOAc (1:1) on silica gel to give 22 mg (25% yield) of a white solid as the title compound. $^1$H NMR (400 MHz, METHANOL-D$_4$) δ 1.41-1.55 (m, 4 H), 1.57 (s, 9 H), 2.26-2.40 (m, 1 H), 2.72 (s, 3 H), 3.30-3.37 (m, 2 H), 3.76 (s, 3 H), 3.86-3.95 (m, 2 H), 4.38 (d, J=7.42 Hz, 2 H), 7.73 (dd, J=8.6, 1.6 Hz, 1 H), 7.78 (d, J=8.2 Hz, 1 H), 8.10 (d, J=0.98 Hz, 1 H); MS (ESI) (M+H)$^+$=396.0; Anal. Calcd for C$_{19}$H$_{29}$N$_3$O$_4$S+0.30 EtOAc (421.96): C, 57.50; H, 7.50; N, 9.96. Found: C, 57.88; H, 7.48; N, 9.95

Example 18

2-tert-Butyl-5-[(3-cyclopropyl-1H-pyrazol-1-yl)sulfonyl]-1-(tetrahydro-2H-pyran-4-ylmethyl)-1H-benzimidazole

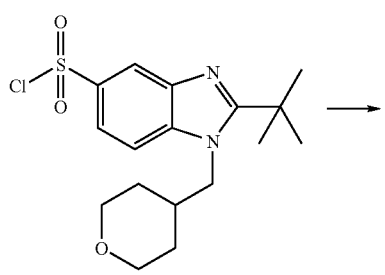

-continued

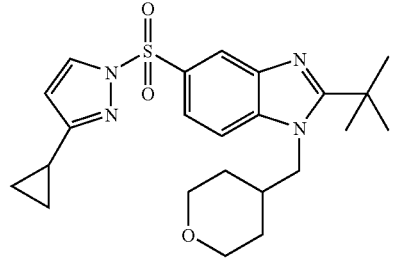

Following the same procedure in Example 1, Step A, using 2-tert-butyl-1-(tetrahydro-2H-pyran-4-ylmethyl)-1H-benzimidazole-5-sulfonyl chloride (93 mg, 0.25 mmol), 3-cyclopropyl-1H-pyrazole (54 mg, 0.50 mmol) and DMAP (92 mg, 0.75 mmol) in MeCN (5 mL). The crude product was purified by MPLC using Hex/EtOAc (1:2) on silica gel to give 30 mg (27% yield) of a white solid as the title compound. $^1$H NMR (400 MHz, METHANOL-D$_4$) δ 0.62-0.75 (m, 2 H), 0.87-0.99 (m, 2 H), 1.43-1.59 (m, 4 H), 1.61 (s, 9 H), 1.81-1.96 (m, 1 H), 2.24-2.42 (m, 1 H), 3.31-3.39 (m, 2 H), 3.91 (m, 2 H), 4.43 (d, J=7.42 Hz, 2 H), 6.18 (d, J=2.73 Hz, 1H), 7.91 (d, J=8.8 Hz, 1 H), 7.95 (dd, J=8.7, 1.5 Hz, 1 H), 8.15 (d, J=2.73 Hz, 1 H), 8.28 (d, J=1.56 Hz, 1 H); MS (ESI) (M+H)$^+$=442.8; Anal. Calcd for C$_{23}$H$_{30}$N$_4$O$_3$S+1.10 TFA+0.10H$_2$O (569.31): C, 53.12; H, 5.54; N, 9.83. Found: C, 53.13; H, 5.62; N, 9.76.

Example 19

2-tert-Butyl-5-[(4-methyl-1H-pyrazol-1-yl)sulfonyl]-1-(tetrahydro-2H-pyran-4-ylmethyl)-1H-benzimidazole

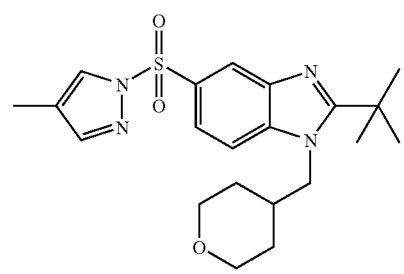

Following the same procedure in Example 1, Step A, using 2-tert-butyl-1-(tetrahydro-2H-pyran-4-ylmethyl)-1H-benzimidazole-5-sulfonyl chloride (371 mg, 1.0 mmol), 4-methyl-1H-pyrazole (164 mg, 2.0 mmol) and DMAP (366 mg, 3.0 mmol) in MeCN (10 mL). The crude product was purified by MPLC using Hex/EtOAc (1:2) on silica gel to give 165 mg (40% yield) of a white solid as the title compound. $^1$H NMR (400 MHz, METHANOL-D$_4$) δ 1.41-1.58 (m, 4 H), 1.61 (s, 9 H), 2.05 (s, 3 H), 2.22-2.47 (m, 1 H), 3.30-3.40 (m, 2 H), 3.91 (m, 2 H), 4.43 (d, J=7.62 Hz, 2 H), 7.60 (s, 1 H), 7.91 (d, J=8.2 Hz, 1 H), 7.95 (dd, J=8.8, 1.8 Hz, 1H), 8.05-8.14 (m, 1 H), 8.28 (d, J=1.17 Hz, 1 H); MS (ESI) (M+H)$^+$=416.8.

Example 20

2-tert-Butyl-5-[(3-methyl-1H-pyrazol-1-yl)sulfonyl]-1-(tetrahydro-2H-pyran-4-ylmethyl)-1H-benzimidazole

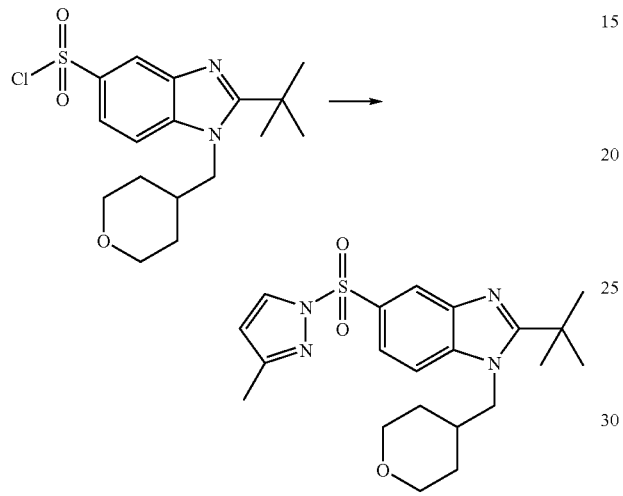

Following the same procedure in Example 1, Step A, using 2-tert-butyl-1-(tetrahydro-2H-pyran-4-ylmethyl)-1H-benzimidazole-5-sulfonyl chloride (371 mg, 1.0 mmol), 3-methyl-1H-pyrazole (164 mg, 2.0 mmol) and DMAP (367 mg, 3.0 mmol) in MeCN (10 mL). The crude product was purified by MPLC using Hex/EtOAc (1:2) on silica gel to give 116 mg (28%) of a white solid as the title compound. $^1$H NMR (400 MHz, METHANOL-D$_4$) δ 1.39-1.57 (m, 4 H), 1.59 (s, 9 H), 2.17 (s, 3 H), 2.23-2.33 (m, 1 H), 3.27-3.36 (m, 2 H), 3.88 (m, 2 H), 4.42 (d, J=7.62 Hz, 2 H), 6.31 (d, J=2.54 Hz, 1 H), 7.88-7.99 (m, 2 H), 8.18 (d, J=2.73 Hz, 1 H), 8.28 (d, J=1.76 Hz, 1 H); MS (ESI) (M+H)$^+$=416.8.

Example 21

1-{[2-tert-Butyl-1-(tetrahydro-2H-pyran-4-ylmethyl)-1H-benzimidazol-5-yl]sulfonyl}-1H-pyrazol-3-amine

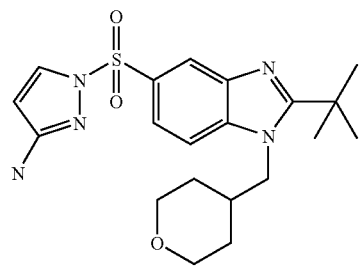

Step A: 1-{[2-tert-butyl-1-(tetrahydro-2H-pyran-4-ylmethyl)-1H-benzimidazol-5-yl]sulfonyl}-1H-pyrazol-3-amine

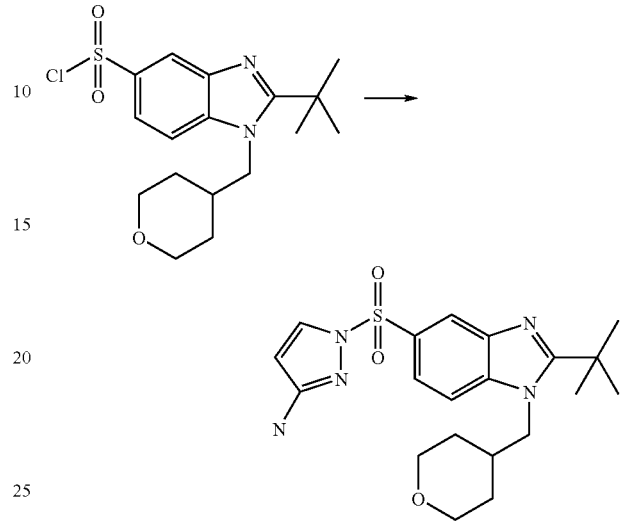

Following the same procedure in Example 1, Step A, using 2-tert-butyl-1-(tetrahydro-2H-pyran-4-ylmethyl)-1H-benzimidazole-5-sulfonyl chloride (1.46 g, 3.93 mmol), tert-butyl 1H-pyrazol-3-ylcarbamate (0.80 g, 4.33 mmol) (see following step B for preparation), and DMAP (1.47 g, 12.0 mmol) in MeCN (40 mL). The crude product was purified by MPLC using EtOAc on silica gel to give 0.31 g (19%) of a white solid as the title compound. $^1$H NMR (400 MHz, DMSO-D$_6$) δ 1.25-1.44 (m, 4 H), 1.46 (s, 9 H), 2.05-2.24 (m, 1 H), 3.15 (m, 2 H), 3.77 (m, 2 H), 4.28 (d, J=7.03 Hz, 2 H), 5.38 (s, 2 H), 5.78 (d, J=2.93 Hz, 1 H), 7.63 (dd, J=8.79, 1.76 Hz, 1 H), 7.82 (d, J=8.59 Hz, 1 H), 7.97 (d, J=1.76 Hz, 1 H), 8.00 (d, J=2.93 Hz, 1 H); MS (ESI) (M+H)$^+$=417.8; Anal. Calcd for C$_{20}$H$_{27}$N$_5$O$_3$S+1.30 TFA+0.10 EtOAc (575.78): C, 48.19; H, 5.09; N, 12.16. Found: C, 48.12; H, 5.02; N, 12.29.

Step B: tert-butyl 1H-pyrazol-3-ylcarbamate

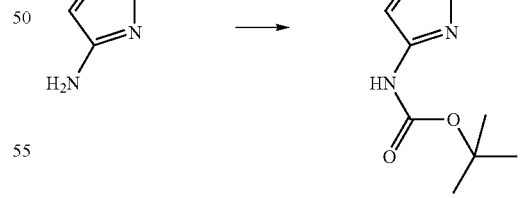

Di-tert-butyl dicarbonate (1.83 g, 8.4 mmol) was added to a solution of 1H-pyrazol-3-amine (0.58 g, 7.0 mmol) in THF (15 mL). The reaction mixture was stirred over weekend at room temperature. After evaporation of the solvent, the crude product was purified by MPLC using Hex/EtOAc (1:1) on silica gel to give 0.84 g (66%) of a white solid as the title compound. $^1$H NMR (400 MHz, DMSO-D$_6$) δ 1.47 (s, 9 H), 3.28 (s, 2 H), 5.74 (d, J=2.93 Hz, 1 H), 7.80 (d, J=2.73 Hz, 1 H); MS (ESI) (M+H)$^+$=183.8.

Example 22

N-(1-{[2-tert-Butyl-1-(tetrahydro-2H-pyran-4-ylmethyl)-1H-benzimidazol-5-yl]sulfonyl}-1H-pyrazol-3-yl)cyclobutanecarboxamide

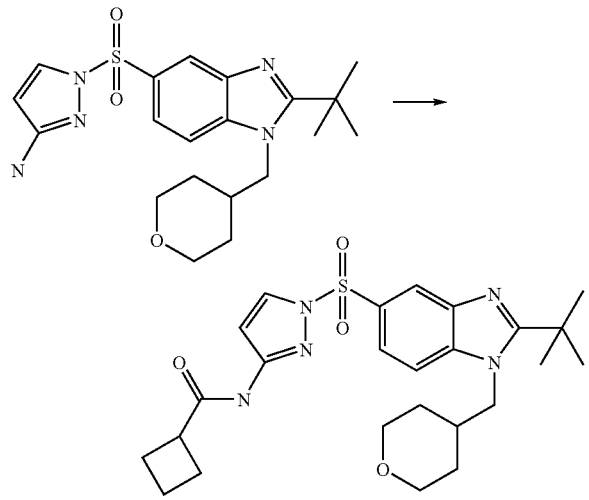

Cyclobutanecarbonyl chloride (30 mg, 30 uL, 0.26 mmol) was added to a solution of 1-{[2-tert-butyl-1-(tetrahydro-2H-pyran-4-ylmethyl)-1H-benzimidazol-5-yl]sulfonyl}-1H-pyrazol-3-amine (37 mg, 0.087 mmol) (see Example 21 for preparation) and DIPEA (34 mg, 46 uL, 0.26 mmol) in $CH_2Cl_2$ (10 mL). The reaction mixture was stirred overnight at room temperature. After evaporation of the solvent, the crude product was purified by MPLC using Hex/EtOAc (1:1) on silica gel to give 14.3 mg (33%) of a white solid as the title compound. $^1$H NMR (400 MHz, METHANOL-D$_4$) δ 1.41-1.56 (m, 4 H), 1.59 (s, 9 H), 1.76-1.88 (m, 1 H), 1.91-2.01 (m, 1 H), 2.06-2.18 (m, 2 H), 2.17-2.27 (m, 2 H), 2.26-2.37 (m, 1 H), 3.10-3.24 (m, 1 H), 3.25-3.35 (m, 2 H), 3.84-3.95 (m, 2 H), 4.41 (d, J=7.62 Hz, 2 H), 6.87 (d, J=2.93 Hz, 1 H), 7.88 (d, J=8.9 Hz, 1 H), 7.92 (dd, J=8.8, 1.5 Hz, 1 H), 8.18 (d, J=2.93 Hz, 1 H), 8.25 (d, J=1.56 Hz, 1 H); MS (ESI) (M+H)$^+$=499.8; Anal. Calcd for $C_{25}H_{33}N_5O_4S$+0.80 TFA+0.20 EtOAc+0.10H$_2$O (612.68): C, 54.11; H, 5.86; N, 11.43. Found: C, 54.12; H, 5.92; N, 11.34.

Example 23

1-{[2-tert-Butyl-1-(tetrahydro-2H-pyran-4-ylmethyl)-1H-benzimidazol-5-yl]sulfonyl}-1H-pyrazole-4-carbaldehyde

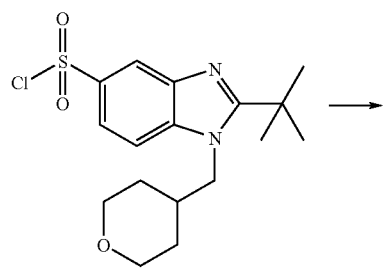

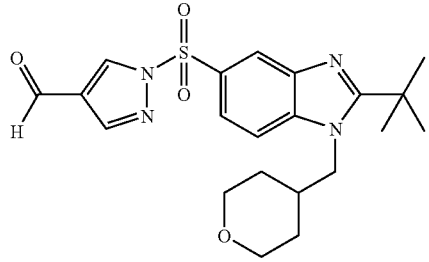

Following the same procedure in Example 1, Step A, using 2-tert-butyl-1-(tetrahydro-2H-pyran-4-ylmethyl)-1H-benzimidazole-5-sulfonyl chloride (3.26 g, 8.8 mmol), 1H-pyrazole-4-carbaldehyde (1.01 g, 10.5 mmol) and DMAP (2.15 g, 17.6 mmol) in MeCN (70 mL). The crude product was purified by MPLC using Hex/EtOAc (1:1) on silica gel to give 1.12 g (30%) of a white solid as the title compound. $^1$H NMR (400 MHz, METHANOL-D4) δ 1.39-1.56 (m, 4 H), 1.58 (s, 9 H), 2.21-2.36 (m, 1 H), 3.29-3.33 (m, 2 H), 3.88 (m, 2 H), 4.40 (d, J=7.42 Hz, 2 H), 5.41 (s, 1 H), 7.69 (s, 1 H), 7.84-7.90 (m, 1 H), 7.92-7.97 (m, 1 H), 8.25 (t, J=0.68 Hz, 1 H), 8.29 (d, J=1.76 Hz, 1 H); MS (ESI) (M+H)$^+$=430.7; Anal. Calcd for $C_{21}H_{26}N_4O_4S$+0.80 TFA+0.30 CH$_3$CN+0.20H$_2$O (537.67): C, 51.83; H, 5.27; N, 11.20. Found: C, 51.79; H, 5.20; N, 11.16.

Example 24

1-{[2-tert-Butyl-1-(tetrahydro-2H-pyran-4-ylmethyl)-1H-benzimidazol-5-yl]sulfonyl}-N-(2-hydroxyethyl)-1H-pyrazole-4-carboxamide

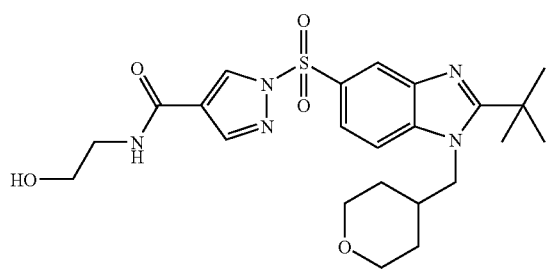

Step A: 1-{[2-tert-butyl-1-(tetrahydro-2H-pyran-4-ylmethyl)-1H-benzimidazol-5-yl]sulfonyl}-N-(2-hydroxyethyl)-1H-pyrazole-4-carboxamide

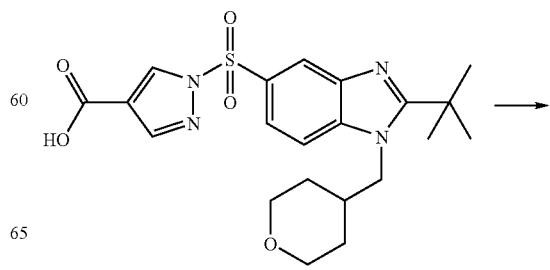

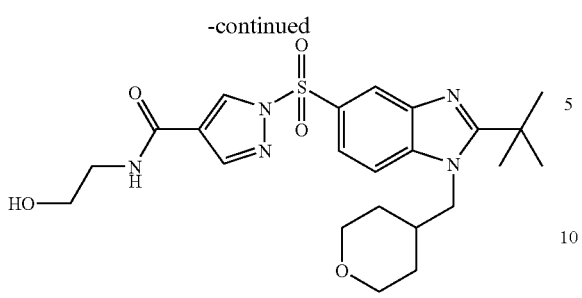

Ethanolamine (29 mg, 0.47 mmol) and DIPEA (122 uL, 90 mg, 0.70 mmol) were added to a solution of 1-{[2-tert-butyl-1-(tetrahydro-2H-pyran-4-ylmethyl)-1H-benzimidazol-5-yl]sulfonyl}-1H-pyrazole-4-carboxylic acid (4.0 mL, 0.23 mmol) (see following step B for preparation). Stirring for 20 min, HATU (117 mg, 0.47 mmol) was added. The reaction mixture was stirred overnight at room temperature, diluted with H$_2$O (100 mL), and extracted with EtOAc (3×50 mL). The combined organic phases were washed with NaCl saturated aqueous solution (2×10 mL) and dried over Na$_2$SO$_4$. The crude product was purified by MPLC using EtOAc/MeOH (20:1-9:1) on silica gel to give 80 mg (71%) of a white solid as the title compound. $^1$H NMR (400 MHz, METHANOL-D4) δ 1.41-1.57 (m, 4 H), 1.60 (s, 9 H), 2.25-2.36 (m, 1 H), 3.24-3.34 (m, 2 H), 3.40 (t, J=5.66 Hz, 2 H), 3.63 (t, J=5.76 Hz, 2 H), 3.86-3.94 (m, 2 H), 4.43 (d, J=7.42 Hz, 2 H), 7.95 (d, J=8.8 Hz, 1 H), 8.02 (dd, J=8.8, 1.8 Hz, 1H), 8.06 (d, J=0.78 Hz, 1 H), 8.35 (d, J=1.17 Hz, 1 H), 8.78 (s, 1 H); MS (ESI) (M+H)$^+$=490.3.

Step B: 1-{[2-tert-butyl-1-(tetrahydro-2H-pyran-4-ylmethyl)-1H-benzimidazol-5-yl]sulfonyl}-1H-pyrazole-4-carboxylic acid

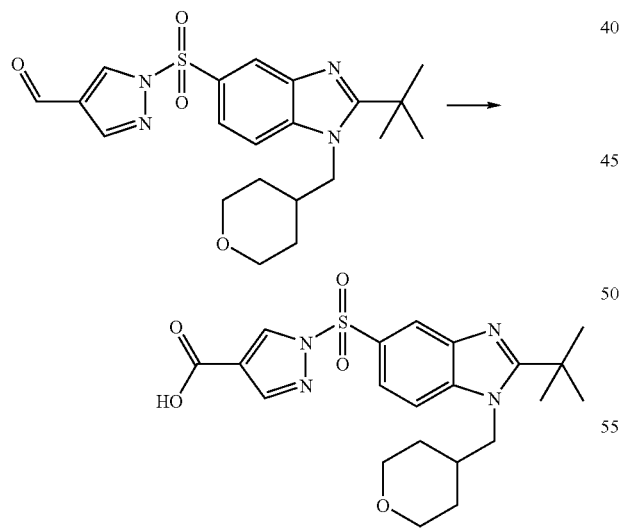

Oxone (344 mg, 0.56 mmol) was added to a solution of 1-{[2-tert-butyl-1-(tetrahydro-2H-pyran-4-ylmethyl)-1H-benzimidazol-5-yl]sulfonyl}-1H-pyrazole-4-carbaldehyde (201 mg, 0.47 mmol) (see example 23 for preparation) in DMF (8 mL). The resulting mixture was stirred overnight at room temperature and used directly for step A. MS (ESI) (M+H)$^+$=447.09.

Example 25

1-{[2-tert-Butyl-1-(tetrahydro-2H-pyran-4-ylmethyl)-1H-benzimidazol-5-yl]sulfonyl}-N-isopropyl-1H-pyrazole-4-carboxamide

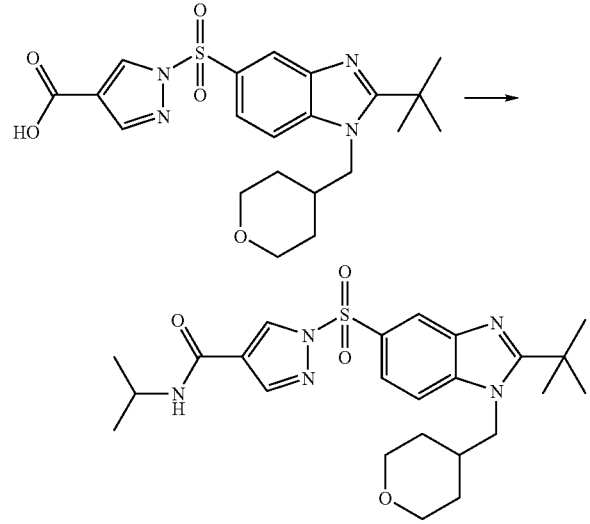

Following the same procedure in Example 24, Step A, using iso-propylamine (9 mg, 0.15 mmol), DIPEA (28 uL, 21 mg, 0.16 mmol), 1-{[2-tert-butyl-1-(tetrahydro-2H-pyran-4-ylmethyl)-1H-benzimidazol-5-yl]sulfonyl}-1H-pyrazole-4-carboxylic acid (0.073 mmol) and HATU (44 mg, 0.12 mmol) in DMF (2.5 mL). The crude product was purified by MPLC using Hex/EtOAc (1:2) on silica gel to give 25 mg (70%) of a white solid as the title compound. $^1$H NMR (400 MHz, METHANOL-D$_4$) δ 1.17 (d, J=6.45 Hz, 6 H), 1.40-1.56 (m, 4 H), 1.59 (s, 9 H), 2.18-2.40 (m, 1 H), 3.23-3.39 (m, 2 H), 3.81-3.96 (m, 2 H), 4.02-4.18 (m, 1 H), 4.41 (d, J=7.42 Hz, 2 H), 7.91 (d, J=8.8 Hz, 1 H), 7.98 (dd, J=8.8, 1.8 Hz, 1 H), 8.04 (s, 1 H), 8.33 (d, J=1.76 Hz, 1 H), 8.77 (d, J=0.78 Hz, 1 H); MS (ESI) (M+H)$^+$=488.0; Anal. Calcd for C$_{24}$H$_{33}$N$_5$O$_4$S+ 0.70 TFA+0.50 EtOAc+0.40H$_2$O (624.71): C, 53.64; H, 6.21; N, 11.21. Found: C, 53.58; H, 6.23; N, 11.28.

Example 26

1-{[2-tert-Butyl-1-(tetrahydro-2H-pyran-4-ylmethyl)-1H-benzimidazol-5-yl]sulfonyl}-N-cyclobutyl-1H-pyrazole-4-carboxamide

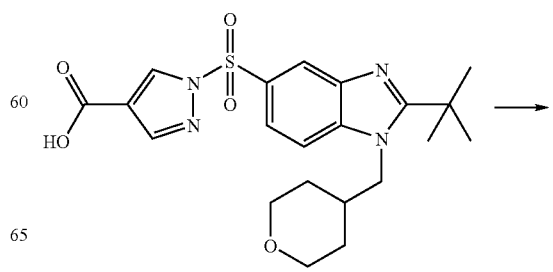

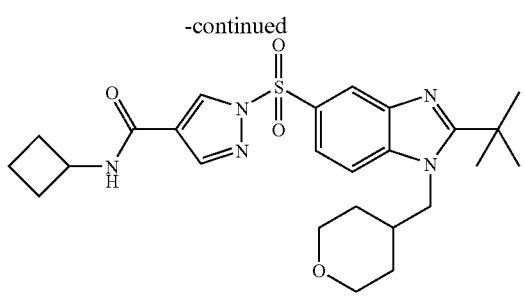

Following the same procedure in Example 24, Step A, using cyclobutylamine (13 uL, 10 mg, 0.15 mmol), DIPEA (28 uL, 21 mg, 0.16 mmol), 1-{[2-tert-butyl-1-(tetrahydro-2H-pyran-4-ylmethyl)-1H-benzimidazol-5-yl]sulfonyl}-1H-pyrazole-4-carboxylic acid (0.073 mmol) and HATU (44 mg, 0.12 mmol) in DMF (2.5 mL). The crude product was purified by MPLC using Hex/EtOAc (1:2) on silica gel to give 17 mg (47%) of a white solid as the title compound. $^1$H NMR (400 MHz, METHANOL-D$_4$) δ 1.40-1.56 (m, 4 H), 1.58 (s, 9 H), 1.67-1.79 (m, 2 H), 1.96-2.09 (m, 2 H), 2.22-2.34 (m, 3 H), 3.25-3.34 (m, 2 H), 3.83-3.94 (m, 2 H), 4.34-4.39 (m, 1 H), 4.41 (d, J=7.62 Hz, 2 H), 7.90 (d, J=8.6 Hz, 1 H), 7.97 (dd, J=8.8, 1.8 Hz, 1 H), 8.04 (d, J=0.59 Hz, 1 H), 8.33 (d, J=1.37 Hz, 1 H), 8.77 (d, J=0.59 Hz, 1 H); MS (ESI) (M+H)$^+$=499.8; Anal. Calcd for C$_{25}$H$_{33}$N$_5$O$_4$S+0.70 TFA+0.30 EtOAc+0.20H$_2$O (613.09): C, 54.66; H, 6.00; N, 11.42. Found: C, 54.63; H, 5.95; N, 11.51.

Example 27

1-{[2-tert-Butyl-1-(tetrahydro-2H-pyran-4-ylmethyl)-1H-benzimidazol-5-yl]sulfonyl}-N-ethyl-1H-pyrazole-4-carboxamide

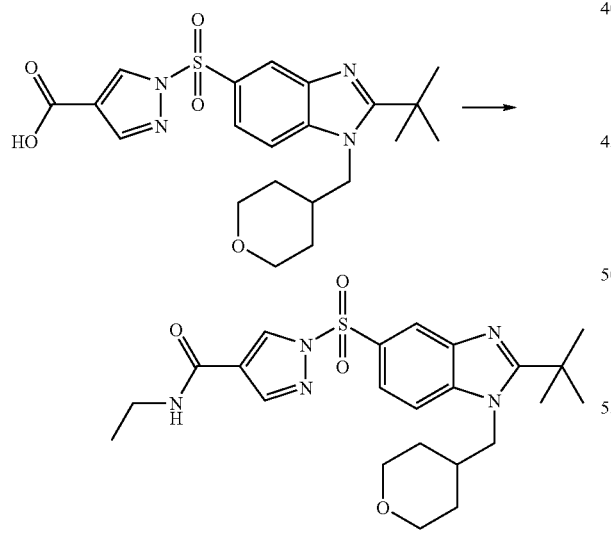

Following the same procedure in Example 24, Step A, using ethylamine (73 uL, 2.0 M in THF, 0.15 mmol), DIPEA (28 uL, 21 mg, 0.16 mmol), 1-{[2-tert-butyl-1-(tetrahydro-2H-pyran-4-ylmethyl)-1H-benzimidazol-5-yl]sulfonyl}-1H-pyrazole-4-carboxylic acid (0.073 mmol) and HATU (44 mg, 0.12 mmol) in DMF (2.5 mL). The crude product was purified by MPLC using Hex/EtOAc (1:2) on silica gel to give 17 mg (48%) of a white solid as the title compound. $^1$H NMR (400 MHz, METHANOL-D$_4$) δ 1.15 (t, J=7.23 Hz, 3 H), 1.40-1.57 (m, 4 H), 1.59 (s, 9H), 2.21-2.41 (m, 1 H), 2.79 (s, 1 H), 3.29-3.35 (m, 4 H), 3.84-3.95 (m, 2 H), 4.41 (d, J=7.42 Hz, 2 H), 7.91 (d, J=9.0 Hz, 1 H), 7.98 (dd, J=9.0, 1.7 Hz, 1 H), 8.03 (s, 1 H), 8.33 (d, J=1.56 Hz, 1 H), 8.74 (s, 1 H); MS (ESI) (M+H)$^+$=474.0; Anal. Calcd for C$_{23}$H$_{31}$N$_5$O$_4$S+0.70 TFA+0.30 EtOAc+0.40H$_2$O (590.66): C, 52.67; H, 5.96; N, 11.86. Found: C, 52.63; H, 5.99; N, 11.81.

Example 28

1-{[2-tert-Butyl-1-(tetrahydro-2H-pyran-4-ylmethyl)-1H-benzimidazol-5-yl]sulfonyl}-N-cyclopropyl-1H-pyrazole-4-carboxamide

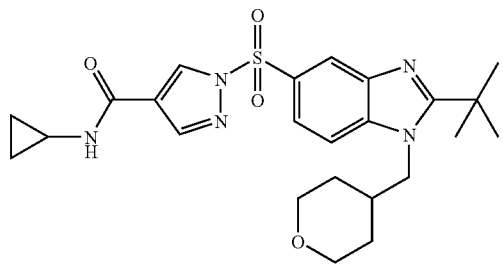

Method A

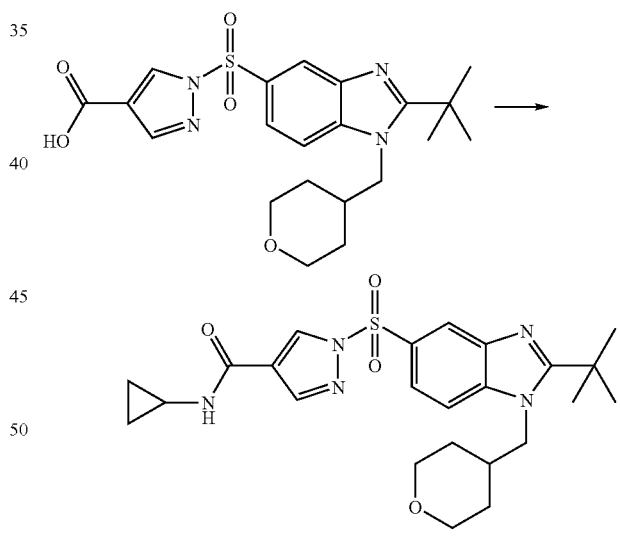

Following the same procedure in Example 24, Step A, using cyclopropylamine (10 uL, 8 mg, 0.15 mmol), DIPEA (28 uL, 21 mg, 0.16 mmol), 1-{[2-tert-butyl-1-(tetrahydro-2H-pyran-4-ylmethyl)-1H-benzimidazol-5-yl]sulfonyl}-1H-pyrazole-4-carboxylic acid (0.073 mmol) and HATU (44 mg, 0.12 mmol) in DMF (2.5 mL). The crude product was purified by MPLC using Hex/EtOAc (1:2) on silica gel to give 27 mg (76%) of a white solid as the title compound. $^1$H NMR (400 MHz, METHANOL-D$_4$) δ 0.51-0.59 (m, 2 H), 0.69-0.79 (m, 2 H), 1.40-1.56 (m, 4 H), 1.59 (s, 9 H), 2.22-2.35 (m, 1 H), 2.70-2.79 (m, 1 H), 3.25-3.34 (m, 2 H), 3.85-3.93 (m, 2 H), 4.41 (d, J=7.42 Hz, 2 H), 7.91 (d, J=8.7 Hz, 1 H), 7.98 (dd, J=8.8, 1.7 Hz, 1 H), 8.02 (d, J=0.59 Hz, 1 H), 8.33 (d, J=1.76 Hz, 1 H), 8.74 (d, J=0.59 Hz, 1 H); MS (ESI) (M+H)$^+$=486.0; Anal. Calcd for $C_{24}H_{31}N_5O_4S$+110 TFA (599.63): C, 52.08; H, 5.38; N, 11.68. Found: C, 52.25H, 5.16; N, 11.92.

Method B

Step A: 1-{[2-tert-butyl-1-(tetrahydro-2H-pyran-4-ylmethyl)-1H-benzimidazol-5-yl]sulfonyl}-N-cyclopropyl-1H-pyrazole-4-carboxamide

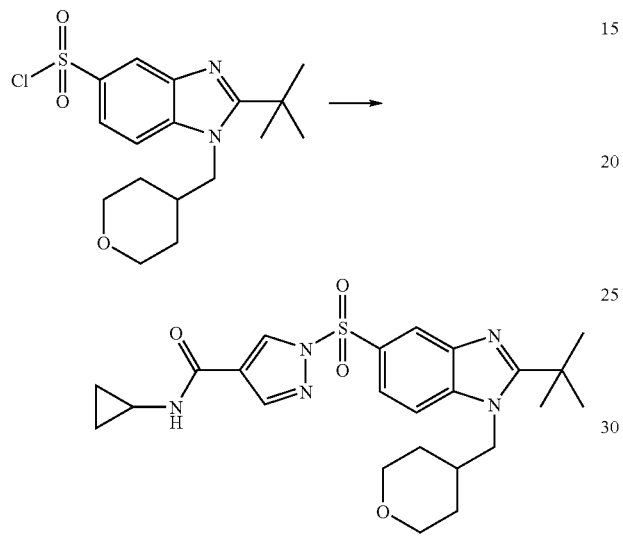

Sodium hydride (0.98 g, 60%, 25 mmol) was added to a solution of N-cyclopropyl-1H-pyrazole-4-carboxamide (0.49 g, 3.5 mmol) (see following steps B and C for preparation) in 40 mL of THF-DMF (3:1) at 0° C. Stirring for 1 h at 0° C. and 0.5 h at room temperature, 2-tert-butyl-1-(tetrahydro-2H-pyran-4-ylmethyl)-1H-benzimidazole-5-sulfonyl chloride (1.30 g, 3.5 mmol) was added. The reaction mixture was stirred for 2 h at 0° C., quenched with NaHCO$_3$ (10 mL) and extracted with EtOAc (3×50 mL). The combined organic phases were washed with NaCl (20 mL) and dried over Na$_2$SO$_4$. The crude product was purified by MPLC using Hex/EtOAc (1:2) on silica gel to give 0.54 g (33%) of a white solid as the title compound. $^1$H NMR (400 MHz, METHANOL-D$_4$) δ 0.52-0.59 (m, 2 H), 0.71-0.79 (m, 2 H), 1.39-1.57 (m, 4 H), 1.60 (s, 9 H), 2.22-2.37 (m, 1 H), 2.71-2.79 (m, 1 H), 3.26-3.34 (m, 2 H), 3.86-3.93 (m, 2 H), 4.43 (d, J=7.62 Hz, 2 H), 7.91-7.95 (m, 1 H), 7.97-8.01 (m, 1 H), 8.03 (d, J=0.78 Hz, 1 H), 8.34 (d, J=1.37 Hz, 1 H), 8.74 (d, J=0.59 Hz, 1 H); MS (ESI) (M+H)$^+$=485.8.

Step B: 1H-pyrazole-4-carbonyl chloride

A mixture of 1H-pyrazole-4-carboxylic acid (1.03 g, 9.2 mmol) in thionyl chloride (20 mL) was heated for 18 h at reflux. Upon evaporation, 1.16 g (97%) of a white solid was obtained.

Step C: N-cyclopropyl-1H-pyrazole-4-carboxamide

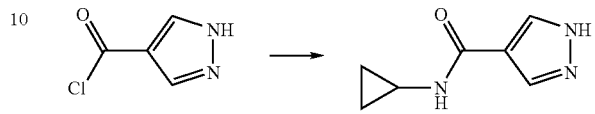

A solution of cyclopropylamine (0.52 mL, 0.43 g, 7.5 mmol) and triethylamine (1.4 mL, 1.01 g, 10.0 mmol) in CH$_2$Cl$_2$ (5 mL) was added to a suspension of 1H-pyrazole-4-carbonyl chloride (0.69 g, 5.3 mmol) in CH$_2$Cl$_2$ (20 mL) at 0° C. The reaction mixture was stirred overnight at room temperature. After evaporation of the solvent, the crude product was purified by MPLC using EtOAc on silica gel to give 0.79 g (99%) of a white solid as the title compound. $^1$H NMR (400 MHz, METHANOL-D4) δ 0.52-0.62 (m, 2 H), 0.72-0.82 (m, 2 H), 2.69-2.86 (m, 1 H), 7.91 (s, 1 H), 8.09 (s, 1 H).

Example 29

2-tert-Butyl-5-(1H-pyrrol-1-ylsulfonyl)-1-(tetrahydro-2H-pyran-4-ylmethyl)-1H-benzimidazole

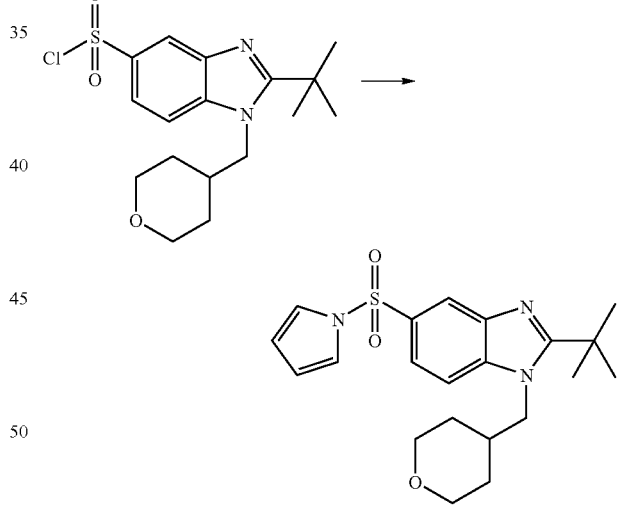

Sodium hydride (139 mg, 60%, 3.5 mmol) was added to a solution of pyrrole (200 uL, 194 mg, 2.9 mmol) in THF (10 mL). Stirring for 3 h at room temperature, 2-tert-butyl-1-(tetrahydro-2H-pyran-4-ylmethyl)-1H-benzimidazole-5-sulfonyl chloride (185 mg, 0.5 mmol) was added. The reaction mixture was stirred overnight at room temperature, quenched with NH$_4$Cl (5 mL), diluted with EtOAc (50 mL), washed with NaCl (2×20 mL) and dried over Na$_2$SO$_4$. The crude product was purified by MPLC using Hex/EtOAc (1:1) on silica gel to give 70 mg (35%) of a white solid as the title compound. $^1$H NMR (400 MHz, METHANOL-D$_4$) δ 1.36-1.53 (m, 4 H), 1.55 (s, 9 H), 2.18-2.38 (m, 1 H), 3.22-3.35 (m, 2 H), 3.88 (m, 2 H), 4.33 (d, J=7.42 Hz, 2 H), 6.22-6.31 (m, 2

H), 7.13-7.29 (m, 2 H), 7.71 (d, J=8.8 Hz, 1 H), 7.77 (dd, J=8.6, 1.8 Hz, 1 H), 8.13 (d, J=1.37 Hz, 1 H); MS (ESI) (M+H)+=401.8; Anal. Calcd for $C_{21}H_{27}N_3O_3S+0.30H_2O$ (406.94): C, 61.98; H, 6.84; N, 10.33. Found: C, 62.10; H, 6.90; N, 10.43.

Example 30

Methyl 1-{[2-tert-butyl-1-(tetrahydro-2H-pyran-4-ylmethyl)-1H-benzimidazol-5-yl]sulfonyl}-1H-pyrrole-3-carboxylate

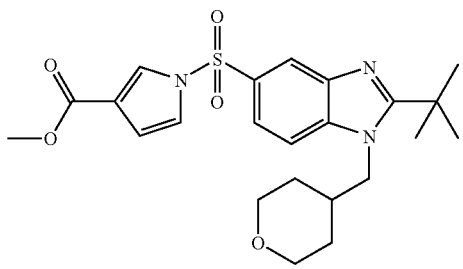

Step A: methyl 1-{[2-tert-butyl-1-(tetrahydro-2H-pyran-4-ylmethyl)-1H-benzimidazol-5-yl]sulfonyl}-1H-pyrrole-3-carboxylate

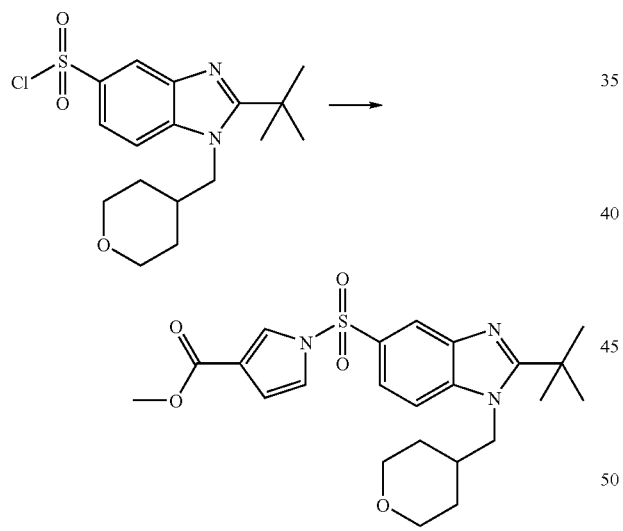

Following the same procedure in Example 29, using methyl 1H-pyrrole-3-carboxylate (0.16 g, 1.3 mmol) (see following step B for preparation), sodium hydride (0.18 g, 60%, 4.5 mmol) and 2-tert-butyl-1-(tetrahydro-2H-pyran-4-ylmethyl)-1H-benzimidazole-5-sulfonyl chloride (0.48 g, 1.3 mmol) in THF (10 mL). The crude product was purified by MPLC using Hex/EtOAc (1:1) on silica gel to give 0.16 g (27%) of a white solid as the title compound. $^1$H NMR (400 MHz, METHANOL-$D_4$) δ 1.46-1.54 (m, 4 H), 1.56 (s, 9 H), 2.15-2.32 (m, 1 H), 3.25-3.37 (m, 2 H), 3.79 (s, 3 H), 3.93-4.03 (m, 2 H), 4.22 (d, J=7.42 Hz, 2 H), 6.62 (dd, J=3.32, 1.56 Hz, 1 H), 7.15 (dd, J=3.32, 2.34 Hz, 1 H), 7.42 (d, J=8.79 Hz, 1 H), 7.74-7.81 (m, 2 H), 8.33 (d, J=1.37 Hz, 1 H); MS (ESI) (M+H)+=459.8; Anal. Calcd for $C_{23}H_{29}N_3O_5S+0.10$ EtOAc+0.30$H_2O$ (474.98): C, 59.43; H, 6.45; N, 8.85. Found: C, 59.34; H, 6.60; N, 8.84.

Step B: methyl 1H-pyrrole-3-carboxylate

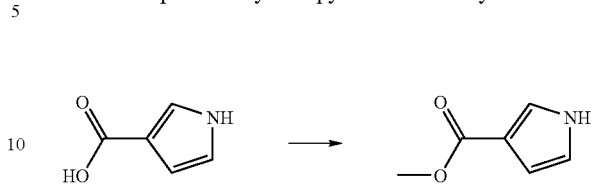

Potassium carbonate (0.65 g, 5.4 mmol) was added to a solution of 1H-pyrrole-3-carboxylic acid (0.50 g, 4.5 mmol) in DMF (10 mL). Stirring for 2 h at room temperature, methyl iodide (0.34 mL, 0.77 g, 5.4 mmol) was added. The mixture was stirred overnight at room temperature, diluted with $H_2O$ (50 mL), and extracted with EtOAc (3×50 mL). The combined organic phases were washed with NaCl (10 mL) and dried over $Na_2SO_4$. The crude product was purified by MPLC using Hex/EtOAc (7:3) on silica gel to give 0.17 g (30%) of a white solid as the title compound. $^1$H NMR (400 MHz, CHLOROFORM-D) δ 3.82 (s, 3 H), 6.56-6.72 (m, 1 H), 6.73-6.83 (m, 1 H), 7.36-7.50 (m, 1 H).

Example 31

1-{[2-tert-Butyl-1-(tetrahydro-2H-pyran-4-ylmethyl)-1H-benzimidazol-5-yl]sulfonyl}-N-ethyl-1H-pyrrole-3-carboxamide

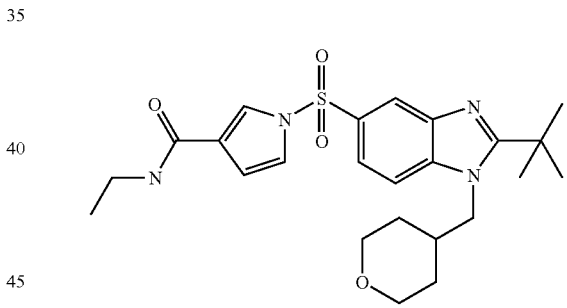

Method A

Step A: 1-{[2-tert-butyl-1-(tetrahydro-2H-pyran-4-ylmethyl)-1H-benzimidazol-5-yl]sulfonyl}-N-ethyl-1H-pyrrole-3-carboxamide

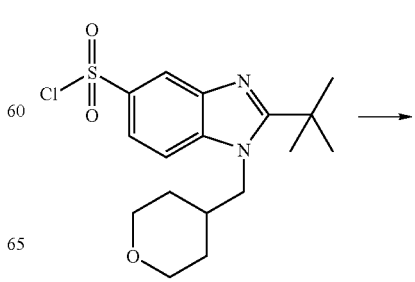

-continued

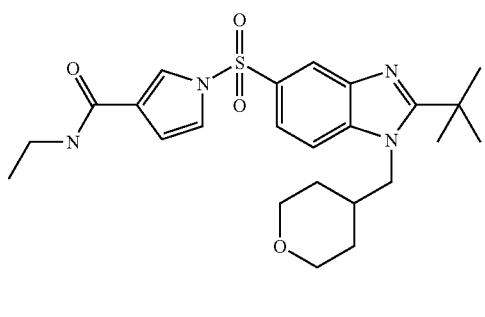

Following the same procedure in Example 29, using N-ethyl-1H-pyrrole-3-carboxamide (2.7 g, 20 mmol) (see following step B for preparation), sodium hydride (4.0 g, 60%, 100 mmol) and 2-tert-butyl-1-(tetrahydro-2H-pyran-4-ylmethyl)-1H-benzimidazole-5-sulfonyl chloride (6.1 g, 16 mmol) in THF (250 mL). The crude product was purified by MPLC using Hex/EtOAc (1:4) on silica gel to give 4.0 g (53%) of a white solid as the title compound. $^1$H NMR (400 MHz, METHANOL-D$_4$) δ 1.13 (t, J=7.23 Hz, 3 H), 1.41-1.58 (m, 4 H), 1.61 (s, 9 H), 2.24-2.38 (m, 1 H), 3.24-3.35 (m, 4 H), 3.85-3.94 (m, 2 H), 4.44 (d, J=7.42 Hz, 2 H), 6.65 (dd, J=3.32, 1.56 Hz, 1 H), 7.29 (dd, J=3.32, 2.34 Hz, 1 H), 7.77-7.82 (m, 1 H), 7.95-7.98 (m, 2 H), 8.24-8.30 (m, 1 H); MS (ESI) (M+H)$^+$=472.8; Anal. Calcd for C$_{24}$H$_{32}$N$_4$O$_4$S+1.20 TFA+ 0.10 EtOAc+0.30H$_2$O (624.86): C, 51.71; H, 5.58; N, 8.97. Found: C, 51.73; H, 5.66; N, 8.91.

Step B: N-ethyl-1H-pyrrole-3-carboxamide

DIPEA (10.4 mL, 7.8 g, 60 mmol) was added to a solution of 1H-pyrrole-3-carboxylic acid (2.2 g, 20 mmol) and ethylamine hydrochloride (2.5 g, 30 mmol) in DMF (50 mL) at 0° C. Stirring for 20 min, HATU (9.9 g, 26 mmol) was added at 0° C. The reaction mixture was stirred overnight at room temperature, diluted with EtOAc (300 mL), washed with H$_2$O (3×30 mL) and dried over Na$_2$SO$_4$. The crude product was purified by MPLC using EtOAc on silica gel to give 4.0 mL of a solution of the desired product in DMF. Small amount of the desired product was purified again by MPLC using EtOAc on silica gel for NMR. $^1$H NMR (400 MHz, CHLOROFORM-D) δ 1.22 (t, J=7.23 Hz, 3 H), 3.39-3.51 (m, 2 H), 5.84 (s, 1 H), 6.37-6.42 (m, 1 H), 6.77 (dd, J=4.98, 2.44 Hz, 1 H), 7.30-7.39 (m, 1 H), 8.85 (t, 1 H).

Method B

Step A: 1-{[2-tert-butyl-1-(tetrahydro-2H-pyran-4-ylmethyl)-1H-benzimidazol-5-yl]sulfonyl}-N-ethyl-1H-pyrrole-3-carboxamide Following the same procedure in Example 24, Step A, using DIPLA (105 uL, 78 mg, 0.60 mmol), 1-{[2-(1,1-dimethylpropyl)-1-(tetrahydro-2H-pyran-4-ylmethyl)-1H-benzimidazol-5-yl]sulfonyl}-1H-pyrrole-3-carboxylic acid (0.85 mmol) (see following Steps B and C for preparation) in DMF (15 mL), HATU (582 mg, 10.53 mmol) and ethylamine hydrochloride (154 mg, 1.87 mmol). The crude product was purified by MPLC on silica gel using EtOAc to give 0.32 g (81%) of a white solid as the title compounds $^1$H NMR (400 MHz, CHLOROFORM-D) δ 1.19 (t, J=7.23 Hz, 3 H), 1.45-1.54 (m, 4 H), 1.56 (s, 9 H), 2.15-2.33 (m, 1 H), 3.26-3.35 (m, 2 H), 3.36-3.44 (m, 2 H), 3.93-4.03 (m, 2 H), 4.22 (d, J=7.42 Hz, 2H), 5.79 (t, J=5.66 Hz, 1 H), 6.47 (dd, J=3.22, 1.66 Hz, 1 H), 7.17 (dd, J=3.32, 2.15 Hz, 1 H), 7.41 (d, J=8.59 Hz, 1 H) 7.62 (dd, J=2.34, 1.76 Hz, 1 H), 7.76 (dd, J=8.69, 1.86 Hz, 1 H), 8.32 (d, J=1.76 Hz, 1 H); MS (ESI) (M+H)$^+$=473.3.

Step B: 1-{[2-tert-butyl-1-(tetrahydro-2H-pyran-4-ylmethyl)-$_{1H}$-benzimidazol-5-yl]sulfonyl}-1H-pyrrole-3-carbaldehyde

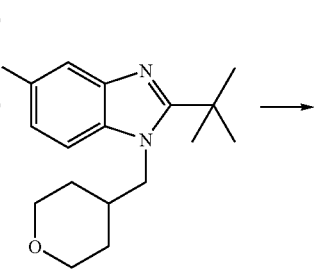

-continued

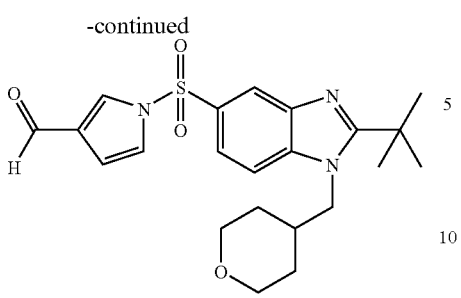

NaH (0.49 mg, 60%, 12.4 mmol) was a solution of 1H-Pyrrole-3-carbaldehyde (0.21 mg, 2.47 mmol) in THF (30 mL) at 0° C. The reaction mixture was allowed to warm to room temperature, stirred for 1 hour at room temperature and cooled down to 0° C. again. 2-tert-Butyl-1-(tetrahydro-2H-pyran-4-ylmethyl)-1H-benzimidazole-5-sulfonyl chloride (1.1 g, 20.97 mmol) was added slowly, allowed the reaction to warm to room temperature and stirred for 1 hour. The reaction mixture was quenched with NaHCO$_3$ (5 mL), diluted with EtOAc (100 mL), washed with brine (2×15 mL) and dried over Na$_2$SO$_4$. The crude product was purified by MPLC on silica gel using Hexane/EtOAc (1:1) to give 0.44 g (34%) of a white solid as the title compound. $^1$H NMR (400 MHz, CHLOROFORM-D) δ 1.45-1.55 (m, 4 H), 1.56 (s, 9 H), 2.16-2.31 (m, 1 H), 3.25-3.35 (m, 2 H), 3.94-4.02 (m, 2 H), 4.22 (d, J=7.42 Hz, 2 H), 6.67 (dd, J=3.42, 1.66 Hz, 1 H), 7.18-7.22 (m, 1 H), 7.44 (d, J=8.79 Hz, 1 H), 7.76-7.82 (m, 2 H) 8.36 (d, J=1.76 Hz, 1 H) 9.79 (s, 1 H); MS (ESI) (M+H)$^+$= 430.00.

Step C: 1-{[2-tert-butyl-1-(tetrahydro-2H-pyran-4-ylmethyl)-1H-benzimidazol-5-yl]sulfonyl}-1H-pyrrole-3-carboxylic acid

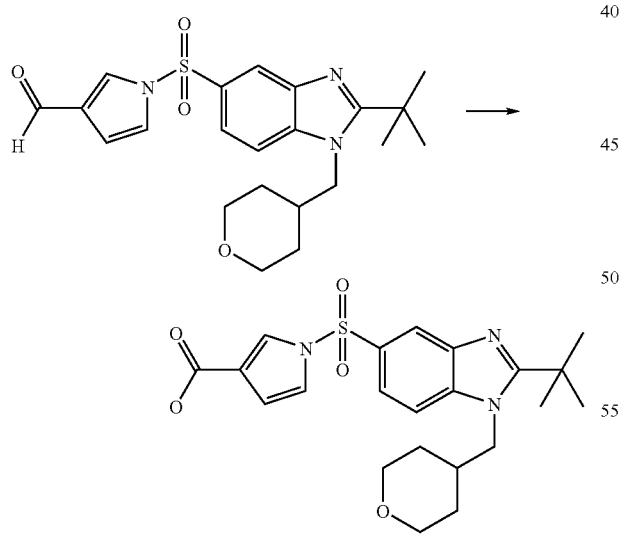

Oxone (784 mg, 1.28 mmol) was added to a solution of 1-{[2-tert-butyl-1-(tetrahydro-2H-pyran-4-ylmethyl)-1H-benzimidazol-5-yl]sulfonyl}-1H-pyrrole-3-carbaldehyde (366 mg, 0.85 mmol) in DMF (15 mL). The reaction mixture was stirred overnight at room temperature and used directly for step A. MS (ESI) (M+H)$^+$=445.88

Example 32

1-{[2-tert-Butyl-1-(tetrahydro-2H-pyran-4-ylmethyl)-1H-benzimidazol-5-yl]sulfonyl}-N-cyclopropyl-1H-pyrrole-3-carboxamide

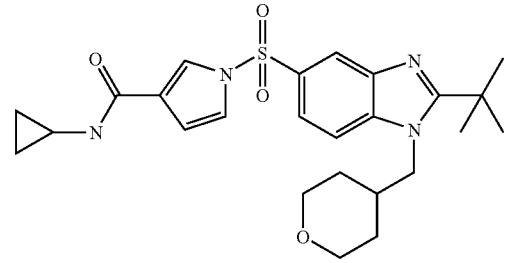

Step A: 1-{[2-tert-butyl-1-(tetrahydro-2H-pyran-4-ylmethyl)-1H-benzimidazol-5-yl]sulfonyl}-N-cyclopropyl-1H-pyrrole-3-carboxamide

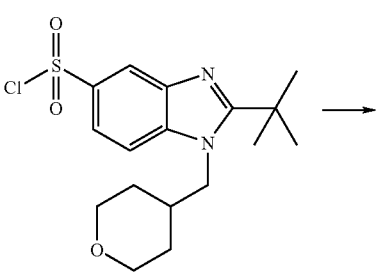

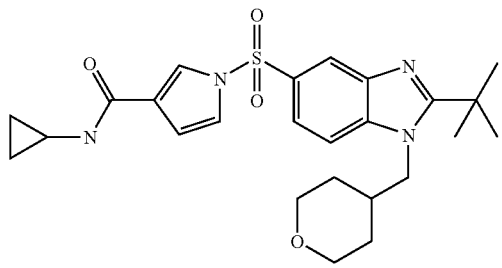

Following the same procedure in Example 29, using N-cyclopropyl-1H-pyrrole-3-carboxamide (49 mg, 0.33 mmol) (see following step B for preparation), sodium hydride (100 mg, 60%, 2.5 mmol) and 2-tert-butyl-1-(tetrahydro-2H-pyran-4-ylmethyl)-1H-benzimidazole-5-sulfonyl chloride (122 mg, 0.33 mmol) in THF (6 mL) and DMF (0.5 mL). The crude product was purified by MPLC using Hex/EtOAc (1:4) on silica gel to give 82 mg (51%) of a white solid as the title compound. $^1$H NMR (400 MHz, METHANOL-D$_4$) δ 0.50-0.56 (m, 2 H), 0.69-0.76 (m, 2 H), 1.40-1.57 (m, 4 H), 1.59 (s, 9 H), 2.29 (m, 1 H), 2.67-2.76 (m, 1 H), 3.24-3.34 (m, 2 H), 3.84-3.93 (m, 2 H), 4.41 (d, J=7.42 Hz, 2 H), 6.64 (dd, J=3.32, 1.56 Hz, 1 H), 7.27 (dd, J=3.32, 2.34 Hz, 1 H), 7.78-7.82 (m, 1 H), 7.90 (d, J=9.0 Hz, 1 H), 7.94 (dd, J=8.6, 1.5 Hz, 1H), 8.25 (d, J=1.56 Hz, 1 H); MS (ESI) (M+H)$^+$=484.7; Anal.

Calcd for $C_{25}H_{32}N_4O_4S+1.10$ TFA+0.10$H_2O$ (611.88): C, 53.40; H, 5.49; N, 9.16. Found: C, 53.44; H, 5.53; N, 9.18.

Step B: N-cyclopropyl-1H-pyrrole-3-carboxamide

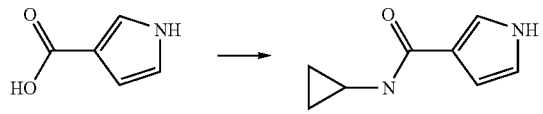

Following the same procedure in Example 31, step B, using DIPEA (0.87 mL, 0.65 g, 5.0 mmol), 1H-pyrrole-3-carboxylic acid (0.25 g, 2.3 mmol), cyclopropylamine (0.14 g, 2.5 mmol) and HATU (1.0 g, 2.7 mmol) in DMF (10 mL). The crude product was purified by MPLC using EtOAc on silica gel to 52 mg (15%) of the title product. $^1$H NMR (400 MHz, METHANOL-D4) δ 0.42-0.63 (m, 2 H), 0.66-0.83 (m, 2 H), 2.60-2.80 (m, 1 H), 6.49 (dd, J=2.93, 1.56 Hz, 1 H), 6.69 (dd, J=2.73, 1.95 Hz, 1 H), 7.30 (t, J=1.76 Hz, 1 H).

Example 33

1-{[2-tert-Butyl-1-(tetrahydro-2H-pyran-4-ylmethyl)-1H-benzimidazol-5-yl]sulfonyl}-N-cyclobutyl-1H-pyrrole-3-carboxamide

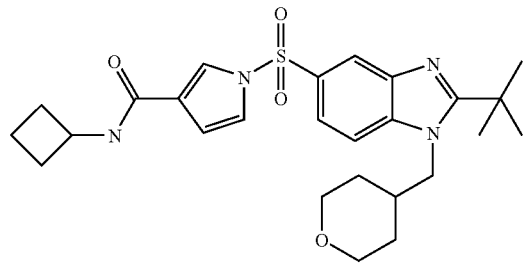

Step A: 1-{[2-tert-butyl-1-(tetrahydro-2H-pyran-4-ylmethyl)-1H-benzimidazol-5-yl]sulfonyl}-N-cyclobutyl-1H-pyrrole-3-carboxamide

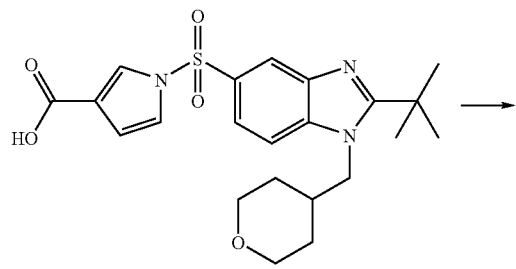

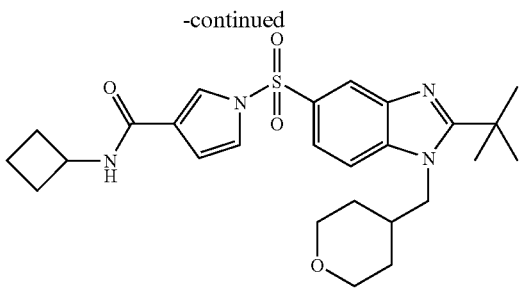

DIPEA (0.1 mL, 74 mg, 0.57 mmol) was added to a solution of 1-{[2-tert-butyl-1-(tetrahydro-2H-pyran-4-ylmethyl)-1H-benzimidazol-5-yl]sulfonyl}-1H-pyrrole-3-carboxylic acid (0.078 mmol) (see following step B for preparation) and cyclobutylamine (0.1 mL, 83 mg, 1.17 mmol) in DMF (5 mL) at 0° C. Stirring for 20 min, HATU (100 mg, 0.31 mmol) was added at 0° C. The reaction mixture was stirred overnight at room temperature, diluted with $H_2O$ (50 mL) and extracted with EtOAc (3×25 mL). The combined organic phases were washed with $H_2O$ (2×10 mL), NaCl (10 mL) and dried over $Na_2SO_4$. The crude product was purified by MPLC using Hex/EtOAc (3:7) on silica gel to 30 mg (78%) of a white solid as the title compound. $^1$H NMR (400 MHz, METHANOL-$D_4$) δ 1.41-1.57 (m, 4 H), 1.60 (s, 9 H), 1.66-1.78 (m, 2 H), 1.95-2.09 (m, 2 H), 2.20-2.35 (m, 3 H), 3.25-3.34 (m, 2 H), 3.85-3.93 (m, 2 H), 4.33-4.41 (m, 1 H), 4.43 (d, J=7.62 Hz, 2 H), 6.67 (dd, J=3.32, 1.56 Hz, 1 H), 7.28 (dd, J=3.32, 2.34 Hz, 1 H), 7.81-7.84 (m, 1 H), 7.91-7.95 (m, 1 H), 7.95-7.99 (m, 1 H), 8.26 (dd, J=1.66, 0.68 Hz, 1 H); MS (ESI) (M+H)$^+$=498.8; Anal. Calcd for $C_{26}H_{34}N_4O_4S+0.90$ TFA+0.80$H_2O$ (615.68): C, 54.23; H, 5.98; N, 9.10. Found: C, 54.25; H, 6.02; N, 9.12.

Step B: 1-{[2-tert-butyl-1-(tetrahydro-2H-pyran-4-ylmethyl)-1H-benzimidazol-5-yl]sulfonyl}-1H-pyrrole-3-carboxylic acid

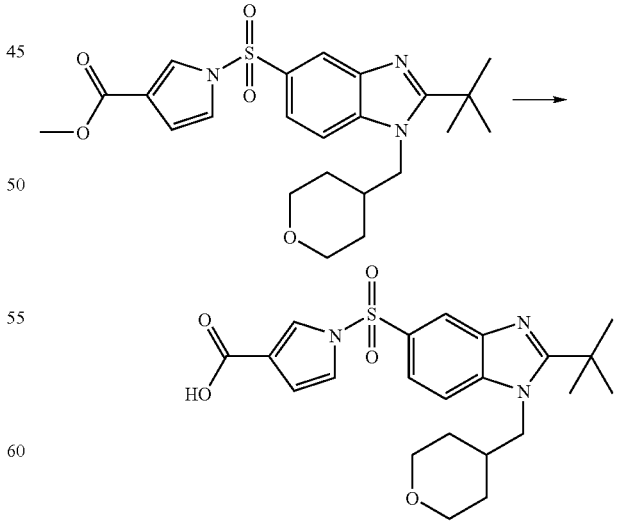

Lithium hydroxide (25 mg, 1.0 mmol) was added to mixture of methyl 1-{[2-tert-butyl-1-(tetrahydro-2H-pyran-4-ylmethyl)-1H-benzimidazol-5-yl]sulfonyl}-1H-pyrrole-3-carboxylate (90 mg, 0.2 mmol) in 10 mL of THF-H$_2$O (7:3) at 0° C. The reaction mixture was stirred overnight at room temperature and acidified to pH=1. Upon evaporation and dried in vacuo, the residue was dissolved in DMF (10 mL) and then used directly for step A. Purity:>80% (checked by LCMS). MS (ESI) (M+H)$^+$=445.99.

Example 34

N-Allyl-1-{[2-tert-butyl-1-(tetrahydro-2H-pyran-4-ylmethyl)-1H-benzimidazol-5-yl]sulfonyl}-1H-pyrrole-3-carboxamide

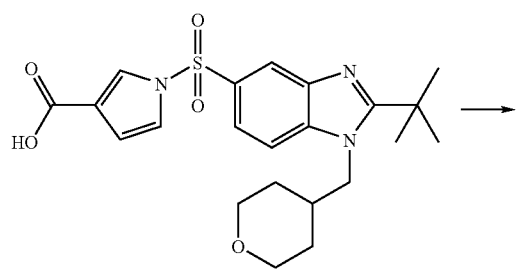

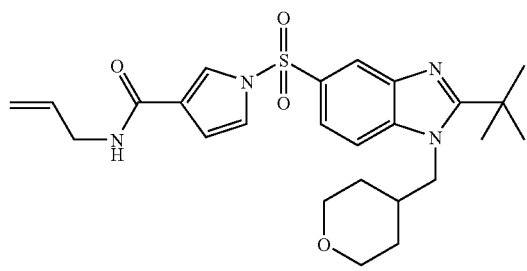

Following the same procedure in Example 33, step A, using DIPEA (0.1 mL, 74 mg, 0.57 mmol), 1-{[2-tert-butyl-1-(tetrahydro-2H-pyran-4-ylmethyl)-1H-benzimidazol-5-yl]sulfonyl}-1H-pyrrole-3-carboxylic acid (0.078 mmol) (see the step B in example 33 for preparation), allylamine (0.1 mL, 76 mg, 1.33 mmol) and HATU (100 mg, 0.31 mmol) in DMF (5 mL). The crude product was purified by MPLC using Hex/EtOAc (3:7) on silica gel to 32 mg (85%) of a white solid as the title compound. $^1$H NMR (400 MHz, METHANOL-D$_4$) δ 1.41-1.57 (m, 4 H), 1.60 (s, 9 H), 2.20-2.41 (m, 1 H), 3.24-3.38 (m, 2 H), 3.84-3.97 (m, 4 H), 4.43 (d, J=7.42 Hz, 2 H), 5.03-5.10 (m, 1 H), 5.10-5.19 (m, 1 H), 5.75-5.94 (m, 1 H), 6.67 (dd, J=3.32, 1.76 Hz, 1 H), 7.30 (dd, J=3.42, 2.25 Hz, 1 H), 7.79-7.85 (m, 1 H), 7.93 (d, J=9.0 Hz, 1H), 7.970 (dd, dd=9.0, 1.8 Hz, 1 H), 8.27 (d, J=1.76 Hz, 1 H); MS (ESI) (M+H)$^+$=484.7; Anal. Calcd for C$_{25}$H$_{32}$N$_4$O$_4$S+0.90 TFA+0.20H$_2$O (590.85): C, 54.48; H, 5.68; N, 9.48. Found: C, 54.53; H, 5.69; N, 9.57.

Example 35

1-{[2-tert-Butyl-1-(tetrahydro-2H-pyran-4-ylmethyl)-1H-benzimidazol-5-yl]sulfonyl}-N-methyl-1H-pyrrole-3-carboxamide

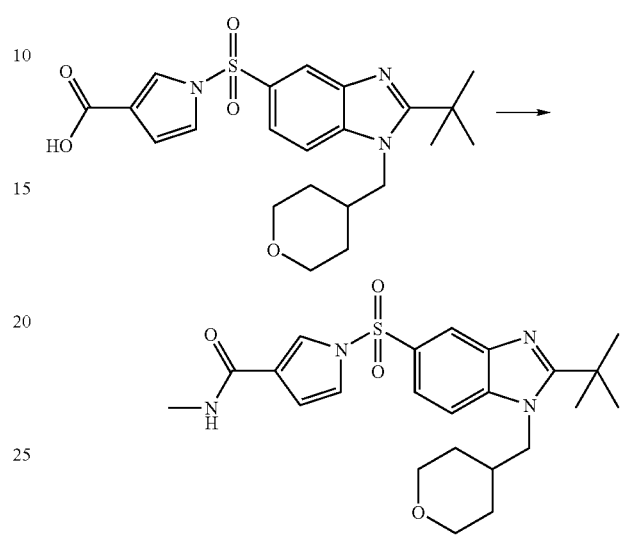

Following the same procedure in Example 33, step A, using DIPEA (0.37 mL, 274 mg, 2.2 mmol), 1-{[2-tert-butyl-1-(tetrahydro-2H-pyran-4-ylmethyl)-1H-benzimidazol-5-yl]sulfonyl}-1H-pyrrole-3-carboxylic acid (0.12 mmol) (see the step B in example 33 for preparation), methylamine hydrochloride (100 mg, 1.45 mmol) and HATU (150 mg, 0.40 mmol) in DMF (5 mL). The crude product was purified by MPLC using Hex/EtOAc (3:7) on silica gel to 25 mg (45%) of a white solid as the title compound. $^1$H NMR (400 MHz, METHANOL-D$_4$) δ 1.41-1.58 (m, 4 H), 1.61 (s, 9 H), 2.21-2.41 (m, 1 H), 2.79 (s, 3 H), 3.23-3.35 (m, 2 H), 3.83-3.96 (m, 2 H), 4.44 (d, J=7.62 Hz, 2 H), 6.63 (dd, J=3.32, 1.76 Hz, 1 H), 7.30 (dd, J=3.32, 2.34 Hz, 1H), 7.75-7.80 (m, 1 H), 7.95 (d, J=8.7 Hz, 1 H), 7.98 (dd, J=8.7, 1.5 Hz, 1 H), 8.27 (d, J=0.98 Hz, 1 H); MS (ESI) (M+H)$^+$=458.8; Anal. Calcd for C$_{23}$H$_{30}$N$_4$O$_4$S+1.50 TFA (629.62): C, 49.60; H, 5.04; N, 8.90. Found: C, 49.53; H, 5.00; N, 9.10.

Example 36

1-{[2-tert-Butyl-1-(tetrahydro-2H-pyran-4-ylmethyl)-1H-benzimidazol-5-yl]sulfonyl}-N-(2-hydroxyethyl)-1H-pyrrole-3-carboxamide

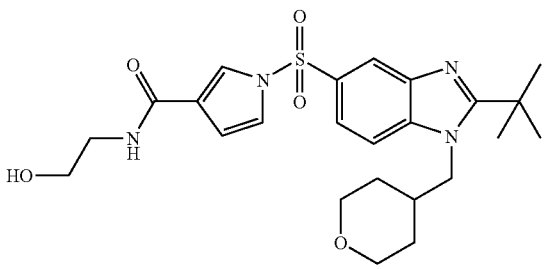

Step A: 1-{[2-tert-butyl-1-(tetrahydro-2H-pyran-4-ylmethyl)-1H-benzimidazol-5-yl]sulfonyl}-N-(2-hydroxyethyl)-1H-pyrrole-3-carboxamide

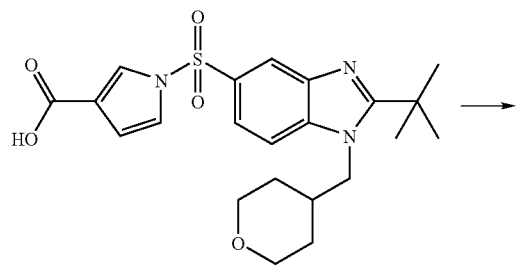

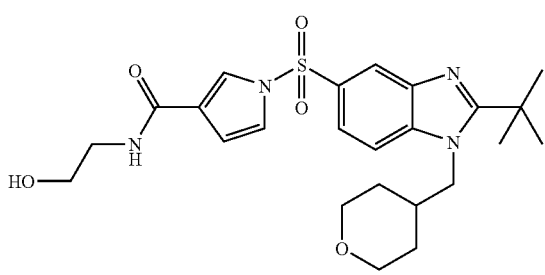

Following the same procedure in Example 33, step A, using DIPEA (47 uL, 35 mg, 0.27 mmol), 1-{[2-tert-butyl-1-(tetrahydro-2H-pyran-4-ylmethyl)-1H-benzimidazol-5-yl]sulfonyl}-1H-pyrrole-3-carboxylic acid (60 mg, 0.14 mmol) (see following step B for preparation), ethanolamine (17 mg, 0.27 mmol) and HATU (103 mg, 0.27 mmol) in DMF (5 mL). The crude product was purified by MPLC using EtOAc/MeOH (9:1) on silica gel to give 48 mg (72%) of a white solid as the title compound. $^1$H NMR (400 MHz, METHANOL-D$_4$) δ 1.42-1.58 (m, 4H), 1.61 (s, 9 H), 2.23-2.36 (m, 1 H), 3.25-3.34 (m, 2 H), 3.38 (t, J=5.76 Hz, 2 H), 3.61 (t, J=5.76 Hz, 2 H), 3.86-3.94 (m, 2 H), 4.44 (d, J=7.42 Hz, 2 H), 6.67 (dd, J=3.32, 1.76 Hz, 1H), 7.30 (dd, J=3.32, 2.34 Hz, 1 H), 7.82-7.85 (m, 1 H), 7.94 (d, J=8.8 Hz, 1 H), 7.98 (d, dd, J=8.7, 1.5 Hz, 1 H), 8.28 (d, J=1.17 Hz, 1 H); MS (ESI) (M+H)$^+$= 489.3.

Step B: 1-{[2-tert-butyl-1-(tetrahydro-2H-pyran-4-ylmethyl)-1H-benzimidazol-5-yl]sulfonyl}-1H-pyrrole-3-carboxylic acid

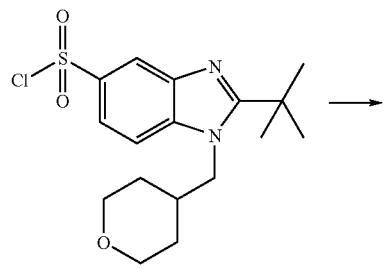

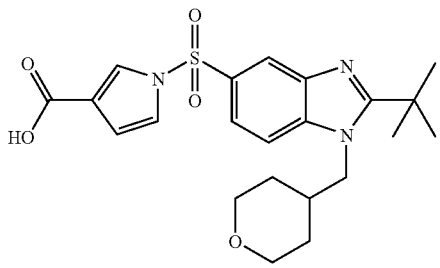

Butyllithium (7.0 mL, 2.0 M, 14 mmol) was added to a solution of 1H-pyrrole-3-carboxylic acid (0.67 g, 6.0 mmol) in THF (35 mL) at −78° C. Stirring for 45 min at −78° C. and 30 min at 0° C., 2-tert-butyl-1-(tetrahydro-2H-pyran-4-ylmethyl)-1H-benzimidazole-5-sulfonyl chloride (1.86 g, 5.0 mmol) was added. The reaction mixture was stirred overnight at room temperature, diluted with EtOAc (200 mL), washed with 2N HCl (2×20 mL), NaCl (20 mL) and dried over Na$_2$SO$_4$. The crude product was purified by MPLC using CH$_2$Cl$_2$/MeOH (20:1) on silica gel to 0.40 g (18%) of a white solid as the title compound. MS (ESI) (M+H)$^+$=445.98.

Example 37

1-{[2-tert-Butyl-1-(tetrahydro-2H-pyran-4-ylmethyl)-1H-benzimidazol-5-yl]sulfonyl}azetidin-3-amine

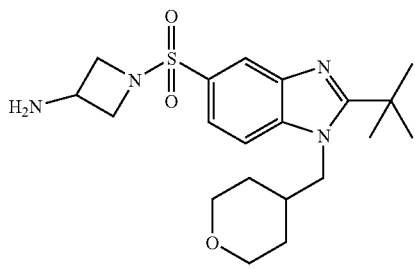

Step A: 1-{[2-tert-butyl-1-(tetrahydro-2H-pyran-4-ylmethyl)-1H-benzimidazol-5-yl]sulfonyl}azetidin-3-amine

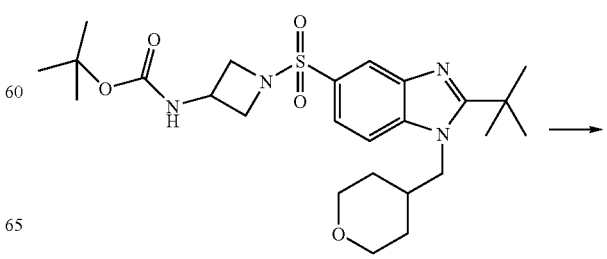

-continued

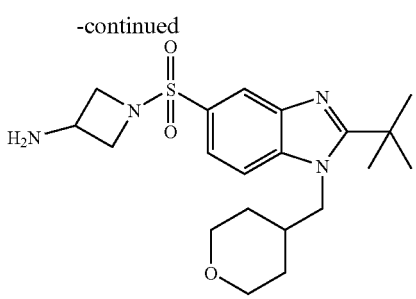

tert-butyl (1-{[2-tert-butyl-1-(tetrahydro-2H-pyran-4-ylmethyl)-1H-benzimidazol-5-yl]sulfonyl}azetidin-3-yl)carbamate (0.84 g, 1.66 mmol) (see following step B for preparation) in CH$_2$Cl$_2$ (10 mL) was treated with TFA (5 mL) for 1 h at room temperature. Upon evaporation, the residue was dissolved in H$_2$O (20 mL), neutralized with 2 N NaOH to pH=10, and extracted with CH$_2$Cl$_2$ (5×30 mL). The combined organic phases were washed with NaCl (10 mL) and dried over Na$_2$SO$_4$. After concentration, 0.58 g (86%) of a white solid was obtained as the title compound. $^1$H NMR (400 MHz, METHANOL-D$_4$) δ 1.45-1.62 (m, 4 H), 1.63 (s, 9 H), 2.28-2.44 (m, 1 H), 3.30-3.39 (m, 2 H), 3.82-3.89 (m, 3 H), 3.89-3.97 (m, 2 H), 3.99-4.10 (m, 2 H), 4.48 (d, J=7.62 Hz, 2 H), 7.85 (dd, J=8.69, 1.66 Hz, 1 H), 7.98 (d, J=8.79 Hz, 1 H), 8.15 (d, J=1.76 Hz, 1 H); MS (ESI) (M+H)$^+$=407.0; Anal. Calcd for C$_{20}$H$_{30}$N$_4$O$_3$S+2.10 TFA+0.20 CH$_3$OH+0.20H$_2$O (656.01): C, 44.67; H, 5.12; N, 8.54. Found: C, 44.68; H, 5.15; N, 8.56.

Step B: tert-butyl (1-{[2-tert-butyl-1-(tetrahydro-2H-pyran-4-ylmethyl)-1H-benzimidazol-5-yl]sulfonyl}azetidin-3-yl)carbamate

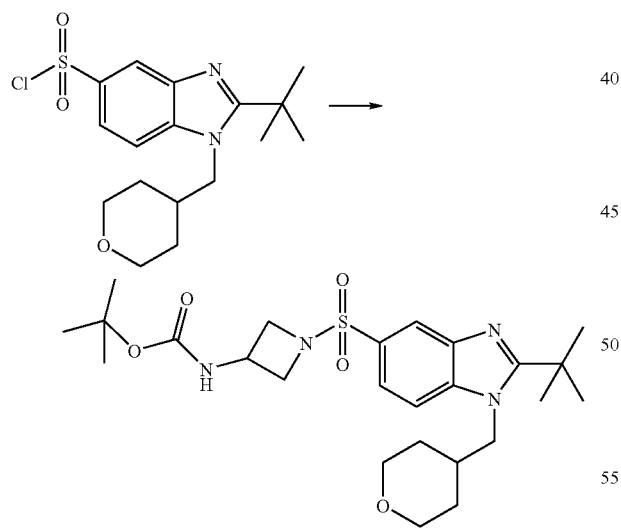

Following the same procedure in Example 1, Step A, using 2-tert-butyl-1-(tetrahydro-2H-pyran-4-ylmethyl)-1H-benzimidazole-5-sulfonyl chloride (0.74 g, 2.0 mmol), tert-butyl azetidin-3-ylcarbamate (0.35 g, 2.0 mmol) and DMAP (0.75 g, 6.1 mmol) in MeCN (60 mL). The crude product was purified by MPLC using Hex/EtOAc (1:1) on silica gel to give 0.84 g (83%) of a white solid as the title compound. $^1$H NMR (400 MHz, METHANOL-D$_4$) δ 1.32 (s, 9 H), 1.49-1.64 (m, 4 H), 1.66 (s, 9 H), 2.29-2.45 (m, 1 H), 3.30-3.41 (m, 2 H), 3.63 (m, 2 H), 3.88-4.01 (m, 4 H), 4.03-4.14 (m, 1 H), 4.52 (d, J=7.62 Hz, 2 H), 7.90 (dd, J=8.59, 1.37 Hz, 1 H), 8.05 (d, J=8.79 Hz, 1 H), 8.15 (d, J=1.17 Hz, 1 H); MS (ESI) (M+H)$^+$= 506.8; Anal. Calcd for C$_{25}$H$_{38}$N$_4$O$_5$S+0.90 TFA+0.10 EtOAc+0.50H$_2$O (628.31): C, 52.19; H, 6.53; N, 8.92. Found: C, 52.13; H, 6.53; N, 8.84.

Example 39

2-tert-Butyl-5-[(3,3-difluoroazetidin-1-yl)sulfonyl]-1-(tetrahydro-2H-pyran-4-ylmethyl)-1H-benzimidazole

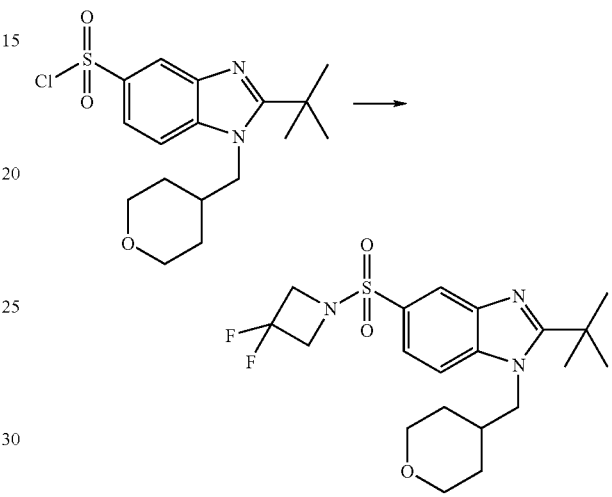

Following the same procedure in Example 1, Step A, using 2-tert-butyl-1-(tetrahydro-2H-pyran-4-ylmethyl)-1H-benzimidazole-5-sulfonyl chloride (90 mg, 0.24 mmol), 3,3-difluoroazetidine (45 mg, 0.49 mmol) and DMAP (59 mg, 0.49 mmol) in MeCN (10 mL). The crude product was purified by MPLC using Hex/EtOAc (1:1) on silica gel to give 68 mg (66%) of a white solid as the title compound. $^1$H NMR (400 MHz, METHANOL-D$_4$) δ 1.46-1.63 (m, 4 H), 1.65 (s, 9 H), 2.27-2.44 (m, 1 H), 3.30-3.39 (m, 2 H), 3.89-3.98 (m, 2 H), 4.20 (t, J=12.30 Hz, 4 H), 4.51 (d, J=7.62 Hz, 2 H), 7.93 (dd, J=8.69, 1.66 Hz, 1 H), 8.05 (d, J=8.79 Hz, 1 H), 8.19 (d, J=1.17 Hz, 1 H); MS (ESI) (M+H)$^+$=427.8; Anal. Calcd for C$_{20}$H$_{27}$F$_2$N$_3$O$_3$S+1.10 TFA+0.3 CH$_3$CN (565.26): C, 48.45; H, 5.17; N, 8.18. Found: C, 48.42; H, 4.86; N, 8.20.

Example 40

2-(1,1-Dimethylpropyl)-5-(1H-pyrazol-1-ylsulfonyl)-1-(tetrahydro-2H-pyran-4-ylmethyl)-1H-benzimidazole

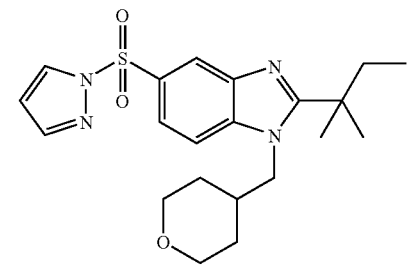

Step A: 2-(1,1-dimethylpropyl)-5-(1H-pyrazol-1-ylsulfonyl)-1-(tetrahydro-2H-pyran-4-ylmethyl)-1H-benzimidazole

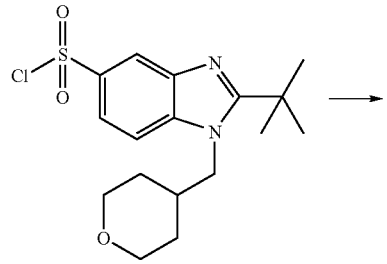

Following the same procedure in Example 1, Step A, using 2-(1,1-dimethylpropyl)-1-(tetrahydro-2H-pyran-4-ylmethyl)-1H-benzimidazole-5-sulfonyl chloride e (287 mg, 0.746 mmol) (see following Steps B, C, D and E for preparation), pyrazol (152 mg, 2.24 mmol) and DMAP (182 mg, 1.49 mmol) in MeCN (15 mL). The crude product was purified by MPLC using Hex/EtOAc (3:7) on silica gel to give 305 mg (98%) of a white solid as the title compound. $^1$H NMR (400 MHz, CHLOROFORM-D) δ 0.73 (t, J=7.52 Hz, 3 H), 1.37-1.52 (m, 4 H), 1.54 (s, 6 H), 1.90 (q, J=7.49 Hz, 2 H), 2.20-2.34 (m, 1 H), 3.24-3.34 (m, 2 H), 3.87-3.90 (m, 2 H), 4.34 (d, J=7.62 Hz, 2 H), 6.47 (dd, J=2.73, 1.56 Hz, 1 H), 7.73 (dd, J=1.56, 0.59 Hz, 1 H), 7.76 (dd, J=8.79, 0.39 Hz, 1 H), 7.86 (dd, J=8.8, 1.8 Hz, 1 H), 8.22-8.27 (m, 1 H), 8.31 (dd, J=2.73, 0.59 Hz, 1 H); MS (ESI) (M+H)$^+$=417.3; Anal. Calcd for $C_{21}H_{28}N_4O_3S$+0.1$H_2O$ (418.35): C, 60.29; H, 6.79; N, 13.39. Found: C, 60.32; H, 6.58; N, 13.77.

Step B: N-{5-(acetylamino)-2-[(tetrahydro-2H-pyran-4-ylmethyl)amino]phenyl}-2,2-dimethylbutanamide

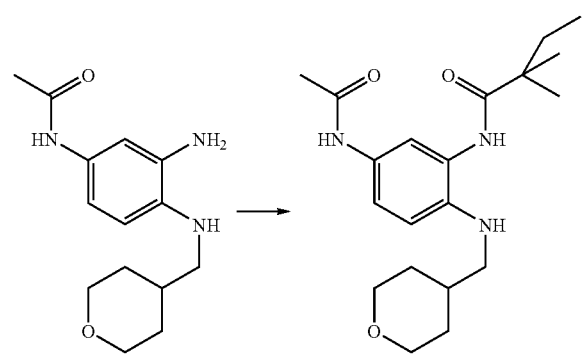

Following the same procedure in Example 1, Step E, using N-{3-Amino-4-[(tetrahydro-2H-pyran-4-ylmethyl)amino] phenyl}acetamide (10.5 g, 40 mmol), DMAP (2.4 g, 20 mmol) and 2,2-dimethylbutyryl chloride (5.9 g, 44 mmol) in 350 mL of DCM. Yield: 14.2 g (98%); $^1$H NMR (400 MHz, CHLOROFORM-D) δ 0.94 (t, J=7.52 Hz, 3 H), 1.29 (s, 6 H), 1.32-1.46 (m, 2 H), 1.66 (q, J=7.42 Hz, 2 H), 1.68-1.75 (m, 2 H), 1.78-1.90 (m, 1 H), 2.13 (s, 3 H), 2.97 (d, J=7.03 Hz, 2 H), 3.34-3.45 (m, 2 H), 3.77-3.86 (m, 1 H), 3.94-4.06 (m, 2 H), 6.75 (d, J=8.79 Hz, 1 H), 7.05 (s, 1 H), 7.21 (dd, J=8.59, 2.54 Hz, 1 H), 7.49 (s, 1 H), 7.55 (d, J=2.34 Hz, 1 H); MS (ESI) (M+H)$^+$=362.06.

Step C: N-[2-(1,1-dimethylpropyl)-1-(tetrahydro-2H-pyran-4-ylmethyl)-1H-benzimidazol-5-yl]acetamide

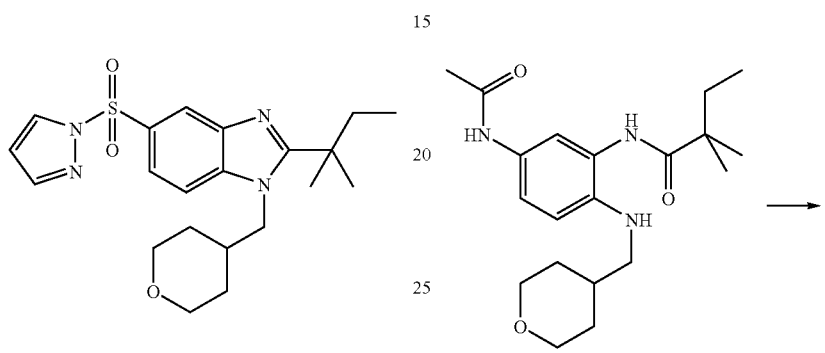

Following the same procedure in Example 1, Step F, using N-{5-(acetylamino)-2-[(tetrahydro-2H-pyran-4-ylmethyl) amino]phenyl}-2,2-dimethylbutanamide (5.12 g, 14.2 mmol) in AcOH (60 mL). Yield: 2.30 g (47%). $^1$H NMR (400 MHz, CHLOROFORM-D): δ 0.78 (t, J=7.42 Hz, 3 H), 1.45-1.60 (m, 10 H), 1.86 (q, J=7.42 Hz, 2 H), 2.19 (s, 3 H), 2.22-2.37 (m, 1 H), 3.24-3.38 (m, 2 H), 3.91-4.02 (m, 2 H), 4.17 (d, J=7.42 Hz, 2 H), 7.26 (d, J=8.5 Hz, 1 H), 7.39 (s, 1 H), 7.53 (dd, J=8.69, 2.05 Hz, 1 H), 7.67 (d, J=1.95 Hz, 1 H); MS (ESI) (M+H)$^+$=344.05.

Step D: 2-(1,1-dimethylpropyl)-1-(tetrahydro-2H-pyran-4-ylmethyl)-1H-benzimidazol-5-amine

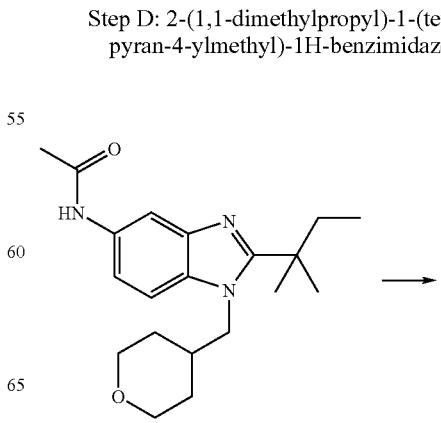

-continued

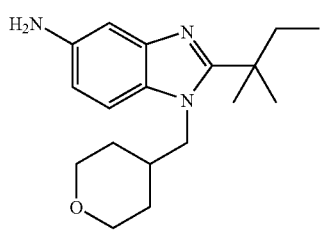

Following the same procedure in Example 1, Step G, using N-[2-(1,1-dimethylpropyl)-1-(tetrahydro-2H-pyran-4-ylmethyl)-1H-benzimidazol-5-yl]acetamide (2.08 g, 6.06 mmol) in 37% HCl (20 mL). Yield: 1.81 g (99%). $^1$H NMR (400 MHz, CHLOROFORM-D): δ 0.79 (t, J=7.52 Hz, 3 H), 1.42-1.51 (m, 4 H), 1.52 (s, 6 H), 1.84 (q, J=7.42 Hz, 2 H), 2.15-2.37 (m, 1 H), 3.25-3.38 (m, 2 H), 3.59 (s, 2 H), 3.92-4.03 (m, 2 H), 4.12 (d, J=7.42 Hz, 2 H), 6.65 (dd, J=8.50, 2.25 Hz, 1 H), 7.06 (d, J=2.15 Hz, 1 H), 7.10 (d, J=8.01 Hz, 1 H); MS (ESI) (M+H)$^+$=301.98.

Step E: 2-(1,1-dimethylpropyl)-1-(tetrahydro-2H-pyran-4-ylmethyl)-1H-benzimidazole-5-sulfonyl chloride

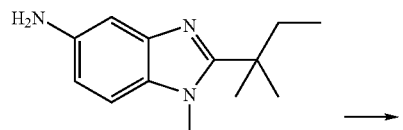

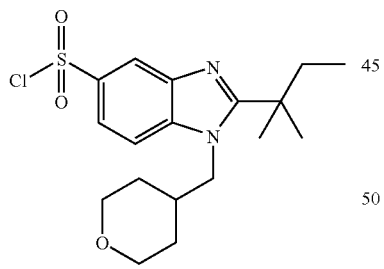

Following the same procedure in Example 1, Step H, using 2-(1,1-dimethylpropyl)-1-(tetrahydro-2H-pyran-4-ylmethyl)-1H-benzimidazol-5-amine (7.44 g, 24.7 mmol) in concentrated hydrochloric acid (50 mL), NaNO$_2$ (2.04 g, 29.6 mmol), CuCl$_2$ (2.00 g, 14.9 mmol) and saturated SO$_2$ in AcOH (100 mL). Yield: 9.04 g (95%) of a yellow solid was obtained. $^1$H NMR (400 MHz, CHLOROFORM-D) δ 0.92 (t, J=7.03 Hz, 3 H), 1.51-1.69 (m, 4 H), 1.82 (s, 6 H), 2.05-2.16 (m, 2 H), 2.27-2.44 (m, 1 H), 3.37 (t, J=11.03 Hz, 2 H), 4.04 (dd, J=11.23, 2.64 Hz, 2 H), 4.51 (dd, J=3.32 Hz, 2 H), 7.86-7.97 (m, J=7.62 Hz, 1 H), 8.12 (d, J=7.03 Hz, 1 H), 8.99 (s, 1 H); MS (ESI) (M+H)$^+$=384.94.

Example 41

1-{[2-(1,1-Dimethylpropyl)-1-(tetrahydro-2H-pyran-4-ylmethyl)-1H-benzimidazol-5-yl]sulfonyl}-N-methyl-1H-pyrazole-4-carboxamide

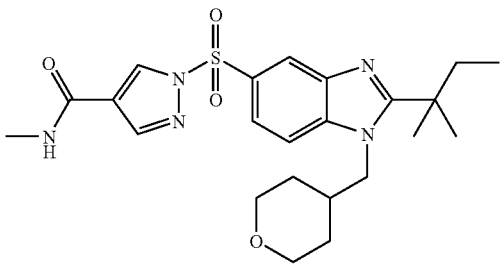

Step A: 1-{[2-(1,1-dimethylpropyl)-1-(tetrahydro-2H-pyran-4-ylmethyl)-1H-benzimidazol-5-yl]sulfonyl}-N-methyl-1H-pyrazole-4-carboxamide

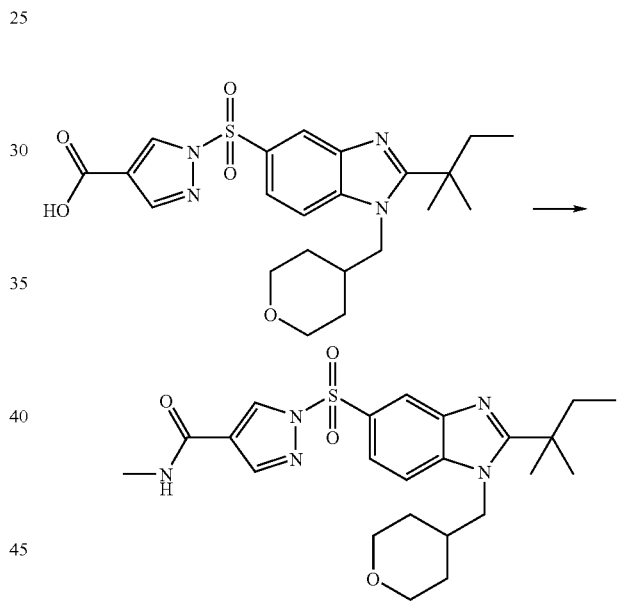

Following the same procedure in Example 24, Step A, using methylamine hydrochloride (24 mg, 0.36 mmol), DIPEA (104 uL, 77 mg, 0.59 mmol), 1-{[2-(1,1-dimethylpropyl)-1-(tetrahydro-2H-pyran-4-ylmethyl)-1H-benzimidazol-5-yl]sulfonyl}-1H-pyrazole-4-carboxylic acid (0.18 mmol) (see following Steps B and C for preparation) and HATU (109 mg, 0.29 mmol) in DMF (3 mL). The crude product was purified by MPLC using Hex/EtOAc (1:9) on silica gel to give 78 mg (92%) of a white solid as the title compound. $^1$H NMR (400 MHz, METHANOL-D$_4$) δ 0.78 (t, J=7.52 Hz, 3 H), 1.40-1.57 (m, 4 H), 1.59 (s, 6 H), 1.95 (q, J=7.29 Hz, 2 H), 2.21-2.37 (m, 1 H), 2.82 (s, 3 H), 3.25-3.35 (m, 2 H), 3.85-3.94 (m, 2 H), 4.42 (d, J=7.42 Hz, 2 H), 7.94 (d, J=9.0 Hz, 1 H), 8.00 (dd, J=8.8, 1.7 Hz, 1 H), 8.02 (d, J=0.59 Hz, 1 H), 8.35 (d, J=1.56 Hz, 1 H), 8.72 (d, J=0.59 Hz, 1 H); MS (ESI) (M+H)$^+$=474.0; Anal. Calcd for C$_{23}$H$_{31}$N$_5$O$_4$S+ 1.10 TFA+0.4H$_2$O (606.23): C, 49.93; H, 5.47; N, 11.55. Found: C, 49.95; H, 5.44; N, 11.48.

Step B: 1-{[2-(1,1-dimethylpropyl)-1-(tetrahydro-2H-pyran-4-ylmethyl)-1H-benzimidazol-5-yl]sulfonyl}-1H-pyrazole-4-carbaldehyde

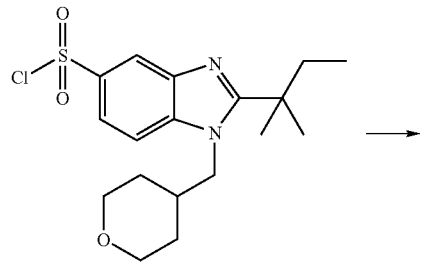

Following the same procedure in Example 1, Step A, using 2-(1,1-dimethylpropyl)-1-(tetrahydro-2H-pyran-4-ylmethyl)-1H-benzimidazole-5-sulfonyl chloride (2.12 g, 5.5 mmol), 1H-pyrazole-4-carbaldehyde (0.48 g, 5.0 mmol) and DMAP (0.73 g, 6.0 mmol) in MeCN (20 mL). The crude product was purified by MPLC using $CH_2Cl_2$/EtOAc (1:1) on silica gel to give 0.53 g (24%) of a white solid as the title compound. MS (ESI) $(M+H)^+$=444.92.

Step C: 1-{[2-(1,1-dimethylpropyl)-1-(tetrahydro-2H-pyran-4-ylmethyl)-1H-benzimidazol-5-yl]sulfonyl}-1H-pyrazole-4-carboxylic acid

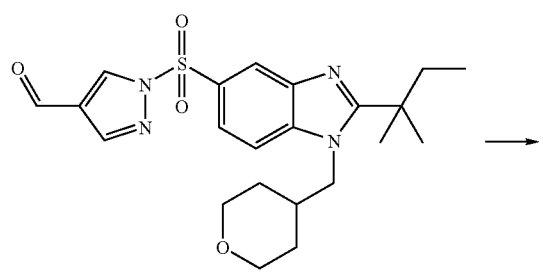

Oxone (534 mg, 0.869 mmol) was added to a solution of 1-{[2-(1,1-dimethylpropyl)-1-(tetrahydro-2H-pyran-4-ylmethyl)-1H-benzimidazol-5-yl]sulfonyl}-1H-pyrazole-4-carbaldehyde (322 mg, 0.724 mmol) in DMF (8 mL). The resulting mixture was stirred overnight at room temperature and used directly for step A. MS (ESI) $(M+H)^+$=460.92.

Example 42

1-{[2-(1,1-Dimethylpropyl)-1-(tetrahydro-2H-pyran-4-ylmethyl)-1H-benzimidazol-5-yl]sulfonyl}-N-ethyl-1H-pyrazole-4-carboxamide

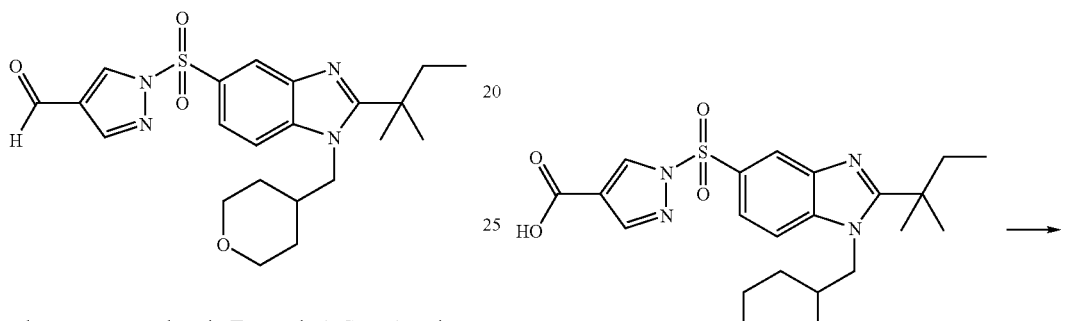

Following the same procedure in Example 24, Step A, using ethylamine hydrochloride (29 mg, 0.36 mmol), DIPEA (104 uL, 77 mg, 0.59 mmol), 1-{[2-(1,1-dimethylpropyl)-1-(tetrahydro-2H-pyran-4-ylmethyl)-1H-benzimidazol-5-yl]sulfonyl}-1H-pyrazole-4-carboxylic acid (0.18 mmol) and HATU (109 mg, 0.29 mmol) in DMF (3 mL). The crude product was purified by MPLC using Hex/EtOAc (1:4) on silica gel to give 53 mg (61%) of a white solid as the title compound. $^1$H NMR (400 MHz, METHANOL-$D_4$) δ 0.77 (t, J=7.42 Hz, 3 H), 1.15 (t, J=7.32 Hz, 3 H), 1.39-1.57 (m, 4 H), 1.58 (s, 6 H), 1.94 (q, J=7.68 Hz, 2 H), 2.19-2.37 (m, 1 H), 3.24-3.40 (m, 4 H), 3.83-3.94 (m, 2 H), 4.41 (d, J=7.23 Hz, 2 H), 7.92 (d, J=8.8 Hz, 1 H), 7.99 (dd, J=8.8, 1.4 Hz, 1 H), 8.04 (s, 1 H), 8.34 (d, J=1.17 Hz, 1 H), 8.74 (s, 1 H); MS (ESI) $(M+H)^+$=488.0; Anal. Calcd for $C_{24}H_{33}N_5O_4S$+0.9 TFA+ 0.3$H_2O$ (595.65): C, 52.02; H, 5.84; N, 11.76. Found: C, 52.01; H, 5.66; N, 11.91.

Example 43

N-Cyclopropyl-1-{[2-(1,1-dimethylpropyl)-1-(tetrahydro-2H-pyran-4-ylmethyl)-1H-benzimidazol-5-yl]sulfonyl}-1H-pyrazole-4-carboxamide

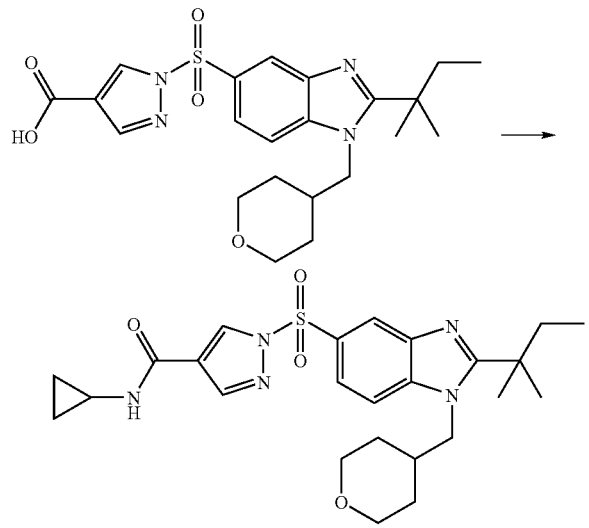

Following the same procedure in Example 24, Step A, using cyclopropylamine (21 mg, 25 uL, 0.36 mmol), DIPEA (104 uL, 77 mg, 0.59 mmol), 1-{[2-(1,1-dimethylpropyl)-1-(tetrahydro-2H-pyran-4-ylmethyl)-1H-benzimidazol-5-yl]sulfonyl}-1H-pyrazole-4-carboxylic acid (0.18 mmol) and HATU (109 mg, 0.29 mmol) in DMF (3 mL). The crude product was purified by MPLC using Hex/EtOAc (1:4) on silica gel to give 38 mg (42%) of a white solid as the title compound. $^1$H NMR (400 MHz, METHANOL-D$_4$) δ 0.54-0.61 (m, 2 H), 0.74-0.82 (m, 5 H), 1.42-1.58 (m, 4 H), 1.60 (s, 6 H), 1.96 (q, J=7.55 Hz, 2 H), 2.22-2.36 (m, 1 H), 2.73-2.80 (m, 1 H), 3.26-3.36 (m, 2 H), 3.86-3.95 (m, 2 H), 4.42 (d, J=7.42 Hz, 2 H), 7.92 (d, J=8.8 Hz, 1 H), 7.98 (dd, J=8.8, 1.8 Hz, 1 H), 8.05 (s, 1 H), 8.34 (d, J=1.76 Hz, 1 H), 8.76 (s, 1 H); MS (ESI) (M+H)$^+$=500.0; Anal. Calcd for C$_{25}$H$_{33}$N$_5$O$_4$S+0.6 TFA+1.0H$_2$O (586.07): C, 53.70; H, 6.12; N, 11.95. Found: C, 53.65; H, 5.98; N, 12.02.

Example 44

1-{[2-(1,1-Dimethylpropyl)-1-(tetrahydro-2H-pyran-4-ylmethyl)-1H-benzimidazol-5-yl]sulfonyl}-N-isopropyl-1H-pyrazole-4-carboxamide

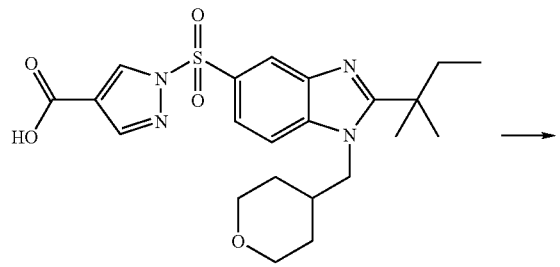

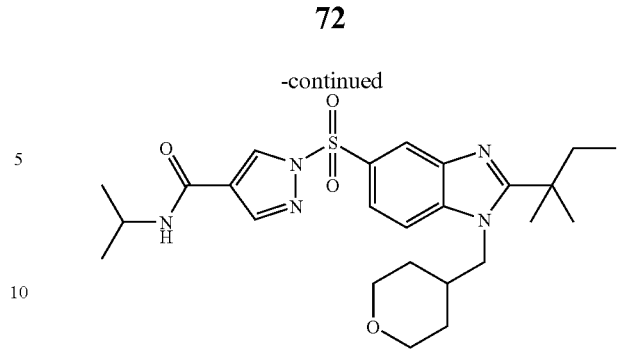

Following the same procedure in Example 24, Step A, using isopropylamine (21 mg, 31 uL, 0.36 mmol), DIPEA (104 uL, 77 mg, 0.59 mmol), 1-{[2-(1,1-dimethylpropyl)-1-(tetrahydro-2H-pyran-4-ylmethyl)-1H-benzimidazol-5-yl]sulfonyl}-1H-pyrazole-4-carboxylic acid (0.18 mmol) and HATU (109 mg, 0.29 mmol) in DMF (3 mL). The crude product was purified by MPLC using Hex/EtOAc (1:2) on silica gel to give 67 mg (74%) of a white solid as the title compound. $^1$H NMR (400 MHz, METHANOL-D$_4$) δ 0.79 (t, J=7.42 Hz, 3 H), 1.20 (d, J=6.64 Hz, 6 H), 1.42-1.58 (m, 4 H), 1.61 (s, 6 H), 1.97 (q, J=7.42 Hz, 2 H), 2.22-2.41 (m, 1 H), 3.26-3.37 (m, 2 H), 3.87-3.96 (m, 2 H), 4.06-4.19 (m, 1 H), 4.43 (d, J=7.62 Hz, 2 H), 7.95 (d, J=8.8 Hz, 1 H), 7.98-8.03 (dd, J=9.0, 2.0 Hz, 1 H), 8.07 (s, 1 H), 8.36 (d, J=1.76 Hz, 1 H), 8.79 (s, 1 H); MS (ESI) (M+H)$^+$=502.0; Anal. Calcd for C$_{25}$H$_{35}$N$_5$O$_4$S+110 TFA+0.6H$_2$O (626.48): C, 51.76; H, 5.99; N, 11.18. Found: C, 51.77; H, 5.96; N, 11.27.

Example 45

1-{[2-(1,1-Dimethylpropyl)-1-(tetrahydro-2H-pyran-4-ylmethyl)-1H-benzimidazol-5-yl]sulfonyl}-1H-pyrazole-4-carboxamide

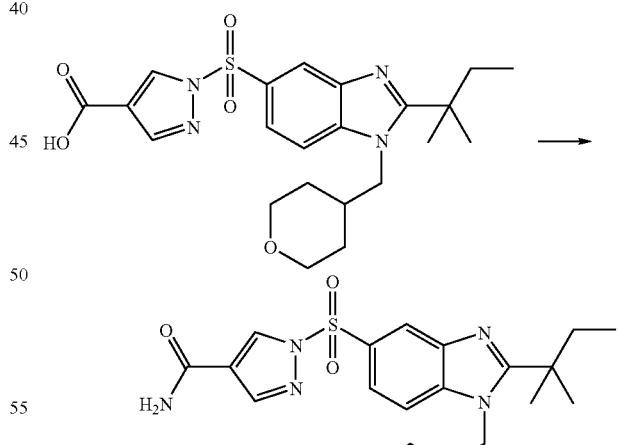

Following the same procedure in Example 24, Step A, using DIPEA (105 uL, 78 mg, 0.60 mmol), 1-{[2-(1,1-dimethylpropyl)-1-(tetrahydro-2H-pyran-4-ylmethyl)-1H-benzimidazol-5-yl]sulfonyl}-1H-pyrazole-4-carboxylic acid (0.20 mmol), HATU (114 mg, 0.30 mmol) and saturated ammonia in DMF (5 mL). The crude product was purified by MPLC using CH$_2$Cl$_2$/MeOH (20:1) on silica gel to give 17 mg (18%) of a white solid as the title compound. $^1$H NMR (400 MHz, METHANOL-D$_4$) δ 0.78 (t, J=7.52 Hz, 3 H), 1.41-1.57 (m, 4 H), 1.59 (s, 6 H), 1.95 (q, J=7.42 Hz, 2 H), 2.20-2.37 (m, 1 H), 3.22-3.38 (m, 2 H), 3.90 (dd, J=11.82, 3.22 Hz, 2 H), 4.42 (d, J=7.42 Hz, 2 H), 7.94 (d, J=8.8 Hz, 1 H), 8.01 (dd, J=8.8, 1.8 Hz, 1 H), 8.05 (s, 1 H), 8.36 (d, J=1.56 Hz, 1 H), 8.79 (d, J=0.59 Hz, 1 H); MS (ESI) (M+H)$^+$=460.3.

Example 46

1-{[2-(1,1-Dimethylpropyl)-1-(tetrahydro-2H-pyran-4-ylmethyl)-1H-benzimidazol-5-yl]sulfonyl}-N-(2-fluoroethyl)-1H-pyrazole-4-carboxamide

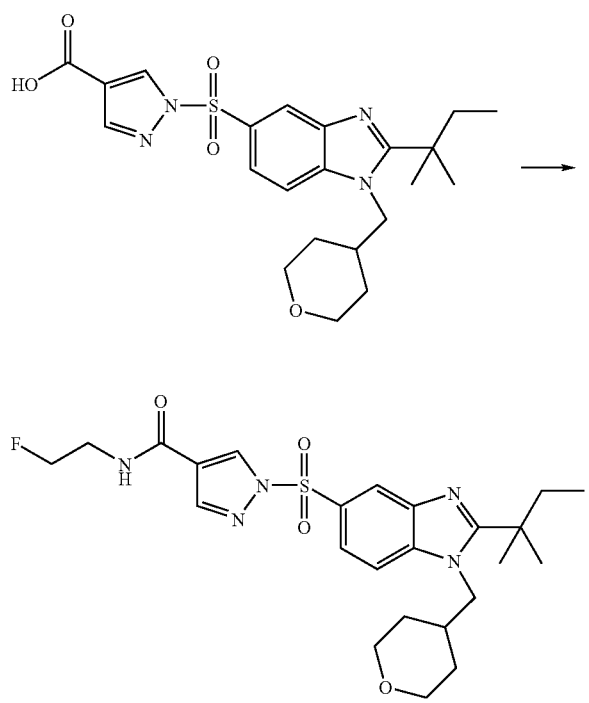

Following the procedure of example 24, step A, using DIPEA (118 uL, 88 mg, 0.68 mmol), 1-{[2-(1,1-dimethylpropyl)-1-(tetrahydro-2H-pyran-4-ylmethyl)-1H-benzimidazol-5-yl]sulfonyl}-1H-pyrazole-4-carboxylic acid (0.22 mmol), HATU (94 mg, 0.25 mmol) and 2-fluoroethylamine hydrochloride (48 mg, 0.45 mmol) in DMF (5 mL). The crude product was purified by reversed-phase HPLC using 10-90% CH$_3$CN/H$_2$O and lyophilized affording the title compound as the corresponding TFA salt. Yield: 73 mg (52%); $^1$H NMR (400 MHz, CDCl$_3$) δ 0.82 (t, J=7.52 Hz, 3 H), 1.40-1.70 (m, 10 H), 1.84-2.01 (m, 2 H), 2.15-2.34 (m, 1 H), 3.31 (td, J=11.18, 2.44 Hz, 2 H), 3.65 (q, J=4.95 Hz, 1 H), 3.72 (q, J=5.01 Hz, 1 H), 4.00 (d, J=11.13 Hz, 2 H), 4.22-4.38 (m, 2 H), 4.54 (dt, J=47.31, 4.76 Hz, 2 H), 7.13 (t, J=5.57 Hz, 1 H), 7.49-7.64 (m, 1 H), 7.92-8.05 (m, 2 H), 8.50-8.61 (m, 2 H); MS (ESI) (M+H)$^+$ 506.2.

Example 47

1-{[2-(1,1-Dimethylpropyl)-1-(tetrahydro-2H-pyran-4-ylmethyl)-1H-benzimidazol-5-yl]sulfonyl}-1H-pyrrole-3-carboxamide

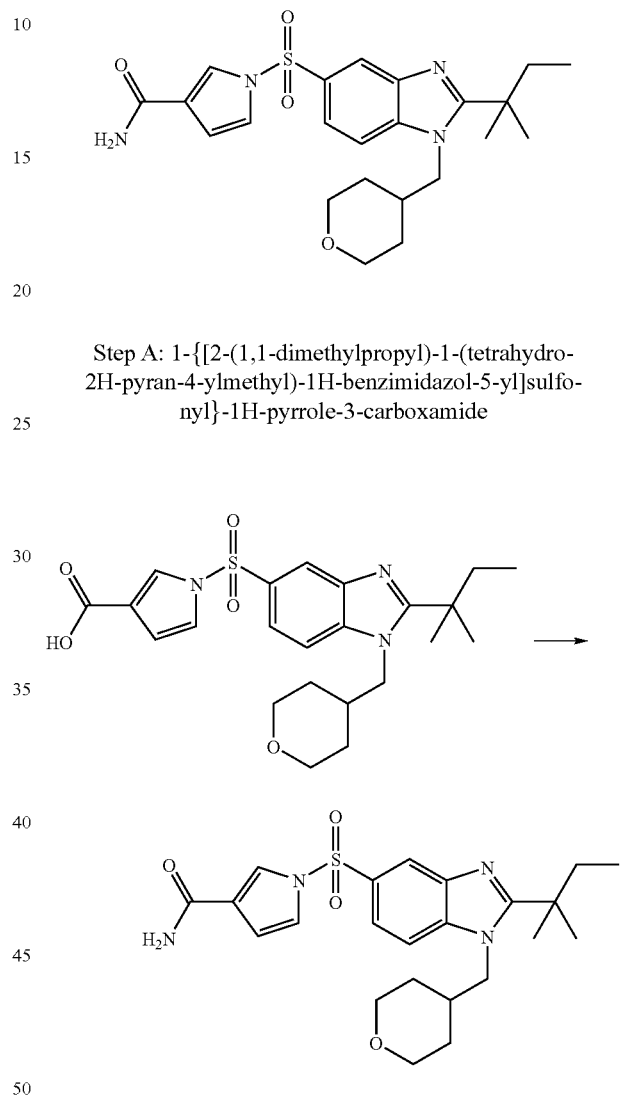

Step A: 1-{[2-(1,1-dimethylpropyl)-1-(tetrahydro-2H-pyran-4-ylmethyl)-1H-benzimidazol-5-yl]sulfonyl}-1H-pyrrole-3-carboxamide Following the same procedure in Example 24, Step A, using DIPEA (105 uL, 78 mg, 0.60 mmol), 1-{[2-(1,1-dimethylpropyl)-1-(tetrahydro-2H-pyran-4-ylmethyl)-1H-benzimidazol-5-yl]sulfonyl}-1H-pyrrole-3-carboxylic acid (0.20 mmol) (see following Steps B and C for preparation), HATU (114 mg, 0.30 mmol) and saturated ammonia in DMF (5 mL). The crude product was purified by reversed HPLC using CH$_3$CN/H$_2$O (30-60%) to give 52 mg (45%) of a white solid as the title compound. $^1$H NMR (400 MHz, CD$_3$OD) δ 0.78 (t, J=7.52 Hz, 3 H), 1.41-1.57 (m, 4 H), 1.59 (s, 6 H), 1.95 (q, J=7.42 Hz, 2 H), 2.20-2.37 (m, 1 H), 3.22-3.38 (m, 2 H), 3.90 (dd, J=11.82, 3.22 Hz, 2 H), 4.42 (d, J=7.42 Hz, 2 H), 7.94 (d, J=8.8 Hz, 1 H), 8.01 (dd, J=8.8, 1.8 Hz, 1 H), 8.05 (s, 1 H), 8.36 (d, J=1.56 Hz, 1 H), 8.79 (d, J=0.59 Hz, 1 H); MS (ESI) (M+H)$^+$=460.3.

Step B: 1-{[2-(1,1-dimethylpropyl)-1-(tetrahydro-2H-pyran-4-ylmethyl)-1H-benzimidazol-5-yl]sulfonyl}-1H-pyrrole-3-carbaldehyde

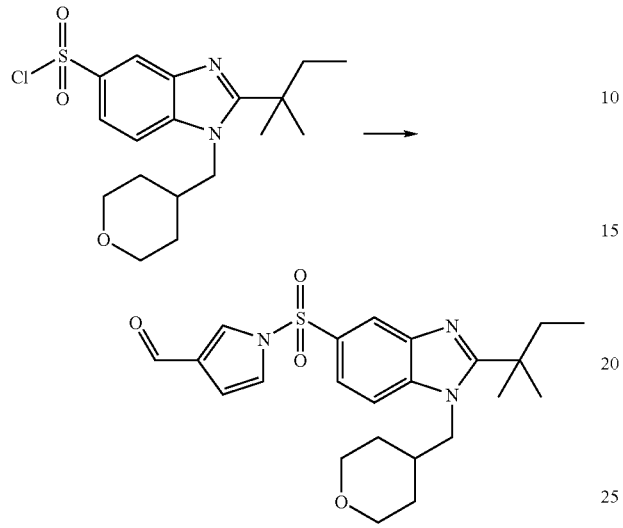

Following the same procedure in Example 29, using 2-(1,1-dimethylpropyl)-1-(tetrahydro-2H-pyran-4-ylmethyl)-1H-benzimidazole-5-sulfonyl chloride (0.66 g, 1.7 mmol), 1H-pyrrole-3-carbaldehyde (0.14 g, 1.4 mmol) and sodium hydride (0.29 g, 60%, 7.2 mmol) in THF (15 mL). The crude product was purified by MPLC using Hex/EtOAc (1:1) on silica gel to give 0.45 g (71%) of a white solid as the title compound. MS (ESI) (M+H)$^+$=443.93

Step C: 1-{[2-(1,1-dimethylpropyl)-1-(tetrahydro-2H-pyran-4-ylmethyl)-1H-benzimidazol-5-yl]sulfonyl}-1H-pyrrole-3-carboxylic acid

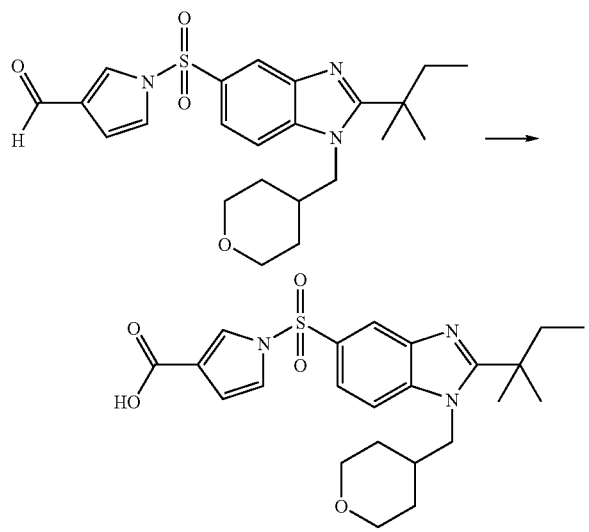

Oxone (148 mg, 0.24 mmol) was added to a solution of 1-{[2-(1,1-dimethylpropyl)-1-(tetrahydro-2H-pyran-4-ylmethyl)-1H-benzimidazol-5-yl]sulfonyl}-1H-pyrrole-3-carbaldehyde (89 mg, 0.20 mmol) in DMF (8 mL). The resulting mixture was stirred overnight at room temperature and used directly for step A. MS (ESI) (M+H)$^+$=460.06.

Example 48

1-{[2-(1,1-Dimethylpropyl)-1-(tetrahydro-2H-pyran-4-ylmethyl)-1H-benzimidazol-5-yl]sulfonyl}-N-methyl-1H-pyrrole-3-carboxamide

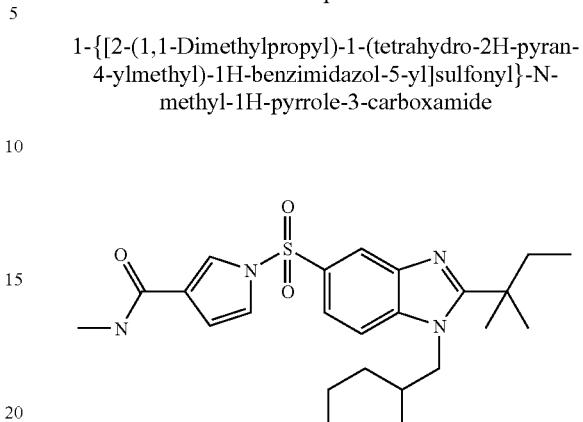

Step A: 1-{[2-(1,1-dimethylpropyl)-1-(tetrahydro-2H-pyran-4-ylmethyl)-1H-benzimidazol-5-yl]sulfonyl}-N-methyl-1H-pyrrole-3-carboxamide

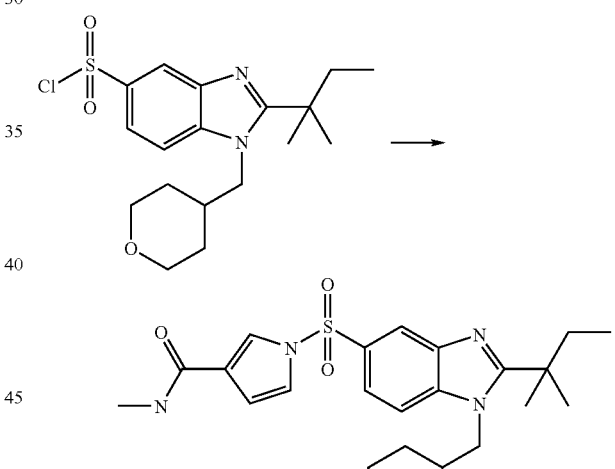

Following the same procedure in Example 29, using N-methyl-1H-pyrrole-3-carboxamide (57 mg, 0.46 mmol) (see following step B for preparation), sodium hydride (110 mg, 60%, 2.76 mmol), 2-(1,1-dimethylpropyl)-1-(tetrahydro-2H-pyran-4-ylmethyl)-1H-benzimidazole-5-sulfonyl chloride (352 mg, 0.92 mmol) in THF (10 mL). The crude product was purified by MPLC using EtOAc on silica gel to give 134 mg (62%) of a white solid as the title compound. $^1$H NMR (400 MHz, METHANOL-D$_4$) δ 0.77 (t, J=7.42 Hz, 3 H), 1.40-1.56 (m, 4 H), 1.59 (s, 6 H), 1.94 (q, J=7.42 Hz, 2 H), 2.19-2.37 (m, 1 H), 2.79 (s, 3 H), 3.24-3.36 (m, 2 H), 3.84-3.94 (m, 2 H), 4.41 (d, J=7.62 Hz, 2 H), 6.63 (dd, J=3.32, 1.56 Hz, 1 H), 7.29 (dd, J=3.32, 2.34 Hz, 1 H), 7.78 (dd, J=2.15, 1.76 Hz, 1 H), 7.88-7.92 (m, 1 H), 7.92-7.98 (m, 1 H), 8.26 (dd, J=1.56, 0.59 Hz, 1 H); MS (ESI) (M+H)$^+$=473.0; Anal. Calcd for C$_{24}$H$_{32}$N$_4$O$_4$S+1.0 TFA (586.63): C, 53.23; H, 5.67; N, 9.55. Found: C, 53.28; H, 5.77; N, 9.42.

Step B: N-methyl-1H-pyrrole-3-carboxamide

DIPEA (284 mg, 381 uL, 2.2 mmol) was added to a solution of 1H-pyrrole-3-carboxylic acid (111 g, 1.0 mmol) and methylamine hydrochloride (222 mg, 3.3 mmol) in DMF (10 mL) at 0° C. Stirring for 20 min, HATU (570 g, 1.5 mmol) was added at 0° C. The reaction mixture was stirred overnight at room temperature, diluted with EtOAc (100 mL), washed with H$_2$O (3×10 mL) and dried over Na$_2$SO$_4$. The crude product was purified by MPLC using EtOAc on silica gel. Yield: 57 mg (46%). $^1$H NMR (400 MHz, CHLOROFORM-D) δ 2.89 (s, 3 H), 5.89 (s, 1 H), 6.36-6.44 (m, 1 H), 6.75-6.79 (m, 1 H), 7.34-7.40 (m, 1 H).

Example 49

1-{[2-(1,1-Dimethylpropyl)-1-(tetrahydro-2H-pyran-4-ylmethyl)-1H-benzimidazol-5-yl]sulfonyl}-N-ethyl-1H-pyrrole-3-carboxamide

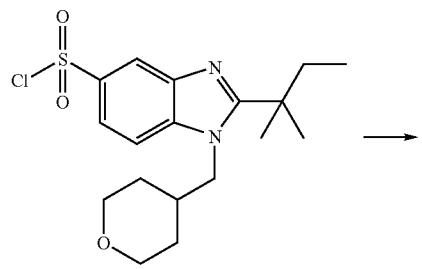

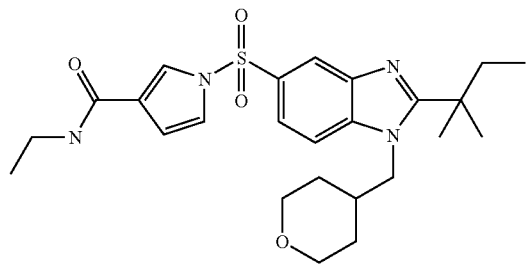

Following the same procedure in Example 29, using N-ethyl-1H-pyrrole-3-carboxamide (166 mg, 1.2 mmol) (see the step B in example 31 for preparation), sodium hydride (240 mg, 60%, 6.0 mmol) and 2-(1,1-dimethylpropyl)-1-(tetrahydro-2H-pyran-4-ylmethyl)-1H-benzimidazole-5-sulfonyl chloride (385 mg, 1.0 mmol) in THF (20 mL). The crude product was purified by MPLC using EtOAc on silica gel to give 195 mg (40%) of a white solid as the title compound. $^1$H NMR (400 MHz, METHANOL-D$_4$) δ 0.78 (t, J=7.42 Hz, 3 H), 1.13 (t, J=7.23 Hz, 3 H), 1.41-1.56 (m, 4 H), 1.59 (s, 6 H), 1.95 (q, J=7.49 Hz, 2 H), 2.21-2.35 (m, 1 H), 3.24-3.34 (m, 4 H), 3.85-3.94 (m, 2 H), 4.42 (d, J=7.62 Hz, 2 H), 6.65 (dd, J=3.32, 1.76 Hz, 1 H), 7.29 (dd, J=3.32, 2.34 Hz, 1 H), 7.78-7.82 (m, 1 H), 7.92 (d, J=8.8 Hz, 1 H), 7.96 (dd, J=8.8, 1.8 Hz, 1 H), 8.27 (d, J=1.56 Hz, 1 H); MS (ESI) (M+H)$^+$= 487.0; Anal. Calcd for C$_{25}$H$_{34}$N$_4$O$_4$S+110 TFA+0.1H$_2$O (602.46): C, 53.83; H, 5.89; N, 9.30. Found: C, 53.79; H, 6.00; N, 9.19.

Example 50

N-Cyclopropyl-1-{[2-(1,1-dimethylpropyl)-1-(tetrahydro-2H-pyran-4-ylmethyl)-1H-benzimidazol-5-yl]sulfonyl}-1H-pyrrole-3-carboxamide

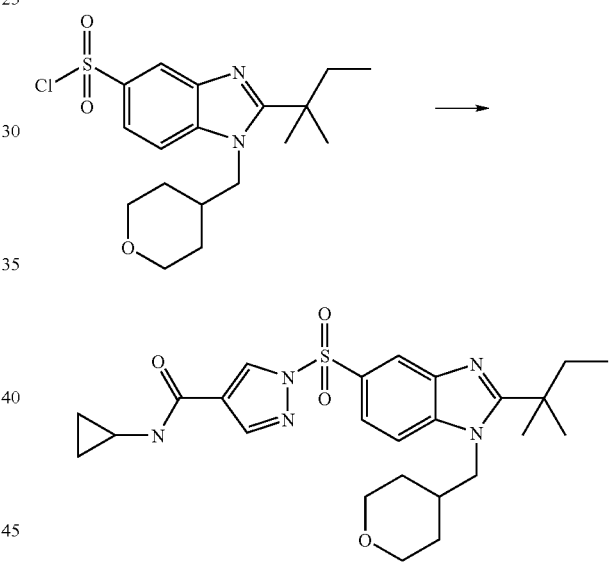

Following the same procedure in Example 29, using N-cyclopropyl-1H-pyrrole-3-carboxamide (49 mg, 0.33 mmol) (see the step B in example 32 for preparation), sodium hydride (110 mg, 60%, 2.75 mmol) and 2-(1,1-dimethylpropyl)-1-(tetrahydro-2H-pyran-4-ylmethyl)-1H-benzimidazole-5-sulfonyl chloride (354 mg, 0.92 mmol) in THF (10 mL). The crude product was purified by MPLC using Hex/EtOAc (3:7) on silica gel to give 137 mg (83%) of a white solid as the title compound. $^1$H NMR (400 MHz, METHANOL-D$_4$) δ 0.50-0.57 (m, 2 H), 0.69-0.75 (m, 2 H), 0.78 (t, J=7.42 Hz, 3 H), 1.42-1.56 (m, 4 H), 1.60 (s, 6 H), 1.95 (q, J=7.62 Hz, 2 H), 2.21-2.37 (m, 1 H), 2.67-2.75 (m, 1 H), 3.23-3.35 (m, 2 H), 3.84-3.93 (m, 2 H), 4.43 (d, J=7.42 Hz, 2 H), 6.65 (dd, J=3.32, 1.76 Hz, 1 H), 7.28 (dd, J=3.32, 2.15 Hz, 1 H), 7.77-7.84 (m, 1 H), 7.90-8.01 (m, 2 H), 8.26 (d, J=0.78 Hz, 1 H); MS (ESI) (M+H)$^+$=499.0; Anal. Calcd for C$_{26}$H$_{34}$N$_4$O$_4$S+1.2 TFA (635.48): C, 53.68; H, 5.58; N, 8.82. Found: C, 53.65; H, 5.61; N, 8.56.

Example 51

1-{[2-(1,1-Dimethylpropyl)-1-(tetrahydro-2H-pyran-4-ylmethyl)-1H-benzimidazol-5-yl]sulfonyl}-N-isopropyl-1H-pyrrole-3-carboxamide

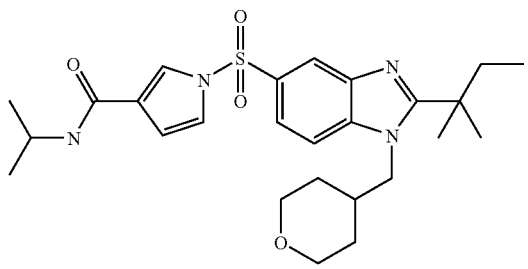

Step A: 1-{[2-(1,1-dimethylpropyl)-1-(tetrahydro-2H-pyran-4-ylmethyl)-1H-benzimidazol-5-yl]sulfonyl}-N-isopropyl-1H-pyrrole-3-carboxamide

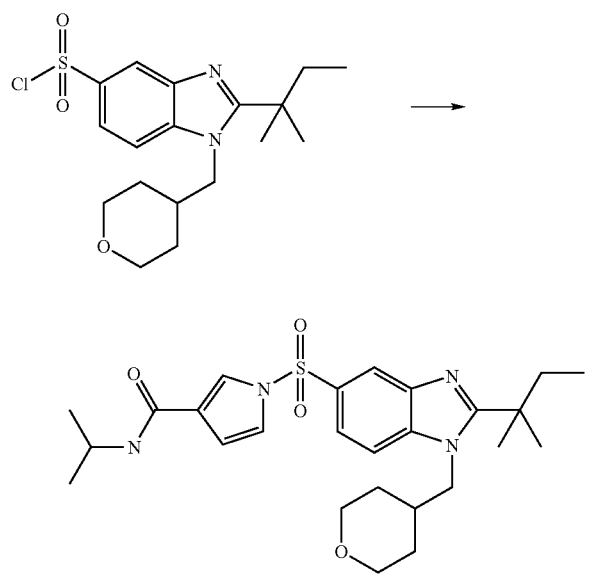

Following the same procedure in Example 29, using N-isopropyl-1H-pyrrole-3-carboxamide (76 mg, 0.50 mmol) (see following step B for preparation), sodium hydride (159 mg, 60%, 3.97 mmol) and 2-(1,1-dimethylpropyl)-1-(tetrahydro-2H-pyran-4-ylmethyl)-1H-benzimidazole-5-sulfonyl chloride (535 mg, 1.39 mmol) in THF (15 mL). The crude product was purified by MPLC using Hex/EtOAc (3:7) on silica gel to give 158 mg (64%) of a white solid as the title compound. $^1$H NMR (400 MHz, METHANOL-$D_4$) δ 0.77 (t, J=7.42 Hz, 3 H), 1.15 (d, J=6.64 Hz, 6 H), 1.39-1.56 (m, 4 H), 1.59 (s, 6 H), 1.94 (q, J=7.42 Hz, 2 H), 2.19-2.38 (m, 1 H), 3.23-3.35 (m, 2 H), 3.83-3.96 (m, 2 H), 4.01-4.15 (m, 1 H), 4.41 (d, J=7.62 Hz, 2 H), 6.67 (dd, J=3.32, 1.56 Hz, 1 H), 7.28 (dd, J=3.12, 2.34 Hz, 1 H), 7.79-7.86 (m, 1 H), 7.88-7.99 (m, 2 H) 8.26 (d, J=1.17 Hz, 1 H); MS (ESI) (M+H)$^+$=501.3; Anal. Calcd for $C_{26}H_{36}N_4O_4S$+1.2 TFA+0.1$H_2O$ (615.50): C, 55.33; H, 6.11; N, 9.09. Found: C, 55.38; H, 6.16; N, 9.04.

Step B: N-isopropyl-1H-pyrrole-3-carboxamide

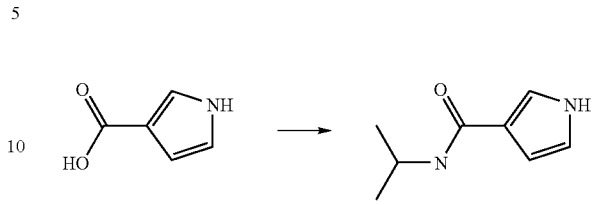

DIPEA (284 mg, 381 uL, 2.2 mmol) was added to a solution of 1H-pyrrole-3-carboxylic acid (111 g, 1.0 mmol) and isopropylamine (118 mg, 170 uL, 2.0 mmol) in DMF (10 mL) at 0° C. Stirring for 20 min, HATU (570 g, 1.5 mmol) was added at 0° C. The reaction mixture was stirred overnight at room temperature, diluted with EtOAc (100 mL), washed with $H_2O$ (3×10 mL) and dried over $Na_2SO_4$. The crude product was purified by MPLC using EtOAc on silica gel. Yield: 80 mg (52%). $^1$H NMR (400 MHz, CHLOROFORM-D) δ 1.19 (d, J=6.64 Hz, 6 H), 3.95-4.31 (m, 1 H), 6.52 (dd, J=2.93, 1.56 Hz, 1 H), 6.70 (dd, J=2.93, 2.15 Hz, 1 H), 7.31 (t, J=1.76 Hz, 1 H), 7.58 (s, 1 H).

Example 52

1-{[2-(1,1-Dimethylpropyl)-1-(tetrahydro-2H-pyran-4-ylmethyl)-1H-benzimidazol-5-yl]sulfonyl}-N-(2-fluoroethyl)-1H-pyrrole-3-carboxamide

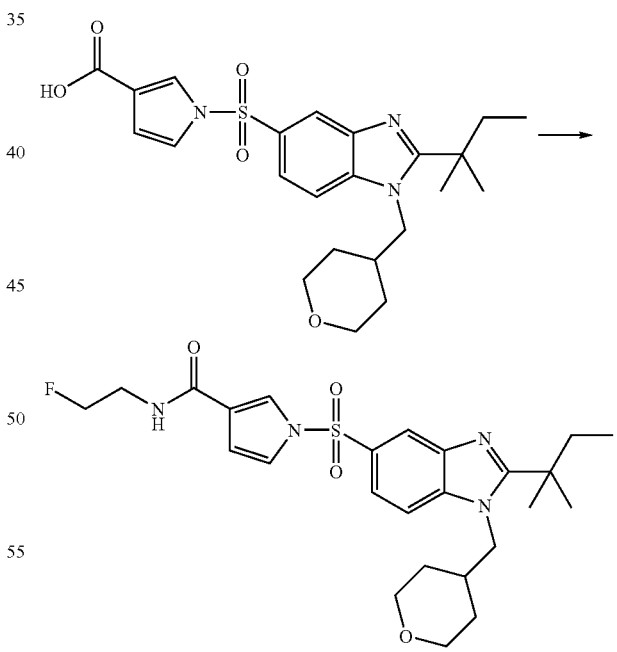

Following the procedure of example 24, step A, using 1-{[2-(1,1-dimethylpropyl)-1-(tetrahydro-2H-pyran-4-ylmethyl)-1H-benzimidazol-5-yl]sulfonyl}-1H-pyrrole-3-carboxylic acid (0.22 mmol), 2-fluoroethylamine hydrochloride (48 mg, 0.45 mmol), DIPEA (118 uL, 88 mg, 0.68 mmol) and HATU (94 mg, 0.25 mmol) in DMF (5 mL). The crude product was purified by reversed-phase HPLC using 10-90%

CH$_3$CN/H$_2$O and lyophilized affording the title compound as the corresponding TFA salt. Yield: 63 mg (45%); $^1$H NMR (400 MHz, CDCl$_3$) δ 0.84 (t, J=7.52 Hz, 3 H), 1.44-1.60 (m, 4 H), 1.64 (s, 6 H), 1.95 (q, J=7.49 Hz, 2 H), 2.15-2.35 (m, 1 H), 3.24-3.42 (m, 2 H), 3.64 (q, J=5.14 Hz, 1 H), 3.70 (q, J=5.01 Hz, 1H), 3.94-4.09 (m, 2 H), 4.32 (d, J=7.23 Hz, 2 H), 4.52 (dt, J=47.21, 4.91 Hz, 2 H), 6.57 (dd, J=3.32, 1.56 Hz, 1 H), 7.01 (t, J=5.47 Hz, 1 H), 7.13 (dd, J=3.22, 2.25 Hz, 1 H), 7.57 (d, J=8.79 Hz, 1 H), 7.73 (t, J=1.86 Hz, 1 H), 7.92 (dd, J=8.69, 1.66 Hz, 1 H), 8.58 (d, J=1.37 Hz, 1H); MS (ESI) (M+H)$^+$=505.3.

Example 53

1-{[2-tert-Butyl-1-(tetrahydro-2H-pyran-4-ylmethyl)-1H-benzimidazol-5-yl]sulfonyl}-N-methyl-1H-pyrazole-4-carboxamide

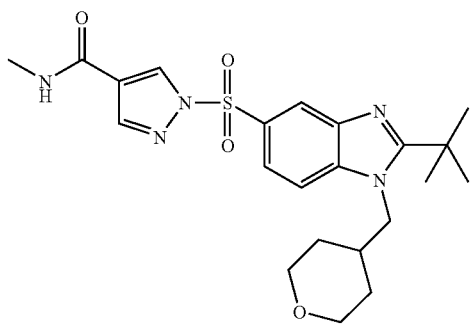

Step A: 1-{[2-tert-Butyl-1-(tetrahydro-2H-pyran-4-ylmethyl)-1H-benzimidazol-5-yl]sulfonyl}-N-methyl-1H-pyrazole-4-carboxamide

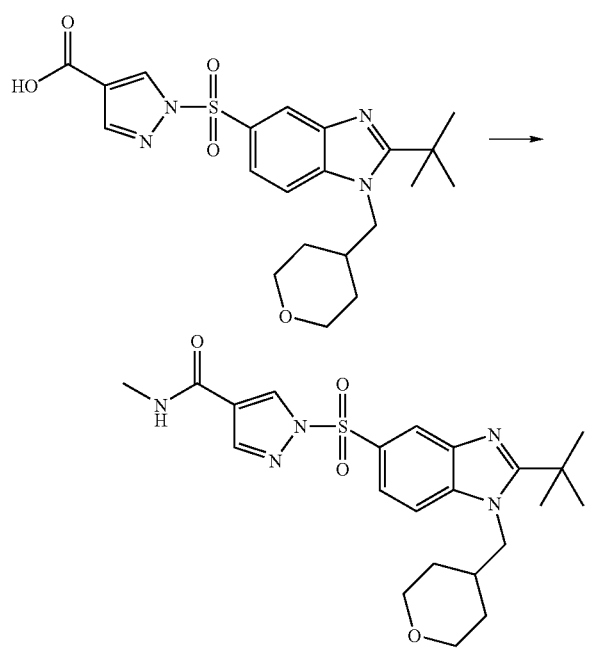

Following the same procedure in Example 24, Step A, using HATU (37 mg, 0.09 mmol), methylamine in THF (0.07 mL, 2M, 0.14 mmol), DIPEA (0.02 mL, 0.10 mmol) and 1-{[2-tert-butyl-1-(tetrahydro-2H-pyran-4-ylmethyl)-1H-benzimidazol-5-yl]sulfonyl}-1H-pyrazole-4-carboxylic acid (40 mg, 0.09 mmol) (see following step B for preparation) in DMF (5 mL). The crude product was purified by MPLC on silica gel using EtOAc/DCM (1:1) to provide the title compound as a white solid. The product was converted to its TFA salt. Yield: 15 mg (29%); $^1$H NMR (400 MHz, CD$_3$OD) δ 1.38-1.46 (m, 2 H), 1.46-1.54 (m, 2 H), 1.54-1.59 (s, 9 H), 2.22-2.36 (m, 1 H), 2.83 (s, 3 H), 3.25-3.35 (m, 2 H), 3.89 (dd, J=11.43, 3.61 Hz, 2 H), 4.36 (d, J=7.42 Hz, 2 H), 7.79 (d, J=8.59 Hz, 1 H), 7.90 (dd, J=8.69, 1.86 Hz, 1 H), 8.01 (s, 1 H), 8.29 (d, J=1.95 Hz, 1 H), 8.72 (s, 1 H); MS (ESI) (M+H)$^+$= 459.8; Anal. Calcd for C$_{22}$H$_{29}$N$_5$O$_4$S+0.1H$_2$O: C, 57.27; H, 6.38; N, 15.18. Found: C, 57.49; H, 6.55; N, 14.34.

Step B: 1-{[2-tert-butyl-1-(tetrahydro-2H-pyran-4-ylmethyl)-1H-benzimidazol-5-yl]sulfonyl}-1H-pyrazole-4-carboxylic acid

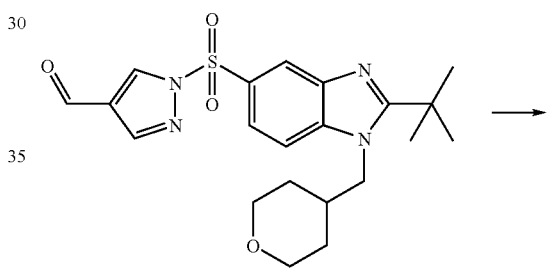

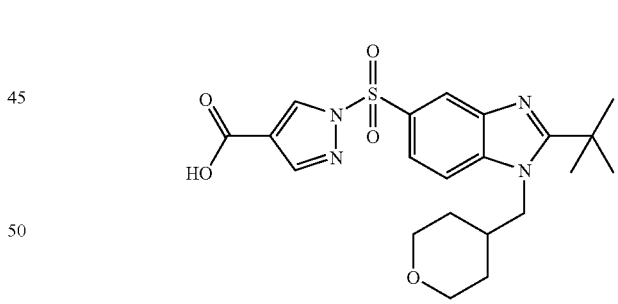

Oxone (596 mg, 0.97 mmol) was added to a solution of 1-{[2-tert-butyl-1-(tetrahydro-2H-pyran-4-ylmethyl)-1H-benzimidazol-5-yl]sulfonyl}-1H-pyrazole-4-carbaldehyde (380 mg, 0.88 mmol) (see example 23 for preparation) in DMF (15 mL). The resulting mixture was stirred overnight at room temperature and the solvent was concentrated. The residue was dissolved in DCM, washed with 10% HCl solution and dried over anhydrous Na$_2$SO$_4$. The solvent was concentrated to provide the title compound as white solid Yield: 330 mg (74%); MS (ESI) (M+H)$^+$=447.09.

Example 54

1-{[2-tert-Butyl-1-(tetrahydro-2H-pyran-4-ylmethyl)-1H-benzimidazol-5-yl]sulfonyl}-N-propyl-1H-pyrazole-4-carboxamide

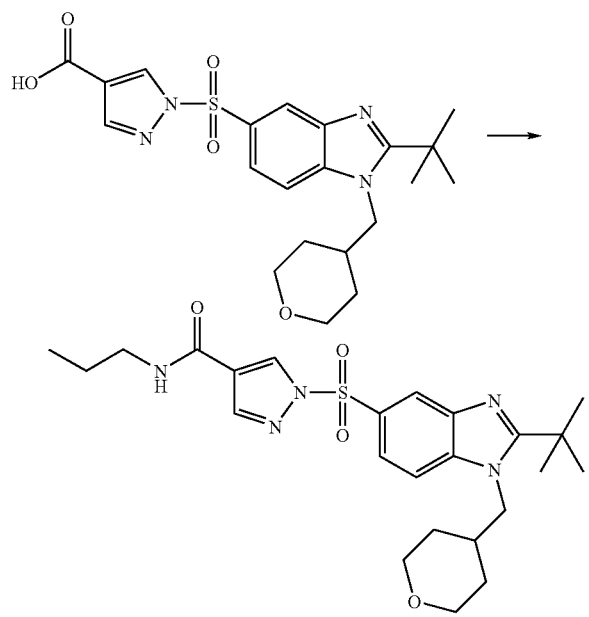

Following the same procedure in Example 53, Step A, using n-propylamine (8 mg, 0.13 mmol), HATU (37 mg, 0.09 mmol), DIPEA (0.02 mL, 0.10 mmol) and 1-{[2-tert-butyl-1-(tetrahydro-2H-pyran-4-ylmethyl)-1H-benzimidazol-5-yl]sulfonyl}-1H-pyrazole-4-carboxylic acid (40 mg, 0.09 mmol) in DMF (5 mL). The crude product was purified by MPLC on silica gel using EtOAc/DCM (1:1) to provide the title compound as a white solid. The product was converted to its TFA salt. Yield: 32 mg (59%); $^1$H NMR (400 MHz, CD$_3$OD) δ 0.93 (t, J=7.52 Hz, 3 H), 1.43-1.52 (m, 2 H), 1.52-1.62 (m, 4 H), 1.64 (s, 9 H), 2.25-2.37 (m, 1 H), 3.28-3.36 (m, 4 H), 3.91 (dd, J=11.43, 3.22 Hz, 2 H), 4.48 (d, J=7.62 Hz, 2 H), 7.99-8.11 (m, 3 H), 8.39 (d, J=1.37 Hz, 1 H), 8.77 (s, 1 H); MS (ESI) (M+H)$^+$=487.8; Anal. Calcd for C$_{24}$H$_{33}$N$_5$O$_4$S+1.7 TFA+1.8H$_2$O: C, 46.10; H, 5.41; N, 9.81. Found: C, 46.15; H, 5.56; N, 9.48.

Example 55

1-{[2-tert-Butyl-1-(tetrahydro-2H-pyran-4-ylmethyl)-1H-benzimidazol-5-yl]sulfonyl}-N-cyclopropylmethyl)-1H-pyrazole-4-carboxamide

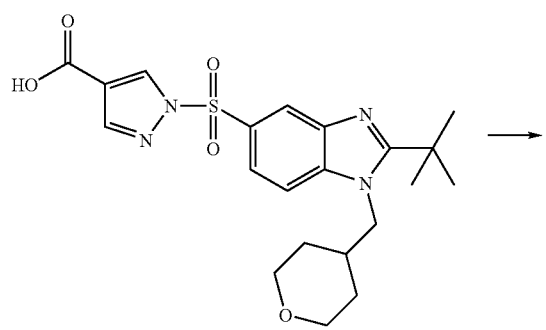

-continued

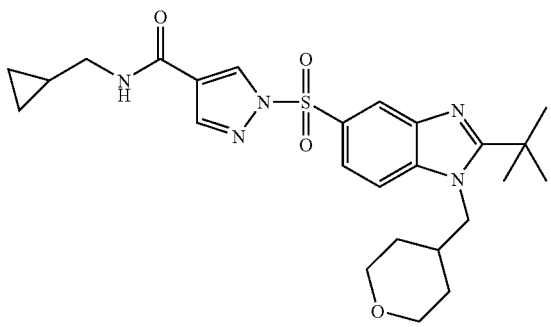

Following the same procedure in Example 53, Step A, step A, using (cyclopropylmethyl)amine (10 mg, 0.13 mmol), HATU (37 mg, 0.09 mmol), DIPEA (0.02 mL, 0.10 mmol) and 1-{[2-tert-butyl-1-(tetrahydro-2H-pyran-4-ylmethyl)-1H-benzimidazol-5-yl]sulfonyl}-1H-pyrazole-4-carboxylic acid (40 mg, 0.09 mmol) in DMF (5 mL). The crude product was purified by MPLC on silica gel using EtOAc/DCM (1:1) to provide the title compound as a white solid. The product was converted to its TFA salt. Yield: 28 mg (50%); $^1$H NMR (400 MHz, CD$_3$OD) δ 0.17-0.27 (m, 2 H), 0.45-0.54 (m, 2 H), 0.98-1.07 (m, 1 H), 1.43-1.52 (m, 3 H), 1.55 (dd, J=12.60, 3.81 Hz, 1 H), 1.62 (s, 9 H), 2.26-2.38 (m, 1 H), 3.15 (d, J=7.03 Hz, 2 H), 3.27-3.36 (m, 2 H), 3.90 (dd, J=11.03, 3.61 Hz, 2 H), 4.45 (d, J=7.62 Hz, 2 H), 7.93-8.04 (m, 2 H), 8.07 (s, 1 H), 8.36 (d, J=1.37 Hz, 1 H), 8.78 (s, 1 H); MS (ESI) (M+H)$^+$=499.8; Anal. Calcd for C$_{25}$H$_{33}$N$_5$O$_4$S+1.6 TFA+4.5H$_2$O: C, 44.38; H, 5.76; N, 9.18. Found: C, 44.45; H, 5.88; N, 8.93.

Example 56

1-{[2-tert-Butyl-1-(tetrahydro-2H-pyran-4-ylmethyl)-1H-benzimidazol-5-yl]sulfonyl}-N-(cyclobutylmethyl)-1H-pyrazole-4-carboxamide

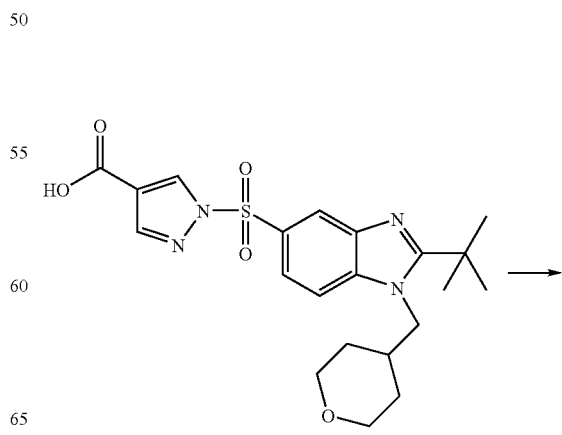

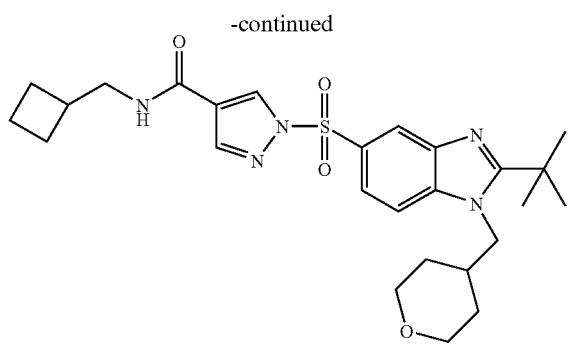

Following the same procedure in example 53, step A, using (cyclobutylmethyl)amine (12 mg, 0.13 mmol), HATU (37 mg, 0.09 mmol), DIPEA (0.02 mL, 0.10 mmol) and 1-{[2-tert-butyl-1-(tetrahydro-2H-pyran-4-ylmethyl)-1H-benzimidazol-5-yl]sulfonyl}-1H-pyrazole-4-carboxylic acid (40 mg, 0.09 mmol) in DMF (5 mL). The crude product was purified by MPLC on silica gel using EtOAc/DCM (1:1) to provide the title compound as a white solid. The product was converted to its TFA salt. Yield: 27 mg (48%); $^1$H NMR (400 MHz, CD$_3$OD) δ 1.43-1.51 (m, 3 H), 1.55 (dd, J=12.30, 3.91 Hz, 1 H), 1.61 (s, 9 H), 1.66-1.78 (m, 2 H), 1.81-1.93 (m, 2 H), 1.99-2.10 (m, 2 H), 2.26-2.37 (m, 1 H), 2.48-2.59 (m, 1 H), 3.26-3.36 (m, 4 H), 3.90 (dd, J=11.13, 3.71 Hz, 2 H), 4.45 (d, J=7.42 Hz, 2 H), 7.94-8.04 (m, 2 H), 8.05 (d, J=0.78 Hz, 1 H), 8.36 (d, J=1.37 Hz, 1 H), 8.76 (s, 1 H); MS (ESI) (M+H)$^+$= 513.7; Anal. Calcd for C$_{26}$H$_{35}$N$_5$O$_4$S+1.8 TFA+2.4H$_2$O: C, 46.65; H, 5.50; N, 9.19. Found: C, 46.74; H, 5.61; N, 8.97.

Example 57

2-tert-Butyl-5-[(3-methylpiperidin-1-yl)sulfonyl]-1-(tetrahydro-2H-pyran-4-ylmethyl)-1H-benzimidazole

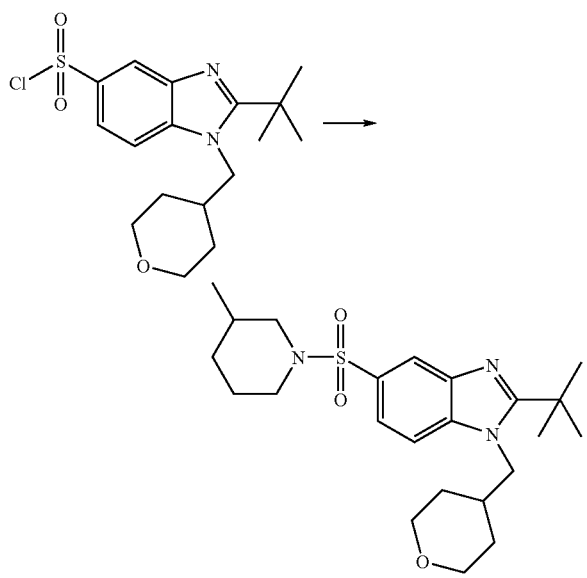

Following the same procedure in Example 1, Step A, using 2-tert-Butyl-1-(tetrahydro-2H-pyran-4-ylmethyl)-1H-benzimidazole-5-sulfonyl chloride (120 mg, 0.29 mmol), 3-methylpiperidine (146 mg, 1.47 mmol), DMAP (180 mg, 1.47 mmol) in MeCN (10 mL). The crude product was purified by reverse-phase preparative HPLC using 10-90% MeCN/H$_2$O and lyophilized affording the title compound as the corresponding TFA salt. Yield: 41 mg (25%); $^1$H NMR (400 MHz, CD$_3$OD) δ 0.88 (d, J=6.45 Hz, 3 H), 1.50-1.65 (m, 4 H), 1.64-1.78 (m, 14 H), 1.90-2.00 (m, 1 H), 2.24-2.33 (m, 1 H), 2.33-2.44 (m, 1 H), 3.31-3.40 (m, 2.64 Hz, 2 H), 3.57-3.69 (m, 2 H), 3.90-4.00 (m, 2 H), 4.53 (d, J=7.42 Hz, 2 H), 7.85 (dd, J=8.79, 1.76 Hz, 1 H), 8.04 (d, J=8.79 Hz, 1 H), 8.08 (d, J=1.17 Hz, 1 H); MS (ESI) (M+H)$^+$=434.0; Anal. Calcd for C$_{23}$H$_{35}$N$_3$O$_3$S+1.3 TFA+0.1H$_2$O: C, 52.68; H, 6.30; N, 7.20. Found: C, 52.65; H, 6.20; N, 7.23

Example 58

2-tert-Butyl-5-[(3-phenylpiperidin-1-yl)sulfonyl]-1-(tetrahydro-2H-pyran-4-ylmethyl)-1H-benzimidazole

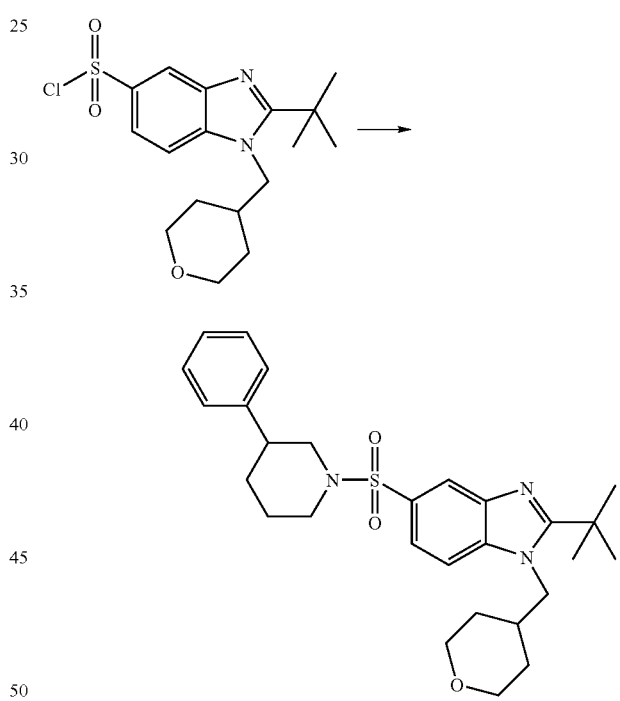

Following the same procedure in Example 1, step A, using 3-phenylpiperidine (238 mg, 1.47 mmol), 2-tert-Butyl-1-(tetrahydro-2H-pyran-4-ylmethyl)-1H-benzimidazole-5-sulfonyl chloride (120 mg, 0.29 mmol), DMAP (180 mg, 1.47 mmol) in MeCN (10 mL). The crude product was purified by reverse-phase preparative HPLC using 10-90% MeCN/H$_2$O and lyophilized affording the title compound as the corresponding TFA salt. Yield: 22 mg (12%); $^1$H NMR (400 MHz, CD$_3$OD) δ 1.41-1.64 (m, 5 H), 1.66 (s, 9 H), 1.68-1.80 (m, 1 H), 1.80-1.93 (m, 2 H), 2.25-2.44 (m, 3 H), 2.77-2.89 (m, 1 H), 3.35 (t, J=11.23 Hz, 2 H), 3.75-3.89 (m, 2 H), 3.94 (dd, J=10.94, 3.52 Hz, 2 H), 4.52 (d, J=7.62 Hz, 2 H), 7.13-7.22 (m, 3 H), 7.27 (t, J=7.13 Hz, 2 H), 7.84 (dd, J=8.79, 1.56 Hz, 1 H), 8.03 (d, J=8.79 Hz, 1 H), 8.07 (d, J=1.17 Hz, 1 H); MS

Example 59

2-tert-butyl-1-(tetrahydro-2H-pyran-4-ylmethyl)-5-{[4-(trifluoromethyl)piperidin-1-yl]sulfonyl}-1H-benzimidazole

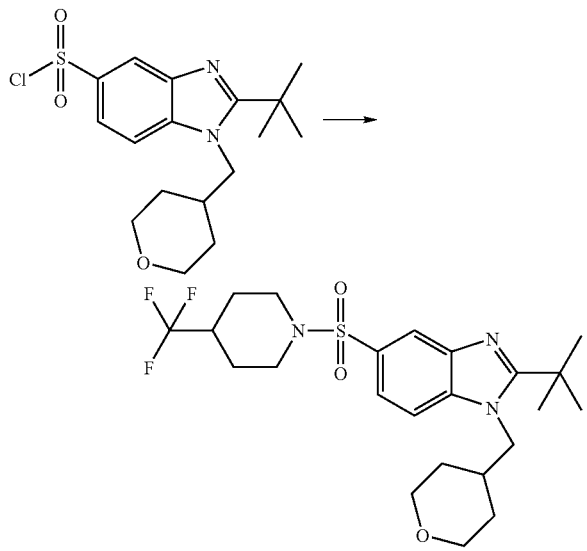

Following the same procedure in Example 1, step A, using 4-(trifluoromethyl)piperidine (225 mg, 1.47 mmol), 2-tert-Butyl-1-(tetrahydro-2H-pyran-4-ylmethyl)-1H-benzimidazole-5-sulfonyl chloride (120 mg, 0.29 mmol), DMAP (180 mg, 1.47 mmol) in MeCN (10 mL). The crude product was purified by reverse-phase preparative HPLC using 10-90% MeCN/H$_2$O and lyophilized affording the title compound as the corresponding TFA salt. Yield: 98 mg (55%); $^1$H NMR (400 MHz, CD$_3$OD) δ 1.49-1.57 (m, 4 H), 1.57-1.64 (m, 2 H), 1.67 (s, 9 H), 1.92 (d, J=11.33 Hz, 2 H), 2.08-2.21 (m, 1 H), 2.38 (td, J=12.30, 2.34 Hz, 2 H), 3.35 (td, J=11.67, 2.44 Hz, 2 H), 3.85-3.99 (m, 4 H), 4.53 (d, J=7.42 Hz, 2 H), 7.87 (dd, J=8.79, 1.76 Hz, 1 H), 8.05 (d, J=8.79 Hz, 1 H), 8.11 (d, J=2.15 Hz, 1 H); MS (ESI) (M+H)$^+$=487.8; Anal. Calcd for C$_{23}$H$_{32}$F$_3$N$_3$O$_3$S+1.5 TFA: C, 47.42; H, 5.13; N, 6.38. Found: C, 47.42; H, 5.14; N, 6.26.

Example 60

2-tert-Butyl-5-[(4-methoxypiperidin-1-yl)sulfonyl]-1-(tetrahydro-2H-pyran-4-ylmethyl)-1H-benzimidazole

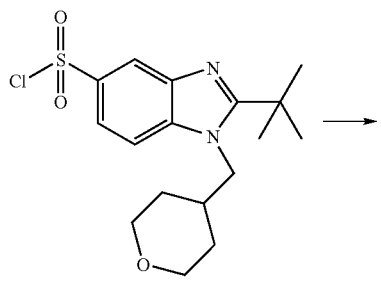

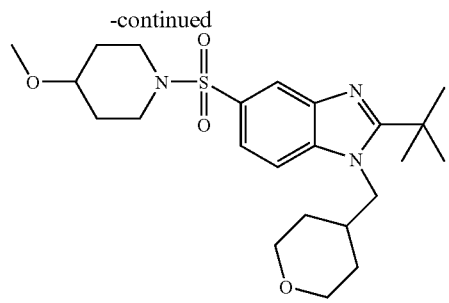

Following the same procedure in Example 1, step A, using 4-methoxypiperidine hydrochloride (223 mg, 1.47 mmol), 2-tert-Butyl-1-(tetrahydro-2H-pyran-4-ylmethyl)-1H-benzimidazole-5-sulfonyl chloride (120 mg, 0.29 mmol), DMAP (180 mg, 1.47 mmol) in MeCN (10 mL). The crude product was purified by reverse-phase preparative HPLC using 10-90% MeCN/H$_2$O and lyophilized affording the title compound as the corresponding TFA salt. Yield: 42 mg (25%); $^1$H NMR (400 MHz, CD$_3$OD) δ 1.50-1.59 (m, 2 H), 1.59-1.66 (m, 3 H), 1.68 (s, 9 H), 1.82-1.92 (m, 2 H), 2.32-2.44 (m, 1 H), 2.96-3.06 (m, 2 H), 3.07-3.16 (m, 2 H), 3.18-3.23 (m, 3 H), 3.25-3.29 (m, 1 H), 3.36 (td, J=11.52, 2.73 Hz, 2 H), 3.95 (dd, J=12.01, 2.83 Hz, 2 H), 4.55 (d, J=7.42 Hz, 2 H), 7.88 (dd, J=8.79, 1.76 Hz, 1 H), 8.05-8.12 (m, 2 H); MS (ESI) (M+H)$^+$= 450.0; Anal. Calcd for C$_{23}$H$_{35}$N$_3$O$_4$S+1.4 TFA+0.2H$_2$O: C, 50.56; H, 6.05; N, 6.86. Found: C, 50.71; H, 6.13; N, 6.31.

Example 61

2-tert-Butyl-5-[(4,4-difluoropiperidin-1-yl)sulfonyl]-1-(tetrahydro-2H-pyran-4-ylmethyl)-1H-benzimidazole

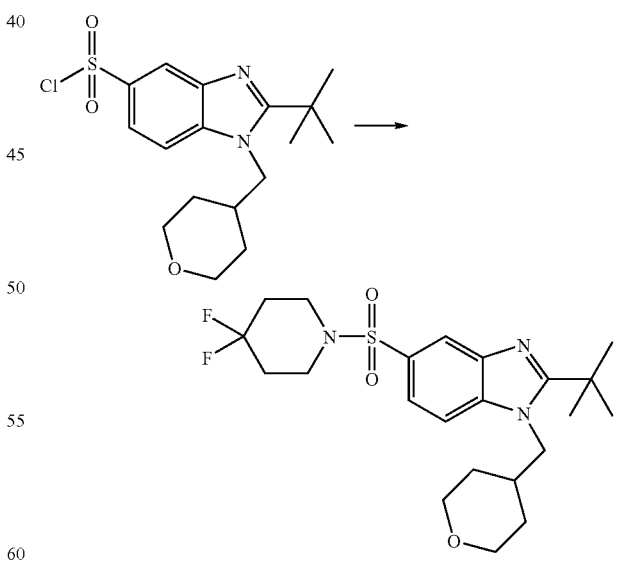

Following the same procedure in Example 1, step A, using 4,4-difluoropiperidine hydrochloride (231 mg, 1.47 mmol), 2-tert-Butyl-1-(tetrahydro-2H-pyran-4-ylmethyl)-1H-benzimidazole-5-sulfonyl chloride (120 mg, 0.29 mmol), DMAP (180 mg, 1.47 mmol) in MeCN (10 mL). The crude product was purified by reverse-phase preparative HPLC using (ESI) (M+H)$^+$=496.0; Anal. Calcd for C$_{28}$H$_{37}$N$_3$O$_3$S+1.3 TFA+0.2H$_2$O: C, 56.76; H, 6.02; N, 6.49. Found: C, 56.85; H, 5.82; N, 6.08.

Example 62

2-tert-Butyl-5-[(3,3-difluoropiperidin-1-yl)sulfonyl]-1-(tetrahydro-2H-pyran-4-ylmethyl)-1H-benzimidazole

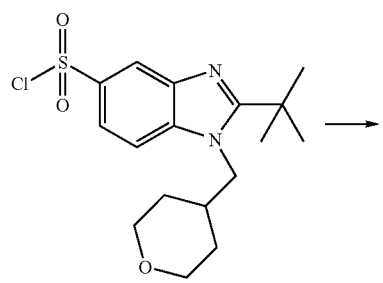

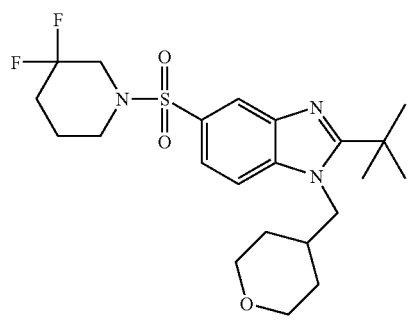

Following the same procedure in Example 1, step A, using 3,3-difluoropiperidine hydrochloride (231 mg, 1.47 mmol), 2-tert-Butyl-1-(tetrahydro-2H-pyran-4-ylmethyl)-1H-benzimidazole-5-sulfonyl chloride (120 mg, 0.29 mmol), DMAP (180 mg, 1.47 mmol) in MeCN (10 mL). The crude product was purified by reverse-phase preparative HPLC using 10-90% MeCN/H$_2$O and lyophilized affording the title compound as the corresponding TFA salt. Yield: 73 mg (43%); $^1$H NMR (400 MHz, CD$_3$OD) δ 1.49-1.64 (m, 4 H), 1.67 (s, 9 H), 1.72-1.82 (m, 2 H), 1.82-1.96 (m, 2 H), 2.30-2.45 (m, 1 H), 3.10-3.17 (m, 2 H), 3.31-3.40 (m, 4 H), 3.94 (dd, J=11.33, 3.32 Hz, 2 H), 4.53 (d, J=7.42 Hz, 2 H), 7.88 (dd, J=8.79, 1.56 Hz, 1 H), 8.05 (d, J=8.79 Hz, 1 H), 8.12 (d, J=1.56 Hz, 1 H); MS (ESI) (M+H)$^+$=456.0; Anal. Calcd for C$_{22}$H$_{31}$F$_2$N$_3$O$_3$S+ 1.5 TFA: C, 47.92; H, 5.23; N, 6.71. Found: C, 48.14; H, 5.37; N, 6.23.

Example 63

2-tert-Butyl-5-[(2-ethylpiperidin-1-yl)sulfonyl]-1-(tetrahydro-2H-pyran-4-ylmethyl)-1H-benzimidazole

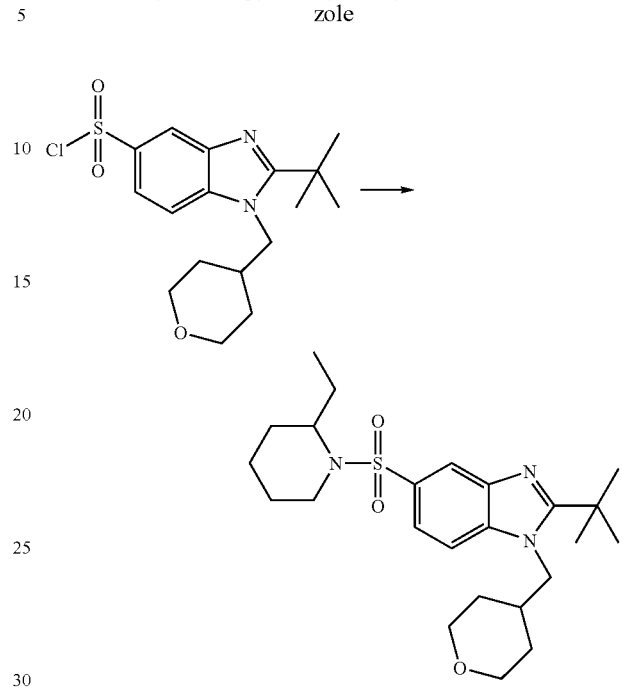

Following the same procedure in Example 1, step A, using 2-ethylpiperidine (167 mg, 1.47 mmol), 2-tert-Butyl-1-(tetrahydro-2H-pyran-4-ylmethyl)-1H-benzimidazole-5-sulfonyl chloride (120 mg, 0.29 mmol), DMAP (180 mg, 1.47 mmol) in MeCN (10 mL). The crude product was purified by reverse-phase preparative HPLC using 10-90% MeCN/H$_2$O and lyophilized affording the title compound as the corresponding TFA salt. Yield: 40 mg (24%); $^1$H NMR (400 MHz, CD$_3$OD) δ 0.86 (t, J=7.42 Hz, 3 H), 1.07-1.21 (m, 1 H), 1.29-1.46 (m, 2 H), 1.46-1.64 (m, 6 H), 1.66-1.70 (m, 1 H), 2.30-2.44 (m, 1 H), 3.1 (m, 1 H), 3.31-3.40 (m, 3 H), 3.8 (m, 1 H), 3.89-4.02 (m, 3 H), 4.53 (d, J=7.42 Hz, 2 H), 7.92-7.99 (m, 1 H), 8.01-8.07 (m, 1 H), 8.17 (d, J=1.17 Hz, 1 H); MS (ESI) (M+H)$^+$=448.0; Anal. Calcd for C$_{24}$H$_{37}$N$_3$O$_3$S+1.6 TFA: C, 51.85; H, 6.18; N, 6.67. Found: C, 51.91; H, 5.93; N, 6.50.

Example 64

2-tert-Butyl-5-[(3-phenylpyrrolidin-1-yl)sulfonyl]-1-(tetrahydro-2H-pyran-4-ylmethyl)-1H-benzimidazole

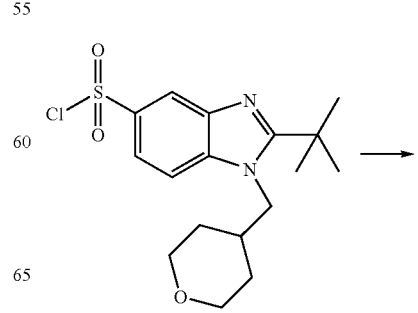

-continued

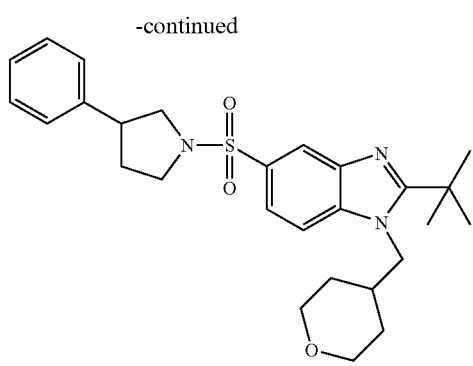

Following the same procedure in Example 1, step A, using 3-phenylpyrrolidine (217 mg, 1.47 mmol), 2-tert-Butyl-1-(tetrahydro-2H-pyran-4-ylmethyl)-1H-benzimidazole-5-sulfonyl chloride (120 mg, 0.29 mmol) and DMAP (180 mg, 1.47 mmol) in MeCN (10 mL). The crude product was purified by reverse-phase preparative HPLC using 10-90% MeCN/H$_2$O and lyophilized affording the title compound as the corresponding TFA salt. Yield: 50 mg (28%); $^1$H NMR (400 MHz, CD$_3$OD) δ 1.50-1.58 (m, 2 H), 1.61 (dd, J=12.30, 3.91 Hz, 1 H), 1.68 (s, 9H), 1.79-1.91 (m, 1 H), 2.12-2.23 (m, 1 H), 2.33-2.42 (m, 1 H), 3.15-3.25 (m, 2 H), 3.31-3.43 (m, 4 H), 3.51-3.61 (m, 1 H), 3.70-3.79 (m, 1 H), 3.94 (dd, J=10.84, 3.81 Hz, 2 H), 4.53 (d, J=7.42 Hz, 2 H), 7.05-7.11 (m, 2 H), 7.12-7.24 (m, 3 H), 7.91-7.97 (m, 1 H), 8.00-8.06 (m, 1 H), 8.17 (d, J=1.56 Hz, 1 H); MS (ESI) (M+H)$^+$=482.0; Anal. Calcd for C$_{27}$H$_{35}$N$_3$O$_3$S+1.1 TFA: C, 57.77; H, 5.99; N, 6.92. Found: C, 58.04; H, 5.81; N, 6.48.

Example 65

2-tert-Butyl-5-{[2-(methoxymethyl)pyrrolidin-1-yl]sulfonyl}-1-(tetrahydro-2H-pyran-4-ylmethyl)-1H-benzimidazole

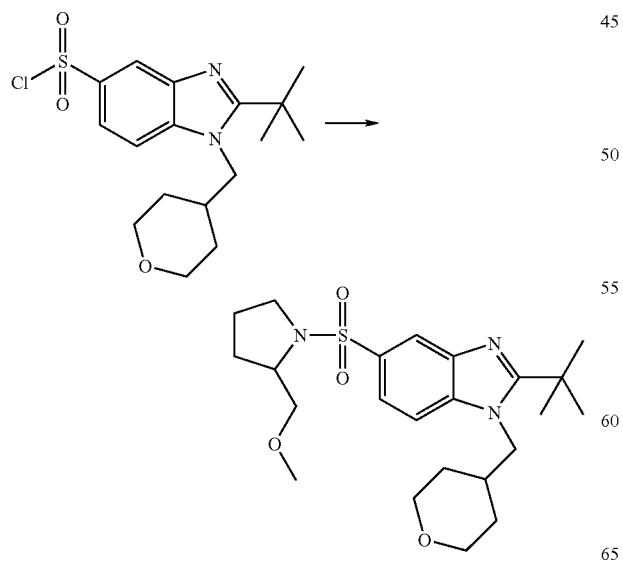

Following the same procedure in Example 1, step A, using 2-(methoxymethyl)pyrrolidine (170 mg, 10.47 mmol), 2-tert-Butyl-1-(tetrahydro-2H-pyran-4-ylmethyl)-1H-benzimidazole-5-sulfonyl chloride (120 mg, 0.29 mmol) and DMAP (180 mg, 1.47 mmol) in MeCN (10 mL). The crude product was purified by reverse-phase preparative HPLC using 10-90% MeCN/H$_2$O and lyophilized affording the title compound as the corresponding TFA salt. Yield: 53 mg (31%); $^1$H NMR (400 MHz, CD$_3$OD) δ 1.47-1.58 (m, 4 H), 1.58-1.67 (m, 2 H), 1.68 (s, 9 H), 1.78-1.92 (m, 2 H), 2.29-2.42 (m, 1 H), 3.12-3.22 (m, 1 H), 3.3 (m, 1 H), 3.35 (s, 3 H), 3.37-3.46 (m, 3 H), 3.58 (dd, J=9.47, 3.81 Hz, 1 H), 3.71-3.81 (m, 1 H), 3.95 (dd, J=11.23, 3.42 Hz, 2 H), 4.48-4.57 (m, 2 H), 7.93-7.99 (m, 1 H), 8.01-8.07 (m, 1 H), 8.17 (d, J=1.17 Hz, 1H); MS (ESI) (M+H)$^+$=450.0; Anal. Calcd for C$_{23}$H$_{35}$N$_3$O$_4$S+1.8 TFA: C, 48.65; H, 5.68; N, 6.40. Found: C, 48.61; H, 5.70; N, 6.42.

Example 66

2-tert-Butyl-5-[(3,3-difluoropyrrolidin-1-yl)sulfonyl]-1-(tetrahydro-2H-pyran-4-ylmethyl)-1H-benzimidazole

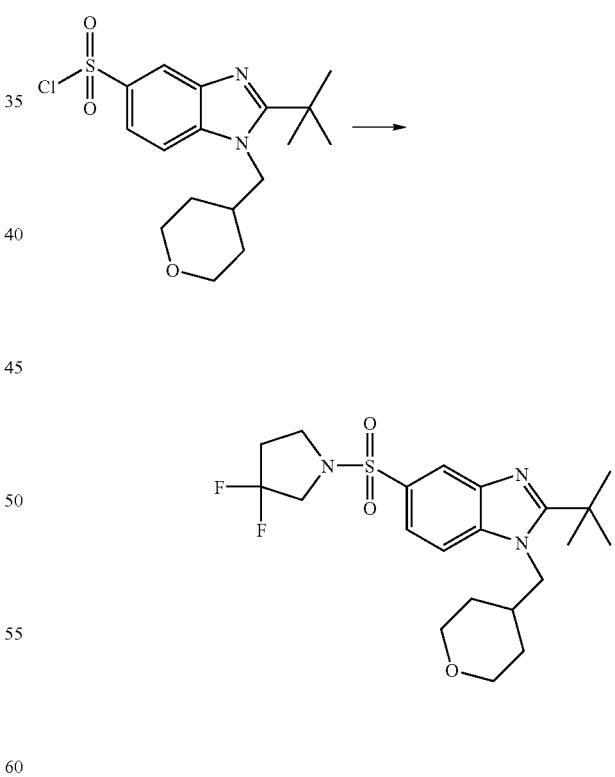

Following the same procedure in Example 1, step A, using 3,3-difluoropyrrolidine hydrochloride (210 mg, 10.47 mmol), 2-tert-Butyl-1-(tetrahydro-2H-pyran-4-ylmethyl)-1H-benzimidazole-5-sulfonyl chloride (120 mg, 0.29 mmol) and DMAP (180 mg, 1.47 mmol) in MeCN (10 mL). The crude product was purified by reverse-phase preparative HPLC using 10-90% MeCN/H$_2$O and lyophilized affording the title compound as the corresponding TFA salt. Yield: 108 mg (65%); $^1$H NMR (400 MHz, CD$_3$OD) δ 1.46-1.54 (m, 2 H), 1.55-1.63 (m, 2 H), 1.65 (s, 9 H), 2.21-2.42 (m, 3 H), 3.34 (td, J=11.77, 2.44 Hz, 2 H), 3.45 (t, J=7.32 Hz, 2 H), 3.58 (t, J=12.89 Hz, 2 H), 3.94 (dd, J=10.84, 4.00 Hz, 2 H), 4.48 (d, J=7.62 Hz, 2 H), 7.87 (dd, J=8.69, 1.66 Hz, 1 H), 7.94-8.00 (m, 1 H), 8.15 (d, J=1.17 Hz, 1 H); MS (ESI) (M+H)$^+$=442.0; Anal. Calcd for C$_{21}$H$_{29}$F$_2$N$_3$O$_3$S+0.8 TFA+0.1H$_2$O: C, 50.78; H, 5.66; N, 7.86. Found: C, 50.75; H, 5.55; N, 7.42.

Example 67

2-tert-Butyl-5-(pyrrolidin-1-ylsulfonyl)-1-(tetrahydro-2H-pyran-4-ylmethyl)-1H-benzimidazole

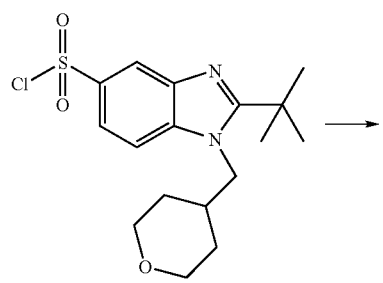

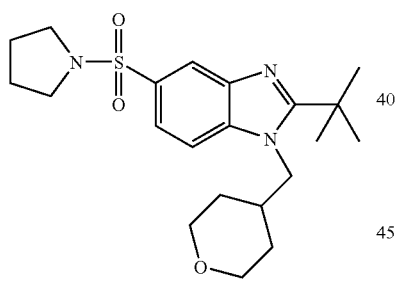

Following the same procedure in Example 1, step A, using pyrrolidine (105 mg, 1.47 mmol), 2-tert-Butyl-1-(tetrahydro-2H-pyran-4-ylmethyl)-1H-benzimidazole-5-sulfonyl chloride (120 mg, 0.29 mmol) and DMAP (180 mg, 1.47 mmol) in MeCN (10 mL). The crude product was purified by reverse-phase preparative HPLC using 10-90% MeCN/H$_2$O and lyophilized affording the title compound as the corresponding TFA salt. Yield: 54 mg (35%); $^1$H NMR (400 MHz, CD$_3$OD) δ 1.51-1.58 (m, 2 H), 1.58-1.67 (m, 2 H), 1.69 (s, 9 H), 1.71-1.78 (m, 4 H), 2.31-2.44 (m, 1 H), 3.22-3.28 (m, 4 H), 3.35 (td, J=11.57, 2.64 Hz, 2 H), 3.90-3.99 (m, 2 H), 4.54 (d, J=7.42 Hz, 2 H), 7.95 (dd, J=8.79, 1.76 Hz, 1 H), 8.07 (d, J=8.79 Hz, 1 H), 8.15 (d, J=1.76 Hz, 1 H); MS (ESI) (M+H)$^+$= 406.0; Anal. Calcd for C$_{21}$H$_{31}$N$_3$O$_3$S+0.1 MeCN: C, 48.96; H, 5.51; N, 7.49. Found: C, 49.17; H, 5.34; N, 7.13.

Example 68

5-[(3-Benzylpyrrolidin-1-yl)sulfonyl]-2-tert-butyl-1-(tetrahydro-2H-pyran-4-ylmethyl)-1H-benzimidazole

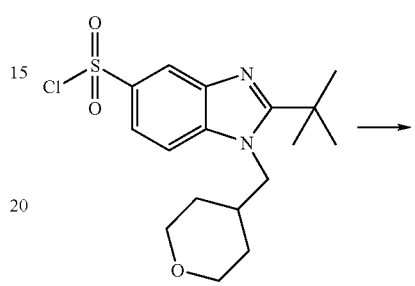

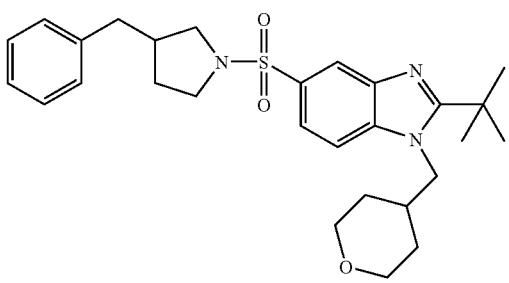

Following the same procedure in Example 1, step A, using 3-benzylpyrrolidine (238 mg, 1.47 mmol), 2-tert-Butyl-1-(tetrahydro-2H-pyran-4-ylmethyl)-1H-benzimidazole-5-sulfonyl chloride (120 mg, 0.29 mmol) and DMAP (180 mg, 1.47 mmol) in MeCN (10 mL). The crude product was purified by reverse-phase preparative HPLC using 10-90% MeCN/H$_2$O and lyophilized affording the title compound as the corresponding TFA salt. Yield: 49 mg (27%); $^1$H NMR (400 MHz, CD$_3$OD) δ 1.40-1.53 (m, 3 H), 1.52-1.62 (m, 3 H), 1.65 (s, 9 H), 1.76-1.91 (m, 1 H), 2.20-2.40 (m, 2 H), 2.40-2.48 (m, 2 H), 2.66-2.80 (m, 1 H), 2.92 (dd, J=9.96, 7.23 Hz, 1 H), 3.19-3.34 (m, 2 H), 3.35-3.44 (m, 1 H), 3.90 (dd, J=11.43, 3.81 Hz, 2 H), 4.48 (d, J=7.42 Hz, 2 H), 6.94-7.05 (m, 1 H), 7.08-7.16 (m, 1 H), 7.16-7.23 (m, 2 H), 7.24-7.33 (m, 1 H), 7.85 (dd, J=8.79, 1.76 Hz, 1 H), 7.96 (d, J=8.79 Hz, 1 H), 8.11 (d, J=1.17 Hz, 1 H); MS (ESI) (M+H)$^+$=496.0; Anal. Calcd for C$_{28}$H$_{37}$N$_3$O$_3$S+0.9 TFA: C, 59.82; H, 6.38; N, 7.02. Found: C, 59.82; H, 6.25; N, 6.93.

Example 69

1-{[2-tert-Butyl-1-(tetrahydro-2H-pyran-4-ylmethyl)-1H-benzimidazol-5-yl]sulfonyl}-N-cyclopropylpiperidine-4-carboxamide

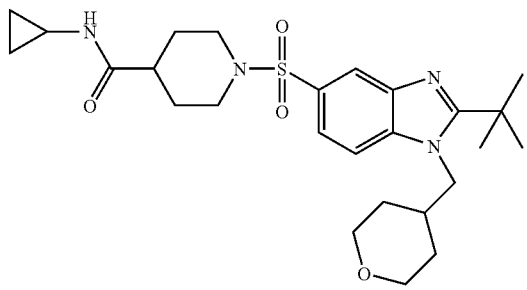

Step A: 1-{[2-tert-butyl-1-(tetrahydro-2H-pyran-4-ylmethyl)-1H-benzimidazol-5-yl]sulfonyl}-N-cyclopropylpiperidine-4-carboxamide

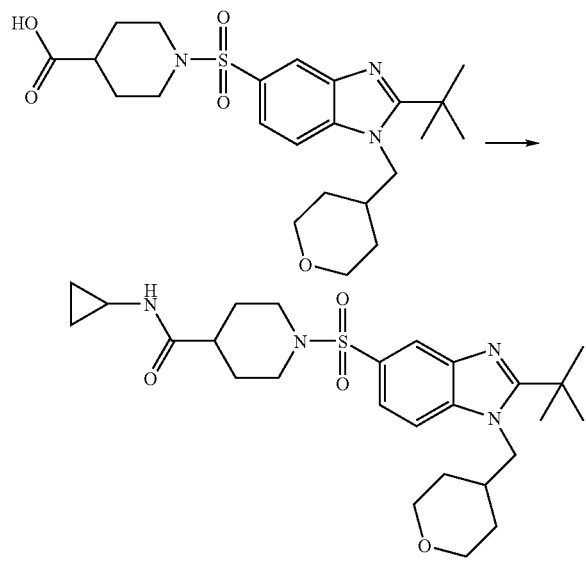

HATU (45 mg, 0.11 mmol) and cyclopropylamine (10 mg, 0.16 mmol) were added to a solution of 1-{[2-tert-butyl-1-(tetrahydro-2H-pyran-4-ylmethyl)-1H-benzimidazol-5-yl]sulfonyl}piperidine-4-carboxylic acid (50 mg, 0.10 mmol) (see following steps B and C for preparation) and DIPLA (20 uL, 0.11 mmol) in DMF (5 mL) at 0° C. The reaction mixture was stirred for 1 hr. and the solvent was concentrated. The crude product was purified by reverse-phase preparative HPLC using 10-50% MeCN/H$_2$O and lyophilized affording the title compound as the corresponding TFA salt. Yield: 30 mg (45%); $^1$H NMR (400 MHz, CD$_3$OD) δ 0.36-0.44 (m, 2 H), 0.62-0.70 (m, 2 H), 1.51-1.61 (m, 4 H), 1.61-1.67 (m, 2 H), 1.69 (s, 9 H), 1.71-1.80 (m, 3 H), 2.01-2.11 (m, 1 H), 2.32-2.39 (m, 1 H), 2.43 (td, J=11.77, 3.03 Hz, 2 H), 2.53-2.61 (m, 1 H), 3.35 (td, J=11.52, 2.73 Hz, 2 H), 3.73-3.81 (m, 2 H), 3.94 (dd, J=10.84, 3.22 Hz, 2 H), 4.55 (d, J=7.62 Hz, 2 H), 7.88 (dd, J=8.79, 1.76 Hz, 1 H), 8.05-8.12 (m, 2 H); MS (ESI) (M+H)$^+$=502.8; Anal. Calcd for C$_{26}$H$_{38}$N$_4$O$_4$S+2.0 TFA+0.8H$_2$O: C, 48.36; H, 5.63; N, 7.52. Found: C, 48.37; H, 5.65; N, 7.32.

Step B: methyl 1-{[2-tert-butyl-1-(tetrahydro-2H-pyran-4-ylmethyl)-1H-benzimidazol-5-yl]sulfonyl}piperidine-4-carboxylate

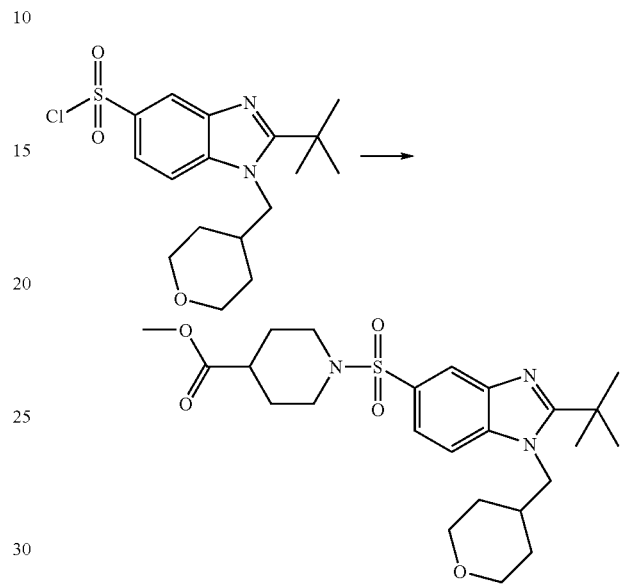

2-tert-Butyl-1-(tetrahydro-2H-pyran-4-ylmethyl)-1H-benzimidazole-5-sulfonyl chloride (400 mg, 0.98 mmol) was added to a solution of methyl piperidine-4-carboxylate (703 mg, 4.90 mmol) and DMAP (600 mg, 4.90 mmol) in MeCN (50 mL). The reaction mixture was stirred overnight at ambient temperature and the solvent was concentrated. The product was purified by MPLC using 50-90% EtOAc/Heptane on silica gel to provide the title compound as colorless oil. Yield: 182 mg (38%); $^1$H NMR (400 MHz, CDCl$_3$) δ 1.48-1.57 (m, 4 H), 1.59 (s, 9 H), 1.76-1.89 (m, 2 H), 1.91-2.00 (m, 2 H), 2.17-2.34 (m, 2 H), 2.48 (td, J=11.28, 2.83 Hz, 2 H), 3.27-3.39 (m, 2 H), 3.64 (s, 3 H), 3.65-3.70 (m, 1 H), 3.95-4.04 (m, 2 H), 4.25 (d, J=7.42 Hz, 2 H), 7.42 (dd, J=8.59, 0.59 Hz, 1 H), 7.64 (dd, J=8.40, 1.76 Hz, 1 H), 8.17 (dd, J=1.66, 0.49 Hz, 1 H); MS (ESI) (M+H)$^+$=478.0.

Step C: 1-{[2-tert-butyl-1-(tetrahydro-2H-pyran-4-ylmethyl)-1H-benzimidazol-5-yl]sulfonyl}piperidine-4-carboxylic acid

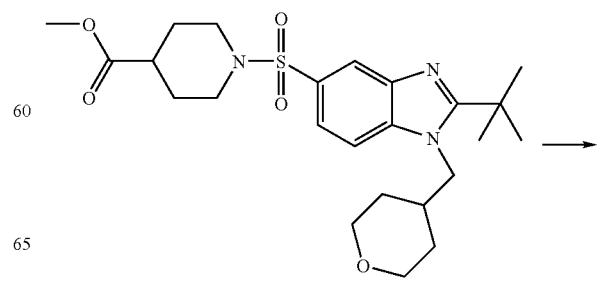

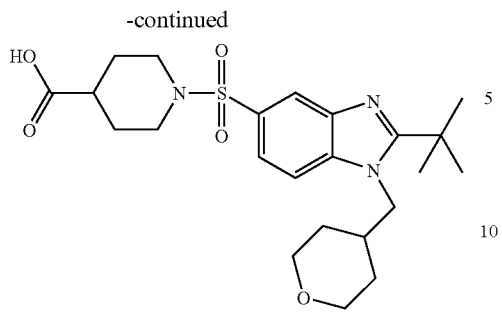

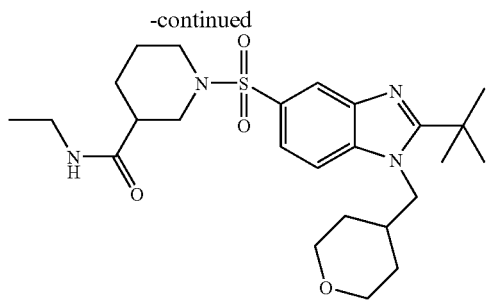

NaOH (0.75 mL, 2M, 1.5 mmol) was added to a solution of methyl 1-{[2-tert-butyl-1-(tetrahydro-2H-pyran-4-ylmethyl)-1H-benzimidazol-5-yl]sulfonyl}piperidine-4-carboxylate (173 mg, 0.36 mmol) in 10 mL MeOH—H$_2$O (1:1) at ambient temperature. The reaction mixture was stirred overnight and diluted with water (40 mL). The solvent was concentrated to 40 mL. The resulting solution was neutralized with HCl solution and the product was extracted with EtOAc and dried over anhydrous Na$_2$SO$_4$. The solvent was concentrated to provide the title compound as white solid. Yield: 60 mg (95%); MS (ESI) (M+H)$^+$=464.0.

Example 70

1-{[2-tert-Butyl-1-(tetrahydro-2H-pyran-4-ylmethyl)-1H-benzimidazol-5-yl]sulfonyl}-N-ethylpiperidine-3-carboxamide HATU (45 mg, 0.11 mmol) and ethylamine 2M solution in THF (80 mg, 0.16 mmol) were added to a solution of 1-{[2-tert-butyl-1-(tetrahydro-2H-pyran-4-ylmethyl)-1H-benzimidazol-5-yl]sulfonyl}piperidine-3-carboxylic acid (50 mg, 0.10 mmol) (see following steps B and C for preparation) and DIPEA (20 μL, 0.11 mmol) in DMF (5 mL) at 0° C. The reaction mixture was stirred for 1 h and the solvent was concentrated. The crude product was purified by reverse-phase preparative HPLC using 10-50% MeCN/H$_2$O and lyophilized affording the title compound as the corresponding TFA salt. Yield: 46 mg (70%); $^1$H NMR (400 MHz, CD$_3$OD) δ 1.09 (t, J=7.23 Hz, 3 H), 1.26-1.39 (m, 1 H), 1.50-1.58 (m, 2 H), 1.58-1.66 (m, 2 H), 1.68 (s, 9 H), 1.76-1.87 (m, 2 H), 2.23 (td, J=11.77, 2.83 Hz, 1 H), 2.30-2.42 (m, 2 H), 2.43-2.52 (m, 1 H), 3.16 (q, J=7.36 Hz, 2 H), 3.36 (td, J=11.57, 2.64 Hz, 2 H), 3.71-3.82 (m, 2 H), 3.94 (dd, J=11.13, 3.32 Hz, 2 H), 4.54 (d, J=7.42 Hz, 2 H), 7.85 (dd, J=8.79, 1.76 Hz, 1 H), 8.06 (d, J=8.79 Hz, 1 H), 8.09 (d, J=1.56 Hz, 1 H); MS (ESI) (M+H)$^+$=490.8; Anal. Calcd for C$_{25}$H$_{38}$N$_4$O$_4$S+1.3 TFA+0.3H$_2$O: C, 51.45; H, 6.24; N, 8.70. Found: C, 51.41; H, 6.27; N, 8.64.

Step B: ethyl 1-{[2-tert-butyl-1-(tetrahydro-2H-pyran-4-ylmethyl)-1H-benzimidazol-5-yl]sulfonyl}piperidine-3-carboxylate

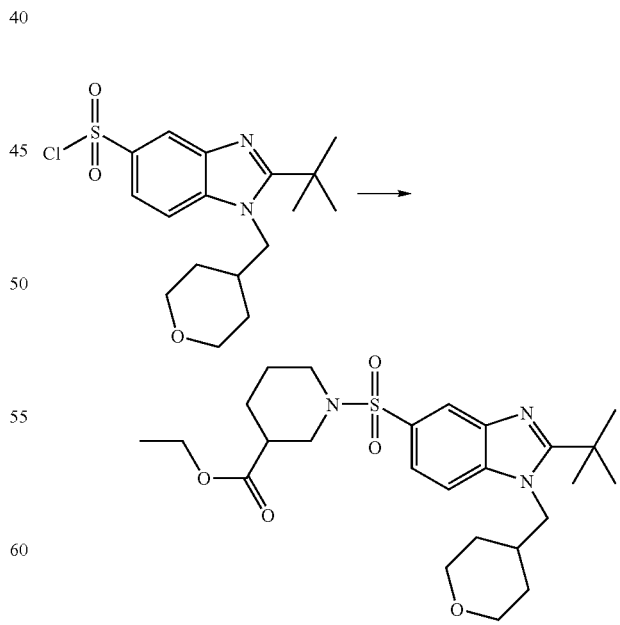

Step A: 1-{[2-tert-butyl-1-(tetrahydro-2H-pyran-4-ylmethyl)-1H-benzimidazol-5-yl]sulfonyl}-N-ethylpiperidine-3-carboxamide

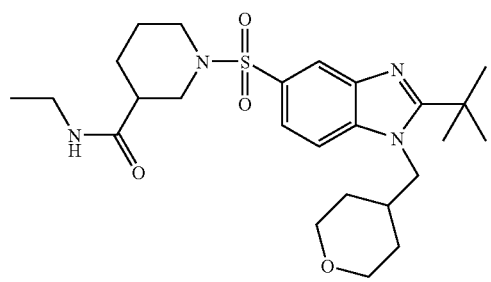

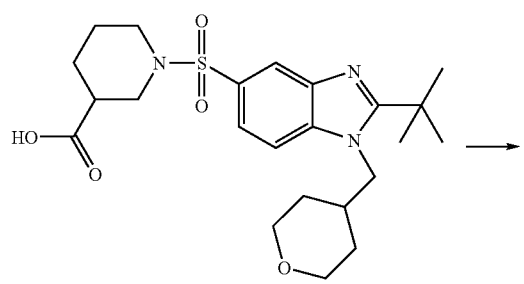

2-tert-Butyl-1-(tetrahydro-2H-pyran-4-ylmethyl)-1H-benzimidazole-5-sulfonyl chloride (400 mg, 0.98 mmol) was added to a solution of ethyl piperidine-3-carboxylate (771 mg, 4.90 mmol) and DMAP (600 mg, 4.90 mmol) in MeCN (50 mL). The reaction mixture was stirred overnight at ambient temperature and the solvent was concentrated. The product was purified by MPLC using 50-90% EtOAc/Heptane on silica gel to provide the title compound as colorless oil. Yield: 182 mg (38%); $^1$H NMR (400 MHz, CDCl$_3$) δ 1.26 (t, J=7.13 Hz, 3 H), 1.29-1.38 (m, 1 H), 1.49-1.57 (m, 4 H), 1.59 (s, 9 H), 1.63-1.83 (m, 2 H), 1.91-2.02 (m, 1 H), 2.30 (td, J=11.43, 2.93 Hz, 2 H), 2.44 (t, J=11.13 Hz, 1 H), 2.57-2.69 (m, 1 H), 3.28-3.40 (m, 2 H), 3.65-3.75 (m, 1 H), 3.91 (dd, J=11.82, 3.81 Hz, 1 H), 3.96-4.05 (m, 2 H), 4.13 (q, J=7.03 Hz, 2 H), 4.25 (d, J=7.23 Hz, 2 H), 7.43 (d, J=8.20 Hz, 1 H), 7.64 (dd, J=8.59, 1.76 Hz, 1 H), 8.19 (d, J=1.56 Hz, 1 H); MS (ESI) (M+H)$^+$ 491.9.

Step C: 1-{[2-tert-butyl-1-(tetrahydro-2H-pyran-4-ylmethyl)-1H-benzimidazol-5-yl]sulfonyl}piperidine-3-carboxylic acid

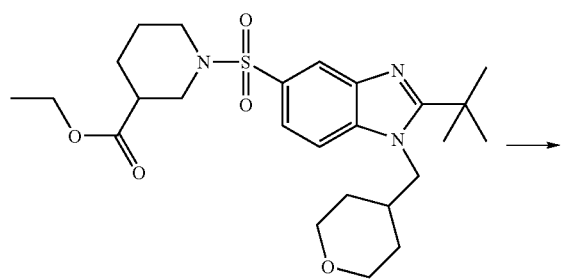

NaOH (0.75 mL, 2M, 1.5 mmol) was added to a solution of ethyl 1-{[2-tert-butyl-1-(tetrahydro-2H-pyran-4-ylmethyl)-1H-benzimidazol-5-yl]sulfonyl}piperidine-3-carboxylate (158 mg, 0.36 mmol) in 10 mL of MeOH—H$_2$O (1:1) at ambient temperature. The reaction mixture was stirred overnight and diluted with water (40 mL). The solvent was concentrated to 40 mL. The resulting solution was neutralized with HCl solution and the product was extracted with EtOAc and dried over anhydrous Na$_2$SO$_4$. The solvent was concentrated to provide the title compound as white solid. Yield: 108 mg (72%); MS (ESI) (M+H)$^+$=464.0.

Example 71

1-{[2-tert-Butyl-1-(tetrahydro-2H-pyran-4-ylmethyl)-1H-benzimidazol-5-yl]sulfonyl}-N-cyclopropylpiperidine-3-carboxamide

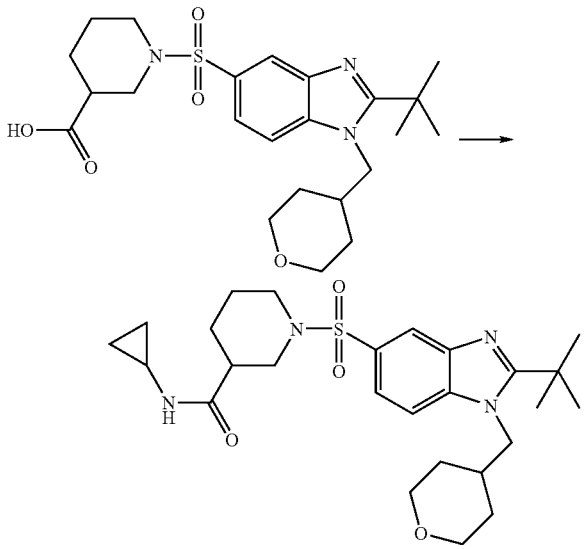

Following the same procedure in example 70 step A, using cyclopropylamine (9 mg, 0.16 mmol), HATU (45 mg, 0.11 mmol), 1-{[2-tert-butyl-1-(tetrahydro-2H-pyran-4-ylmethyl)-1H-benzimidazol-5-yl]sulfonyl}piperidine-3-carboxylic acid (50 mg, 0.10 mmol) and DIPEA (20 μL, 0.11 mmol) in DMF (5 mL). The crude product was purified by reverse-phase preparative HPLC using 10-50% MeCN/H$_2$O and lyophilized affording the title compound as the corresponding TFA salt. Yield: 40 mg (60%); $^1$H NMR (400 MHz, CD$_3$OD) δ 0.39-0.52 (m, 2 H), 0.63-0.74 (m, 2 H), 1.26-1.39 (m, 1 H), 1.50-1.59 (m, 3 H), 1.61 (dd, J=12.01, 4.20 Hz, 2 H), 1.68 (s, 9 H), 1.75-1.85 (m, 2 H), 2.22 (td, J=11.82, 2.15 Hz, 1 H), 2.34 (t, J=11.13 Hz, 1 H), 2.37-2.48 (m, 2 H), 2.57-2.65 (m, 1 H), 3.36 (td, J=11.52, 2.54 Hz, 2 H), 3.69-3.80 (m, 2 H), 3.95 (dd, J=11.52, 3.52 Hz, 2 H), 4.54 (d, J=7.42 Hz, 2 H), 7.86 (dd, J=8.79, 1.76 Hz, 1 H), 8.07 (d, J=8.79 Hz, 1 H), 8.09 (d, J=1.76 Hz, 1 H); MS (ESI) (M+H)$^+$=502.8; Anal. Calcd for C$_{26}$H$_{38}$N$_4$O$_4$S+1.6 TFA+0.1H$_2$O: C, 51.06; H, 5.84; N, 8.16. Found: C, 51.17; H, 5.97; N, 7.63.

Example 72

1-({2-tert-Butyl-1-[(4,4-difluorocyclohexyl)methyl]-1H-benzimidazol-5-yl}sulfonyl)-N-methyl-1H-pyrazole-4-carboxamide

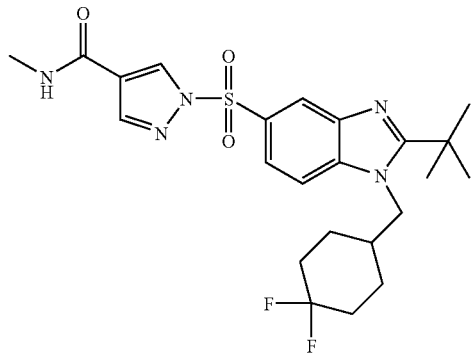

101

Step A: 1-({2-tert-butyl-1-[(4,4-difluorocyclohexyl)methyl]-1H-benzimidazol-5-yl}sulfonyl)-N-methyl-1H-pyrazole-4-carboxamide

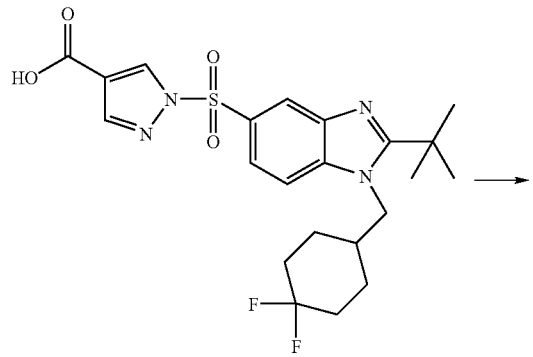

HATU (39 mg, 0.10 mmol) and methylamine (50 uL, 2M in THF, 0.10 mmol) were added to a solution of 1-({2-tert-butyl-1-[(4,4-difluorocyclohexyl)methyl]-1H-benzimidazol-5-yl}sulfonyl)-1H-pyrazole-4-carboxylic acid (45 mg, 0.09 mmol) (see following steps B, C, D, E, F, G, H, I and J for preparation) and DIPEA (20 uL, 0.11 mmol) in DMF (10 mL). The reaction mixture was stirred for 4 hrs. and the solvent was concentrated. The crude product was purified by reverse-phase preparative HPLC using 10-90% MeCN/H$_2$O and lyophilized affording the title compound as the corresponding TFA salt. Yield: 15 mg (26%); $^1$H NMR (400 MHz, CDCl$_3$) δ 1.44-1.60 (m, 3 H), 1.62 (s, 9 H), 1.64-1.78 (m, 3 H), 2.03-2.20 (m, 3 H), 2.93 (d, J=4.69 Hz, 3 H), 4.32 (d, J=7.42 Hz, 2 H), 6.73-6.80 (m, 1 H), 7.51-7.58 (m, 1 H), 7.93 (s, 1 H), 8.01 (dd, J=8.79, 1.76 Hz, 1 H), 8.49 (s, 1 H), 8.57 (d, J=1.56 Hz, 1 H); MS (ESI) (M+H)$^+$=494.3; Anal. Calcd for C$_{23}$H$_{29}$F$_2$N$_5$O$_3$S+1.0 TFA+0.2H$_2$O: C, 49.13; H, 5.01; N, 11.46. Found: C, 49.22; H, 5.00; N, 11.32.

102

Step B. tert-Butyl[(4,4-difluorocyclohexyl)methyl]carbamate

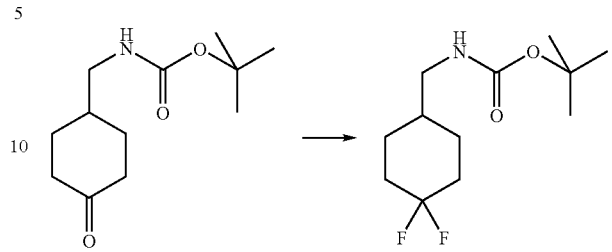

4-N-Boc-aminomethyl cyclohexanone (1.00 g, 4.4 mmol) was dissolved in 30 mL of DCM at 0° C. DAST (1.45 mL, 11.0 mmol) was added dropwise and the solution was stirred at rt overnight. The solution washed with aqueous 5% KHSO$_4$ solution, saturated aqueous NaHCO$_3$ solution, brine and dried over anhydrous MgSO$_4$. The crude product was purified by flash chromatography using hexane/EtOAc (3:1) on silica gel. Yield: 508 mg (46%); $^1$H NMR (400 MHz, CDCl$_3$) δ 1.19-1.36 (m, 2 H), 1.44 (s, 9 H), 1.51-1.56 (m, 1 H), 1.59-1.75 (m, 2 H), 1.75-1.84 (m, 2 H), 2.01-2.16 (m, 2 H), 3.03 (t, J=6.54 Hz, 2 H), 4.62 (br.s, 1 H).

Step C. [(4,4-Difluorocyclohexyl)methyl]amine hydrochloride

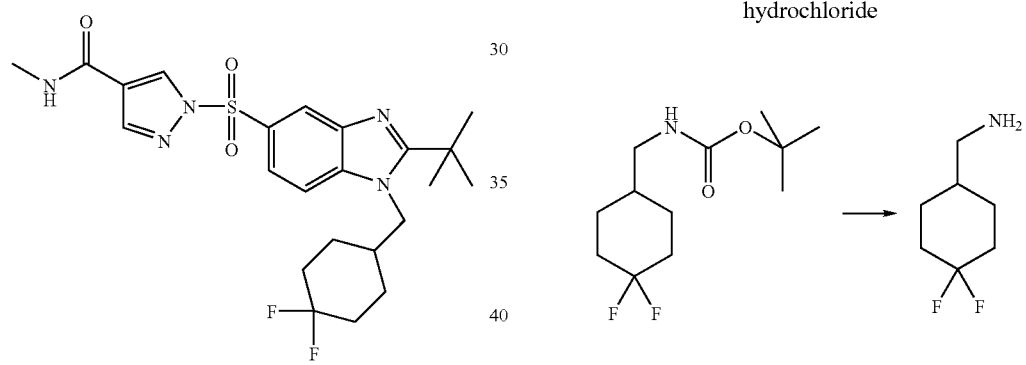

tert-Butyl[(4,4-difluorocyclohexyl)methyl]carbamate (505 mg, 2.03 mmol) was stirred in 5 mL of 1M HCl/AcOH at rt for 2 h. The solvent was evaporated. The residue washed with ether, filtered and dried. Yield: 330 mg (88%); $^1$H NMR (400 MHz, CD$_3$OD) δ 1.28-1.40 (m, 2 H), 1.71-1.82 (m, 2 H), 1.84 (d, J=3.12 Hz, 2 H), 1.86-1.89 (m, 1 H), 2.03-2.15 (m, 2 H), 2.85 (d, J=7.03 Hz, 2 H).

Step D: N-(4-{[(4,4-Difluorocyclohexyl)methyl]amino}-3-nitrophenyl)acetamide

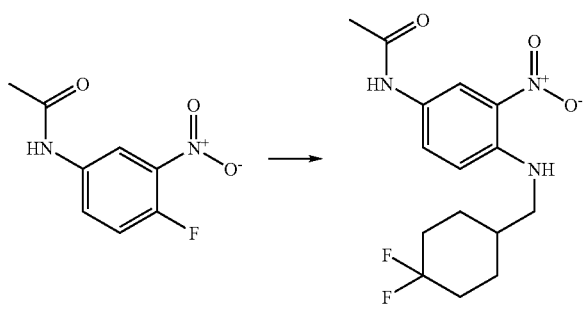

N-(4-Fluoro-3-nitrophenyl)acetamide (1.15 g, 5.84 mmol) and [(4,4-difluorocyclohexyl)methyl]amine hydrochloride (1.30 g, 7.59 mmol) were stirred in 30 mL of EtOH containing TEA (2.40 mL, 17.5 mmol) at 80° C. for 48 h. The solvent was evaporated. The residue was dissolved in EtOAc and washed with aqueous 5% KHSO₄ solution, saturated aqueous NaHCO₃ solution, saturated aqueous NaCl solution and dried over anhydrous Na₂SO₄. The product was crystallized from EtOAc. The left over mother liquor was purified by flash chromatography on silica gel using hexane/acetone (2:1) as eluent. Yield: 1.50 g (78%); ¹H NMR (400 MHz, CDCl₃) δ 1.33-1.47 (m, 2 H), 1.66-1.77 (m, 2 H), 1.77-1.86 (m, 1 H), 1.89-1.93 (m, 1 H), 1.93-1.97 (m, 1 H), 2.10-2.17 (m, 2 H), 2.18 (s, 3 H), 3.23 (dd, J=6.74, 5.76 Hz, 2 H), 6.83 (d, J=9.37 Hz, 1 H), 7.15 (s, 1 H), 7.80 (dd, J=9.18, 2.54 Hz, 1 H), 8.09 (d, J=2.54 Hz, 2 H).

Step E: N-(3-Amino-4-{[(4,4-difluorocyclohexyl)methyl]amino}phenyl)acetamide

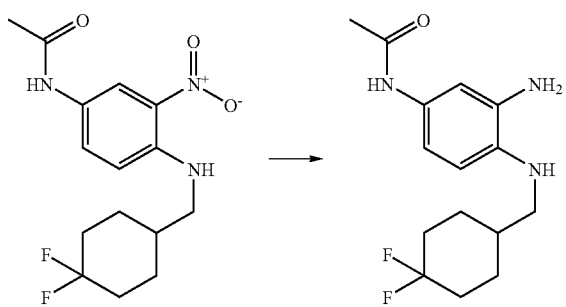

N-(4-{[(4,4-Difluorocyclohexyl)methyl]amino}-3-nitrophenyl)acetamide (1.48 g, 4.52 mmol) was dissolved in 50 mL of EtOAc containing a catalytic amount of 10% Pd/C. The solution was shaken in a Parr hydrogenation apparatus under H₂ atmosphere (45 psi) at rt for 24 h. The solution was filtered through Celite and the solvent was evaporated. Yield: 1.32 g (98%); ¹H NMR (400 MHz, CDCl₃) δ 1.31-1.43 (m, 2 H), 1.64-1.73 (m, 2 H), 1.74-1.82 (m, 1 H), 1.89-1.93 (m, 1 H), 1.93-1.96 (m, 1 H), 2.08-2.17 (m, 5 H), 3.00 (d, J=6.64 Hz, 2 H), 3.27-3.46 (m, 2 H), 6.55 (d, J=8.40 Hz, 1 H), 6.70 (dd, J=8.40, 2.34 Hz, 1 H), 7.01 (s, 1 H), 7.13 (d, J=2.34 Hz, 1 H).

Step F: N-{2-tert-Butyl-1-[(4,4-difluorocyclohexyl)methyl]-1H-benzimidazol-5-yl}acetamide

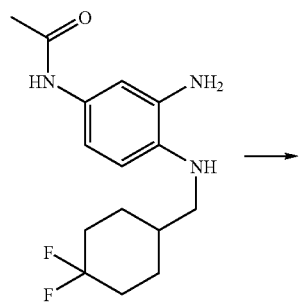

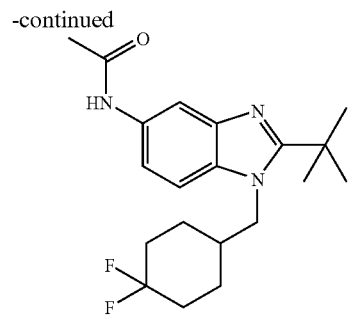

N-(3-Amino-4-{[(4,4-difluorocyclohexyl)methyl]amino}phenyl)acetamide (1.32 g, 4.44 mmol) was dissolved in 100 mL of DCM containing DMAP (108 mg, 0.89 mmol). Trimethylacetyl chloride (0.60 mL, 4.88 mmol) was added dropwise and the solution was stirred at rt for 2 h. The solution washed with saturated aqueous NaHCO₃ solution, saturated aqueous NaCl solution and dried over anhydrous Na₂SO₄. Part of the product precipitated during the washings and was filtered. The organic phase was evaporated and combined with the precipitate. The product was dissolved in 30 mL of AcOH and placed in 6 sealed tubes (5 mL/tube). Each tube was heated at 150° C. in a Personal Chemistry microwaves instrument for 2.5 h. The fractions were pooled and the solvent was evaporated. The product was dissolved in EtOAc and washed with aqueous NaHCO₃ solution, saturated aqueous NaCl solution and dried over anhydrous Na₂SO₄. The product was purified by flash chromatography on silica gel using acetone/hexanes (2:1) as eluent. Yield: 1.11 g (68%); ¹H NMR (400 MHz, CD₃OD) δ 1.40-1.49 (m, 2 H), 1.52 (s, 9 H), 1.60-1.65 (m, 2 H), 1.67-1.77 (m, 1 H), 1.96-2.06 (m, 3 H), 2.11 (s, 3 H), 2.15-2.23 (m, 1 H), 4.28 (d, J=7.62 Hz, 2 H), 7.35-7.39 (m, 1 H), 7.40-7.44 (m, 1 H), 7.85 (d, J=1.76 Hz, 1 H).

Step G: 2-tert-Butyl-1-[(4,4-difluorocyclohexyl)methyl]-1H-benzimidazol-5-amine

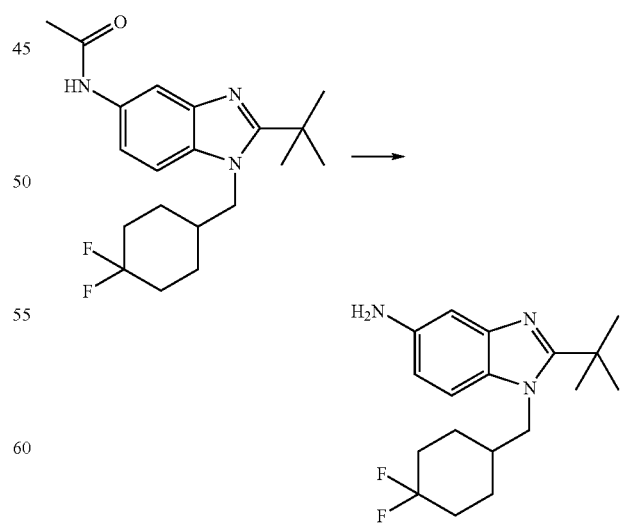

N-{2-tert-Butyl-1-[(4,4-difluorocyclohexyl)methyl]-1H-benzimidazol-5-yl}acetamide (500 mg, 1.37 mmol) was dissolved in 10 mL of 2 M HCl-EtOH (1:1). The solution was Step H. 2-tert-butyl-1-[(4,4-difluorocyclohexyl)methyl]-1H-benzimidazole-5-sulfonyl chloride divided into two sealed tubes (5 mL/tube). Each tube was heated at 120° C. in a Personal Chemistry microwaves instrument for 1 h. The fractions were pooled and the solvent was evaporated. The residue was diluted with 2 M NaOH and extracted (3×) with EtOAc. The organic phase was washed with saturated aqueous NaCl solution and dried over anhydrous Na$_2$SO$_4$. The solvent was evaporated. Yield: 440 mg (99%); $^1$H NMR (400 MHz, CDCl$_3$) δ 1.40-1.52 (m, 2 H), 1.52-1.54 (m, 9 H), 1.56-1.66 (m, 4 H), 1.68-1.75 (m, 2 H), 2.07-2.17 (m, 3 H), 4.14 (d, J=7.62 Hz, 2 H), 6.65 (dd, J=8.50, 2.25 Hz, 1 H), 7.04-7.09 (m, 2 H).

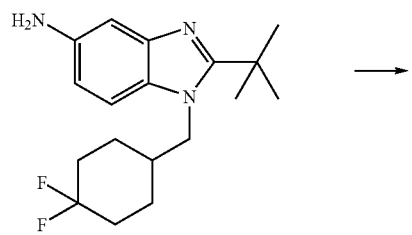

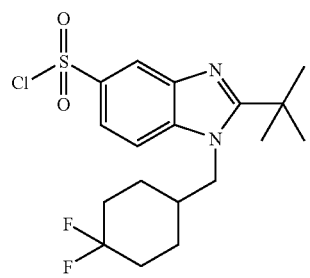

A solution of NaNO$_2$ (1.8 g, 26 mmol) in water (6 mL) was slowly added to a solution of 2-tert-Butyl-1-[(4,4-difluorocyclohexyl)methyl]-1H-benzimidazol-5-amine (7.7 g, 23 mmol) in 60 mL of 37% HCl—AcOH (2:1) at 0° C. The reaction mixture was stirred for 1 h at 0° C. The reaction mixture was added to a mixture of liquid SO$_2$ (~60 mL), CuCl$_2$.2H$_2$O (1.6 g, 9 mmol) and AcOH (30 mL) at −20° C. The resulting mixture was allowed to warm to 0° C. and stirred for 5 h. The reaction mixture was poured over ice (500 mL) while vigorously shaking. The quenched reaction mixture was stirred for 30 min at 0° C. The product was extracted with cold DCM and the organic layers were combined and dried over anhydrous Na$_2$SO$_4$. The solvent was concentrated to provide the pure title compound as beige solid. Yield: 9.5 g (95%); MS (ESI) (M+H)$^+$=404.9.

Step I. 1-({2-tert-butyl-1-[(4,4-difluorocyclohexyl)methyl]-1H-benzimidazol-5-yl}sulfonyl)-1H-pyrazole-4-carbaldehyde

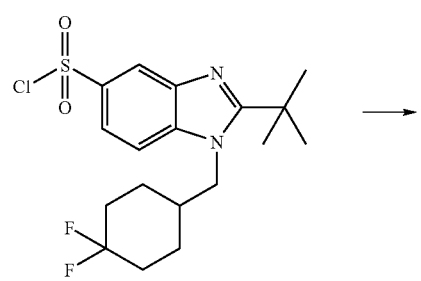

2-tert-Butyl-1-[(4,4-difluorocyclohexyl)methyl]-1H-benzimidazole-5-sulfonyl chloride (0.8 g, 1.9 mmol) was added to a solution of 1H-pyrazole-4-carbaldehyde (0.6 g, 6.2 mmol) and DMAP (1.5 g, 12 mmol) in DCE (70 mL) at 0° C. The reaction mixture was allowed to warm to ambient temperature and stirred for 3 h. The solvent was concentrated and the product was purified by flash chromatography on silica gel using DCM/EtOAc (1:1) as eluent to provide the title compound as white solid. Yield: 0.34 g (36%); MS (ESI) (M+H)$^+$=465.0.

Step J. 1-({2-tert-butyl-1-[(4,4- difluorocyclohexyl)methyl]-1H-benzimidazol-5-yl}sulfonyl)-1H-pyrazole-4-carboxylic acid

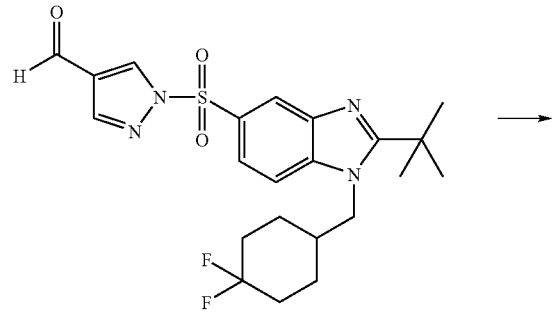

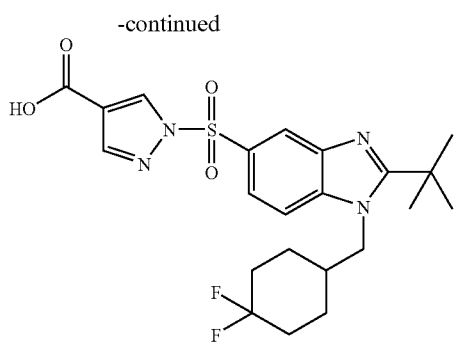

Oxone® (0.60 g, 0.97 mmol) was added to a solution of 1-({2-tert-butyl-1-[(4,4-difluorocyclohexyl)methyl]-1H-benzimidazol-5-yl}sulfonyl)-1H-pyrazole-4-carbaldehyde (0.41 g, 0.88 mmol) in DMF (15 mL). The reaction mixture was stirred overnight at ambient temperature and the solvent was concentrated. The product was recovered in DCM, washed with 10% HCl solution, brine and dried over anhydrous $Na_2SO_4$, The solvent was concentrated to provide the pure title compound as white solid. Yield: 0.38 g (89%); $^1$H NMR (400 MHz, $CDCl_3$) δ 1.42-1.53 (m, 2 H), 1.56 (s, 9 H), 1.59-1.75 (m, 4 H), 2.02-2.20 (m, 3 H), 4.25 (d, J=7.42 Hz, 2 H), 7.46 (d, J=8.59 Hz, 1 H), 7.99 (dd, J=8.69, 1.86 Hz, 1 H), 8.01-8.08 (m, 2 H), 8.47 (d, J=1.56 Hz, 1 H), 8.68 (d, J=0.59 Hz, 1 H); MS (ESI) (M+H)$^+$=481.0.

Example 73

1-({2-tert-Butyl-1-[(4,4-difluorocyclohexyl)methyl]-1H-benzimidazol-5-yl}sulfonyl)-N-ethyl-1H-pyrazole-4-carboxamide

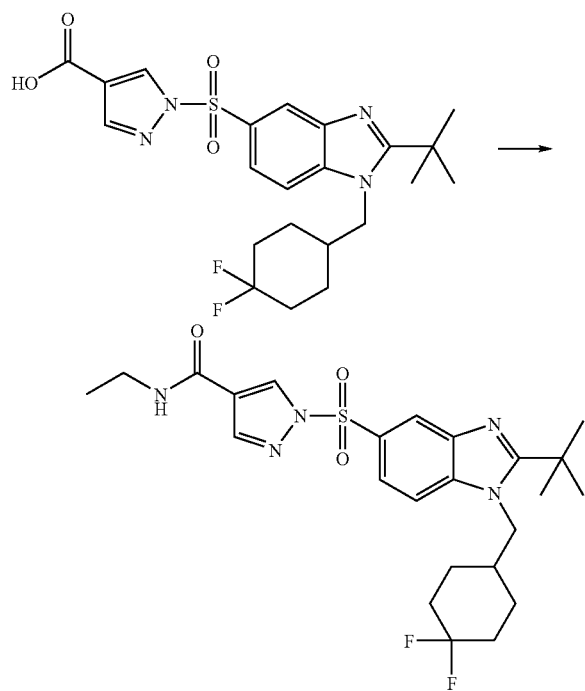

Following the same procedure in example 72, step A, using ethylamine (51 uL, 2 M in THF, 0.10 mmol), HATU (39 mg, 0.10 mmol), 1-({2-tert-butyl-1-[(4,4-difluorocyclohexyl)methyl]-1H-benzimidazol-5-yl}sulfonyl)-1H-pyrazole-4-carboxylic acid (45 mg, 0.09 mmol) and DIPEA (20 uL, 0.11 mmol) in DMF (10 mL). The crude product was purified by reverse-phase preparative HPLC using 10-90% MeCN/$H_2O$ and lyophilized affording the title compound as the corresponding TFA salt. Yield: 20 mg (34%); $^1$H NMR (400 MHz, $CDCl_3$) δ 1.20 (t, J=7.32 Hz, 3 H), 1.43-1.57 (m, 2 H), 1.59 (s, 9 H), 1.61-1.76 (m, 3 H), 2.03-2.23 (m, 2 H), 3.28-3.47 (m, 4 H), 4.29 (d, J=7.42 Hz, 2 H), 6.35 (t, J=5.57 Hz, 1 H), 7.49 (d, J=8.59 Hz, 1 H), 7.94 (d, J=0.59 Hz, 1 H), 7.97 (dd, J=8.69, 1.86 Hz, 1 H), 8.48 (d, J=0.59 Hz, 1 H), 8.49 (d, J=1.56 Hz, 1 H); MS (ESI) (M+H)$^+$=507.8; Anal. Calcd for $C_{24}H_{31}F_2N_5O_3S$+0.4 TFA+0.2$H_2O$: C, 53.32; H, 5.77; N, 12.54. Found: C, 53.36; H, 5.77; N, 12.53.

Example 74

1-({2-tert-Butyl-1-[(4,4-difluorocyclohexyl)methyl]-1H-benzimidazol-5-yl}sulfonyl)-N-propyl-1H-pyrazole-4-carboxamide

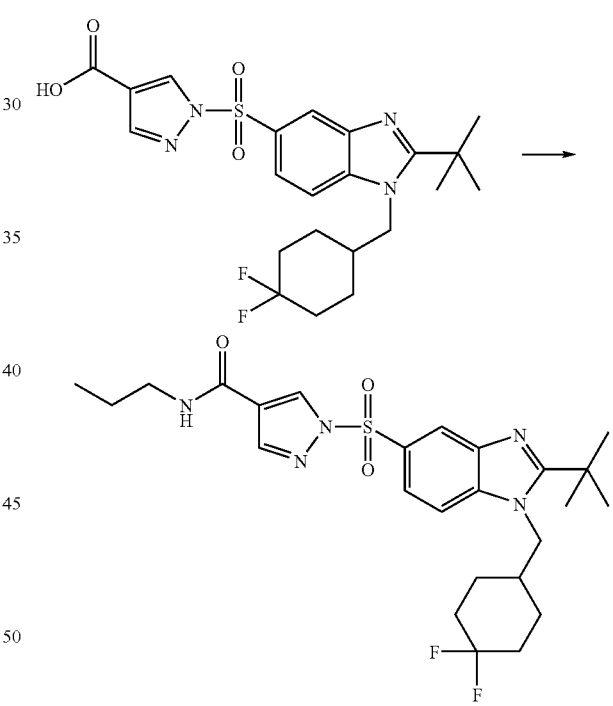

Following the same procedure in Example 72, step A, using n-propylamine (120 uL, 86 mg, 1.5 mmol), HATU (39 mg, 0.10 mmol), 1-({2-tert-butyl-1-[(4,4-difluorocyclohexyl)methyl]-1H-benzimidazol-5-yl}sulfonyl)-1H-pyrazole-4-carboxylic acid (45 mg, 0.09 mmol) and DIPEA (20 uL, 0.11 mmol) in DMF (10 mL). The crude product was purified by reverse-phase preparative HPLC using 10-90% MeCN/$H_2$n and lyophilized affording the title compound as the corresponding TFA salt corresponding TFA salt. Yield: 19 mg (31%); $^1$H NMR (400 MHz, $CDCl_3$) δ 0.95 (t, J=7.42 Hz, 3 H), 1.5 (m, 2 H), 1.56 (s, 9 H), 1.58-1.76 (m, 4 H), 2.01-2.20 (m, 3 H), 2.31 (m, 2 H), 3.28-3.38 (m, 2 H), 4.25 (d, J=7.42

Hz, 2 H), 6.03 (t, J=5.66 Hz, 1 H), 7.44 (d, J=8.79 Hz, 1 H), 7.88-7.97 (m, 2 H), 8.42 (d, J=1.56 Hz, 1 H), 8.47 (s, 1 H); MS (ESI) (M+H)$^+$=521.8.

Example 75

1-({2-tert-Butyl-1-[(4,4-difluorocyclohexyl)methyl]-1H-benzimidazol-5-yl}sulfonyl)-N-cyclopropyl-1H-pyrazole-4-arboxamide

Example 76

1-({2-tert-Butyl-1-[(4,4-difluorocyclohexyl)methyl]-1H-benzimidazol-5-yl}sulfonyl)-N-cyclobutyl-1H-pyrazole-4-carboxamide

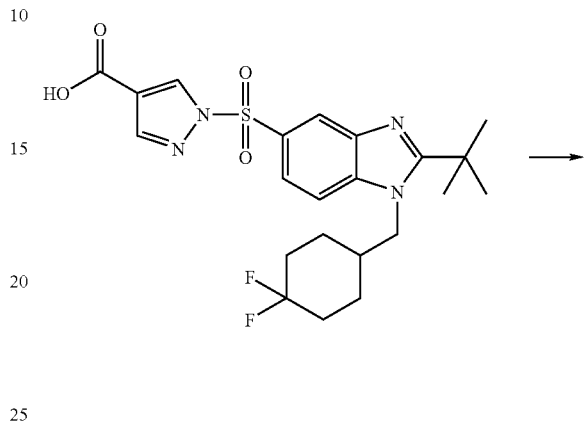

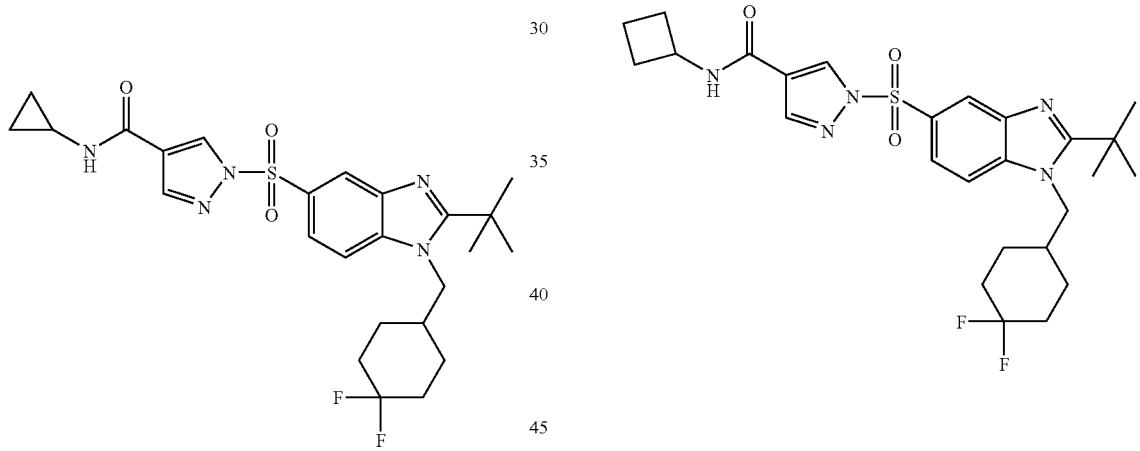

Following the same procedure in Example 72, step A, using cyclopropylamine (120 uL, 98 mg, 1.7 mmol), HATU (39 mg, 0.10 mmol), 1-({2-tert-butyl-1-[(4,4-difluorocyclohexyl)methyl]-1H-benzimidazol-5-yl}sulfonyl)-1H-pyrazole-4-carboxylic acid (45 mg, 0.09 mmol) and DIPLA (20 uL, 0.11 mmol) in DMF (10 mL). The crude product was purified by reverse-phase preparative HPLC using 10-90% MeCN/H$_2$O and lyophilized affording the title compound as the corresponding TFA salt. Yield: 20 mg (33%); $^1$H NMR (400 MHz, CDCl$_3$) δ 0.53-0.64 (m, 2 H), 0.76-0.88 (m, 2 H), 1.38-1.53 (m, 2 H), 1.52-1.59 (m, 9 H), 1.59-1.77 (m, 3 H), 2.01-2.22 (m, 3 H), 2.73-2.93 (m, 2 H), 4.26 (d, J=7.42 Hz, 2 H), 6.39 (d, J=1.95 Hz, 1 H), 7.45 (d, J=8.59 Hz, 1 H), 7.85-7.96 (m, 2 H), 8.39 (d, J=1.56 Hz, 1 H), 8.46 (s, 1 H); MS (ESI) (M+H)$^+$= 519.8; Anal. Calcd for C$_{25}$H$_{31}$F$_2$N$_5$O$_3$S+1.0 TFA+0.1 MeCN: C, 51.23; H, 5.11; N, 11.20. Found: C, 51.37; H, 5.06; N, 11.17.

Following the same procedure in Example 72, step A, using cyclobutylamine (120 uL, 100 mg, 1.4 mmol), HATU (39 mg, 0.10 mmol), 1-({2-tert-butyl-1-[(4,4-difluorocyclohexyl)methyl]-1H-benzimidazol-5-yl}sulfonyl)-1H-pyrazole-4-carboxylic acid (45 mg, 0.09 mmol) and DIPEA (20 uL, 0.11 mmol) in DMF (10 mL). The crude product was purified by reverse-phase preparative HPLC using 10-90% MeCN/H$_2$O and lyophilized affording the title compound as the corresponding TFA salt. Yield: 22 mg (36%); $^1$H NMR (400 MHz, CDCl$_3$) δ 1.40-1.55 (m, 2 H), 1.57 (s, 9 H), 1.60-1.81 (m, 4 H), 1.87-2.02 (m, 2 H), 2.03-2.22 (m, 3 H), 2.28-2.45 (m, 2 H), 2.68 (m, 2 H), 4.26 (d, J=7.42 Hz, 2 H), 4.43-4.58 (m, 1 H), 6.22 (d, J=7.62 Hz, 1 H), 7.45 (d, J=8.79 Hz, 1 H), 7.89-7.96 (m, 2 H), 8.42 (d, J=1.76 Hz, 1 H), 8.46 (d, J=0.78 Hz, 1 H); MS (ESI) (M+H)$^+$=533.8; Anal. Calcd for C$_{26}$H$_{33}$F$_2$N$_5$O$_3$S+0.6 TFA+0.2H$_2$O: C, 53.94; H, 5.66; N, 11.56. Found: C, 53.92; H, 5.51; N, 11.57.

Example 77

1-({2-tert-Butyl-1-[(4,4-difluorocyclohexyl)methyl]-1H-benzimidazol-5-yl}sulfonyl)-N-(cyclopropylmethyl)-1H-pyrazole-4-carboxamide

Example 78

1-({2-tert-Butyl-1-[(4,4-difluorocyclohexyl)methyl]-1H-benzimidazol-5-yl}sulfonyl)-N-(cyclobutylmethyl)-1H-pyrazole-4-carboxamide

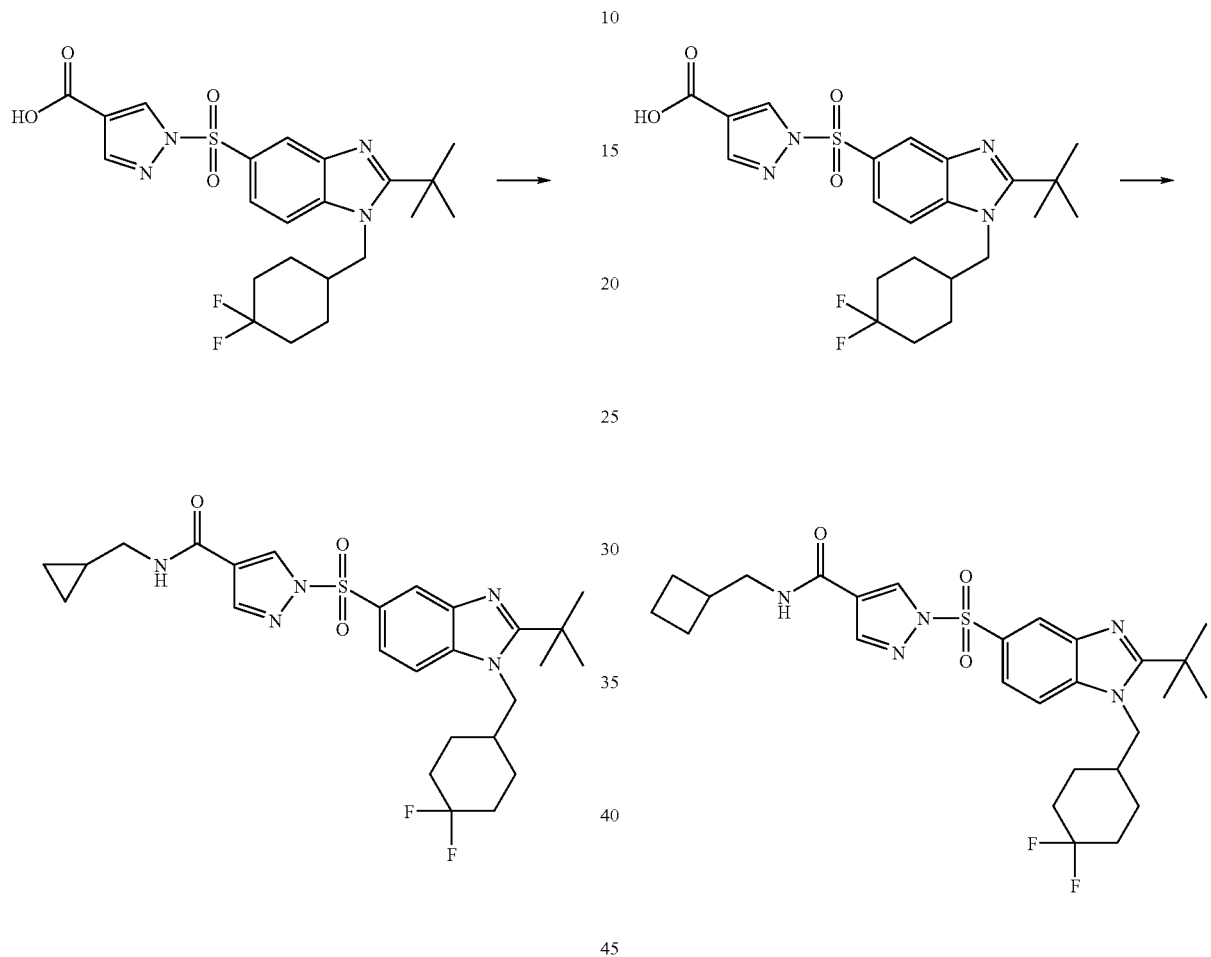

Following the same procedure in Example 72, step A, using (cyclopropylmethyl)amine (120 uL, 98 mg, 1.4 mmol), HATU (39 mg, 0.10 mmol), 1-({2-tert-butyl-1-[(4,4-difluorocyclohexyl)methyl]-1H-benzimidazol-5-yl}sulfonyl)-1H-pyrazole-4-carboxylic acid (45 mg, 0.09 mmol) and DIPEA (20 uL, 0.11 mmol) in DMF (10 mL). The crude product was purified by reverse-phase preparative HPLC using 10-90% MeCN/H$_2$O and lyophilized affording the title compound as the corresponding TFA salt. Yield: 17 mg (28%); $^1$H NMR (400 MHz, CDCl$_3$) δ 0.20-0.28 (m, 2 H), 0.49-0.57 (m, 2 H), 0.94-1.07 (m, 1 H), 1.42-1.55 (m, 2 H), 1.57 (s, 9 H), 1.60-1.76 (m, 3 H), 2.02-2.20 (m, 3 H), 3.24 (dd, J=7.23, 5.47 Hz, 2 H), 3.32 (s, 1 H), 4.27 (d, J=7.42 Hz, 2 H), 6.29 (t, J=5.37 Hz, 1 H), 7.46 (d, J=8.40 Hz, 1H), 7.93 (dd, J=8.69, 1.86 Hz, 1 H), 7.96 (d, J=0.78 Hz, 1 H), 8.43 (d, J=1.56 Hz, 1 H), 8.49 (d, J=0.78 Hz, 1 H); MS (ESI) (M+H)$^+$ 533.8; Anal. Calcd for C$_{26}$H$_{33}$F$_2$N$_5$O$_3$S+1.0 TFA: C, 51.93; H, 5.29; N, 10.81. Found: C, 51.98; H, 5.31; N, 10.81.

Following the same procedure in Example 72, step A, using (cyclobutylmethyl)amine (120 uL, 100 mg, 1.17 mmol), HATU (39 mg, 0.10 mmol), 1-({2-tert-butyl-1-[(4,4-difluorocyclohexyl)methyl]-1H-benzimidazol-5-yl}sulfonyl)-1H-pyrazole-4-carboxylic acid (45 mg, 0.09 mmol) and DIPEA (20 uL, 0.11 mmol) in DMF (10 mL). The crude product was purified by reverse-phase preparative HPLC using 10-90% MeCN/H$_2$O and lyophilized affording the title compound as the corresponding TFA salt. Yield: 23 mg (37%); $^1$H NMR (400 MHz, CDCl$_3$) δ 1.41-1.54 (m, 1 H), 1.56 (s, 9 H), 1.60-1.77 (m, 5 H), 1.83-1.98 (m, 2 H), 2.00-2.20 (m, 5 H), 2.26 (s, 2 H), 2.45-2.59 (m, 1 H), 3.40 (dd, J=7.32, 5.76 Hz, 2 H), 4.25 (d, J=7.62 Hz, 2 H), 5.97 (t, J=5.66 Hz, 1 H), 7.44 (d, J=8.59 Hz, 1 H), 7.88-7.95 (m, 2 H), 8.41 (d, J=1.37 Hz, 1 H), 8.46 (d, J=0.78 Hz, 1 H); MS (ESI) (M+H)$^+$=547.8; Anal. Calcd for C$_{27}$H$_{35}$F$_2$N$_5$O$_3$S+0.3 TFA+0.2H$_2$O: C, 56.62; H, 6.15; N, 11.96. Found: C, 56.71; H, 6.16; N, 11.86.

Example 79

1-({2-tert-Butyl-1-[(4,4-difluorocyclohexyl)methyl]-1H-benzimidazol-5-yl}sulfonyl)-N-isopropyl-1H-pyrazole-4-carboxamide

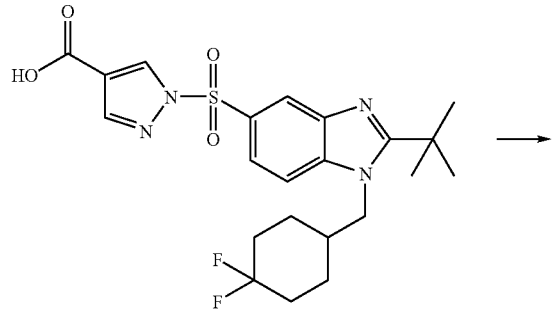

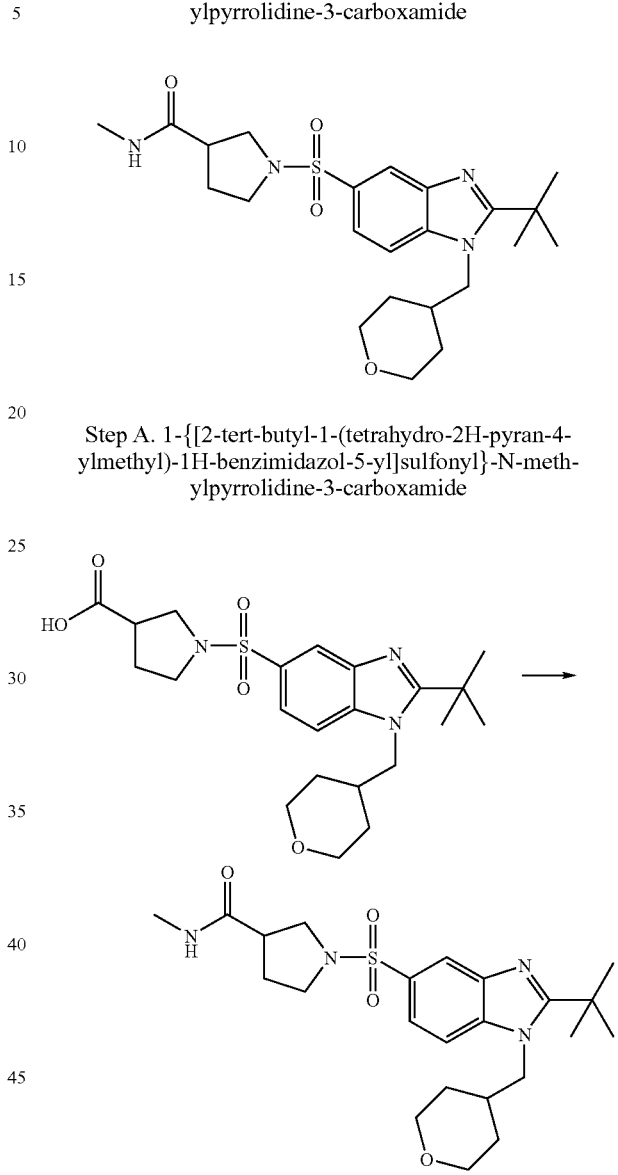

Following the same procedure in Example 72, step A, using isopropylamine (120 uL, 83 mg, 1.4 mmol), HATU (39 mg, 0.10 mmol), 1-({2-tert-butyl-1-[(4,4-difluorocyclohexyl)methyl]-1H-benzimidazol-5-yl}sulfonyl)-1H-pyrazole-4-carboxylic acid (45 mg, 0.09 mmol) and DIPEA (20 uL, 0.11 mmol) in DMF (10 mL). The crude product was purified by reverse-phase preparative HPLC using 10-90% MeCN/H$_2$O and lyophilized affording the title compound as the corresponding TFA salt. Yield: 28 mg (47%); $^1$H NMR (400 MHz, CDCl$_3$) δ 1.22 (d, J=6.44 Hz, 6 H), 1.43-1.54 (m, 2 H), 1.57 (s, 9 H), 1.59-1.75 (m, 3 H), 2.03-2.20 (m, 3 H), 2.81 (s, 1 H), 4.16-4.23 (m, 1 H), 4.26 (d, J=7.42 Hz, 2 H), 5.89 (d, J=7.81 Hz, 1 H), 7.42-7.49 (m, 1 H), 7.89-7.95 (m, 2 H), 8.41 (d, J=1.56 Hz, 1 H), 8.46 (d, J=0.78 Hz, 1 H); MS (ESI) (M+H)$^+$= 521.8; Anal. Calcd for C$_{25}$H$_{33}$F$_2$N$_5$O$_3$S+0.3 TFA+0.3H$_2$O: C, 54.79; H, 6.09; N, 12.48. Found: C, 54.78; H, 6.19; N, 12.46.

Example 80

1-{[2-tert-Butyl-1-(tetrahydro-2H-pyran-4-ylmethyl)-1H-benzimidazol-5-yl]sulfonyl}-N-methylpyrrolidine-3-carboxamide Step A. 1-{[2-tert-butyl-1-(tetrahydro-2H-pyran-4-ylmethyl)-1H-benzimidazol-5-yl]sulfonyl}-N-methylpyrrolidine-3-carboxamide HATU (70 mg, 0.18 mmol) and methylamine (0.6 mL, 2 M s in THF, 1.2 mmol) were added to a solution of 1-{[2-tert-butyl-1-(tetrahydro-2H-pyran-4-ylmethyl)-1H-benzimidazol-5-yl]sulfonyl}pyrrolidine-3-carboxylic acid (75 mg, 0.16 mmol) (see following steps B and C for preparation) and DIPEA (35 uL, 0.20 mmol) in DMF (5 mL). The reaction mixture was stirred for 4 h and the solvent was concentrated. The crude product was purified by reverse-phase preparative HPLC using 10-90% MeCN/H$_2$O and lyophilized affording the title compound as the corresponding TFA salt. Yield: 25 mg (26%); $^1$H NMR (400 MHz, CDCl$_3$) δ 1.51-1.66 (m, 4 H), 1.73 (s, 9 H), 1.84-1.96 (m, 1 H), 2.11-2.25 (m, 1 H), 2.25-2.39 (m, 1 H), 2.72 (d, J=4.49 Hz, 4 H), 3.01-3.14 (m, 1 H), 3.25-3.45 (m, 4 H), 3.85 (dd, J=10.64, 8.11 Hz, 1 H), 4.04 (d, J=11.13 Hz, 2 H), 4.41 (d, J=7.42 Hz, 2 H), 7.63 (d, J=8.59 Hz, 1 H), 7.86 (d, J=8.79 Hz, 1 H), 8.33 (s, 1 H); MS (ESI) (M+H)$^+$=462.8; Anal. Calcd for C$_{23}$H$_{34}$N$_4$O$_4$S+1.7 TFA+0.2H$_2$O: C, 48.04; H, 5.51; N, 8.49. Found: C, 48.01; H, 5.46; N, 8.33.

Step B. methyl 1-{[2-tert-butyl-1-(tetrahydro-2H-pyran-4-ylmethyl)-1H-benzimidazol-5-yl]sulfonyl}pyrrolidine-3-carboxylate

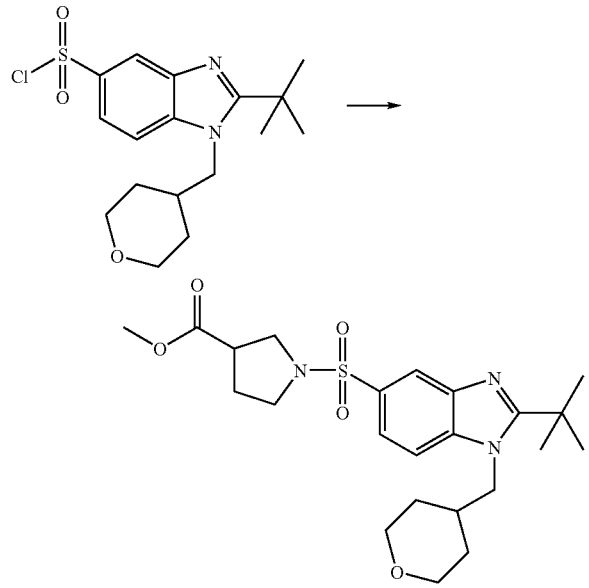

A suspension of 2-tert-butyl-1-(tetrahydro-2H-pyran-4-ylmethyl)-1H-benzimidazole-5-sulfonyl chloride (1.21 g, 3.26 mmol) in DCL (25 mL) was slowly added to a solution of 3-(methoxycarbonyl)pyrrolidine hydrochloride (0.46 g, 3.58 mmol) and DIPLA (5.6 mL, 32.6 mmol) in DCE (80 mL). The reaction mixture was stirred for 3 h and the solvent was concentrated. The product was purified by MPLC on silica gel using EtOAc as eluent to provide the title compound as white solid. Yield: 0.60 g (39%); $^1$H NMR (400 MHz, CDCl$_3$) δ 1.49-1.56 (m, 3 H), 1.55-1.58 (m, 1 H), 1.59 (s, 9 H), 1.93-2.13 (m, 2 H), 2.20-2.36 (m, 1 H), 2.89-3.01 (m, 1 H), 3.28-3.41 (m, 5 H), 3.60 (s, 3 H), 3.61-3.66 (m, 1 H), 3.94-4.06 (m, 2 H), 4.25 (d, J=7.42 Hz, 2 H), 7.44 (dd, J=8.50, 0.49 Hz, 1 H), 7.72 (dd, J=8.59, 1.76 Hz, 1 H), 8.24 (dd, J=1.76, 0.59 Hz, 1 H); MS (ESI) (M+H)$^+$=464.0.

Step C. 1-{[2-tert-butyl-1-(tetrahydro-2H-pyran-4-ylmethyl)-1H-benzimidazol-5-yl]sulfonyl}pyrrolidine-3-carboxylic acid

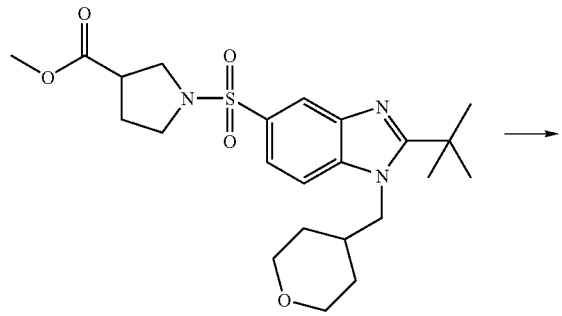

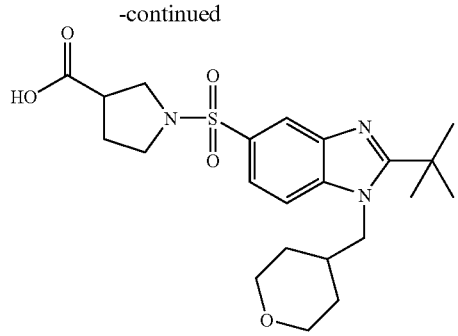

NaOH (2 mL, 2 M, 4.0 mmol) was added to a solution of methyl 1-{[2-tert-butyl-1-(tetrahydro-2H-pyran-4-ylmethyl)-1H-benzimidazol-5-yl]sulfonyl}pyrrolidine-3-carboxylate (570 mg, 1.22 mmol) in a 1:1 mixture of MeOH:H$_2$O (30 mL) at ambient temperature. The reaction mixture was stirred overnight and diluted with water (100 mL). The solvent was concentrated to 100 mL. The resulting solution was neutralized with HCl solution, the product was extracted with EtOAc and dried over anhydrous Na$_2$SO$_4$. The solvent was concentrated to provide the title compound as white solid. Yield: 480 mg (87%); MS (ESI) (M+H)$^+$=450.1.

Example 81

1-{[2-tert-Butyl-1-(tetrahydro-2H-pyran-4-ylmethyl)-1H-benzimidazol-5-yl]sulfonyl}-N-cyclopropylpyrrolidine-3-carboxamide

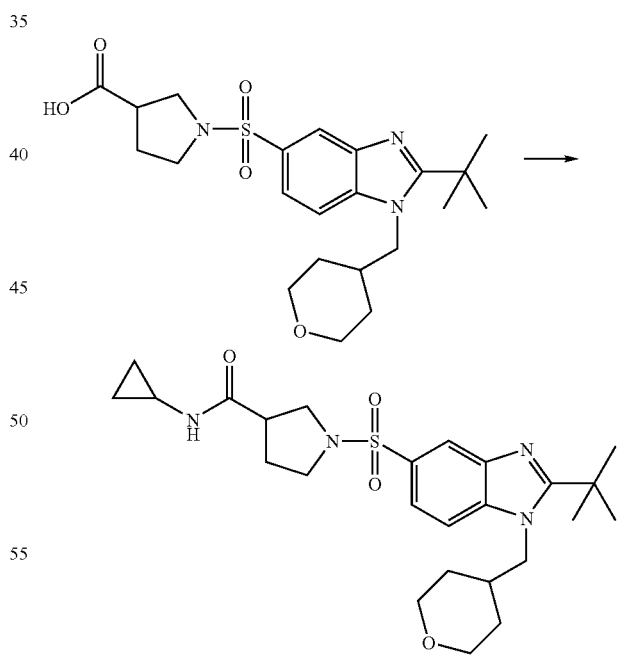

Following the same procedure in Example 80, step A, using cyclopropylamine (100 uL, 82 mg, 1.4 mmol), HATU (70 mg, 0.18 mmol), 1-{[2-tert-butyl-1-(tetrahydro-2H-pyran-4-ylmethyl)-1H-benzimidazol-5-yl]sulfonyl}pyrrolidine-3-carboxylic acid (75 mg, 0.16 mmol) and DIPEA (35 uL, 0.20 mmol) in DMF (5 mL). The crude product was purified by reverse-phase preparative HPLC using 10-90% MeCN/H$_2$O and lyophilized affording the title compound as the corresponding TFA salt. Yield: 27 mg (26%); $^1$H NMR (400 MHz, CDCl$_3$) δ 0.39-0.52 (m, 2 H), 0.62-0.74 (m, 2 H), 1.50-1.67 (m, 4 H), 1.74 (s, 9 H), 1.82-1.95 (m, 1 H), 2.04-2.21 (m, 1 H), 2.26-2.40 (m, 1 H), 2.54-2.75 (m, 2 H), 3.02-3.14 (m, 1 H), 3.26 (t, J=9.96 Hz, 1 H), 3.31-3.46 (m, 3 H), 3.69 (dd, J=10.35, 8.01 Hz, 1 H), 4.03 (d, J=11.13 Hz, 2 H), 4.42 (d, J=7.23 Hz, 2 H), 6.95 (d, J=2.73 Hz, 1 H), 7.65 (d, J=8.59 Hz, 1 H), 7.79 (dd, J=8.69, 1.27 Hz, 1 H), 8.18 (s, 1 H); MS (ESI) (M+H)$^+$=488.7; Anal. Calcd for C$_{25}$H$_{36}$N$_4$O$_4$S+1.6 TFA+0.4H$_2$O: C, 49.94; H, 5.71; N, 8.26. Found: C, 49.87; H, 5.70; N, 8.29.

Example 82

1-{[2-tert-Butyl-1-(tetrahydro-2H-pyran-4-ylmethyl)-1H-benzimidazol-5-yl]sulfonyl}-N-isopropylpyrrolidine-3-carboxamide

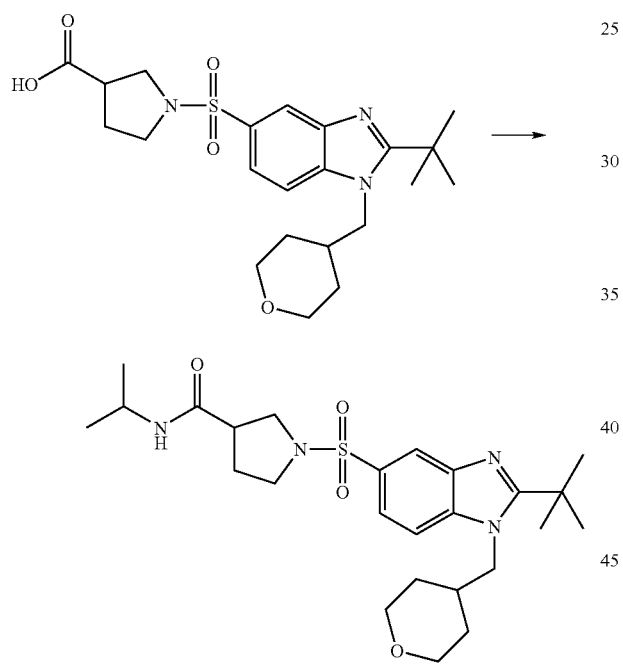

Following the same procedure in Example 80, step A, using isopropylamine (100 uL, 69 mg, 1.17 mmol), HATU (70 mg, 0.18 mmol), 1-{[2-tert-butyl-1-(tetrahydro-2H-pyran-4-ylmethyl)-1H-benzimidazol-5-yl]sulfonyl}pyrrolidine-3-carboxylic acid (75 mg, 0.16 mmol) and DIPEA (35 uL, 0.20 mmol) in DMF (5 mL The crude product was purified by reverse-phase preparative HPLC using 10-90% MeCN/H$_2$O and lyophilized affording the title compound as the corresponding TFA salt. Yield: 47 mg (46%); $^1$H NMR (400 MHz, CDCl$_3$) δ 1.08 (dd, J=6.44, 2.73 Hz, 6 H), 1.53-1.68 (m, 4 H), 1.74 (s, 9 H), 1.84-1.99 (m, 1 H), 2.01-2.16 (m, 1 H), 2.27-2.42 (m, 1 H), 2.60-2.76 (m, 1 H), 3.04-3.17 (m, 1 H), 3.20-3.29 (m, 1 H), 3.30-3.45 (m, 3 H), 3.62 (dd, J=10.25, 8.11 Hz, 1 H), 3.88-4.00 (m, 1 H), 4.03 (d, J=11.13 Hz, 2H), 4.43 (d, J=7.23 Hz, 2 H), 6.41 (d, J=7.62 Hz, 1 H), 7.66 (d, J=8.79 Hz, 1 H), 7.76 (dd, J=8.79, 1.37 Hz, 1 H), 8.11 (d, J=1.17 Hz, 1 H); MS (ESI) (M+H)$^+$=491.0; Anal. Calcd for C$_{25}$H$_{38}$N$_4$O$_4$S+2.1 TFA: C, 48.04; H, 5.54; N, 7.67. Found: C, 48.06; H, 5.56; N, 7.60.

Example 83

1-{[2-tert-Butyl-1-(tetrahydro-2H-pyran-4-ylmethyl)-1H-benzimidazol-5-yl]sulfonyl}-N-cyclobutylpyrrolidine-3-carboxamide

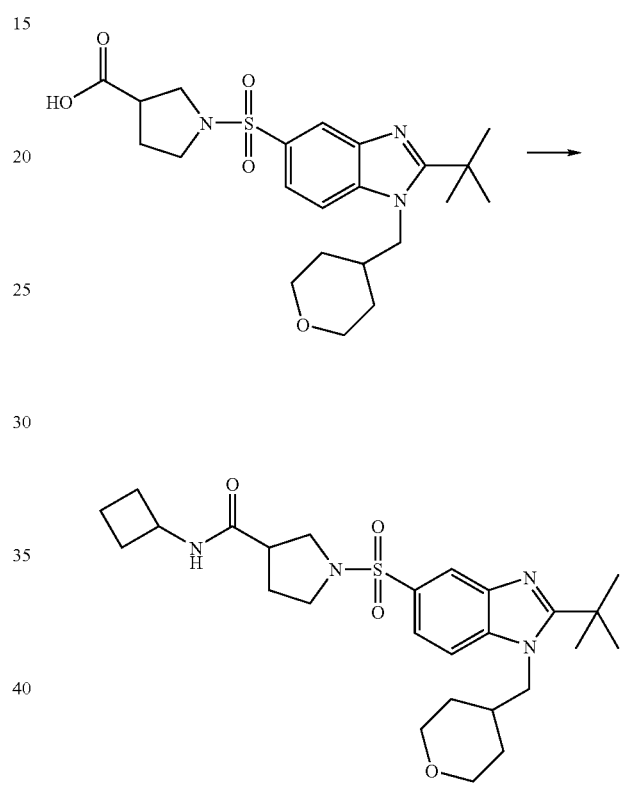

Following the same procedure in Example 80, step A, using cyclobutylamine (100 uL, 83 mg, 1.17 mmol), HATU (70 mg, 0.18 mmol), 1-{[2-tert-butyl-1-(tetrahydro-2H-pyran-4-ylmethyl)-1H-benzimidazol-5-yl]sulfonyl}pyrrolidine-3-carboxylic acid (75 mg, 0.16 mmol) and DIPLA (35 uL, 0.20 mmol) in DMF (5 mL). The crude product was purified by reverse-phase preparative HPLC using 10-90% MeCN/H$_2$O and lyophilized affording the title compound as the corresponding TFA salt. Yield: 72 mg (70%); $^1$H NMR (400 MHz, CDCl$_3$) δ 10.53-10.63 (m, 4 H), 1.66 (dd, J=10.55, 7.81 Hz, 2 H), 1.74 (s, 9 H), 1.79-1.95 (m, 3 H), 2.02-2.15 (m, 1 H), 2.16-2.28 (m, 2 H), 2.28-2.40 (m, 1 H), 2.62-2.74 (m, 1 H), 3.05-3.15 (m, 1 H), 3.24 (t, J=9.96 Hz, 1 H), 3.29-3.43 (m, 3 H), 3.67 (dd, J=10.25, 8.11 Hz, 1 H), 4.03 (d, J=11.33 Hz, 2 H), 4.19-4.32 (m, 1 H), 4.42 (d, J=7.23 Hz, 2 H), 6.81 (d, J=7.62 Hz, 1 H), 7.64 (d, J=8.79 Hz, 1 H), 7.77 (dd, J=8.69, 1.07 Hz, 1 H), 8.17 (s, 1 H); MS (ESI) (M+H)$^+$=503.0; Anal. Calcd for C$_{26}$H$_{38}$N$_4$O$_4$S+1.6 TFA+0.2H$_2$O: C, 50.92; H, 5.85; N, 8.13. Found: C, 50.95; H, 5.85; N, 7.89.

Example 84

(3S)-1-{[2-tert-Butyl-1-(tetrahydro-2H-pyran-4-ylmethyl)-1H-benzimidazol-5-yl]sulfonyl}-N-cyclopropylpiperidine-3-carboxamide

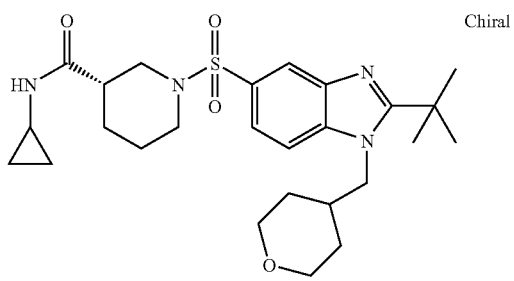

Step A. (3S)-1-{[2-tert-butyl-1-(tetrahydro-2H-pyran-4-ylmethyl)-1H-benzimidazol-5-yl]sulfonyl}-N-cyclopropylpiperidine-3-carboxamide

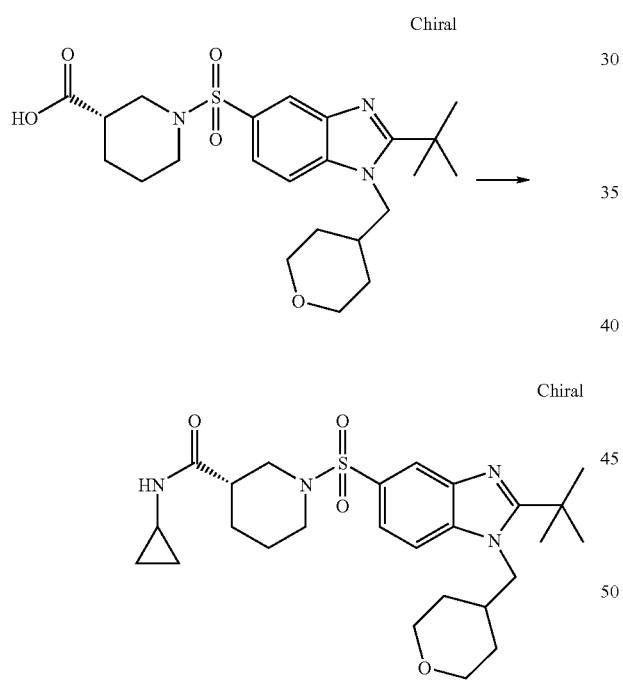

HATU (198 mg, 0.52 mmol) and cyclopropylamine (30 mg, 0.52 mmol) were added to a solution of (3S)-1-{[2-tert-butyl-1-(tetrahydro-2H-pyran-4-ylmethyl)-1H-benzimidazol-5-yl]sulfonyl}piperidine-3-carboxylic acid (220 mg, 0.47 mmol) (see following steps B and C for preparation) and DIPEA (100 uL, 0.56 mmol) in DMF (20 mL). The reaction mixture was stirred overnight at ambient temperature and the solvent was concentrated. The crude product was purified by reverse-phase preparative HPLC using 10-90% MeCN/H$_2$O and lyophilized affording the title compound as the corresponding TFA salt. Yield: 108 mg (37%); [α]$_D$ −66.0° (c=1.28, MeOH); $^1$H NMR (400 MHz, CDCl$_3$) δ 0.44-0.59 (m, 2 H), 0.68-0.80 (m, 2 H), 1.37-1.50 (m, 1 H), 1.51-1.64 (m, 5 H), 1.65-1.82 (m, 1 H), 2.24-2.43 (m, 2 H), 2.53 (td, J=11.38, 2.25 Hz, 1 H), 2.62-2.75 (m, 2 H), 3.28-3.44 (m, 2 H), 3.55 (d, J=11.91 Hz, 1 H), 3.66 (dd, J=12.40, 3.22 Hz, 1 H), 3.96-4.10 (m, 2 H), 4.38 (d, J=7.23 Hz, 2 H), 6.63 (d, J=2.93 Hz, 1 H), 7.59 (d, J=8.79 Hz, 1 H), 7.70 (dd, J=8.69, 1.66 Hz, 1 H), 8.20 (d, J=1.17 Hz, 1 H); MS (ESI) (M+H)$^+$= 502.8; Anal. Calcd for C$_{26}$H$_{38}$N$_4$O$_4$S+1.2 TFA+0.5H$_2$O Calculated: C, 52.60; H, 6.25; N, 8.64. Found: C, 52.53; H, 6.19; N, 8.63.

Step B. Ethyl (3S)-1-{[2-tert-butyl-1-(tetrahydro-2H-pyran-4-ylmethyl)-1H-benzimidazol-5-yl]sulfonyl}piperidine-3-carboxylate

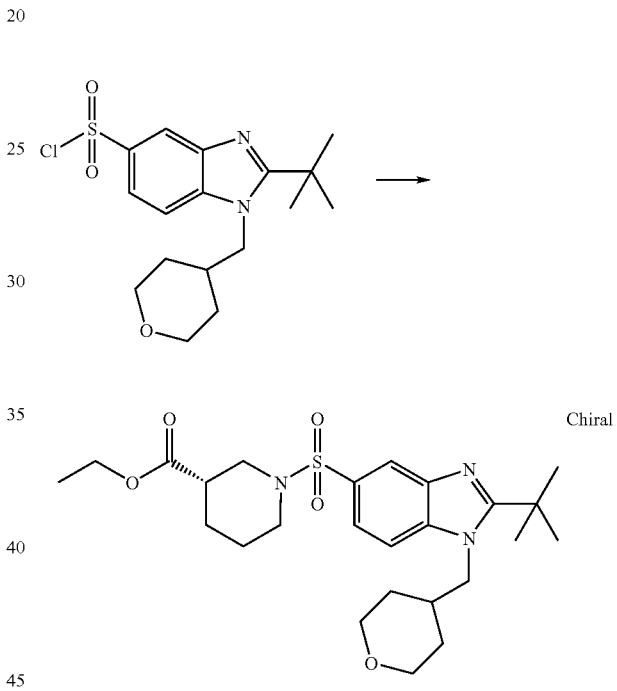

A suspension of 2-tert-butyl-1-(tetrahydro-2H-pyran-4-ylmethyl)-1H-benzimidazole-5-sulfonyl chloride (300 mg, 0.80 mmol) in DCE (5 mL) was slowly added to a solution of ethyl (3S)-piperidine-3-carboxylate (140 mg, 0.88 mmol) and DIPEA (1.4 mL, 8.0 mmol) in DCE (25 mL). The reaction mixture was stirred overnight at ambient temperature and the solvent was concentrated. The product was purified by MPLC on silica gel using 60-90% EtOAc/heptane as eluent to provide the title compound as white solid. Yield: 276 mg (69%). $^1$H NMR (400 MHz, CDCl$_3$) δ 1.26 (t, J=7.13 Hz, 3 H), 1.33 (td, J=12.21, 3.32 Hz, 1 H), 1.50-1.57 (m, 3 H), 1.59 (s, 9 H), 1.62-1.73 (m, 2 H), 1.73-1.83 (m, 1 H), 1.91-2.01 (m, 1 H), 2.30 (td, J=11.43, 2.93 Hz, 2 H), 2.44 (t, J=11.13 Hz, 1 H), 2.58-2.69 (m, 1 H), 3.28-3.40 (m, 2 H), 3.65-3.74 (m, 1 H), 3.91 (dd, J=11.43, 3.81 Hz, 1 H), 4.01 (dd, J=11.33, 2.93 Hz, 2 H), 4.13 (q, J=7.23 Hz, 2H), 4.25 (d, J=7.42 Hz, 2 H), 7.43 (d, J=8.59 Hz, 1 H), 7.64 (dd, J=8.59, 1.76 Hz, 1 H), 8.19 (d, J=1.76 Hz, 1 H). MS (ESI) (M+H)$^+$=492.0.

Step C. (3S)-1-{[2-tert-butyl-1-(tetrahydro-2H-pyran-4-ylmethyl)-1H-benzimidazol-5-yl]sulfonyl}piperidine-3-carboxylic acid

Step A. (3R)-1-{[2-tert-butyl-1-(tetrahydro-2H-pyran-4-ylmethyl)-1H-benzimidazol-5-yl]sulfonyl}-N-cyclopropylpiperidine-3-carboxamide

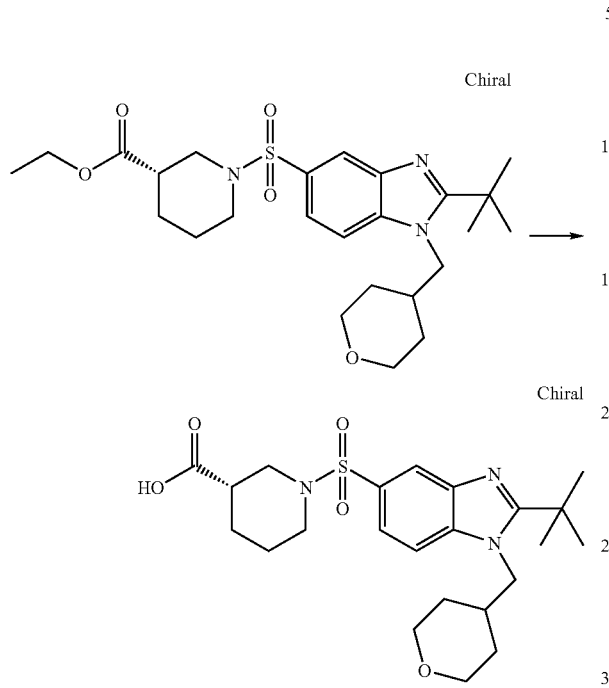

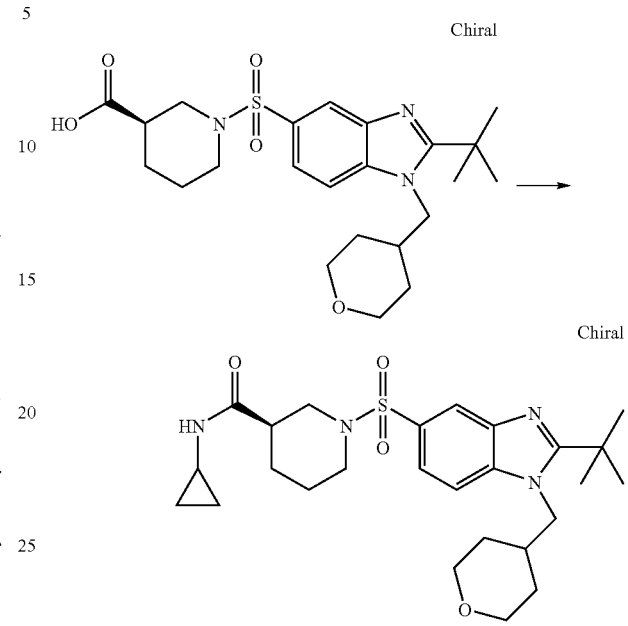

NaOH (0.15 mL, 2M, 0.3 mmol) was added to a solution of ethyl (3S)-1-{[2-tert-butyl-1-(tetrahydro-2H-pyran-4-ylmethyl)-1H-benzimidazol-5-yl]sulfonyl}piperidine-3-carboxylate (265 mg, 0.54 mmol) in a 1:1 mixture of MeOH:H$_2$O (10 mL) at ambient temperature. The reaction mixture was stirred overnight and diluted with water (50 mL). The solvent was concentrated to 50 mL. The resulting solution was neutralized with HCl solution, the product was extracted with EtOAc and dried over anhydrous Na$_2$SO$_4$. The solvent was concentrated to provide the title compound as white solid. Yield: 220 mg (88%); MS (ESI) (M+H)$^+$=464.1.

Example 85

(3R)-1-{[2-tert-Butyl-1-(tetrahydro-2H-pyran-4-ylmethyl)-1H-benzimidazol-5-yl]sulfonyl}-N-cyclopropylpiperidine-3-carboxamide HATU (212 mg, 0.56 mmol) and cyclopropylamine (32 mg, 0.56 mmol) were added to a solution of (3R)-1-{[2-tert-butyl-1-(tetrahydro-2H-pyran-4-ylmethyl)-1H-benzimidazol-5-yl]sulfonyl}piperidine-3-carboxylic acid (236 mg, 0.51 mmol) (see following steps B and C for preparation) and DIPEA (105 uL, 0.61 mmol) in DMF (20 mL). The reaction mixture was stirred overnight at ambient temperature and the solvent was concentrated. The crude product was purified by reverse-phase preparative HPLC using 10-90% MeCN/H$_2$O and lyophilized affording the title compound as the corresponding TFA salt. Yield: 164 mg (52%); [α]$_D$ +64.9° (c=1.34, MeOH); $^1$H NMR (400 MHz, CDCl$_3$) δ0.45-0.58 (m, 2 H), 0.67-0.82 (m, 2 H), 1.50-1.64 (m, 5 H), 1.63-1.84 (m, 12H), 2.25-2.46 (m, 2 H), 2.55 (t, J=9.67 Hz, 1 H), 2.62-2.78 (m, 2 H), 3.26-3.44 (m, 2 H), 3.50-3.61 (m, 1 H), 3.62-3.74 (m, 1 H), 3.95-4.11 (m, 2 H), 4.37 (d, J=7.03 Hz, 2 H), 7.59 (d, J=8.98 Hz, 1 H), 7.68-7.79 (m, 1 H), 8.16-8.28 (m, 1 H); MS (ESI) (M+H)$^+$=502.8; Anal. Calcd for C$_{26}$H$_{38}$N$_4$O$_4$S+1.2 TFA+0.7H$_2$O: C, 52.31; H, 6.28; N, 8.59. Found: C, 52.24; H, 6.23; N, 8.59.

Step B. Ethyl (3R)-1-{[2-tert-butyl-1-(tetrahydro-2H-pyran-4-ylmethyl)-1H-benzimidazol-5-yl]sulfonyl}piperidine-3-carboxylate

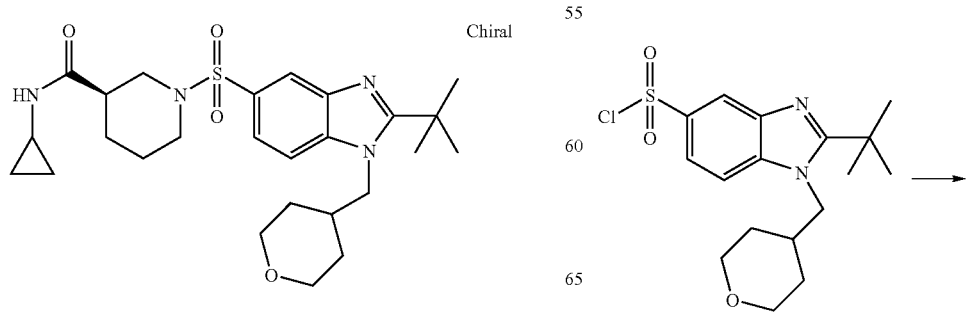

-continued

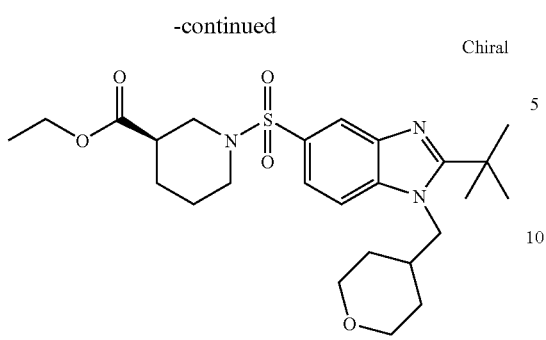

A suspension of 2-tert-butyl-1-(tetrahydro-2H-pyran-4-yl-methyl)-1H-benzimidazole-5-sulfonyl chloride (300 mg, 0.80 mmol) in DCE (5 mL) was slowly added to a solution of ethyl (3R)-piperidine-3-carboxylate (140 mg, 0.88 mmol) and DIPEA (1.4 mL, 8.0 mmol) in DCE (25 mL). The reaction mixture was stirred overnight at ambient temperature and the solvent was concentrated. The product was purified by MPLC on silica gel using 60-90% EtOAc/Heptane to provide the title compound as white solid. Yield: 265 mg (66%); $^1$H NMR (400 MHz, CDCl3) δ 1.26 (t, J=7.13 Hz, 3 H), 1.33 (td, J=12.55, 4.00 Hz, 1 H), 1.50-1.57 (m, 3 H), 1.59 (s, 9 H), 1.62-1.71 (m, 2 H), 1.72-1.84 (m, 1 H), 1.90-2.02 (m, 1 H), 2.22-2.38 (m, 2 H), 2.44 (t, J=11.03 Hz, 1 H), 2.57-2.69 (m, 1 H), 3.28-3.41 (m, 2 H), 3.70 (d, J=11.33 Hz, 1 H), 3.91 (dd, J=11.43, 3.81 Hz, 1 H), 4.01 (dd, J=11.23, 2.83 Hz, 2 H), 4.13 (q, J=7.16 Hz, 2 H), 4.25 (d, J=7.42 Hz, 2 H), 7.43 (d, J=8.59 Hz, 1 H), 7.64 (dd, J=8.40, 1.76 Hz, 1 H), 8.18 (d, J=1.17 Hz, 1 H); MS (ESI) (M+H)$^+$=492.0.

Step C. (3R)-1-{[2-tert-butyl-1-(tetrahydro-2H-pyran-4-ylmethyl)-1H-benzimidazol-5-yl]sulfonyl}piperidine-3-carboxylic acid

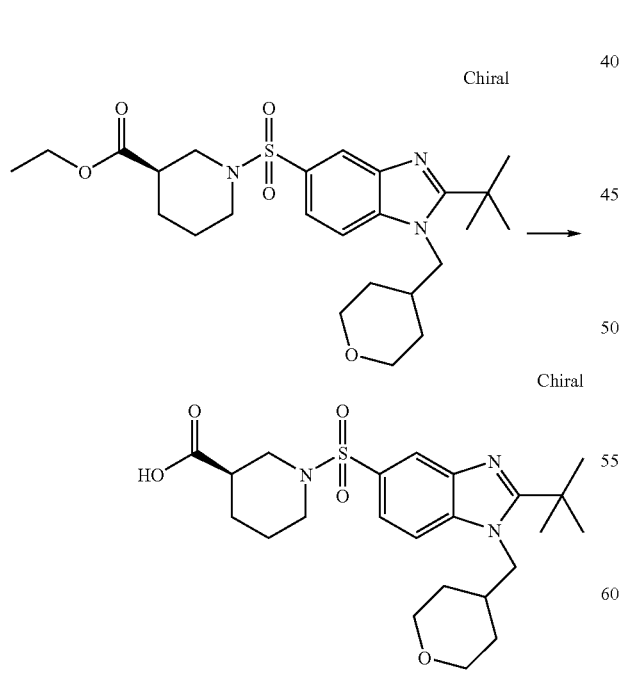

NaOH (0.5 mL, 2 M, 1.0 mmol) was added to a solution of ethyl (3R)-1-{[2-tert-butyl-1-(tetrahydro-2H-pyran-4-ylmethyl)-1H-benzimidazol-5-yl]sulfonyl}piperidine-3-car-boxylate (255 mg, 0.52 mmol) in a 1:1 mixture of MeOH:H$_2$O (10 mL) at ambient temperature. The reaction mixture was stirred overnight and diluted with water (50 mL). The solvent was concentrated to 50 mL. The resulting solution was neutralized with HCl solution, the product was extracted with EtOAc and dried over anhydrous Na$_2$SO$_4$. The solvent was concentrated to provide the title compound as white solid. Yield: 236 mg (98%); MS (ESI) (M+H)$^+$=464.1.

Example 86

4-({2-tert-Butyl-1-[(4,4-difluorocyclohexyl)methyl]-1H-benzimidazol-5-yl}sulfonyl)-N-cyclopropylmorpholine-2-carboxamide

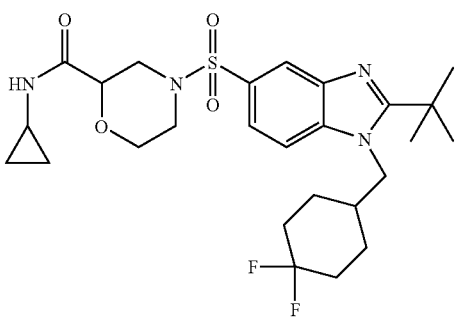

Step A. 4-({2-tert-butyl-1-[(4,4-difluorocyclohexyl)methyl]-1H-benzimidazol-5-yl}sulfonyl)-N-cyclopropylmorpholine-2-carboxamide

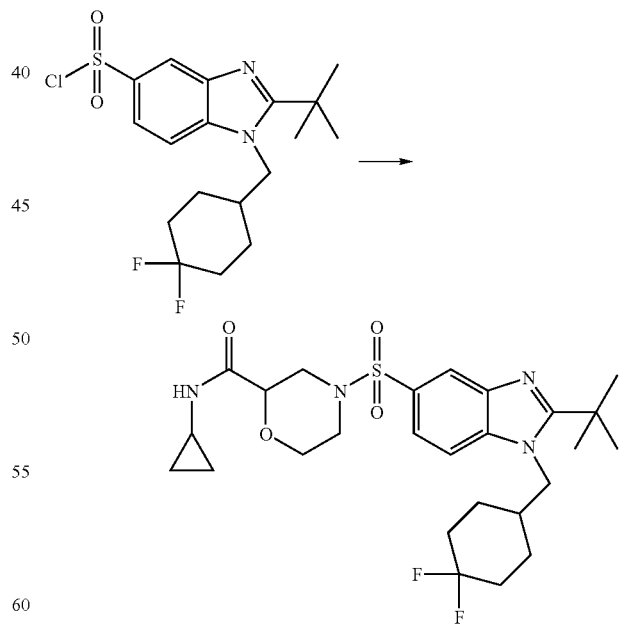

2-tert-Butyl-1-[(4,4-difluorocyclohexyl)methyl]-1H-benzimidazole-5-sulfonyl chloride (0.95 g, 2.35 mmol) was added to a solution of N-cyclopropylmorpholine-2-carboxamide (0.8 g, 2.6 mmol) (see following steps B and C for preparation) and DIPEA (0.82 mL, 4.7 mmol) in DCE (80 mL) at 80° C. The reaction mixture was stirred for 1 h and the solvent was concentrated. The product was purified by MPLC on silica gel using 60-90% EtOAc/Heptane to provide the title compound as white solid. Yield: 1.1 g (71%); $^1$H NMR (400 MHz, CDCl$_3$) δ 0.39-0.54 (m, 2 H), 0.69-0.80 (m, 2 H), 1.49-1.69 (m, 3 H), 1.72 (s, 9 H), 1.75-1.86 (m, 3 H), 2.09 (t, J=10.84 Hz, 1 H), 2.2 (m, 3 H), 2.38-2.50 (m, 1 H), 2.61-2.71 (m, 1 H), 3.56 (d, J=11.91 Hz, 1 H), 3.67 (td, J=11.52, 1.95 Hz, 1 H), 3.91-4.06 (m, 3 H), 4.44 (d, J=7.03 Hz, 2 H), 6.58 (d, J=3.12 Hz, 1 H), 7.63-7.73 (m, 2 H), 8.04 (s, 1 H); MS (ESI) (M+H)$^+$=538.8; Anal. Calcd for C$_{26}$H$_{36}$F$_2$N$_4$O$_4$S+2.2 TFA: C, 46.25; H, 4.88; N, 7.10. Found: C, 46.26; H, 5.00; N, 6.95.

Step B. 9H-fluoren-9-ylmethyl 2-[(cyclopropylamino)carbonyl]morpholine-4-carboxylate

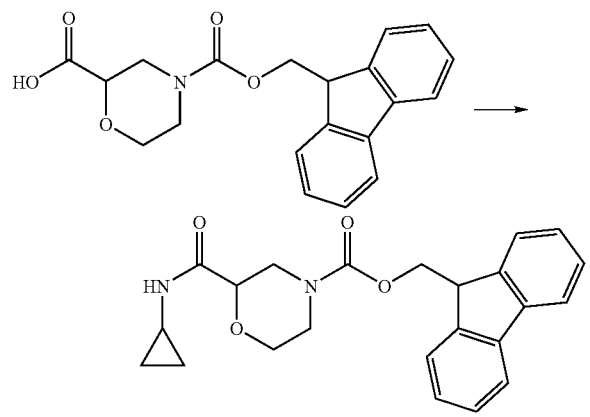

HATU (1.17 g, 3.0 mmol) and cyclopropylamine (0.17 g, 3.0 mmol) were added to a solution of 4-[(9H-fluoren-9-ylmethoxy)carbonyl]morpholine-2-carboxylic acid (1.0 g, 2.9 mmol) and DIPEA (0.56 mL, 3.2 mmol) in DMF (50 mL). The reaction mixture was stirred for 2 hrs. at ambient temperature and the solvent was concentrated. The product was recovered in EtOAc and washed with water, saturated NaHCO$_3$ solution, water and brine. The organic layer was dried over anhydrous MgSO$_4$ and the solvent was concentrated to provide the title compound that was used for the next step without further purification. MS (ESI) (M+H)$^+$=393.0.

Step C. N-cyclopropylmorpholine-2-carboxamide

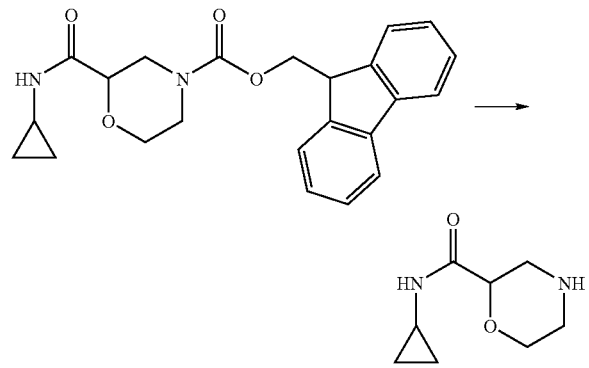

NaOH (1 mL, 2 M, 2.0 mmol) was slowly added to a solution of 9H-fluoren-9-ylmethyl 2-[(cyclopropylamino)carbonyl]morpholine-4-carboxylate (1.0 g, 2.6 mmol) in MeOH (70 mL) at ambient temperature. The reaction mixture was stirred for 3 h and the solvent was concentrated. The product was recovered in water (50 mL) and the mixture was neutralized to pH 7 using HCl solution. The product was extracted with EtOAc and dried over anhydrous Na$_2$SO$_4$. The solvent was concentrated to provide the title compound that was used for the next step without further purification. Yield: 0.8 g.

Example 87

4-{[2-tert-Butyl-1-(tetrahydro-2H-pyran-4-ylmethyl)-1H-benzimidazol-5-yl]sulfonyl}-N-cyclopropylmorpholine-2-carboxamide

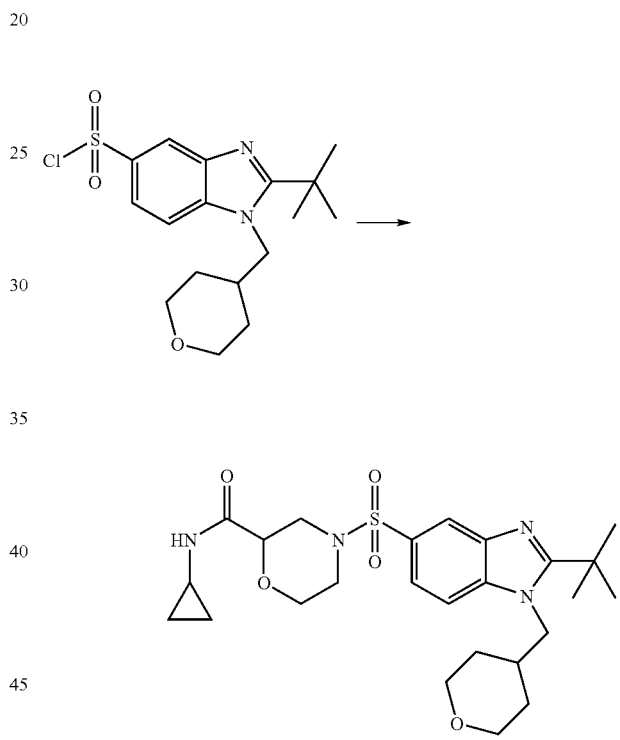

2-tert-Butyl-1-(tetrahydro-2H-pyran-4-ylmethyl)-1H-benzimidazole-5-sulfonyl chloride (0.50 g, 1.3 mmol) was added to a solution of N-cyclopropylmorpholine-2-carboxamide (0.34 g, 2.0 mmol) and DIPEA (1.1 mL, 6.7 mmol) in DCE at 50° C. The reaction mixture was stirred for 4 h and the solvent was concentrated. The crude product was purified by reverse-phase preparative HPLC using 10-90% MeCN/H$_2$O and lyophilized affording the title compound as the corresponding TFA salt. Yield: 0.38 g (46%); $^1$H NMR (400 MHz, CDl$_3$) δ 0.37-0.55 (m, 2 H), 0.68-0.80 (m, 2 H), 1.52-1.65 (m, 4 H), 1.72 (s, 9 H), 2.11 (t, J=11.72 Hz, 1 H), 2.26-2.38 (m, 1 H), 2.47 (td, J=11.62, 2.93 Hz, 1 H), 2.60-2.71 (m, 1 H), 3.30-3.43 (m, 2 H), 3.59 (d, J=11.72 Hz, 1 H), 3.68 (td, J=11.57, 2.44 Hz, 1 H), 3.92-4.10 (m, 5 H), 4.41 (d, J=7.23 Hz, 2 H), 6.54 (d, J=3.52 Hz, 1 H), 7.63-7.69 (m, 1 H), 7.70-7.77 (m, 1 H), 8.14 (d, J=1.37 Hz, 1H); MS (ESI) (M+H)$^+$=504.8.

Example 88

(3S)-1-{[2-tert-Butyl-1-(tetrahydro-2H-pyran-4-ylmethyl)-1H-benzimidazol-5-yl]sulfonyl}-N-cyclopropylpyrrolidine-3-carboxamide

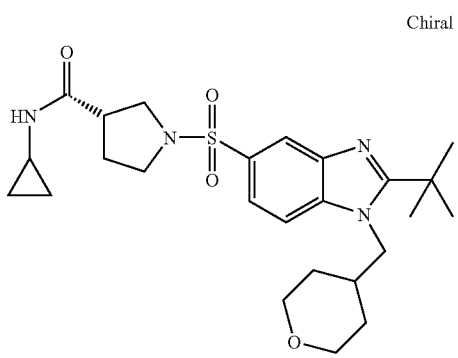

Step A. (3S)-1-{[2-tert-butyl-1-(tetrahydro-2H-pyran-4-ylmethyl)-1H-benzimidazol-5-yl]sulfonyl}-N-cyclopropylpyrrolidine-3-carboxamide

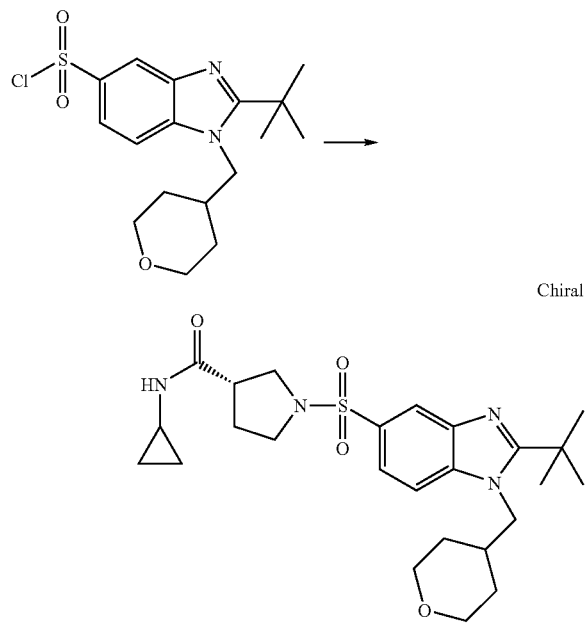

2-tert-Butyl-1-(tetrahydro-2H-pyran-4-ylmethyl)-1H-benzimidazole-5-sulfonyl chloride (95 mg, 0.25 mmol) was added to a solution of (3S)-3-[(cyclopropylamino)carbonyl]pyrrolidinium trifluoroacetate (100 mg, 0.38 mmol) (see following step B for preparation) and DIPEA (0.22 mL, 1.27 mmol) in DCE (15 mL) at 50° C. The reaction mixture was stirred for 3 h and the solvent was concentrated. The crude product was purified by reverse-phase preparative HPLC using 10-90% MeCN/H$_2$O and lyophilized affording the title compound as the corresponding TFA salt. Yield: 41 mg (26%); [α]$_D$ −10.5° (c=0.43, MeOH); $^1$H NMR (400 MHz, CDCl$_3$) δ 0.40-0.56 (m, 2 H), 0.62-0.74 (m, 2 H), 1.50-1.66 (m, 4 H), 1.73 (s, 9 H), 1.85-1.99 (m, 1 H), 2.05-2.21 (m, 1 H), 2.25-2.41 (m, 1 H), 2.57-2.68 (m, 1 H), 2.71-2.84 (m, 1 H), 3.04-3.16 (m, 1 H), 3.26 (t, J=9.96 Hz, 1 H), 3.30-3.43 (m, 3 H), 3.72 (dd, J=10.16, 8.01 Hz, 1 H), 4.02 (d, J=11.33 Hz, 2 H), 4.41 (d, J=7.42 Hz, 2 H), 7.01 (s, 1 H), 7.64 (d, J=8.59 Hz, 1 H), 7.79 (d, J=8.01 Hz, 1 H), 8.29 (s, 1 H); MS (ESI) (M+H)$^+$=488.7.

Step B.
(3S)-3-[(cyclopropylamino)carbonyl]pyrrolidinium trifluoroacetate

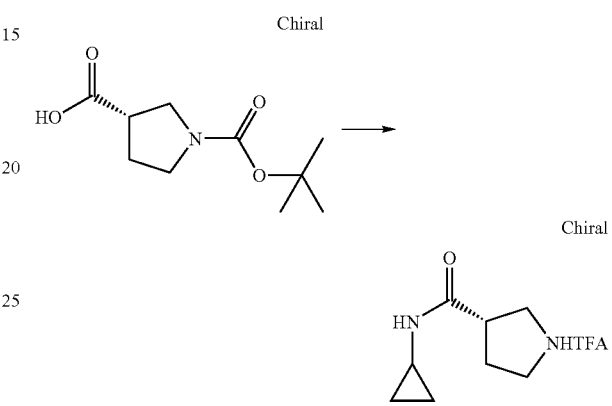

HATU (0.97 g, 2.5 mmol) and cyclopropylamine (0.14 g, 2.5 mmol) were added to a solution of (3S)-1-(tert-butoxycarbonyl)pyrrolidine-3-carboxylic acid (0.50 g, 2.3 mmol) and DIPEA (0.48 mL, 2.7 mmol) in DMF (15 mL). The reaction mixture was stirred for 3 h and the solvent was concentrated. The product was recovered in EtOAc and washed with water, saturated NaHCO$_3$ solution, water and brine. The organic layer was dried over anhydrous MgSO$_4$ and the solvent was concentrated to provide tert-butyl (3S)-3-[(cyclopropylamino)carbonyl]pyrrolidine-1-carboxylate as white solid. The intermediate was recovered in TFA (5 mL) and stirred for 2 h. The solvent was concentrated to provide the title compound as yellow oil that was used for the next step without further purification. Yield: 0.21 g (33%).

Example 89

(3S)-1-({2-tert-Butyl-1-[(4,4-difluorocyclohexyl)methyl]-1H-benzimidazol-5-yl}sulfonyl)-N-cyclopropylpyrrolidine-3-carboxamide

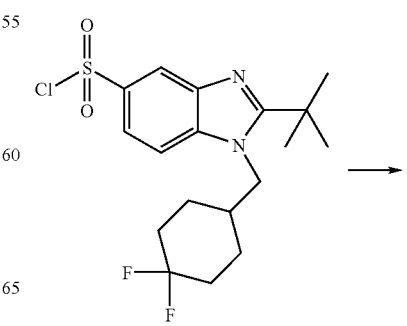

-continued

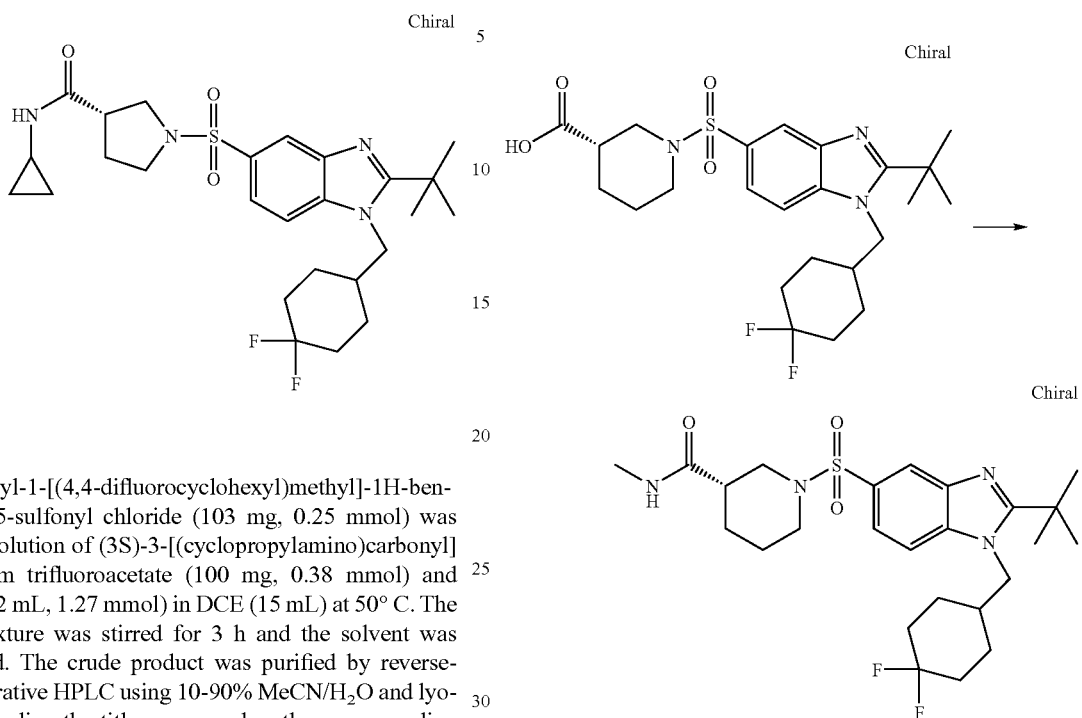

2-tert-Butyl-1-[(4,4-difluorocyclohexyl)methyl]-1H-benzimidazole-5-sulfonyl chloride (103 mg, 0.25 mmol) was added to a solution of (3S)-3-[(cyclopropylamino)carbonyl]pyrrolidinium trifluoroacetate (100 mg, 0.38 mmol) and DIPEA (0.22 mL, 1.27 mmol) in DCE (15 mL) at 50° C. The reaction mixture was stirred for 3 h and the solvent was concentrated. The crude product was purified by reverse-phase preparative HPLC using 10-90% MeCN/H$_2$O and lyophilized affording the title compound as the corresponding TFA salt. Yield: 53 mg (32%); $^1$H NMR (400 MHz, CDCl$_3$) δ 0.39-0.52 (m, 2 H), 0.62-0.73 (m, 2 H), 1.48-1.85 (m, 16H), 2.03-2.28 (m, 4 H), 2.62 (s, 1 H), 2.66-2.77 (m, 1 H), 3.04-3.19 (m, 1 H), 3.26 (t, J=9.28 Hz, 1 H), 3.35 (t, J=8.11 Hz, 1 H), 3.64-3.76 (m, 1 H), 4.42 (d, J=7.03 Hz, 2 H), 6.87 (s, 1 H), 7.61 (d, J=8.20 Hz, 1 H), 7.78 (d, J=8.01 Hz, 1 H), 8.23 (s, 1 H); MS (ESI) (M+H)$^+$=522.8.

Example 90

(3S)-1-({2-tert-Butyl-1-[(4,4-difluorocyclohexyl)methyl]-1H-benzimidazol-5-yl}sulfonyl)-N-methylpiperidine-3-carboxamide

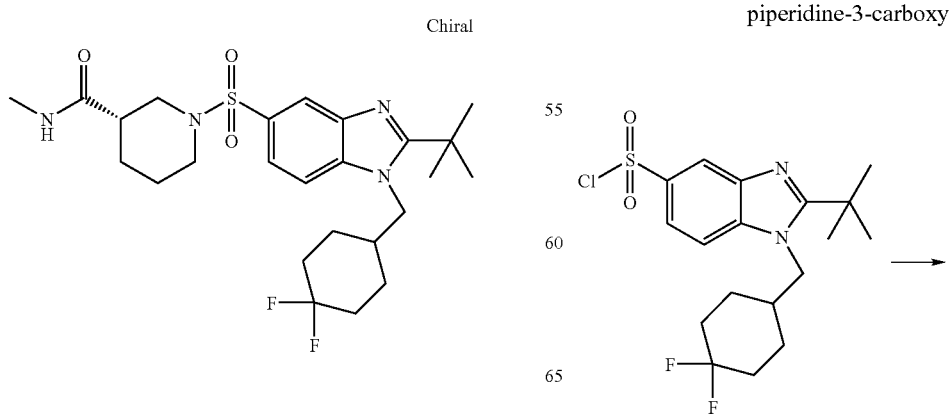

Step A. (3S)-1-({2-tert-butyl-1-[(4,4-difluorocyclohexyl)methyl]-1H-benzimidazol-5-yl}sulfonyl)-N-methylpiperidine-3-carboxamide HATU (80 mg, 0.21 mmol) and methylamine (0.1 mL, 2 M in THF, 0.21 mmol) were added to a solution of (3S)-1-({2-tert-butyl-1-[(4,4-difluorocyclohexyl)methyl]-1H-benzimidazol-5-yl}sulfonyl)piperidine-3-carboxylic acid (100 mg, 0.20 mmol) (see following steps B and C for preparation) and DIPEA (40 uL, 0.22 mmol) in DMF (15 mL). The reaction mixture was stirred overnight at ambient temperature and the solvent was concentrated. The crude product was purified by reverse-phase preparative HPLC using 10-90% MeCN/H$_2$O and lyophilized affording the title compound as the corresponding TFA salt. Yield: 75 mg (60%); [α]$_D$ −46.2° (c=1.17, MeOH); $^1$H NMR (400 MHz, CDCl$_3$) δ 1.31-1.67 (m, 6 H), 1.71 (s, 9 H), 1.8 (m, 4 H), 2.08-2.28 (m, 4 H), 2.34-2.52 (m, 2 H), 2.66 (t, J=11.43 Hz, 1 H), 2.78 (d, J=4.49 Hz, 3 H), 3.78 (dd, J=12.01, 3.22 Hz, 1 H), 4.42 (d, J=7.23 Hz, 2 H), 6.84 (d, J=4.49 Hz, 1 H), 7.55-7.63 (m, 1 H), 7.64-7.73 (m, 1 H), 8.22 (s, 1 H); MS (ESI) (M+H)$^+$=510.8.

Step B. ethyl (3S)-1-({2-tert-butyl-1-[(4,4-difluorocyclohexyl)methyl]-1H-benzimidazol-5-yl}sulfonyl)piperidine-3-carboxylate -continued

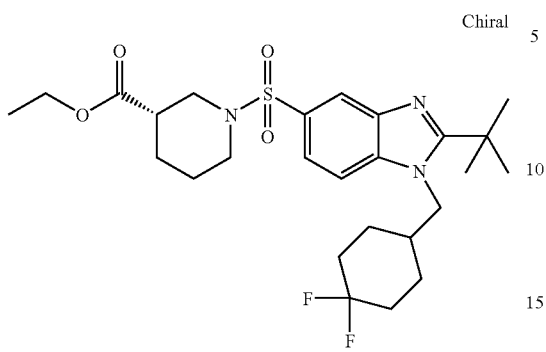

2-tert-Butyl-1-[(4,4-difluorocyclohexyl)methyl]-1H-benzimidazole-5-sulfonyl chloride (1.2 g, 2.9 mmol) was slowly added to a solution of ethyl (3S)-piperidine-3-carboxylate (0.7 g, 4.4 mmol) and DIPLA (2.6 mL, 14 mmol) in DCL (50 mL) at 80° C. The reaction mixture was stirred for 1 h and the solvent was concentrated. The product was purified by MPLC on silica gel using 60-90% EtOAc/Heptane to provide the title compound as white solid. Yield: 1.5 g (96%); MS (ESI) (M+H)$^+$=526.0.

Step C. (3S)-1-({2-tert-butyl-1-[(4,4-difluorocyclohexyl)methyl]-1H-benzimidazol-5-yl}sulfonyl)piperidine-3-carboxylic acid

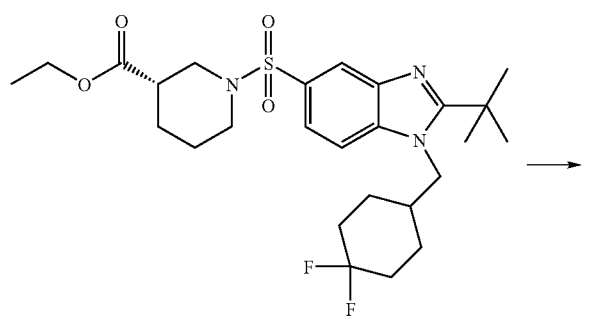

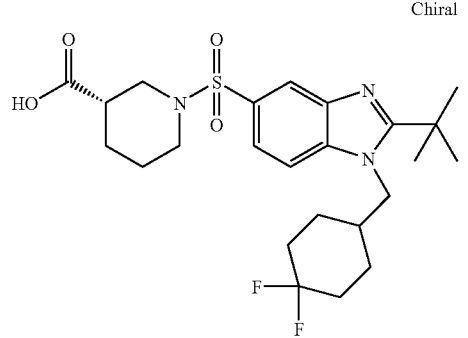

NaOH (2 mL, 2 M, 4.0 mmol) was added to a solution of ethyl (3S)-1-({2-tert-butyl-1-[(4,4-difluorocyclohexyl)methyl]-1H-benzimidazol-5-yl}sulfonyl)piperidine-3-carboxylate (1.4 g, 2.7 mmol) in 80 mL of MeOH—H$_2$O (1:1) at ambient temperature. The reaction mixture was stirred overnight and diluted with water (80 mL). The solvent was concentrated to 80 mL. The resulting solution was neutralized with 2 N HCl. The product was extracted with EtOAc and dried over anhydrous Na$_2$SO$_4$. The solvent was concentrated to provide the title compound as white solid. Yield: 1.3 g (95%); $^1$H NMR (400 MHz, CDCl$_3$) δ 1.24-1.27 (m, 1 H), 1527-1.39 (m, 1 H), 1.45-1.59 (m, 2 H), 1.62 (s, 9 H), 1.68 (s, 3 H), 1.70-1.86 (m, 4 H), 1.93-2.06 (m, 1 H), 2.08-2.25 (m, 2 H), 2.33 (t, J=12.11 Hz, 1 H), 2.46 (t, J=10.94 Hz, 1 H), 2.53-2.66 (m, 1 H), 3.69 (d, J=11.72 Hz, 1 H), 3.89 (d, J=9.96 Hz, 1 H), 4.31 (d, J=7.23 Hz, 2 H), 7.48 (d, J=8.79 Hz, 1 H), 7.67 (d, J=8.20 Hz, 1 H), 8.26 (s, 1 H); MS (ESI) (M+H)$^+$= 498.1.

Example 91

(3S)-1-({2-tert-Butyl-1-[(4,4-difluorocyclohexyl)methyl]-1H-benzimidazol-5-yl}sulfonyl)-N-ethylpiperidine-3-carboxamide

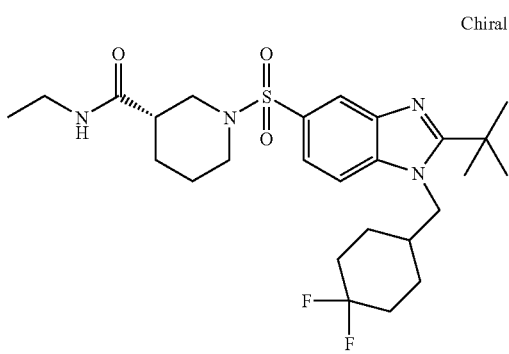

Following the same procedure in Example 90, step A, using ethylamine (0.1 mL, 2 M in TH, 0.21 mmol), HATU (80 mg, 0.21 mmol), (3S)-1-({2-tert-butyl-1-[(4,4-difluorocyclohexyl)methyl]-1H-benzimidazol-5-yl}sulfonyl)piperidine-3-carboxylic acid (100 mg, 0.20 mmol) and DIPEA (40 uL, 0.22 mmol) in DMF (15 mL). The crude product was purified by reverse-phase preparative HPLC using 10-90% MeCN/H$_2$O and lyophilized affording the title compound as the corresponding TFA salt. Yield: 64 mg (50%); [α]$_D$ −51.4° (c=1.16, MeOH); $^1$H NMR (400 MHz, CDCl$_3$) δ 1.13 (t, J=7.23 Hz, 3 H), 1.36-1.66 (m, 4 H), 1.71 (s, 11 H), 1.74-1.87 (m, 4 H), 2.09-2.28 (m, 3 H), 2.35-2.53 (m, 2 H), 2.66 (t, J=11.03 Hz, 1 H), 3.19-3.33 (m, 2 H), 3.57 (d, J=12.30 Hz, 1 H), 3.72 (dd, J=11.72, 2.73 Hz, 1 H), 4.41 (d, J=7.23 Hz, 2 H), 6.58 (t, J=5.37 Hz, 1 H), 7.59 (d, J=8.59 Hz, 1 H), 7.65-7.73 (m, 1 H), 8.20 (s, 1 H); MS (ESI) (M+H)$^+$=524.8;

Example 92

(3S)-1-({2-tert-Butyl-1-[(4,4-difluorocyclohexyl)methyl]-1H-benzimidazol-5-yl}sulfonyl)-N-propylpiperidine-3-carboxamide

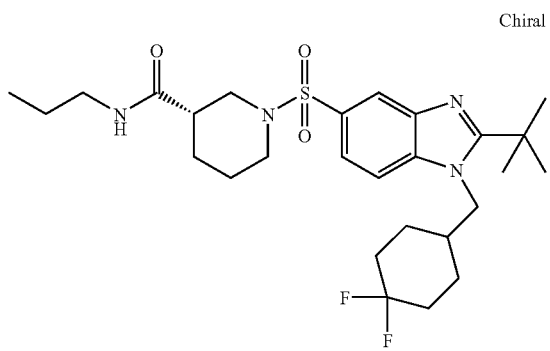

Following the same procedure in Example 90, step A, using n-propylamine (0.15 mL, 108 mg, 1.8 mmol), HATU (80 mg, 0.21 mmol), (3S)-1-({2-tert-butyl-1-[(4,4-difluorocyclohexyl)methyl]-1H-benzimidazol-5-yl}sulfonyl)piperidine-3-carboxylic acid (100 mg, 0.20 mmol) and DIPEA (40 uL, 0.22 mmol) in DMF (15 mL). The crude product was purified by reverse-phase preparative HPLC using 10-90% MeCN/H$_2$O and lyophilized affording the title compound as the corresponding TFA salt. Yield: 60 mg (45%); $[\alpha]_D$ −54.6° (c=1.18, MeOH); $^1$H NMR (400 MHz, CDCl$_3$) δ 0.91 (t, J=7.32 Hz, 3 H), 1.40-1.58 (m, 5 H), 1.58-1.66 (m, 1 H), 1.66-1.71 (m, 10 H), 1.71-1.84 (m, 4 H), 2.10-2.26 (m, 3 H), 2.38-2.47 (m, 1 H), 2.53 (t, J=10.06 Hz, 1 H), 2.69 (t, J=11.03 Hz, 1 H), 3.14-3.25 (m, 2 H), 3.53 (d, J=11.91 Hz, 1 H), 3.67 (dd, J=12.30, 3.12 Hz, 1 H), 4.40 (d, J=7.42 Hz, 2 H), 6.50 (t, J=5.27 Hz, 1 H), 7.57 (d, J=8.79 Hz, 1 H), 7.68 (dd, J=8.59, 1.56 Hz, 1 H), 8.21 (d, J=1.37 Hz, 1 H); MS (ESI) (M+H)$^+$=538.8;

Example 93

(3S)-1-({2-tert-Butyl-1-[(4,4-difluorocyclohexyl)methyl]-1H-benzimidazol-5-yl}sulfonyl)-N-cyclopropylpiperidine-3-carboxamide

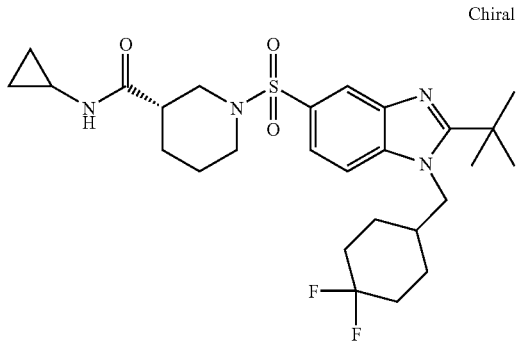

Following the same procedure in Example 90, step A, using cyclopropylamine (0.15 mL, 123 mg, 2.1 mmol)), HATU (80 mg, 0.21 mmol), (3S)-1-({2-tert-butyl-1-[(4,4-difluorocyclohexyl)methyl]-1H-benzimidazol-5-yl}sulfonyl)piperidine-3-carboxylic acid (100 mg, 0.20 mmol) and DIPEA (40 uL, 0.22 mmol) in DMF (15 mL). The crude product was purified by reverse-phase preparative HPLC using 10-90% MeCN/H$_2$O and lyophilized affording the title compound as the corresponding TFA salt. Yield: 72 mg (55%); $[\alpha]_D$ −56.6° (c=1.14, MeOH); $^1$H NMR (400 MHz, CDCl$_3$) δ 0.46-0.57 (m, 2 H), 0.68-0.81 (m, 2 H), 1.35-1.50 (m, 1 H), 1.50-1.62 (m, 3 H), 1.63-1.69 (m, 2 H), 1.68-1.73 (m, 9 H), 1.73-1.87 (m, 4 H), 2.10-2.28 (m, 3 H), 2.31-2.43 (m, 1 H), 2.51 (t, J=10.16 Hz, 1 H), 2.60-2.74 (m, 2 H), 3.54 (d, J=12.69 Hz, 1 H), 3.66 (d, J=10.74 Hz, 1 H), 4.41 (d, J=7.23 Hz, 2 H), 6.65 (d, J=1.37 Hz, 1 H), 7.55-7.63 (m, 1 H), 7.65-7.72 (m, 1 H), 8.12-8.21 (m, 1 H); MS (ESI) (M+H)$^+$=536.8.

Example 94

(3S)-1-({2-tert-Butyl-1-[(4,4-difluorocyclohexyl)methyl]-1H-benzimidazol-5-yl}sulfonyl)-N-cyclobutylpiperidine-3-carboxamide

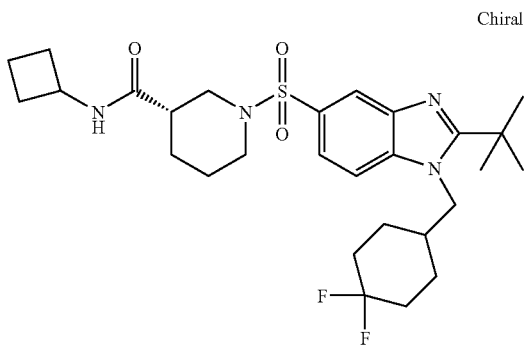

Following the same procedure in Example 90, step A, using cyclobutylamine (0.15 mL, 124 mg, 1.8 mmol), HATU (80 mg, 0.21 mmol), (3S)-1-({2-tert-butyl-1-[(4,4-difluorocyclohexyl)methyl]-1H-benzimidazol-5-yl}sulfonyl)piperidine-3-carboxylic acid (100 mg, 0.20 mmol) and DIPEA (40 uL, 0.22 mmol) in DMF (15 mL). The crude product was purified by reverse-phase preparative HPLC using 10-90% MeCN/H$_2$O and lyophilized affording the title compound as the corresponding TFA salt. Yield: 68 mg (51%); $[\alpha]_D$ −63.0° (c=1.23, MeOH); $^1$H NMR (400 MHz, CDCl$_3$) δ 1.40-1.63 (m, 4 H), 1.63-1.69 (m, 2 H), 1.70-1.73 (m, 11 H), 1.73-1.84 (m, 4 H), 1.83-1.99 (m, 2 H), 2.11-2.24 (m, 3 H), 2.24-2.33 (m, 2 H), 2.33-2.43 (m, 1 H), 2.49 (t, J=10.35 Hz, 1 H), 2.63 (t, J=11.13 Hz, 1 H), 3.53 (d, J=12.69 Hz, 1 H), 3.64 (dd, J=12.40, 3.22 Hz, 1 H), 4.27-4.38 (m, 1 H), 4.41 (d, J=7.42 Hz, 2 H), 6.53 (d, J=7.62 Hz, 1 H), 7.55-7.63 (m, 1 H), 7.64-7.71 (m, 1 H), 8.15 (d, J=1.17 Hz, 1 H); MS (ESI) (M+H)$^+$=551.0.

Example 95

(3S)-1-({2-tert-Butyl-1-[(4,4-difluorocyclohexyl)methyl]-1H-benzimidazol-5-yl}sulfonyl)-N-(cyclopropylmethyl)piperidine-3-carboxamide

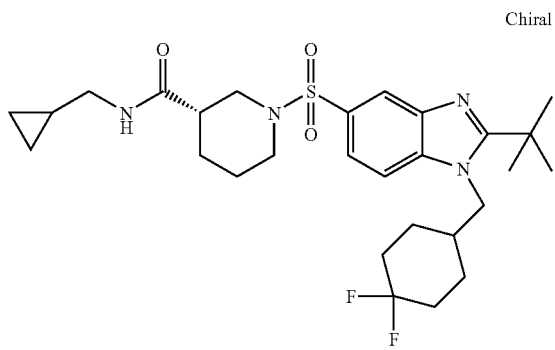

Following the same procedure in Example 90, step A, using (cyclopropylmethyl)amine (0.15 mL, 122 mg, 1.7 mmol), HATU (80 mg, 0.21 mmol), (3S)-1-({2-tert-butyl-1-[(4,4-difluorocyclohexyl)methyl]-1H-benzimidazol-5-yl}sulfonyl)piperidine-3-carboxylic acid (100 mg, 0.20 mmol) and DIPEA (40 uL, 0.22 mmol) in DMF (15 mL). The crude product was purified by reverse-phase preparative HPLC using 10-90% MeCN/H$_2$O and lyophilized affording the title compound as the corresponding TFA salt. Yield: 60 mg (44%); [α]$_D$ −55.5° (c=1.11, MeOH); $^1$H NMR (400 MHz, CDCl$_3$) δ 0.20 (m, 2 H), 0.45-0.54 (m, 2 H), 0.89-1.02 (m, 1 H), 1.42-1.63 (m, 4 H), 1.70 (s, 10 H), 1.72-1.86 (m, 5 H), 2.10-2.26 (m, 3 H), 2.39-2.54 (m, 2 H), 2.65 (t, J=10.94 Hz, 1 H), 3.05-3.13 (m, 2 H), 3.56 (d, J=11.52 Hz, 1 H), 3.70 (dd, J=11.72, 2.73 Hz, 1 H), 4.41 (d, J=7.42 Hz, 2 H), 6.51 (t, J=5.08 Hz, 1 H), 7.56-7.62 (m, 1 H), 7.68 (dd, J=8.79, 1.37 Hz, 1 H), 8.19 (d, J=1.37 Hz, 1 H); MS (ESI) (M+H)$^+$=550.8.

Example 96

(3S)-1-({2-tert-Butyl-1-[(4,4-difluorocyclohexyl)methyl]-1H-benzimidazol-5-yl}sulfonyl)-N-(cyclobutylmethyl)piperidine-3-carboxamide

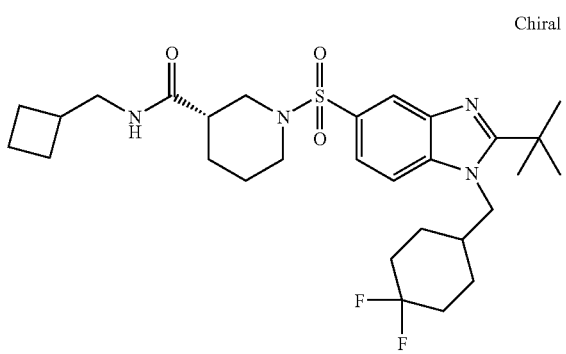

Following the same procedure in Example 90, step A, using (cyclobutylmethyl)amine (0.15 mL, 124 mg, 1.5 mmol), HATU (80 mg, 0.21 mmol), (3S)-1-({2-tert-butyl-1-[(4,4-difluorocyclohexyl)methyl]-1H-benzimidazol-5-yl}sulfonyl)piperidine-3-carboxylic acid (100 mg, 0.20 mmol) and DIPEA (40 uL, 0.22 mmol) in DMF (15 mL). The crude product was purified by reverse-phase preparative HPLC using 10-90% MeCN/H$_2$O and lyophilized affording the title compound as the corresponding TFA salt. Yield: 55 mg (40%); [α]$_D$ −53.4° (c=1.12, MeOH); $^1$H NMR (400 MHz, CDCl$_3$) δ 1.42-1.62 (m, 4 H), 1.62-1.68 (m, 2 H), 1.70 (s, 11 H), 1.73-1.82 (m, 4 H), 1.82-1.95 (m, 2 H), 1.98-2.09 (m, 2 H), 2.11-2.25 (m, 3H), 2.38-2.51 (m, 2 H), 2.55 (t, J=10.74 Hz, 1 H), 2.71 (t, J=10.94 Hz, 1 H), 3.21-3.31 (m, 2 H), 3.49 (d, J=12.11 Hz, 1 H), 3.61 (dd, J=12.30, 3.32 Hz, 1 H), 4.41 (d, J=7.23 Hz, 2 H), 6.39 (t, J=5.76 Hz, 1 H), 7.59 (d, J=8.79 Hz, 1 H), 7.69 (dd, J=8.69, 1.27 Hz, 1 H), 8.18 (d, J=1.17 Hz, 1 H); MS (ESI) (M+H)$^+$=564.8.

Example 97

(3S)-1-({2-tert-Butyl-1-[(4,4-difluorocyclohexyl)methyl]-1H-benzimidazol-5-yl}sulfonyl)-N-isopropylpiperidine-3-carboxamide

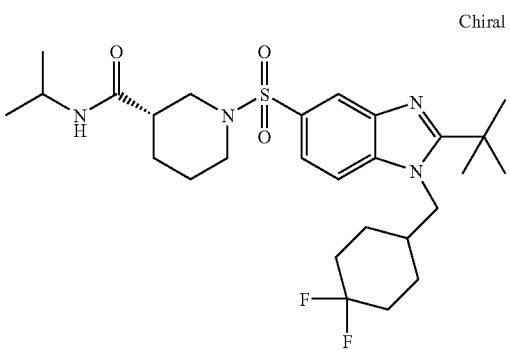

Following the same procedure in Example 90, step A, using isopropylamine (0.15 mL, 104 mg, 1.75 mmol), HATU (80 mg, 0.21 mmol), (3S)-1-({2-tert-butyl-1-[(4,4-difluorocyclohexyl)methyl]-1H-benzimidazol-5-yl}sulfonyl)piperidine-3-carboxylic acid (100 mg, 0.20 mmol) and DIPEA (40 uL, 0.22 mmol) in DMF (15 mL). The crude product was purified by reverse-phase preparative HPLC using 10-90% MeCN/H$_2$O and lyophilized affording the title compound as the corresponding TFA salt. Yield: 75 mg (57%); [α]$_D$ −55.1° (c=1.35, MeOH); $^1$H NMR (400 MHz, CDCl$_3$) δ 1.15 (d, J=6.93 Hz, 6 H), 1.44-1.62 (m, 4 H), 1.62-1.73 (m, 11H), 1.73-1.84 (m, 4 H), 2.10-2.27 (m, 3 H), 2.32-2.43 (m, 1 H), 2.50 (t, J=10.55 Hz, 1 H), 2.65 (t, J=11.03 Hz, 1 H), 3.53 (d, J=11.72 Hz, 1 H), 3.63 (dd, J=11.23, 3.03 Hz, 1 H), 3.95-4.09 (m, 1 H), 4.41 (d, J=7.42 Hz, 2 H), 6.13 (d, J=7.03 Hz, 1 H), 7.56-7.63 (m, 1 H), 7.65-7.72 (m, 1 H), 8.15 (s, 1 H); MS (ESI) (M+H)$^+$=538.8.

Example 98

(3S)-1-({2-tert-Butyl-1-[(4,4-difluorocyclohexyl)methyl]-1H-benzimidazol-5-yl}sulfonyl)-N-methylpyrrolidine-3-carboxamide

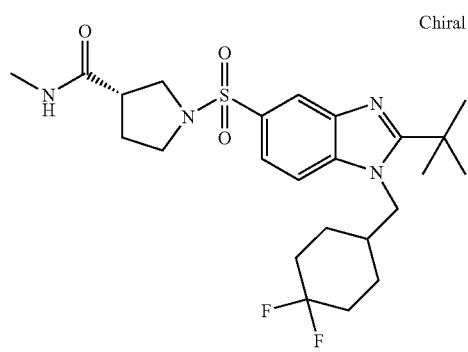

Step A. (3S)-1-({2-tert-butyl-1-[(4,4-difluorocyclohexyl)methyl]-1H-benzimidazol-5-yl}sulfonyl)-N-methylpyrrolidine-3-carboxamide

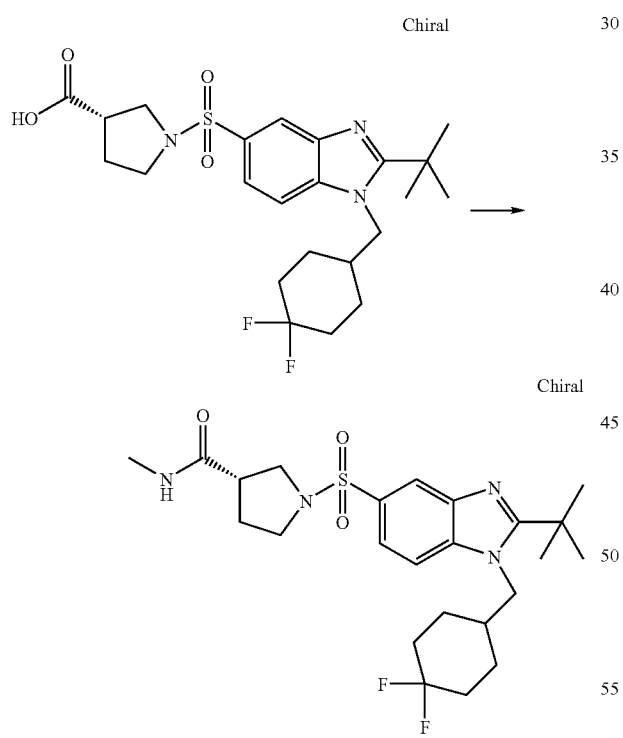

HATU (86 mg, 0.22 mmol) and methylamine (0.8 mL, 2 M in THF, 1.6 mmol) were added to a solution of (3S)-1-({2-tert-butyl-1-[(4,4-difluorocyclohexyl)methyl]-1H-benzimidazol-5-yl}sulfonyl)pyrrolidine-3-carboxylic acid (100 mg, 0.20 mmol) (see following steps B and C for preparation) and DIPEA (72 uL, 0.22 mmol) in DMF (15 mL). The reaction mixture was stirred for 1 h. and the solvent was concentrated. The crude product was purified by reverse-phase preparative HPLC using 10-90% MeCN/H$_2$O and lyophilized affording the title compound as the corresponding TFA salt. Yield: 65 mg (53%); [α]$_D$ –7.3° (c=1.04, MeOH); $^1$H NMR (400 MHz, CDCl$_3$) δ 1.50-1.69 (m, 3 H), 1.72 (s, 9 H), 1.74-1.84 (m, 3 H), 1.86-1.97 (m, 1 H), 2.10-2.25 (m, 4 H), 2.72 (d, J=4.69 Hz, 4 H), 3.02-3.12 (m, 1 H), 3.27 (t, J=10.16 Hz, 1 H), 3.36 (td, J=9.37, 3.32 Hz, 1 H), 3.78 (dd, J=10.45, 7.91 Hz, 1 H), 4.43 (d, J=7.42 Hz, 2 H), 6.98 (d, J=4.30 Hz, 1 H), 7.60 (d, J=8.79 Hz, 1 H), 7.79 (dd, J=8.69, 1.46 Hz, 1H), 8.29 (d, J=1.17 Hz, 1 H); MS (ESI) (M+H)$^+$=497.2.

Step B. (3S)-3-carboxypyrrolidinium trifluoroacetate

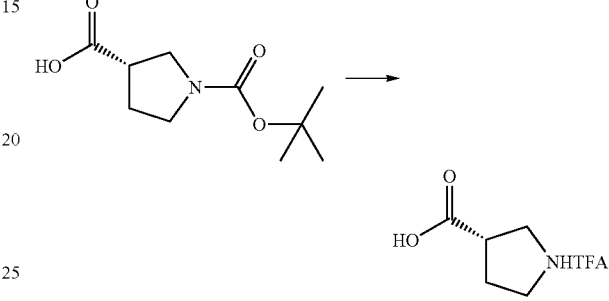

(3S)-1-(tert-Butoxycarbonyl)pyrrolidine-3-carboxylic acid (0.5 g, 2.34 mmol) was stirred in TFA (20 mL) for 3 h. The solvent was removed to provide the title compound as yellow oil that was used for the next step without further purification. Yield: 0.50 g (99%).

Step C. (3S)-1-({2-tert-butyl-1-[(4,4-difluorocyclohexyl)methyl]-1H-benzimidazol-5-yl}sulfonyl)pyrrolidine-3-carboxylic acid

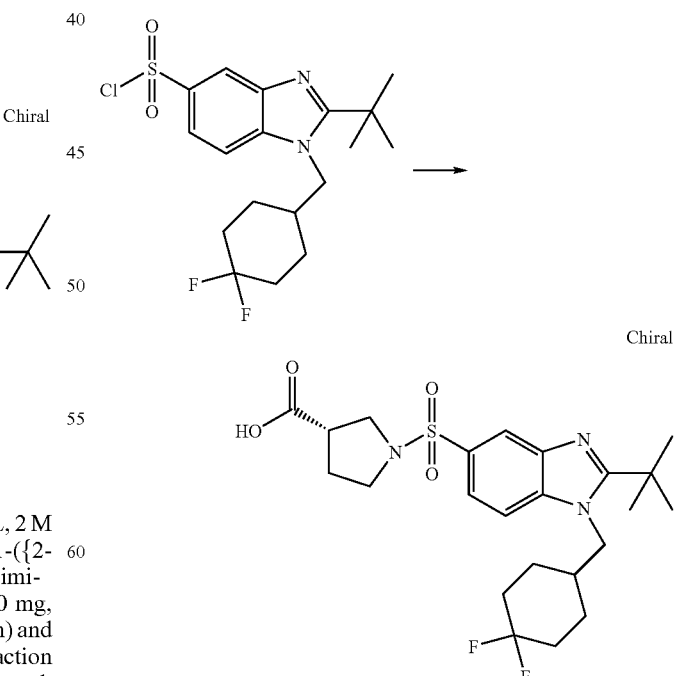

2-tert-Butyl-1-[(4,4-difluorocyclohexyl)methyl]-1H-benzimidazole-5-sulfonyl chloride (1.2 g, 2.9 mmol) was added to a solution of (3S)-3-carboxypyrrolidinium trifluoroacetate (0.50 g, 2.3 mmol) and DIPEA (3 mL, 17 mmol) in DCE (20 mL) at 80° C. The reaction mixture was stirred for 2 hrs. and the solvent was concentrated. The product was purified by MPLC on silica gel using 30% acetone in DCM containing 1% of AcOH to provide the title compound as white solid. Yield: 600 mg (42%); MS (ESI) (M+H)$^+$=484.1.

Example 99

(3S)-1-({2-tert-Butyl-1-[(4,4-difluorocyclohexyl)methyl]-1H-benzimidazol-5-yl}sulfonyl)-N-ethylpyrrolidine-3-carboxamide

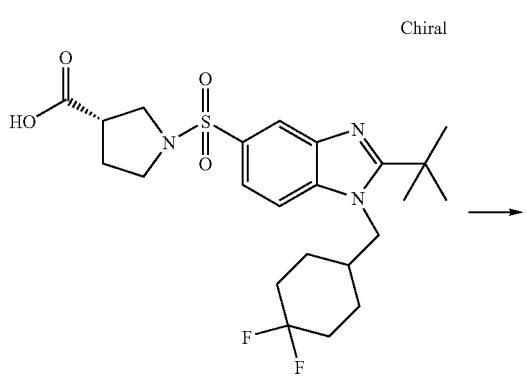

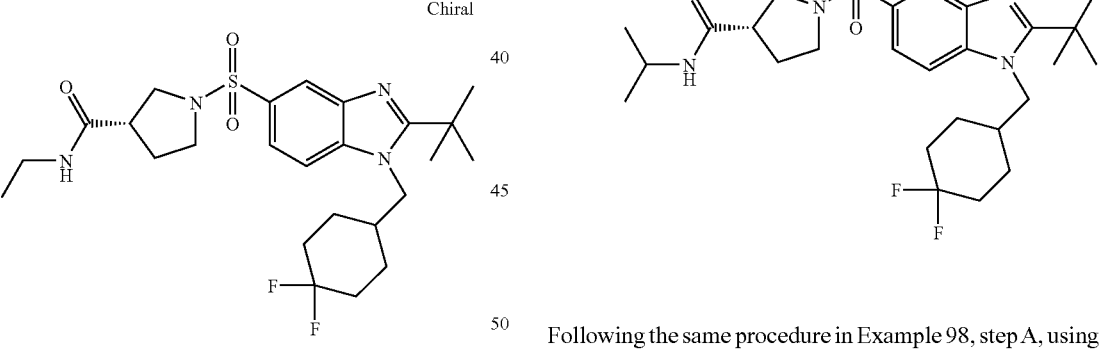

Following the same procedure in Example 98, step A, using ethylamine (0.11 mL, 2 M in TH, 0.22 mmol), HATU (86 mg, 0.22 mmol), (3S)-1-({2-tert-butyl-1-[(4,4-difluorocyclohexyl)methyl]-1H-benzimidazol-5-yl}sulfonyl)pyrrolidine-3-carboxylic acid (100 mg, 0.20 mmol) and DIPEA (72 uL, 0.22 mmol) in DMF (15 mL). The crude product was purified by reverse-phase preparative HPLC using 10-90% MeCN/H$_2$O and lyophilized affording the title compound as the corresponding TFA salt. Yield: 52 mg (40%); [α]$_D$ −8.9° (c=1.17, MeOH); $^1$H NMR (400 MHz, CDCl$_3$) δ 1.07 (t, J=7.32 Hz, 3 H), 1.49-1.62 (m, 2 H), 1.63-1.70 (m, 1 H), 1.72 (s, 9 H), 1.75-1.84 (m, 3 H), 1.85-1.98 (m, 1 H), 2.05-2.28 (m, 4 H), 2.64-2.79 (m, 1 H), 3.04-3.14 (m, 1 H), 3.14-3.30 (m, 3 H), 3.35 (td, J=9.28, 3.71 Hz, 1 H), 3.73 (dd, J=10.45, 8.11 Hz, 1 H), 4.43 (d, J=7.42 Hz, 2 H), 6.76 (t, J=4.78 Hz, 1 H), 7.61 (d, J=8.79 Hz, 1 H), 7.77 (dd, J=8.79, 1.17 Hz, 1 H), 8.24 (s, 1 H); MS (ESI) (M+H)$^+$=511.3.

Example 100

(3S)-1-({2-tert-Butyl-1-[(4,4-difluorocyclohexyl)methyl]-1H-benzimidazol-5-yl}sulfonyl)-N-isopropylpyrrolidine-3-carboxamide

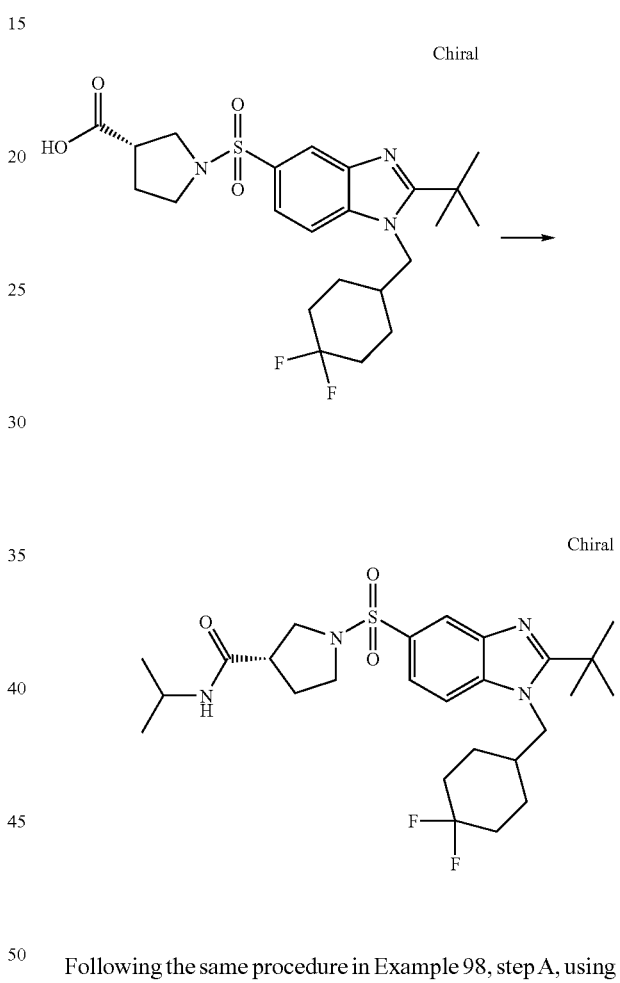

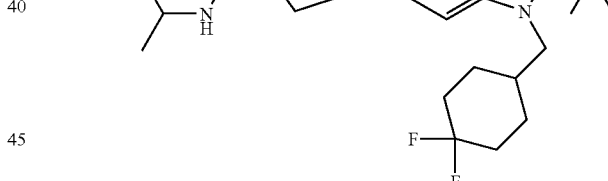

Following the same procedure in Example 98, step A, using isopropylamine (0.15 mL, 103 mg, 1.75 mmol), HATU (86 mg, 0.22 mmol), (3S)-1-({2-tert-butyl-1-[(4,4-difluorocyclohexyl)methyl]-1H-benzimidazol-5-yl}sulfonyl)pyrrolidine-3-carboxylic acid (100 mg, 0.20 mmol) and DIPEA (72 uL, 0.22 mmol) in DMF (15 mL) provided the TFA salt of the title compound as white solid. Yield: 51 mg (39%); [α]$_D$ −10.7° (c=1.10, MeOH); $^1$H NMR (400 MHz, CDCl$_3$) δ 1.08 (dd, J=6.64, 2.54 Hz, 6 H), 1.49-1.63 (m, 2 H), 1.63-1.70 (m, 1 H), 1.73 (s, 9 H), 1.76-1.85 (m, 3 H), 1.85-1.99 (m, 1 H), 2.00-2.12 (m, 1 H), 2.12-2.27 (m, 4 H), 2.62-2.76 (m, 1 H), 3.06-3.17 (m, 1 H), 3.19-3.28 (m, 1 H), 3.32 (td, J=9.18, 3.91 Hz, 1 H), 3.61 (dd, J=10.35, 8.20 Hz, 1 H), 3.88-4.00 (m, 1 H), 4.44 (d, J=7.23 Hz, 2 H), 6.32 (d, J=7.81 Hz, 1 H), 7.73 (dd, J=8.79, 1.37 Hz, 1 H), 8.12 (d, J=1.17 Hz, 1 H); MS (ESI) (M+H)$^+$=525.3.

Example 101 tert-Butyl[1-({2-tert-butyl-1-[(4,4-difluorocyclo-hexyl)methyl]-1H-benzimidazol-5-yl}sulfonyl)azetidin-3-yl]carbamate

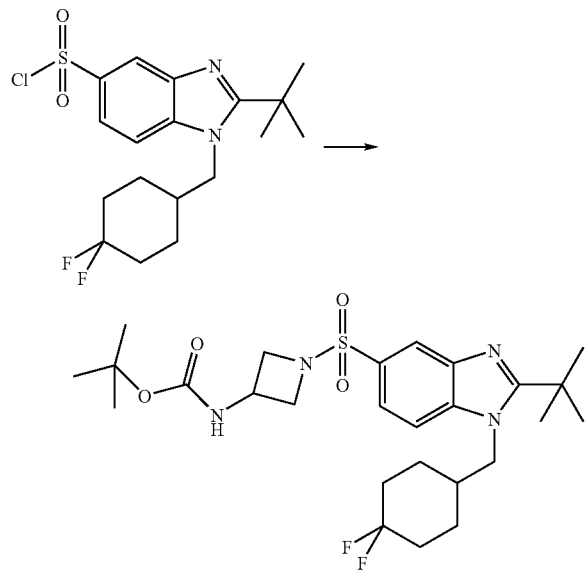

Following the same procedure in Example 1, Step A, using 2-tert-butyl-1-[(4,4-difluorocyclohexyl)methyl]-1H-benzimidazole-5-sulfonyl chloride (0.41 g, 1.0 mmol), tert-butyl azetidin-3-ylcarbamate (0.17 g, 1.0 mmol) and DMAP (0.37 g, 3.0 mmol) in MeCN (20 mL). The crude product was purified by MPLC using Hex/EtOAc (1:1) on silica gel to give 0.40 g (74%) of a white solid as the title compound. $^1$H NMR (400 MHz, METHANOL-D$_4$) δ 1.33 (s, 9 H), 1.48-1.62 (m, 2 H), 1.64 (s, 9 H), 1.67-1.87 (m, 4 H), 1.98-2.15 (m, 2 H), 2.19-2.35 (m, 1 H), 3.62 (t, J=7.03 Hz, 2 H), 3.96 (t, J=8.11 Hz, 2 H), 4.05-4.16 (m, 1 H), 4.51 (d, J=7.42 Hz, 2 H), 7.86 (dd, J=9.18, 1.17 Hz, 1 H), 7.98 (d, J=8.79 Hz, 1 H), 8.14 (d, J=1.56 Hz, 1 H); MS (ESI) (M+H)$^+$=541.3; Anal. Calcd for C$_{26}$H$_{38}$F$_2$N$_4$O$_4$S+1.00 TFA+0.20 EtOAc (674.72): C, 51.62; H, 6.07; N, 8.30. Found: C, 51.73; H, 5.94; N, 8.27.

Example 102

1-({2-tert-Butyl-1-[(4,4-difluorocyclohexyl)methyl]-1H-benzimidazol-5-yl}sulfonyl)azetidin-3-amine

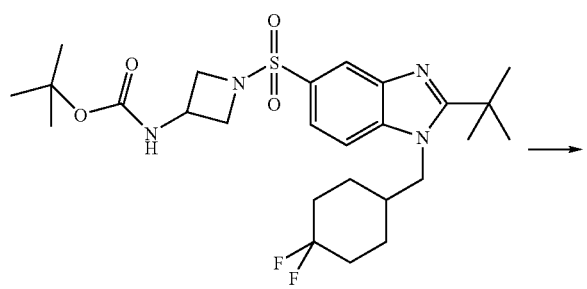

-continued

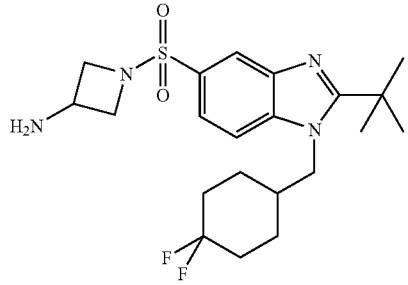

Following the same procedure in Example 37, Step A, using tert-butyl[1-({2-tert-butyl-1-[(4,4-difluorocyclohexyl)methyl]-1H-benzimidazol-5-yl}sulfonyl)azetidin-3-yl]carbamate (0.34 g, 0.63 mmol) and TFA (5 mL) in CH$_2$Cl$_2$ (10 mL). Yield: 0.26 g (93%). $^1$H NMR (400 MHz, METHANOL-D$_4$) δ 1.47-1.57 (m, 2 H), 1.61 (s, 9 H), 1.63-1.84 (m, 4 H), 1.98-2.13 (m, 2 H), 2.16-2.32 (m, 1 H), 3.79-3.90 (m, 3 H), 3.97-4.08 (m, 2 H), 4.45 (d, J=7.42 Hz, 2 H), 7.75-7.84 (m, 1 H), 7.86-7.92 (m, 1 H), 8.14 (d, J=1.37 Hz, 1 H); MS (ESI) (M+H)$^+$=441.3; Anal. Calcd for C$_{21}$H$_{30}$F$_2$N$_4$O$_2$S+2.10 TFA (680.01): C, 44.51; H, 4.76; N, 8.24. Found: C, 44.48; H, 4.65; N, 8.43.

Example 103

N-[1-({2-tert-Butyl-1-[(4,4-difluorocyclohexyl)methyl]-1H-benzimidazol-5-yl}sulfonyl)azetidin-3-yl]cyclopropanecarboxamide

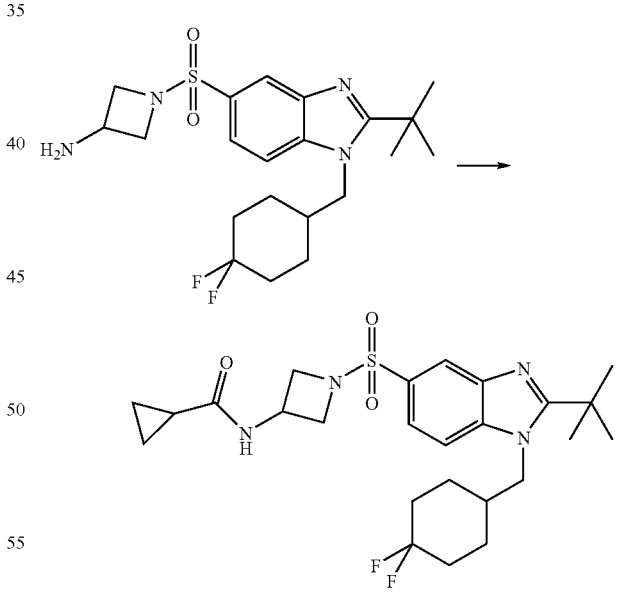

Cyclopropane carbonylchloride (16 uL, 19 mg, 0.18 mmol) was added to a solution of 1-({2-tert-butyl-1-[(4,4-difluorocyclohexyl)methyl]-1H-benzimidazol-5-yl}sulfonyl)azetidin-3-amine (52 mg, 0.12 mmol) (see Example 102 for preparation) and DIPEA (41 uL, 31 mg, 0.24 mmol) in CH$_2$Cl$_2$ (5 mL). The reaction mixture was stirred for 4 h at room temperature, diluted with EtOAc (50 mL), washed with NaHCO$_3$ (2×10 mL) and dried over Na$_2$SO$_4$. The crude product was purified by MPLC using Hex/EtOAc (1:4) on

Example 104

N-[1-({2-tert-Butyl-1-[(4,4-difluorocyclohexyl)methyl]-1H-benzimidazol-5-yl}sulfonyl)azetidin-3-yl] propanamide

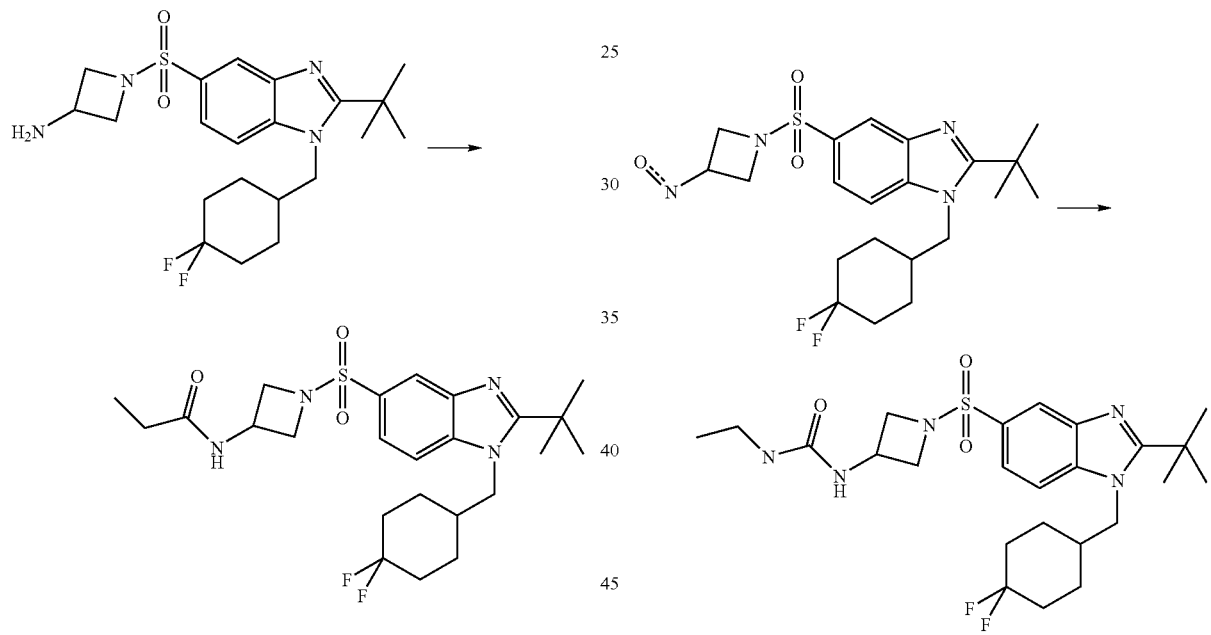

Following the same procedure in Example 103, using propionic anhydride (50 uL, 51 mg, 0.39 mmol), 1-({2-tert-butyl-1-[(4,4-difluorocyclohexyl)methyl]-1H-benzimidazol-5-yl}sulfonyl)azetidin-3-amine (51 mg, 0.12 mmol) (see Example 102 for preparation) and DIPEA (41 uL, 31 mg, 0.24 mmol) in $CH_2Cl_2$ (5 mL). The crude product was purified by MPLC using Hex/EtOAc (1:4) on silica gel to give 60 mg (100%) of a white solid as the title compound. $^1$H NMR (400 MHz, METHANOL-$D_4$) δ 1.00 (t, J=7.62 Hz, 3 H), 1.48-1.63 (m, 2 H), 1.66 (s, 9 H), 1.68-1.84 (m, 4 H), 2.01-2.06 (m, 2 H), 2.07 (q, J=7.62 Hz, 2 H), 2.18-2.35 (m, 1 H), 3.68 (dd, J=8.69, 6.15 Hz, 2 H), 4.00 (dd, J=8.8, 7.8 Hz, 2 H), 4.22-4.33 (m, 1 H), 4.53 (d, J=7.42 Hz, 2 H), 7.90 (dd, J=8.79, 1.76 Hz, 1 H), 8.04 (d, J=8.79 Hz, 1 H), 8.16 (d, J=1.76 Hz, 1 H); MS (ESI) (M+H)$^+$=497.2; Anal. Calcd for $C_{24}H_{34}F_2N_4O_3S$+1.20 TFA+0.40$H_2O$ (640.66): C, 49.49; H, 5.66; N, 8.75. Found: C, 49.49; H, 5.58; N, 8.82.

Example 105

N-[1-({2-tert-Butyl-1-[(4,4-difluorocyclohexyl)methyl]-1H-benzimidazol-5-yl}sulfonyl)azetidin-3-yl]-N'-ethylurea

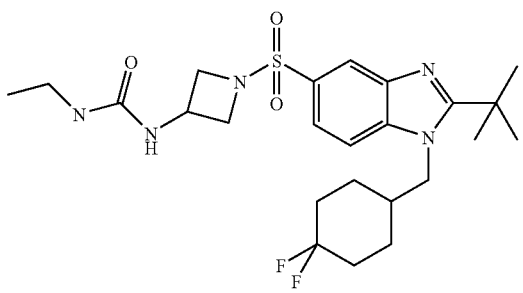

Step A: N-[1-({2-tert-butyl-1-[(4,4-difluorocyclohexyl)methyl]-1H-benzimidazol-5-yl}sulfonyl)azetidin-3-yl]-N'-ethylurea A solution of 2-tert-butyl-1-[(4,4-difluorocyclohexyl)methyl]-5-[(3-isocyanatoazetidin-1-yl)sulfonyl]-1H-benzimidazole in THF (4.0 mL, 0.095 mmol) (see following step B for preparation) was added to a solution of ethylamine (100 uL, 2.0 M in THF, 0.2 mmol) in THF (2.0 mL). The reaction mixture was stirred for 4 h at room temperature, diluted with EtOAc (50 mL), washed with NaHCO$_3$ (2×5 mL) and dried over Na$_2$SO$_4$. The crude product was purified by MPLC using EtOAc/MeOH (20:1) on silica gel to give 21 mg (44%) of a white solid as the title compound. $^1$H NMR (400 MHz, METHANOL-$D_4$) δ 1.02 (t, J=7.13 Hz, 3 H), 1.51-1.64 (m, 2 H), 1.66 (s, 9 H), 1.69-1.87 (m, 4 H), 2.01-2.15 (m, 2 H), 2.21-2.37 (m, 1 H), 3.04 (q, J=7.16 Hz, 2 H), 3.62 (dd, J=8.11, 6.74 Hz, 2 H), 3.99 (t, J=8.10 Hz, 2 H), 4.16-4.29 (m, 1 H), 4.54 (d, J=7.62 Hz, 2 H), 7.90 (dd, J=8.59, 1.56 Hz, 1 H), 8.03 (d, J=8.59 Hz, 1 H), 8.17 (d, J=1.76 Hz, 1 H); MS (ESI) (M+H)$^+$=512.3; Anal. Calcd for $C_{24}H_{35}F_2N_5O_3S$+1.40 TFA+0.50$H_2O$ (680.28): C, 47.32; H, 5.54; N, 10.29. Found: C, 47.36; H, 5.57; N, 10.32.

Step B: 2-tert-butyl-1-[(4,4-difluorocyclohexyl)methyl]-5-[(3-isocyanatoazetidin-1-yl)sulfonyl]-1H-benzimidazole

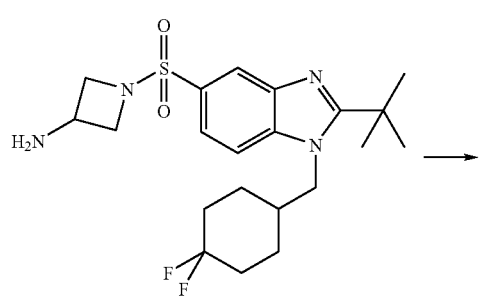

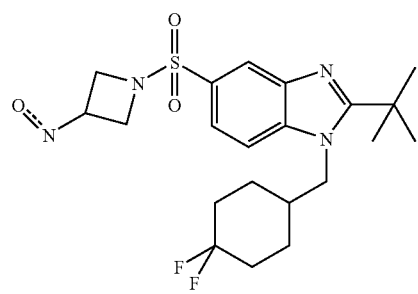

A solution of 1-({2-tert-butyl-1-[(4,4-difluorocyclohexyl)methyl]-1H-benzimidazol-5-yl}sulfonyl)azetidin-3-amine (125 mg, 0.29 mmol) (see Example 102 for preparation) and DIPEA (109 uL, 81 mg, 0.63 mmol) in THF (6 mL) was added to a solution of triphosgene (34 mg, 0.14 mmol) in THF (6 mL) at 0° C. The reaction mixture was stirred for 30 at 0° C. and 30 min at room temperature, then directly used for next step.

Example 106

N-[1-({2-tert-Butyl-1-[(4,4-difluorocyclohexyl)methyl]-1H-benzimidazol-5-yl}sulfonyl)azetidin-3-yl]-N'-cyclopropylurea

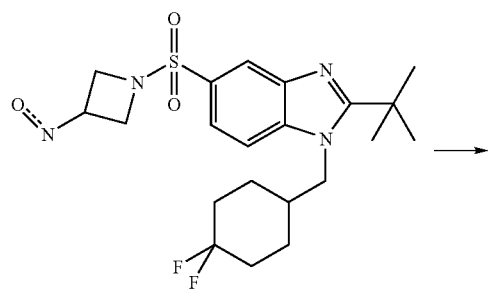

-continued

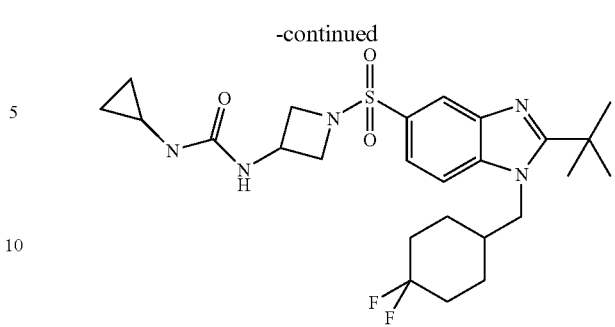

Following the same procedure in Example 105, Step A, using 2-tert-butyl-1-[(4,4-difluorocyclohexyl)methyl]-5-[(3-isocyanatoazetidin-1-yl)sulfonyl]-1H-benzimidazole (0.095 mmol) and cyclopropylamine (13 uL, 11 mg, 0.19 mmol) in THF (6.0 mL). The crude product was purified by MPLC using EtOAc/MeOH (20:1) on silica gel to give 22 mg (44%) of a white solid as the title compound. $^1$H NMR (400 MHz, METHANOL-D$_4$) δ 0.29-0.40 (m, 2 H), 0.57-0.66 (m, 2 H), 1.49-1.64 (m, 2 H), 1.67 (s, 9 H), 1.70-1.86 (m, 4 H), 1.99-2.15 (m, 2 H), 2.20-2.31 (m, 1 H), 2.31-2.41 (m, 1 H), 3.65-3.78 (m, 2 H), 3.94-4.06 (m, 2 H), 4.15-4.30 (m, 1 H), 4.55 (d, J=7.42 Hz, 2 H), 7.92 (dd, J=8.69, 1.66 Hz, 1 H), 8.05 (d, J=8.79 Hz, 1 H), 8.18 (d, J=1.56 Hz, 1 H); MS (ESI) (M+H)$^+$ =524.3; Anal. Calcd for C$_{25}$H$_{35}$F$_2$N$_5$O$_3$S+1.20 TFA+ 0.60H$_2$O+0.40 EtOAc (711.33): C, 49.64; H, 5.75; N, 9.85. Found: C, 49.62; H, 5.71; N, 9.83.

Example 107

N-[1-({2-tert-Butyl-1-[(4,4-difluorocyclohexyl)methyl]-1H-benzimidazol-5-yl}sulfonyl)azetidin-3-yl]-N'-(2-hydroxyethyl)urea

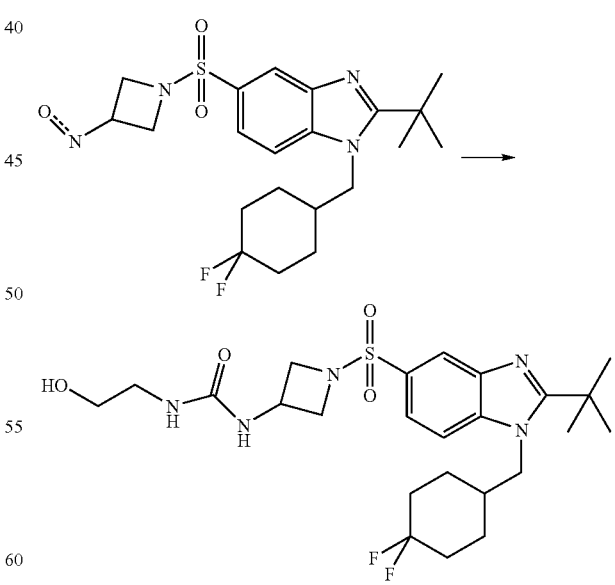

Following the same procedure in Example 105, Step A, using 2-tert-butyl-1-[(4,4-difluorocyclohexyl)methyl]-5-[(3-isocyanatoazetidin-1-yl)sulfonyl]-1H-benzimidazole (0.095 mmol) and ethanolamine (12 uL, 12 mg, 0.19 mmol) in THF (6.0 mL). The crude product was purified by MPLC using EtOAc/MeOH (20:1) on silica gel to give 22 mg (44%) of a white solid as the title compound. ¹H NMR (400 MHz, METHANOL-D₄) δ 1.49-1.65 (m, 2 H), 1.68 (s, 9 H), 1.70-1.86 (m, 4 H), 2.02-2.14 (m, 2 H), 2.19-2.36 (m, 1 H), 3.13 (t, J=5.57 Hz, 2 H), 3.48 (t, J=5.57 Hz, 2 H), 3.64 (dd, J=8.50, 6.35 Hz, 2 H), 3.99 (t, J=8.11 Hz, 2 H), 4.17-4.27 (m, 1 H), 4.55 (d, J=7.42 Hz, 2 H), 7.93 (dd, J=8.79, 1.76 Hz, 1 H), 8.06 (d, J=8.79 Hz, 1 H), 8.17 (d, J=1.37 Hz, 1 H); MS (ESI) (M+H)⁺=528.3; Anal. Calcd for $C_{24}H_{35}F_2N_5O_4S+0.90$ TFA+1.0H₂O+0.10 EtOAc (658.29): C, 47.99; H, 5.93; N, 10.64. Found: C, 47.99; H, 5.95; N, 10.68.

Example 108

5-(Azetidin-1-ylsulfonyl)-2-tert-butyl-1-[(4,4-difluorocyclohexyl)methyl]-1H-benzimidazole

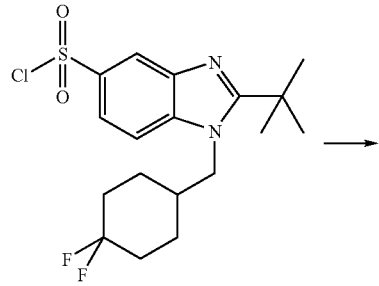

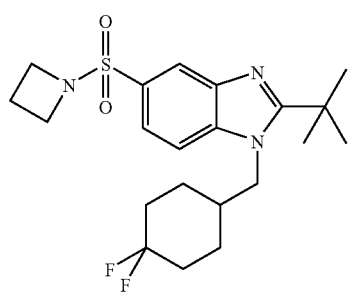

Following the same procedure in Example 1, Step A, using 2-tert-butyl-1-[(4,4-difluorocyclohexyl)methyl]-1H-benzimidazole-5-sulfonyl chloride (122 mg, 0.3 mmol), azetidine (41 uL, 34 mg, 0.6 mmol) and DMAP (73 mg, 0.6 mmol) in MeCN (5 mL). The crude product was purified by MPLC using Hex/EtOAc (1:1) on silica gel to give 88 mg (69%) of a white solid as the title compound. ¹H NMR (400 MHz, METHANOL-D₄) δ 1.49-1.63 (m, 2 H), 1.65 (s, 9 H), 1.69-1.93 (m, 4 H), 1.98-2.19 (m, 4 H), 2.21-2.34 (m, 1 H), 3.73-3.82 (m, 4 H), 4.51 (d, J=7.42 Hz, 2 H), 7.84 (dd, J=8.59, 1.76 Hz, 1 H), 7.98 (d, J=8.59 Hz, 1 H), 8.13 (d, J=1.76 Hz, 1 H); MS (ESI) (M+H)⁺=426.2.

Example 109

2-tert-Butyl-1-[(4,4-difluorocyclohexyl)methyl]-5-(1H-pyrazol-1-ylsulfonyl)-1H-benzimidazole

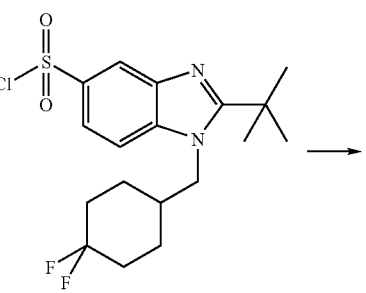

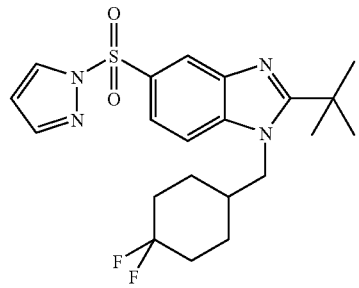

Following the same procedure in Example 1, Step A, using 2-tert-butyl-1-[(4,4-difluorocyclohexyl)methyl]-1H-benzimidazole-5-sulfonyl chloride (202 mg, 0.5 mmol) and pyrazol (186 mg, 2.7 mmol) in MeCN (6 mL). The crude product was purified by MPLC using Hex/EtOAc (1:1) on silica gel to give 164 mg (75%) of a white solid as the title compound. ¹H NMR (400 MHz, CHLOROFORM-D) δ 1.43-1.54 (m, 1 H), 1.56 (s, 9 H), 1.59-1.80 (m, 4 H), 2.01-2.22 (m, 3 H), 2.49-2.79 (m, 1 H), 4.24 (d, J=7.42 Hz, 2 H), 6.38 (dd, J=2.73, 1.56 Hz, 1 H), 7.43 (d, J=8.59 Hz, 1 H), 7.70 (d, J=0.98 Hz, 1 H), 7.96 (dd, J=8.69, 1.66 Hz, 1 H), 8.15 (d, J=2.73 Hz, 1 H), 8.40 (d, J=1.76 Hz, 1 H); MS (ESI) (M+H)⁺=437.3; Anal. Calcd for $C_{21}H_{26}F_2N_4O_2S+0.2H_2O$ (440.13): C, 57.31; H, 6.05; N, 12.73. Found: C, 57.23; H, 6.05; N, 12.83.

Example 110

1-({2-tert-Butyl-1-[(4,4-difluorocyclohexyl)methyl]-1H-benzimidazol-5-yl}sulfonyl)azetidin-3-ol

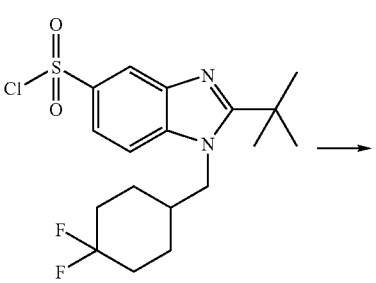

-continued

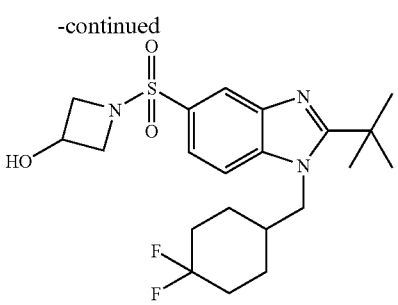

3-Hydroxyazetidine hydrochloride (162 mg, 1.5 mmol) was dissolved in 7 mL of dry dichloromethane. N,N-diisopropylethylamine (0.7 mL, 4 mmol) was added and the mixture was cooled down to 0° C. 2-tert-Butyl-1-[(4,4-difluorocyclohexyl)methyl]-1H-benzimidazole-5-sulfonyl chloride (400 mg, 1 mmol) was slowly added to the reaction mixture which was allowed to warm to room temperature for 2 hours. The mixture was diluted with EtOAc which washed with water then brine and dried over $Na_2SO_4$. The solvent was removed in vacuo to give a crude product that was purified by LCMS using high pH column 40-70% acetonitrile gradient to give 340 mg (62%) of a white solid as the title compound. $^1$H NMR (400 MHz, METHANOL-$D_4$) δ 1.56-1.66 (m, 2 H), 1.69 (s, 9 H), 1.73-1.84 (m, 4 H), 2.01-2.14 (m, 3 H), 3.45-3.51 (m, 2 H), 4.01 (dd, J=8.79, 6.84 Hz, 2 H), 4.34-4.43 (m, 1 H), 4.58 (d, J=7.62 Hz, 2 H), 7.97 (dd, J=8.79, 1.56 Hz, 1 H), 8.13 (d, J=8.79 Hz, 1 H), 8.18 (d, J=1.76 Hz, 1 H); MS (APPI) (M+H)$^+$=442.3; Anal. Calc. for $C_{21}H_{29}F_2N_3O_3S$+4.9$C_2HO_2F_3$+5.0$H_2O$+2.7 $CH_3CN$: C, 39.47; H, 4.14; N, 6.31. Found: C, 39.48; H, 4.14; N, 6.30

Example 111

1-({2-tert-Butyl-1-[(4,4-difluorocyclohexyl)methyl]-1H-benzimidazol-5-yl}sulfonyl)azetidin-3-yl ethylcarbamate

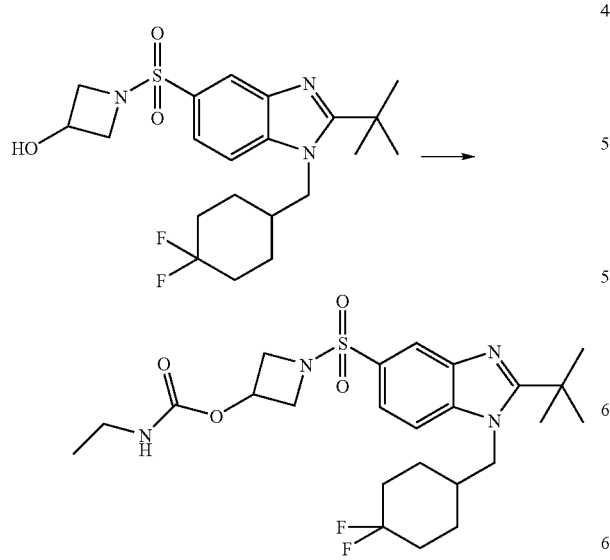

To a solution of 1-({2-tert-butyl-1-[(4,4-difluorocyclohexyl)methyl]-1H-benzimidazol-5-yl}sulfonyl)azetidin-3-ol (100 mg, 0.23 mmol) in 2 mL of dry dichloromethane was added triethylamine (3 uL, 0.023 mmol) and ethyl isocyanate (0.11 mL, 1.4 mmol), respectively. The reaction mixture was stirred at room temperature for 1 hour and then concentrated. The crude product was purified by LCMS using high pH column 40-70% acetonitrile gradient to give 100 mg (85%) of a white solid as the title compound. $^1$H NMR (400 MHz, METHANOL-$D_4$) δ 1.00 (t, J=7.23 Hz, 3 H), 1.48-1.57 (m, 2 H), 1.59 (s, 9 H), 1.63-1.83 (m, 4 H), 2.04 (d, J=26.56 Hz, 2 H), 2.18-2.31 (m, 1 H), 3.00 (q, J=7.23 Hz, 2 H), 3.63 (dd, J=9.18, 5.08 Hz, 2H), 4.01-4.09 (m, 2 H), 4.42 (d, J=7.62 Hz, 2 H), 7.70-7.75 (m, 1 H), 7.79-7.84 (m, 1 H), 8.10 (s, 1 H); MS (APPI) (M+H)$^+$=513.3; Anal. Calc. for $C_{24}H_{34}F_2N_4O_4S$+1.1 TFA: C, 49.32; H, 5.54; N, 8.78. Found: C, 49.31; H, 5.42; N, 8.59.

Example 112 and 113

(2S)-4-({2-tert-butyl-1-[(4,4-difluorocyclohexyl)methyl]-1H-benzimidazol-5-yl}sulfonyl)-N-ethyl-morpholine-2-carboxamide

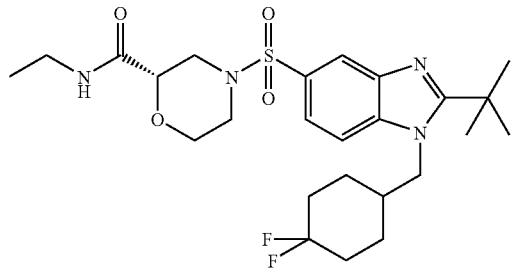

(2R)-4-({2-tert-butyl-1-[(4,4-difluorocyclohexyl)methyl]-1H-benzimidazol-5-yl}sulfonyl)-N-ethyl-morpholine-2-carboxamide

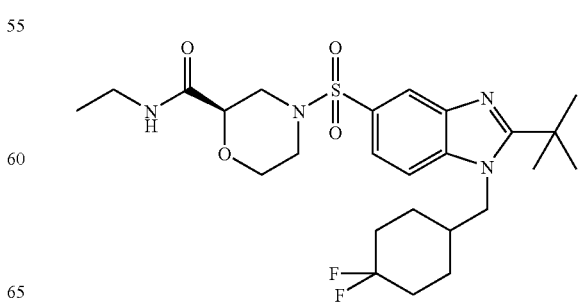

Step A: 4-({2-tert-butyl-1-[(4,4-difluorocyclohexyl)methyl]-1H-benzimidazol-5-yl}sulfonyl)-N-ethyl-morpholine-2-carboxamide

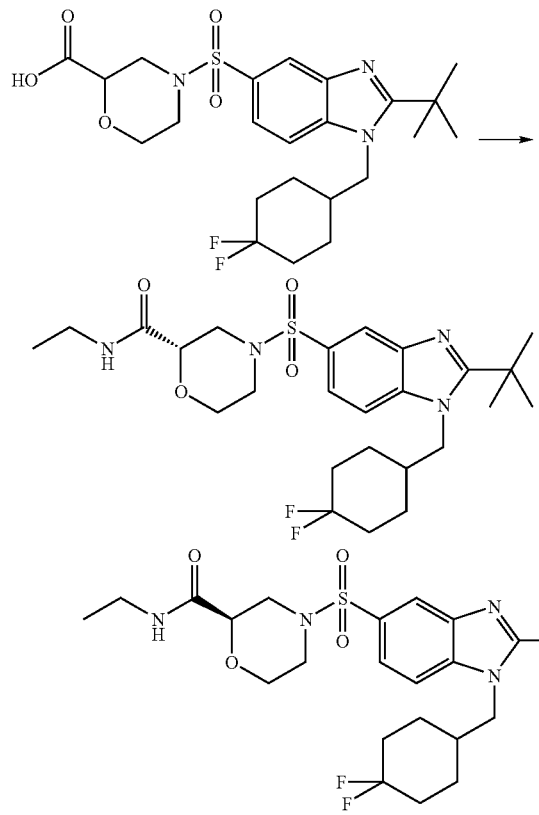

4-({2-tert-butyl-1-[(4,4-difluorocyclohexyl)methyl]-1H-benzimidazol-5-yl}sulfonyl)morpholine-2-carboxylic acid (500 mg, 1 mmol) (see following steps B and C for preparation) was dissolved in DMF (10 mL). Ethylamine hydrochloride (122 mg, 1.5 mmol) and N,N-diisopropylethylamine (1 mL, 5 mmol) were added and the reaction mixture was cooled down to 0° C. HATU (456 mg, 1.2 mmol) was added portionwise and the reaction was stirred overnight at room temperature. The reaction was concentrated, extracted with EtOAc and washed with sodium bicarbonate, water then brine and dried over anhydrous sodium sulfate. The crude product was purified by LCMS using high pH column 40-70% acetonitrile gradient to give 200 mg (40%) as white solid racemic mixture of the title compound. The two enantiomers were separated on a chiral OD 5 microns column using 20% ethanol/hexane. Example 112 (isomer-1): $^1$H NMR (400 MHz, METHANOL-D$_4$) δ 1.04 (t, J=7.23 Hz, 3 H), 1.46-1.56 (m, 2 H), 1.57 (s, 9H), 1.61-1.70 (m, 3 H), 1.70-1.81 (m, 1 H), 1.98-2.08 (m, 2 H), 2.12-2.23 (m, 1 H), 2.39 (m, 1 H), 2.74 (q, J=7.23 Hz, 2 H), 3.17 (dd, J=7.23, 3.91 Hz, 2 H), 3.68 (m, 1 H), 3.87-3.94 (m, 1 H), 4.01 (dd, J=10.45, 2.83 Hz, 2 H), 4.40 (d, J=7.62 Hz, 2H), 7.64 (dd, J=8.59, 1.56 Hz, 1 H), 7.77 (d, J=8.59 Hz, 1 H), 8.03 (d, J=1.76 Hz, 1 H); MS (APPI) (M+H)$^+$=527.3; Anal. Calc. for C$_{21}$H$_{29}$F$_2$N$_3$O$_3$S+4.9C$_2$HO$_2$F$_3$+5.0H$_2$O+2.7 CH$_3$CN: C, 39.47; H, 4.14; N, 6.31. Found: C, 39.48; H, 4.14; N, 6.30.

Example 113 (isomer-2): $^1$H NMR (400 MHz, METHANOL-D$_4$) δ 1.04 (t, J=7.23 Hz, 3 H), 1.46-1.56 (m, 2 H), 1.57 (s, 9H), 1.61-1.70 (m, 3 H), 1.70-1.81 (m, 1 H), 1.98-2.08 (m, 2 H), 2.12-2.23 (m, 1 H), 2.39 (m, 1 H), 2.74 (q, J=7.23 Hz, 2 H), 3.17 (dd, J=7.23, 3.91 Hz, 2 H), 3.68 (m, 1 H), 3.87-3.94 (m, 1 H), 4.01 (dd, J=10.45, 2.83 Hz, 2 H), 4.40 (d, J=7.62 Hz, 2H), 7.64 (dd, J=8.59, 1.56 Hz, 1 H), 7.77 (d, J=8.59 Hz, 1 H), 8.03 (d, J=1.76 Hz, 1 H). MS (APPI) (M+H)$^+$=527.3; Anal. Calc. for C$_{25}$H$_{36}$F$_2$N$_4$O$_4$S+1.7 TFA: C, 47.34; H, 5.27; N, 7.78. Found: C, 47.44; H, 5.20; N, 7.71.

Step B: Morpholine-2-carboxylic acid hydrochloride

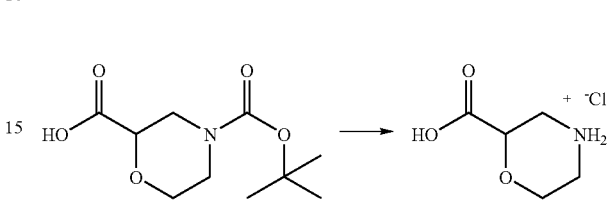

(R,S)-Boc-2-carboxymorpholine (3 g, 13 mmol) was added to 4 N HCl in dioxane (15 mL) at 0° C. The reaction mixture was allowed to warm to room temperature and stirred overnight. Removal of solvent produced 2.2 g (100%) of the desired product as an HCl salt. $^1$H NMR (400 MHz, METHANOL-D$_4$) δ 2.79-2.86 (m, 1 H), 2.87-2.94 (m, 2 H), 3.21 (dd, J=12.50, 3.52 Hz, 1 H), 3.51 (m, 1 H), 3.79 (m, 1 H), 4.07 (dd, J=9.77, 3.12 Hz, 1 H).

Step C: 4-({2-tert-butyl-1-[(4,4-difluorocyclohexyl)methyl]-1H-benzimidazol-5-yl}sulfonyl)morpholine-2-carboxylic acid

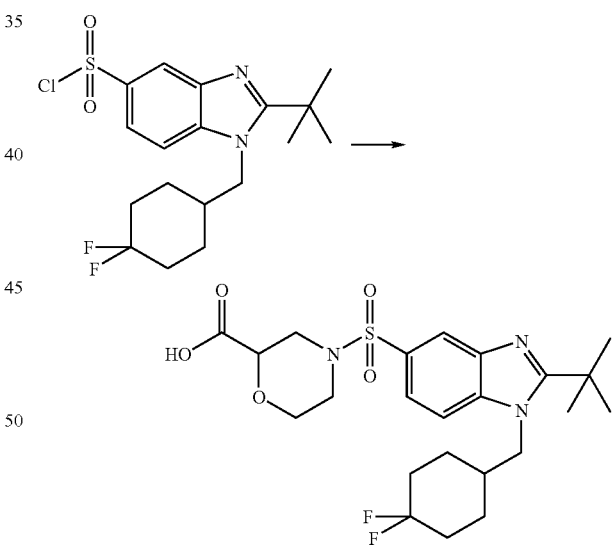

Following the same procedure in Example 1, Step A, using 2-tert-butyl-1-[(4,4-difluorocyclohexyl)methyl]-1H-benzimidazole-5-sulfonyl chloride (1.6 g, 4 mmol), N,N-diisopropylethylamine (3.5 mL, 20 mmol) and morpholine-2-carboxylic acid hydrochloride (1.0 g, 6 mmol) in methylene chloride (10 mL). Obtained 1.5 g of crude product which was carried over to step A. $^1$H NMR (400 MHz, METHANOL-D$_4$) δ 1.53 (d, J=13.67 Hz, 2 H), 1.59 (s, 12 H), 1.63-1.78 (m, 6 H), 1.98-2.12 (m, 3 H), 3.22 (q, J=7.36 Hz, 1 H), 3.72 (m, 1 H), 4.42 (d, J=7.42 Hz, 2 H), 7.69 (d, J=8.40 Hz, 1 H), 7.81 (d, J=8.40 Hz, 1 H), 8.05 (s, 1 H).

Example 114 and 115

(2S)-2-tert-Butyl-5-[(4-methylpiperidin-1-yl)sulfonyl]-1-(tetrahydro-2H-pyran-4-ylmethyl)-1H-benzimidazole (2R)-2-tert-Butyl-5-[(4-methylpiperidin-1-yl)sulfonyl]-1-(tetrahydro-2H-pyran-4-ylmethyl)-1H-benzimidazole

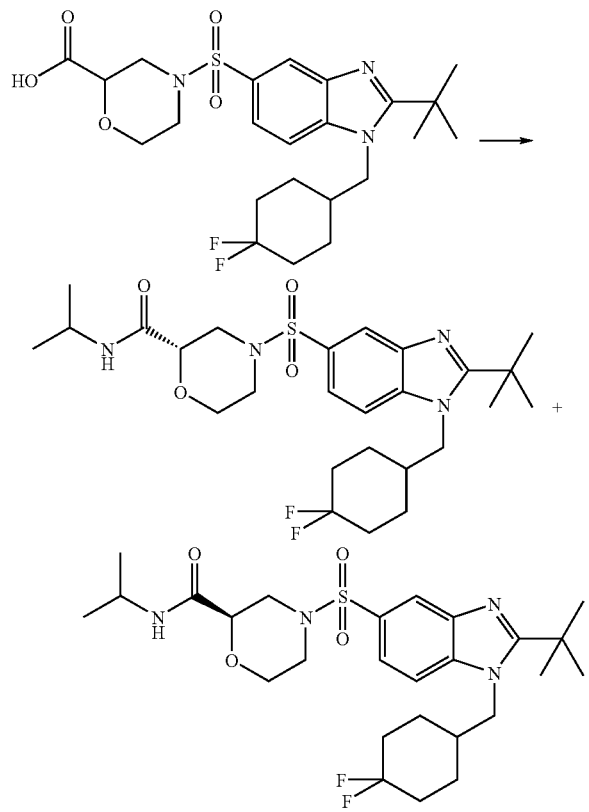

Following the same procedure in Example 112, Step A, using 4-({2-tert-butyl-1-[(4,4-difluorocyclohexyl)methyl]-1H-benzimidazol-5-yl}sulfonyl)morpholine-2-carboxylic acid (500 mg, 1 mmol), N,N-diisopropylethylamine (1 mL, 5 mmol), isopropylamine hydrochloride (143 mg, 1.5 mmol) and HATU (456 mg, 1.2 mmol) in (10 mL) DMF. The crude product was purified by LCMS using high pH column 40-70% acetonitrile gradient to give 410 mg (76%) as white solid racemic mixture of the title compound. The two enantiomers were separated on a chiral OD 5 microns column using 20% ethanol/hexane.

Example 114 (Isomer 1): $[\alpha]_D$: −49.6° (c=1.05, MeOH); $^1$H NMR (400 MHz, METHANOL-D$_4$) δ 0.97 (d, J=6.64 Hz, 3 H), 1.02 (d, J=6.64 Hz, 3 H), 1.38-1.47 (m, 2 H), 1.49 (s, 9 H), 1.53-1.61 (m, 3 H), 1.62-1.73 (m, 1 H), 1.89-2.02 (m, 2 H), 2.05-2.17 (m, 2 H), 2.31 (m, 1 H), 3.48 (d, J=13.09 Hz, 1 H), 3.60 (m, 1 H), 3.78-3.84 (m, 1 H), 3.84-3.89 (m, 1 H), 3.92 (dd, J=10.35, 2.93 Hz, 2 H), 4.31 (d, J=7.42 Hz, 2 H), 7.57 (dd, J=8.69, 1.46 Hz, 1 H), 7.69 (d, J=8.59 Hz, 1 H), 7.94 (d, J=1.76 Hz, 1 H); MS (ESI) (M+H)$^+$=541.3; Anal. Calc. for C$_{26}$H$_{38}$F$_2$N$_4$O$_4$S+1.1 TFA: C, 50.85; H, 5.92; N, 8.41. Found: C, 50.93; H, 5.88; N, 7.75;

Example 115 (Isomer 2): $[\alpha]_D$: +50.0° (c=1.05, MeOH); $^1$H NMR (400 MHz, METHANOL-D$_4$) δ 0.97 (d, J=6.64 Hz, 3 H), 1.02 (d, J=6.64 Hz, 3 H), 1.38-1.47 (m, 2 H), 1.49 (s, 9 H), 1.53-1.61 (m, 3 H), 1.62-1.73 (m, 1 H), 1.89-2.02 (m, 2 H), 2.05-2.17 (m, 2 H), 2.31 (m, 1 H), 3.48 (d, J=13.09 Hz, 1 H), 3.60 (m, 1 H), 3.78-3.84 (m, 1 H), 3.84-3.89 (m, 1 H), 3.92 (dd, J=10.35, 2.93 Hz, 2 H), 4.31 (d, J=7.42 Hz, 2 H), 7.57 (dd, J=8.69, 1.46 Hz, 1 H), 7.69 (d, J=8.59 Hz, 1 H), 7.94 (d, J=1.76 Hz, 1 H). MS (APPI) (M+H)$^+$=541.3; Anal. Calc. for C$_{26}$H$_{38}$F$_2$N$_4$O$_4$S+2.0 TFA: C, 46.87; H, 5.24; N, 7.29. Found: C, 46.90; H, 5.18; N, 7.18.

Example 116

(2R)-4-({2-tert-Butyl-1-[(4,4-difluorocyclohexyl)methyl]-1H-benzimidazol-5-yl}sulfonyl)-N-methyl-morpholine-2-carboxamide

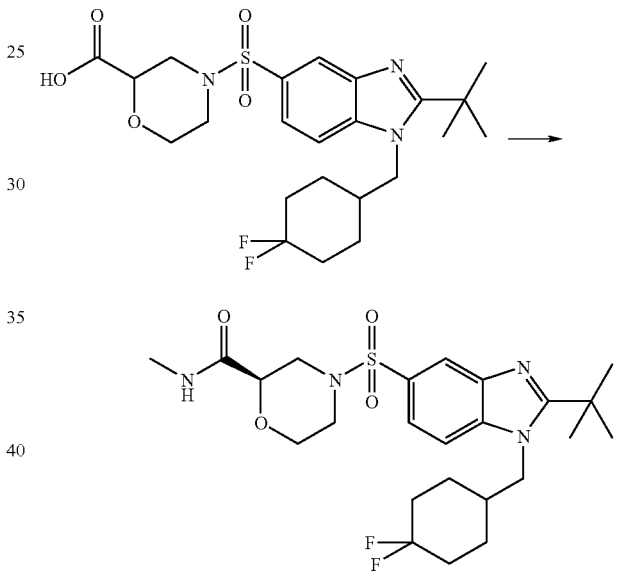

Following the same procedure in Example 112, Step A, using 4-({2-tert-butyl-1-[(4,4-difluorocyclohexyl)methyl]-1H-benzimidazol-5-yl}sulfonyl)morpholine-2-carboxylic acid (500 mg, 1 mmol), N,N-diisopropylethylamine (1 mL, 5 mmol), methylamine (0.75 mL, 2.0M in THF, 1.5 mmol) and HATU (456 mg, 1.2 mmol) in DMF (10 mL). The crude product was purified by LCMS using high pH column 40-70% acetonitrile gradient to give 400 mg (78% yield) as white solid racemic mixture of the title compound. The two enantiomers were separated on a chiral OD 5 microns column using 20% ethanol:hexane. $[\alpha]_D$: +37.4 (c=1.00, MeOH). $^1$H NMR (400 MHz, METHANOL-D$_4$) δ 1.37-1.46 (m, 2 H), 1.48 (s, 9 H), 1.53-1.73 (m, 4 H), 1.88-2.01 (m, 2 H), 2.04-2.18 (m, 2 H), 2.29 (m, 1 H), 2.59 (s, 3 H), 3.43-3.49 (m, 1 H), 3.59 (m, 1 H), 3.77-3.85 (m, 1 H), 3.87-3.96 (m, 2 H), 4.30 (d, J=7.62 Hz, 2 H), 7.54 (dd, J=8.69, 1.66 Hz, 1 H), 7.67 (d, J=8.59 Hz, 1 H), 7.93 (d, J=1.76 Hz, 1 H); MS (APPI) (M+H)$^+$=513.3; Anal. Calc. for C$_{24}$H$_{34}$F$_2$N$_4$O$_4$S+1.5 TFA: C, 47.44; H, 5.23; N, 8.20. Found: C, 47.54; H, 4.91; N, 8.00.

Example 117

(3R)-1-({2-tert-Butyl-1-[(4,4-difluorocyclohexyl)methyl]-1H-benzimidazol-5-yl}sulfonyl)pyrrolidin-3-ol

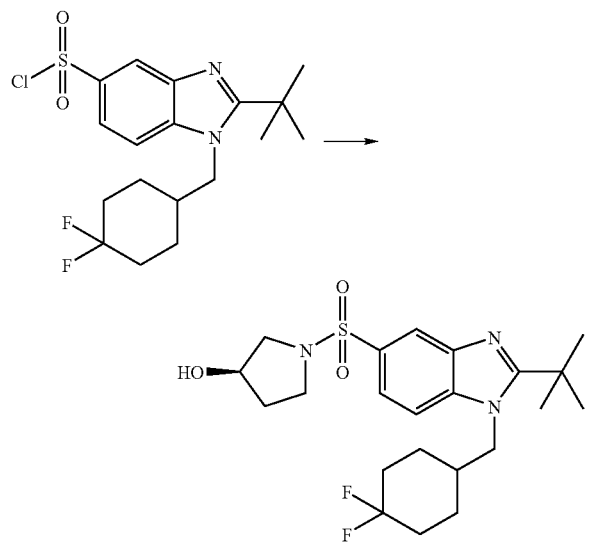

Following the same procedure in Example 1, using 2-tert-butyl-1-[(4,4-difluorocyclohexyl)methyl]-1H-benzimidazole-5-sulfonyl chloride (50 mg, 0.12 mmol), N,N-diisopropylethylamine (0.1 mL, 0.48 mmol) and (R)-(−)-3-pyrrolidinol hydrochloride (23 mg, 0.19 mmol) in (1 mL) methylene chloride. The crude product was purified by LCMS using high pH column 40-70% acetonitrile gradient to give 42 mg (61% yield) of a white solid as the title compound. $^1$H NMR (400 MHz, METHANOL-D$_4$) δ 1.43-1.52 (m, 2 H), 1.56 (s, 9 H), 1.60-1.69 (m, 3 H), 1.90-2.01 (m, 3 H), 2.09-2.21 (m, 1 H), 3.05-3.11 (m, 1 H), 3.20-3.25 (m, 2 H), 3.26-3.34 (m, 3 H), 4.13-4.18 (m, 1 H), 4.44 (d, J=7.62 Hz, 2 H), 7.81 (dd, J=8.79, 1.76 Hz, 1 H), 7.89-7.93 (m, 1 H), 8.04 (d, J=1.17 Hz, 1 H); MS (ESI) (M+H)$^+$=455.2; Anal. Calc. for C$_{22}$H$_{31}$F$_2$N$_3$O$_3$S+1.3 TFA+0.50H$_2$O+0.2 CH$_3$CN: C, 48.75; H, 5.46; N, 7.16. Found: C, 48.78; H, 5.48; N, 7.11.

Example 118

N-[(3R)-1-({2-tert-Butyl-1-[(4,4-difluorocyclohexyl)methyl]-1H-benzimidazol-5-yl}sulfonyl)pyrrolidin-3-yl]acetamide

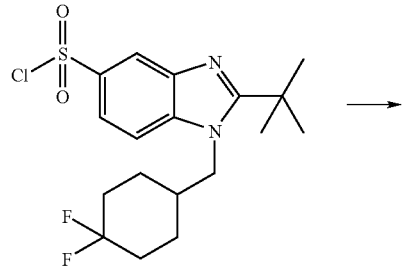

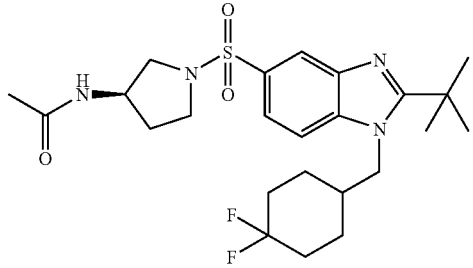

Following the same procedure in Example 1, step A, using 2-tert-butyl-1-[(4,4-difluorocyclohexyl)methyl]-1H-benzimidazole-5-sulfonyl chloride (300 mg, 0.74 mmol), N,N-diisopropylethylamine (0.5 mL, 3 mmol) and (3R)-(+)-3-acetamidopyrrolidine (142 mg, 1.1 mmol) in (1 mL) methylene chloride. The crude product was purified by LCMS using high pH column 40-70% acetonitrile gradient to give 15 mg (4% yield) of a white solid as the title compound. $^1$H NMR (400 MHz, METHANOL-D$_4$) δ 1.51-1.65 (m, 3 H), 1.69 (s, 9 H), 1.71-1.77 (m, 4 H), 1.78 (s, 3 H), 1.93-2.12 (m, 3 H), 2.21-2.33 (m, 1 H), 3.15 (dd, J=10.35, 4.69 Hz, 1 H), 3.21-3.28 (m, 1 H), 3.37-3.49 (m, 2 H), 4.00-4.11 (m, 1 H), 4.58 (d, J=7.42 Hz, 2 H), 7.91 (d, J=8.59 Hz, 1 H), 8.09 (d, J=8.79 Hz, 1 H), 8.12 (s, 1 H); MS (ESI) (M+H)$^+$=496.6; Anal. Calc. for C$_{24}$H$_{34}$F$_2$N$_4$O$_3$S+4.2 TFA+2.9H$_2$O+2.4 CH$_3$CN: C, 39.67; H, 4.58; N, 7.16. Found: C, 39.69; H, 4.61; N, 7.96.

Example 119

(3S)-1-({2-tert-Butyl-1-[(4,4-difluorocyclohexyl)methyl]-1H-benzimidazol-5-yl}sulfonyl)pyrrolidin-3-amine

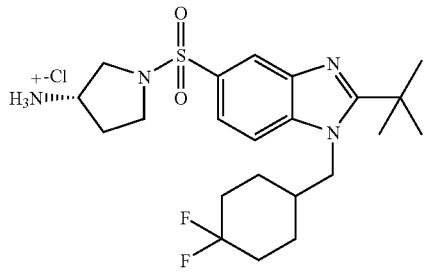

Step A: (3S)-1-({2-tert-butyl-1-[(4,4-difluorocyclohexyl)methyl]-1H-benzimidazol-5-yl}sulfonyl)pyrrolidin-3-amine

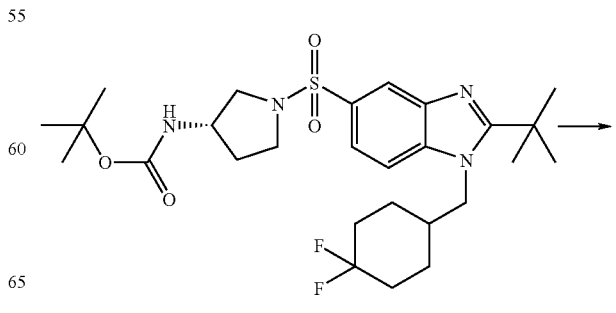

-continued

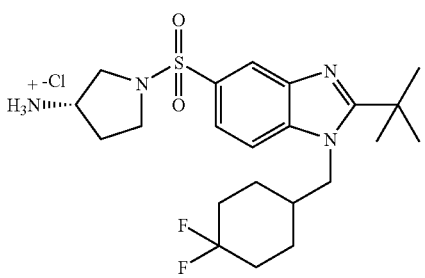

Following the same procedure in Example 112, step B, using tert-butyl[(3S)-1-({2-tert-butyl-1-[(4,4-difluorocyclohexyl)methyl]-1H-benzimidazol-5-yl}sulfonyl)pyrrolidin-3-yl]carbamate (2.8 g, 5 mmol) (see the following step B for preparation), and 4N HCl in dioxane (50 mL). Yield: 2.0 g (82%). $^1$H NMR (400 MHz, METHANOL-D$_4$) δ 1.45-1.56 (m, 3 H), 1.63 (s, 9 H), 1.65-1.80 (m, 4 H), 1.94-2.05 (m, 2 H), 3.10-3.18 (m, 1 H), 3.33-3.42 (m, 2 H), 3.46-3.54 (m, 1 H), 3.54-3.59 (m, 2 H), 3.70-3.80 (m, 1 H), 4.53 (d, J=7.23 Hz, 2 H), 7.96 (d, J=8.98 Hz, 1 H), 8.11 (d, J=8.98 Hz, 1 H), 8.16 (s, 1 H); MS (APPI) (M+H)$^+$=455.3; Anal. Calc. for C$_{22}$H$_{32}$F$_2$N$_4$O$_2$S+2.5HCl+1.2H$_2$O: C, 46.57; H, 6.56; N, 9.88. Found: C, 46.73; H, 6.55; N, 9.40.

Step B: tert-butyl[(3S)-1-({2-tert-butyl-1-[(4,4-difluorocyclohexyl)methyl]-1H-benzimidazol-5-yl}sulfonyl)pyrrolidin-3-yl]carbamate

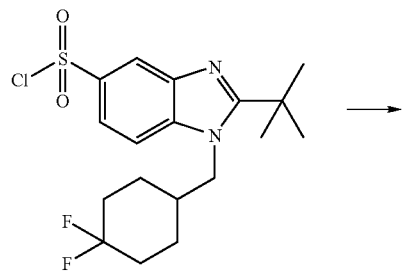

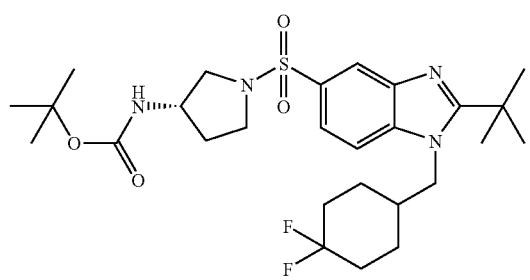

Following the same procedure in Example 1, step A, using 2-tert-butyl-1-[(4,4-difluorocyclohexyl)methyl]-1H-benzimidazole-5-sulfonyl chloride (2 g, 5 mmol), N,N-diisopropylethylamine (3.5 mL, 20 mmol) and (3S)-(−)-3-(tert-butoxycarbonylamino)pyrrolidine (1.4 g, 7.5 mmol) in (10 mL)

methylene chloride. The crude product was purified by MPLC on silica gel using 8-70% EtOAc/hexane. Yield: 2.77 g (100%). $^1$H NMR (400 MHz, METHANOL-D$_4$) δ 1.35 (s, 9 H) 1.52 (d, J=11.72 Hz, 4 H) 1.58 (s, 9 H) 1.62-1.73 (m, 4 H) 1.75-1.81 (m, 1 H) 1.93-2.00 (m, 1 H) 3.03-3.10 (m, 1 H) 3.24-3.29 (m, 2 H) 3.35-3.47 (m, 3 H) 4.40 (d, J=7.42 Hz, 2 H) 7.71-7.78 (m, 2 H) 8.09 (d, J=1.37 Hz, 1 H).

Example 120

N-[(3S)-1-({2-tert-Butyl-1-[(4,4-difluorocyclohexyl)methyl]-1H-benzimidazol-5-yl}sulfonyl)pyrrolidin-3-yl]cyclopropanecarboxamide

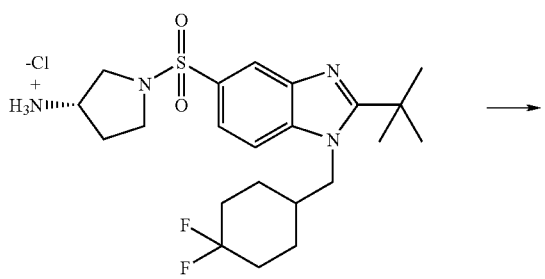

(3S)-1-({2-tert-Butyl-1-[(4,4-difluorocyclohexyl)methyl]-1H-benzimidazol-5-yl}sulfonyl)pyrrolidin-3-amine hydrochloride (200 mg, 0.41 mmol) was dissolved in methylene chloride (3 mL) followed by addition of N,N-diisopropylethylamine (0.3 mL, 1.64 mmol). The reaction mixture was cooled down to 0° C. followed by addition of cyclopropanecarbonyl chloride (43 mg, 0.41 mmol) dropwise and the mixture was allowed to warm to room temperature. The reaction was quenched with methylamine and concentrated under vacuum. The crude product was purified on LCMS using low pH column 30-60% acetonitrile gradient to afford 160 mg (65%) white solid of the title compound. [α]$_D$ −2.2° (c=0.98, MeOH); $^1$H NMR (400 MHz, METHANOL-D$_4$) δ 1.45-1.56 (m, 3 H), 1.63 (s, 9 H), 1.65-1.80 (m, 4 H), 1.94-2.05 (m, 2 H), 3.10-3.18 (m, 1 H), 3.33-3.42 (m, 2 H), 3.46-3.54 (m, 1 H), 3.54-3.59 (m, 2 H), 3.70-3.80 (m, 1 H), 4.53 (d, J=7.23 Hz, 2 H), 7.96 (d, J=8.98 Hz, 1 H), 8.11 (d, J=8.98 Hz, 1 H), 8.16 (s, 1 H); MS (ESI) (M+H)$^+$=523; Anal. Calc. for C$_{26}$H$_{36}$F$_2$N$_4$O$_3$S+2.0 TFA: C, 48.00; H, 5.10; N, 7.46. Found: C, 48.15; H, 5.02; N, 7.25.

Example 121

N-[(3S)-1-({2-tert-Butyl-1-[(4,4-difluorocyclohexyl)methyl]-1H-benzimidazol-5-yl}sulfonyl)pyrrolidin-3-yl]propanamide

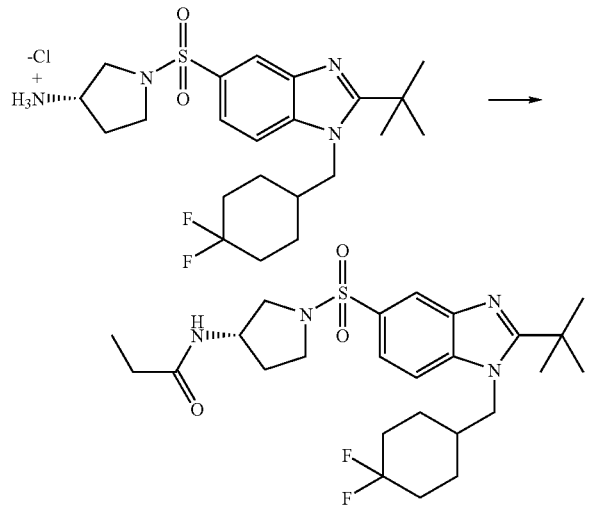

Following the same procedure in Example 120, using (3S)-1-({2-tert-butyl-1-[(4,4-difluorocyclohexyl)methyl]-1H-benzimidazol-5-yl}sulfonyl)pyrrolidin-3-amine hydrochloride (200 mg, 0.41 mmol), N,N-diisopropylethylamine (0.3 mL, 1.64 mmol), propionic anhydride (53 µL, 0.41 mmol) in methylene chloride (3 mL). The crude product was purified on LCMS using low pH column 30-60% acetonitrile gradient to afford 160 mg (62%) white solid of the title compound. $[\alpha]_D$ −2.9° (c=1.10, MeOH); $^1$H NMR (400 MHz, METHANOL-D$_4$) δ 1.01 (t, J=7.62 Hz, 3 H), 1.56-1.65 (m, 2 H), 1.69 (s, 9 H), 1.72-1.83 (m, 5 H), 1.95-2.04 (m, 3 H), 2.04-2.12 (m, 2 H), 2.22-2.31 (m, 1 H), 3.15 (dd, J=10.45, 4.98 Hz, 1 H), 3.25-3.29 (m, 1H), 3.44 (dd, J=10.55, 6.25 Hz, 1 H), 3.46-3.51 (m, 1 H), 4.02-4.09 (m, 1 H), 4.58 (d, J=7.62 Hz, 2 H), 7.94 (dd, J=8.79, 1.76 Hz, 1 H), 8.09 (d, J=8.79 Hz, 1 H), 8.15 (d, J=1.56 Hz, 1 H); MS (ESI) (M+H)$^+$=511; Anal. Calc. for $C_{25}H_{36}F_2N_4O_3S$+1.8 TFA+0.2H$_2$O: C, 47.74; H, 5.35; N, 7.79. Found: C, 47.75; H, 5.33; N, 7.78.

Example 122

N-[(3S)-1-({2-tert-Butyl-1-[(4,4-difluorocyclohexyl)methyl]-1H-benzimidazol-5-yl}sulfonyl)pyrrolidin-3-yl]acetamide

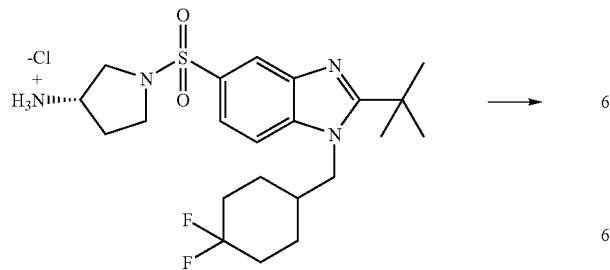

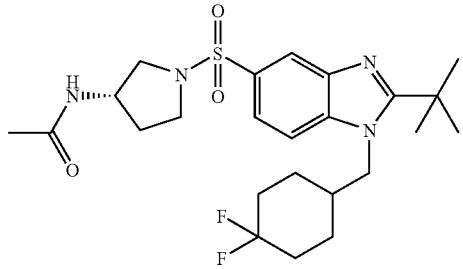

Following the same procedure in Example 120, using (3S)-1-({2-tert-butyl-1-[(4,4-difluorocyclohexyl)methyl]-1H-benzimidazol-5-yl}sulfonyl)pyrrolidin-3-amine (200 mg, 0.41 mmol), N,N-diisopropylethylamine (0.3 mL, 1.64 mmol), acetic anhydride (39 µL, 0.41 mmol) in methylene chloride (3 mL). The crude product was purified on LCMS using low pH column 30-60% acetonitrile gradient to afford 160 mg (64%) white solid of the title compound. $[\alpha]_D$ −3.4° (c=1.10, MeOH); $^1$H NMR (400 MHz, METHANOL-D4) δ 1.53-1.65 (m, 3 H), 1.70 (s, 9 H), 1.72-1.77 (m, 3 H), 1.78 (s, 3 H), 1.95-2.13 (m, 4 H), 2.21-2.33 (m, 1 H), 3.16 (dd, J=10.35, 4.69 Hz, 1 H), 3.24-3.28 (m, 1 H), 3.39-3.42 (m, 1 H), 3.43-3.50 (m, 1 H), 4.01-4.09 (m, 1 H), 4.59 (d, J=7.62 Hz, 2 H), 7.92 (dd, J=8.79, 1.56 Hz, 1 H), 8.10 (d, J=8.98 Hz, 1 H), 8.12 (d, J=1.17 Hz, 1 H); MS (ESI) (M+H)$^+$=497;

Example 123 and 124

(2S)-4-({2-tert-butyl-1-[(4,4-difluorocyclohexyl)methyl]-1H-benzimidazol-5-yl}sulfonyl)-N-cyclopropylmorpholine-2-carboxamide

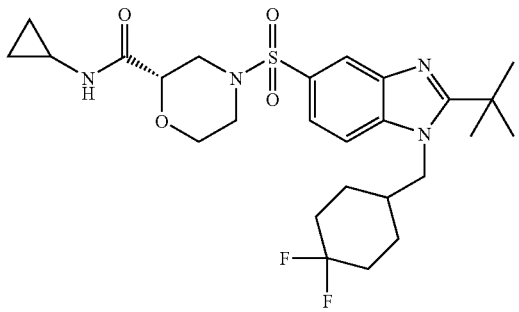

(2R)-4-({2-tert-Butyl-1-[(4,4-difluorocyclohexyl)methyl]-1H-benzimidazol-5-yl}sulfonyl)-N-cyclopropylmorpholine-2-carboxamide

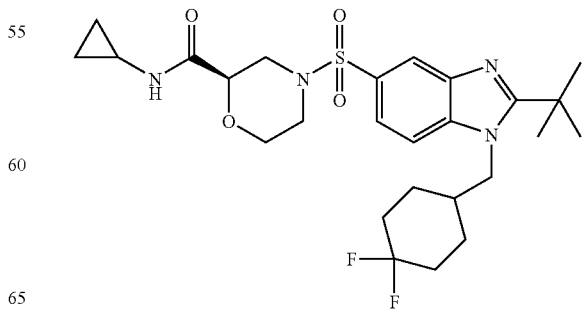

Step A. (2R)-4-({2-tert-butyl-1-[(4,4-difluorocyclohexyl)methyl]-1H-benzimidazol-5-yl}sulfonyl)-N-cyclopropylmorpholine-2-carboxamide

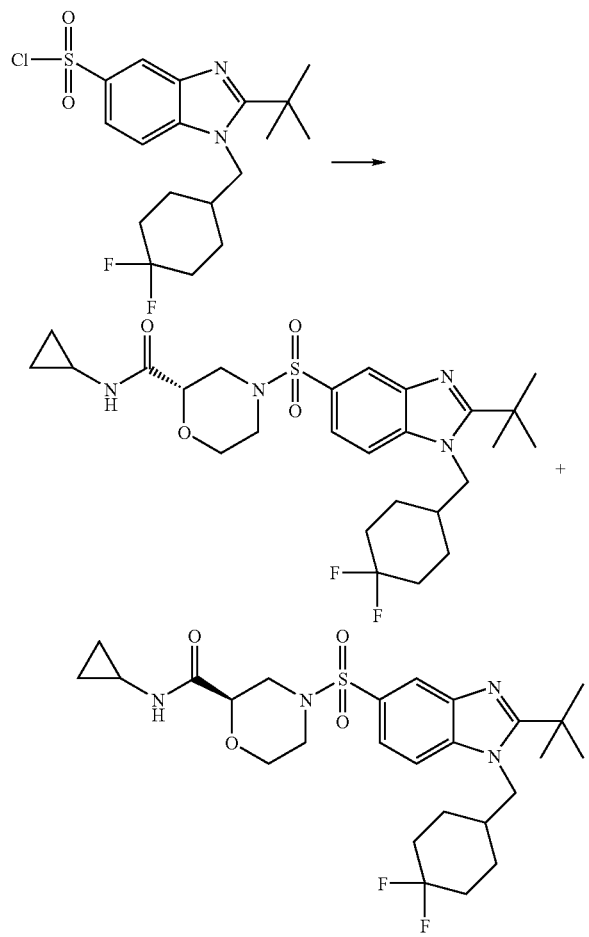

2-tert-Butyl-1-[(4,4-difluorocyclohexyl)methyl]-1H-benzimidazole-5-sulfonyl chloride (1.1 g, 2.7 mmol) was added to a solution of 2-[(cyclopropylamino)carbonyl]morpholin-4-ium trifluoroacetate (0.92 g, 3.2 mmol) (see the following step B for preparation) and DIPEA (1.5 mL, 8.1 mmol) in DCE at 80° C. The reaction mixture was stirred for 1 h and washed with saturated NaHCO₃ solution, water and brine. The solvent was concentrated to provide the racemic title compound as white solid. The enantiomers were separated by chiral preparative HPLC to provide the title compounds.

Example 123 (isomer-1): 76 mg (4%); [α]$_D$: −35.1° (c=1.29, CD₃OD); ¹H NMR (400 MHz, CD₃OD) δ 0.39-0.53 (m, 2 H), 0.62-0.75 (m, 2 H), 1.49-1.65 (m, 2 H), 1.68 (s, 9 H), 1.70-1.86 (m, 4 H), 2.00-2.14 (m, 2 H), 2.24 (dd, J=11.62, 10.45 Hz, 2 H), 2.45 (td, J=11.52, 3.32 Hz, 1 H), 2.57-2.66 (m, 1 H), 3.60 (d, J=11.52 Hz, 1 H), 3.68 (m, 1 H), 3.86-3.94 (m, 1 H), 3.96-4.05 (m, 2 H), 4.56 (d, J=7.62 Hz, 2 H), 7.88 (dd, J=8.69, 1.66 Hz, 1 H), 8.08 (d, J=8.79 Hz, 1 H), 8.12 (d, J=1.56 Hz, 1 H); MS (ESI) (M+H)⁺=539.3.

Example 124 (isomer-2): Yield: 70 mg (4%); [α]$_D$ +40.2° (c=1.05, CD₃OD); ¹H NMR (400 MHz, CD₃OD) δ 0.40-0.54 (m, 2 H), 0.62-0.74 (m, 2 H), 1.48-1.63 (m, 2 H), 1.65 (s, 9 H), 1.68-1.76 (m, J=15.62 Hz, 4 H), 1.77-1.84 (m, 1 H), 1.99-2.13 (m, 2 H), 2.22 (dd, J=11.43, 10.45 Hz, 2 H), 2.43 (m, 1 H), 2.57-2.66 (m, 1 H), 3.67 (td, J=11.47, 2.83 Hz, 1 H), 3.86-3.93 (m, 1 H), 3.96-4.06 (m, 2 H), 4.52 (d, J=7.42 Hz, 2 H), 7.82 (dd, J=8.79, 1.56 Hz, 1 H), 8.01 (d, J=8.79 Hz, 1 H), 8.09 (d, J=1.37 Hz, 1 H); MS (ESI) (M+H)⁺=539.3.

Step B. 2-[(cyclopropylamino)carbonyl]morpholin-4-ium trifluoroacetate

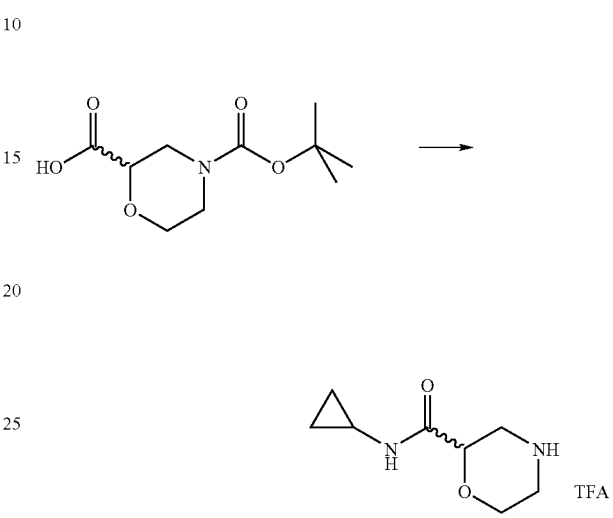

HATU (3.7 g, 9.7 mmol) and cyclopropylamine (0.53 g, 9.3 mmol) were added to a solution of 4-(tert-butoxycarbonyl)morpholine-2-carboxylic acid (2.0 g, 8.9 mmol) in DMF. The reaction mixture was stirred for 3 h and the solvent was concentrated. The residue was recovered in EtOAc and washed with saturated NaHCO₃ solution, water and brine. The solvent was concentrated and the resulting beige solid was treated with TFA (50 mL) for 3 hrs. The solvent was concentrated to provide the title compound as yellow oil that was used for the next step without further purification. Yield: 2.1 g (99%).

Example 125

1-({2-tert-Butyl-1-[(4,4-difluorocyclohexyl)methyl]-1H-benzimidazol-5-yl}sulfonyl)-1H-pyrazole-4-carboxamide

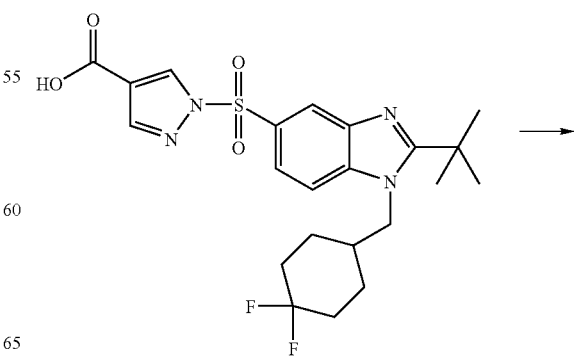

-continued

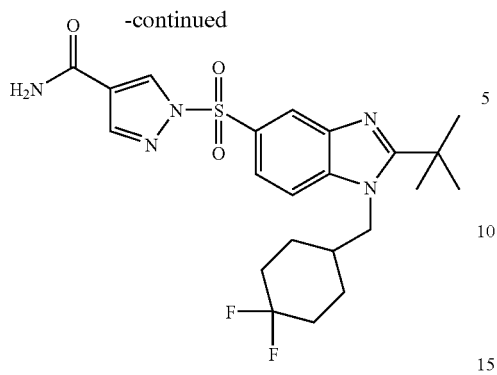

Following the same procedure in Example 72, step A, using HATU (87 mg, 0.22 mmol), 1-({2-tert-butyl-1-[(4,4-difluorocyclohexyl)methyl]-1H-benzimidazol-5-yl}sulfonyl)-1H-pyrazole-4-carboxylic acid (100 mg, 0.20 mmol), DIPEA (0.36 mL, 2.8 mmol) and gaseous ammonia in DMF (6 mL). The crude product was purified by reverse-phase preparative HPLC using 10-90% MeCN/H$_2$O and lyophilized affording the title compound as the corresponding TFA salt. Yield: 46 mg (46%); $^1$H NMR (400 MHz, CD$_3$OD) δ 1.42-1.57 (m, 2 H), 1.60 (s, 9 H), 1.62-1.71 (m, 3 H), 1.71-1.80 (m, 1 H), 1.96-2.10 (m, 4 H), 2.11-2.26 (m, 1 H), 4.44 (d, J=7.42 Hz, 2 H), 7.88-7.94 (m, 1 H), 7.97-8.03 (m, 1 H), 8.06 (d, J=0.59 Hz, 1 H), 8.36 (d, J=1.56 Hz, 1 H), 8.79 (d, J=0.59 Hz, 1 H); MS (ESI) (M+H)$^+$ 479.9.

Example 126

1-({2-tert-Butyl-1-[(4-fluorocyclohexyl)methyl]-1H-benzimidazol-5-yl}sulfonyl)-N-methyl-1H-pyrrole-3-carboxamide

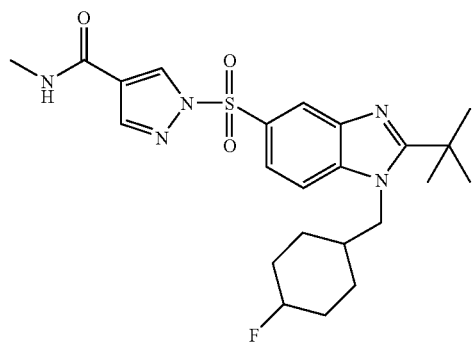

Step A. 1-({2-tert-butyl-1-[(4-fluorocyclohexyl)methyl]-1H-benzimidazol-5-yl}sulfonyl)-N-methyl-1H-pyrrole-3-carboxamide

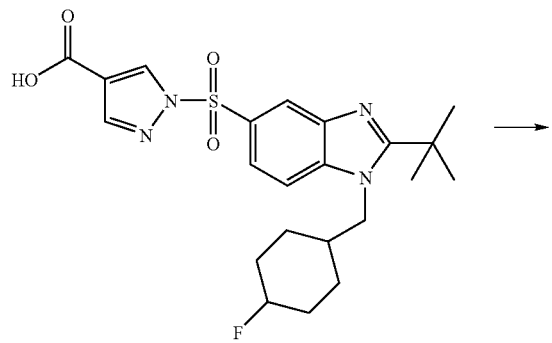

-continued

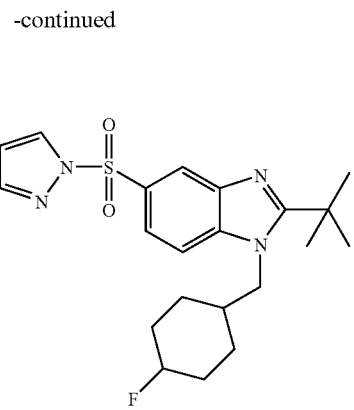

HATU (0.24 g, 0.64 mmol) and methylamine (0.32 mL, 2M in THF, 0.64 mmol) were added to a solution of 1-({2-tert-butyl-1-[(4-fluorocyclohexyl)methyl]-1H-benzimidazol-5-yl}sulfonyl)-1H-pyrrole-3-carboxylic acid (0.28 g, 0.58 mmol) (see following steps B, C, D, E, F, G, H, I, and J for preparation) and DIPEA (0.12 mL, 0.69 mmol) in DMF (5 mL). The reaction mixture was stirred for 1 h and the solvent was concentrated. The crude product was purified by reverse-phase preparative HPLC using 10-90% MeCN/H$_2$O and lyophilized affording the title compound as the corresponding TFA salt. Yield: 0.13 g (55%); $^1$H NMR (400 MHz, CDCl$_3$) δ 1.15-1.33 (m, 1 H), 1.33-1.58 (m, 4 H), 1.59-1.67 (m, 10 H), 1.67-1.81 (m, 1 H), 1.90-2.27 (m, 1 H), 2.90 (d, J=4.88 Hz, 3 H), 4.19-4.34 (m, 2 H), 4.36-4.98 (m, 1 H), 6.49-6.59 (m, 1 H), 6.58-6.89 (m, 1 H), 7.04-7.15 (m, 1 H), 7.42-7.58 (m, 1 H), 7.63-7.74 (m, 1 H), 7.82-7.95 (m, 1 H), 8.48-8.65 (m, 1 H); MS (ESI) (M+H)$^+$=475.3.

Step B: tert-Butyl[(4-fluorocyclohex-3-en-1-yl)methyl]carbamate

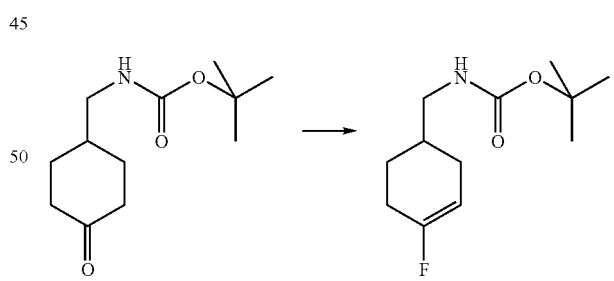

4-N-Boc-aminomethyl cyclohexanone (4.95 g, 21.8 mmol) was dissolved in THF (80 mL). DAST (4.3 mL, 32.7 mmol) was added dropwise and the solution was stirred at 50° C. for 5 h. The solvent was concentrated and the product purified by flash chromatography on silica gel using hexanes/EtOAc (3:1) as eluent. Yield: 1.62 g (30%). $^1$H NMR (400 MHz, CDCl$_3$) δ 1.36-1.42 (m, 1 H), 1.44 (s, 9 H), 1.70-1.80 (m, 2 H), 1.82-1.90 (m, 1 H), 2.09-2.17 (m, 1 H), 2.17-2.29 (m, 2 H), 3.04-3.11 (m, 2 H), 4.61 (s, 1 H), 5.11-5.19 (m, 1 H).

Step C: [(4-Fluorocyclohex-3-en-1-yl)methyl]amine hydrochloride

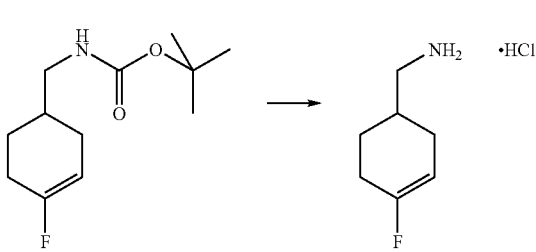

tert-Butyl[(4-fluorocyclohex-3-en-1-yl)methyl]carbamate (1.62 g, 7.06 mmol) was stirred in 25 mL of 1M HCl/AcOH at rt for 2 h. The solvent was evaporated and the product was precipitated in ether, filtered and dried under vacuum. Yield: 1.13 g (97%). $^1$H NMR (400 MHz, CD$_3$OD) δ 1.44-1.53 (m, 1 H), 1.80-1.89 (m, 2 H), 1.90-1.98 (m, 1 H), 2.16-2.23 (m, 2 H), 2.26-2.34 (m, 1 H), 2.88 (d, J=6.25 Hz, 2 H), 5.12-5.19 (m, 1 H).

Step D: N-(4-{[(4-Fluorocyclohex-3-en-1-yl)methyl]amino}-3-nitrophenyl)acetamide

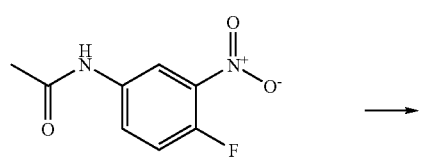

N-(4-Fluoro-3-nitrophenyl)acetamide (460 mg, 2.32 mmol) and [(4-fluorocyclohex-3-en-1-yl)methyl]amine hydrochloride (350 mg, 2.11 mmol) were stirred in 20 mL of EtOH containing TEA (0.735 mL, 5.28 mmol) at 75° C. for 48 h. The solvent was concentrated. The residue was dissolved in EtOAc and washed with aqueous 5% KHSO$_4$, saturated aqueous NaHCO$_3$ solution, brine and dried over anhydrous MgSO$_4$. The crude product was purified by flash chromatography on silica gel using hexanes/acetone (2:1) as eluent. Yield: 553 mg (85%). $^1$H NMR (400 MHz, CDCl$_3$) δ 1.51-1.61 (m, 1 H), 1.84-1.93 (m, 1 H), 1.96-2.03 (m, 2 H), 2.16-2.18 (m, 3 H), 2.22-2.32 (m, 3 H), 3.26 (td, J=6.05, 2.93 Hz, 2 H), 5.19 (dt, J=16.45, 2.61 Hz, 1 H), 6.84 (d, J=9.37 Hz, 1 H), 7.21 (s, 1 H), 7.79 (dd, J=9.18, 2.54 Hz, 1 H), 8.09 (d, J=2.54 Hz, 2 H).

Step E: N-(3-Amino-4-{[(4-fluorocyclohexyl)methyl]amino}phenyl)acetamide

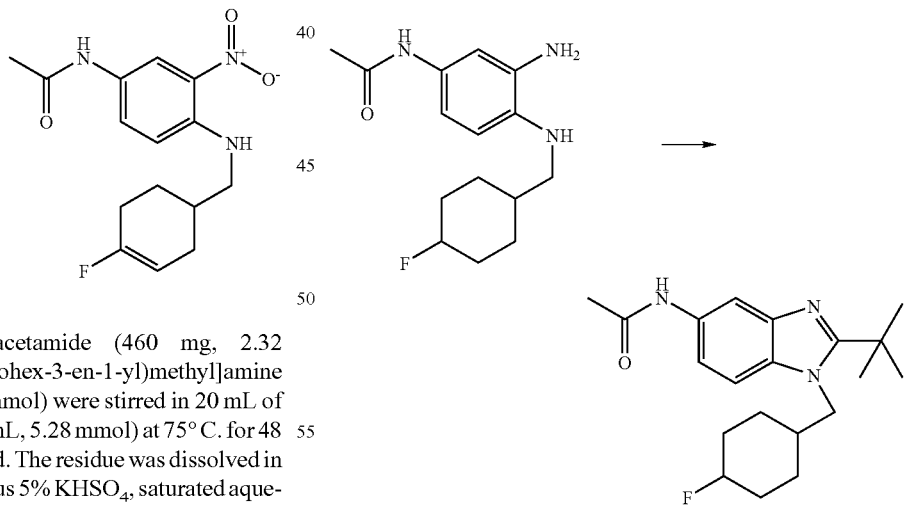

N-(4-{[(4-Fluorocyclohex-3-en-1-yl)methyl]amino}-3-nitrophenyl)acetamide (340 mg, 1.11 mmol) was dissolved in 25 mL of EtOAc containing a catalytic amount of 10% Pd/C. The solution was shaken under H$_2$ atmosphere (40 psi) using a Parr hydrogenation apparatus at rt for 48 h. The solution was filtered through Celite and the solvent was evaporated. Yield: 308 mg (99%). MS (ESI) (M+H)$^-$=279.95.

Step F: N-{2-tert-Butyl-1-[(4-fluorocyclohexyl)methyl]-1H-benzimidazol-5-yl}acetamide N-(3-Amino-4-{[(4-fluorocyclohexyl)methyl]amino}phenyl)acetamide (300 mg, 1.07 mmol) and DMAP (25 mg, 0.214 mmol) were dissolved in DCM (10 mL). Trimethylacetyl chloride (0.145 mL, 1.18 mmol) was added dropwise and the solution was stirred at rt for 1 h. The solution washed with aqueous NaHCO$_3$ solution, brine and dried over anhydrous MgSO$_4$. The residue was dissolved in 5 mL of AcOH and was heated at 150° C. for 2.5 h using a Personal Chemistry microwave apparatus. The solvent was evaporated. The residue was dissolved in EtOAc and washed with aqueous NaHCO$_3$ solution, brine and dried over anhydrous MgSO$_4$. The crude product was purified by flash chromatography on silica gel using acetone/hexane (2:1) as eluent. Yield: 196 mg (53%). $^1$H NMR (400 MHz, CDCl$_3$) δ 1.14-1.25 (m, 2 H), 1.37-1.45 (m, 1 H), 1.43-1.51 (m, 1 H), 1.54-1.57 (m, 9 H), 1.70-1.78 (m, 2 H), 1.70-1.77 (m, 1 H), 2.02-2.08 (m, 1 H), 2.10-2.17 (m, 1 H), 2.19-2.21 (m, 3 H), 4.12-4.19 (m, 2 H), 4.53-4.90 (m, 1 H), 7.21-7.29 (m, 1 H), 7.30 (s, 1 H), 7.50-7.57 (m, 1 H), 7.64-7.67 (m, 1 H).

Step G: 2-tert-Butyl-1-[(4-fluorocyclohexyl)methyl]-1H-benzimidazol-5-amine

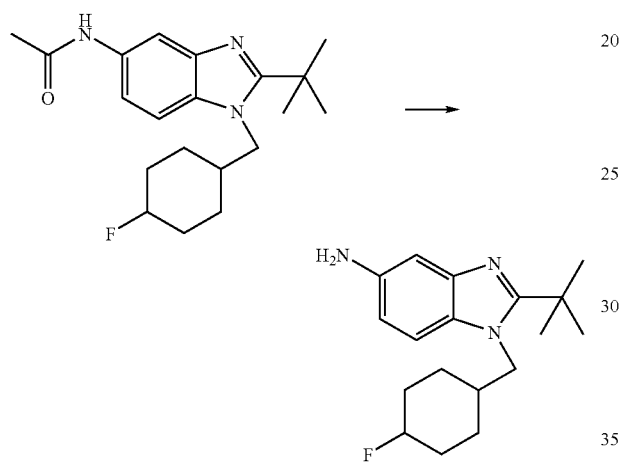

N-{2-tert-Butyl-1-[(4-fluorocyclohexyl)methyl]-1H-benzimidazol-5-yl}acetamide (190 mg, 0.550 mmol) was heated in 5 mL of 2 M HCl/EtOH (1:1) at 120° C. for 1 h using a Personal Chemistry microwaves apparatus. The solvent was evaporated. The residue was basified with 2M NaOH and extracted (3×) with EtOAc. The organic phase washed with saturated aqueous NaCl solution and dried over anhydrous Na$_2$SO$_4$. The solvent was evaporated. Yield: 154 mg (92%). $^1$H NMR (400 MHz, CD$_3$OD) δ 1.28-1.39 (m, 2 H), 1.41-1.50 (m, 1 H), 1.53-1.59 (m, 1 H), 1.61-1.64 (m, 9 H), 1.69 (d, J=7.81 Hz, 2 H), 1.95-2.22 (m, 3 H), 4.37-4.83 (m, 3 H), 7.11-7.13 (m, 1 H), 7.15-7.18 (m, 1 H), 7.67-7.73 (m, 1 H).

Step H. 2-tert-Butyl-1-[(4-fluorocyclohexyl)methyl]-1H-benzimidazole-5-sulfonyl chloride

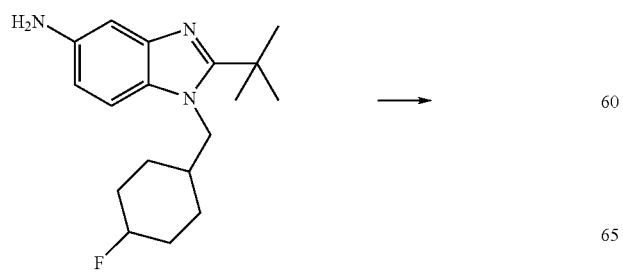

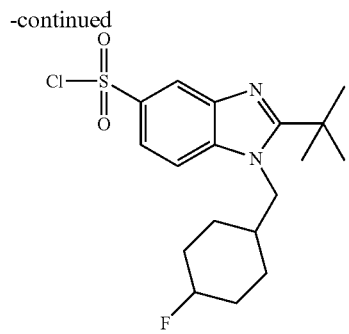

A solution of NaNO$_2$ (0.21 g, 3.0 mmol) in water (0.5 mL) was slowly added to a solution of 2-tert-Butyl-1-[(4-fluorocyclohexyl)methyl]-1H-benzimidazol-5-amine (0.84 g, 2.7 mmol) in 6 mL of AcOH/HCl (1:2) at 0° C. The reaction mixture was stirred for 1 h at 0° C. The reaction mixture was added to a mixture of liquid SO$_2$ (~6 mL), CuCl$_2$.2H$_2$O (0.19 g, 1.1 mmol) and AcOH (3 mL) at −20° C. The resulting mixture was allowed to warm to 0° C. and stirred for 3 h. The reaction mixture was poured over ice (50 mL) while vigorously shaking. The quenched reaction mixture was stirred for 30 min at 0° C. The product was extracted with cold DCM and the organic layers were combined and dried over anhydrous Na$_2$SO$_4$. The solvent was concentrated to provide the pure title compound as beige solid. Yield: 0.98 g (92%); MS (ESI) (M+H)$^+$=387.2.

Step I. 1-({2-tert-Butyl-1-[(4-fluorocyclohexyl)methyl]-1H-benzimidazol-5-yl}sulfonyl)-1H-pyrrole-3-carbaldehyde

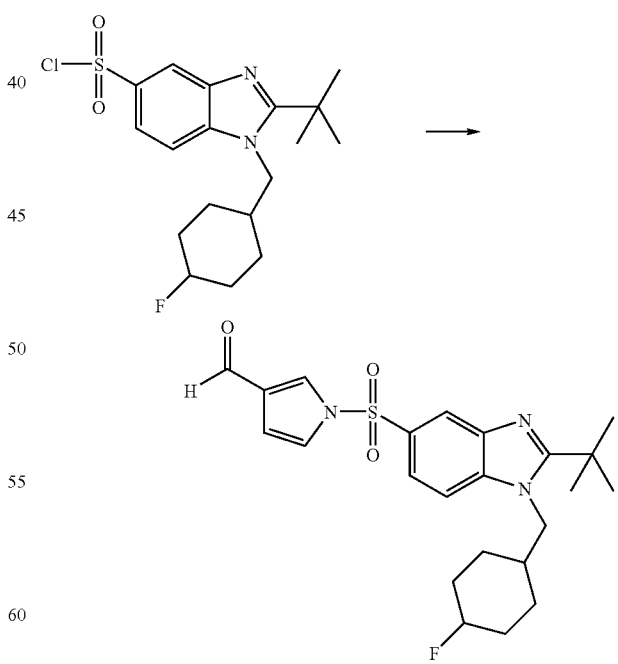

NaH (0.19 g, 60%, 4.8 mmol) was added to a solution of 1H-pyrrole-3-carbaldehyde (0.13 g, 1.4 mmol) in THF (30 mL) at 0° C. The reaction mixture was allowed to warm to ambient temperature, stirred for 1 h and cooled to 0° C.

2-tert-Butyl-1-[(4-fluorocyclohexyl)methyl]-1H-benzimidazole-5-sulfonyl chloride (0.37 g, 0.96 mmol) was added to the reaction mixture and stirred for 1 h. The reaction mixture was quenched with saturated NaHCO$_3$ solution (30 mL) and the solvent was concentrated. Water (50 mL) was added to the residue and the product was extracted with DCM (workup). The solvent was concentrated and the product was purified by MPLC on silica gel using 50-80% EtOAc/heptane to provide the title compound as white solid. Yield: 0.25 g (57%); MS (ESI) (M+H)$^+$=445.9.

Step J. 1-({2-tert-Butyl-1-[(4-fluorocyclohexyl)methyl]-1H-benzimidazol-5-yl}sulfonyl)-1H-pyrrole-3-carboxylic acid

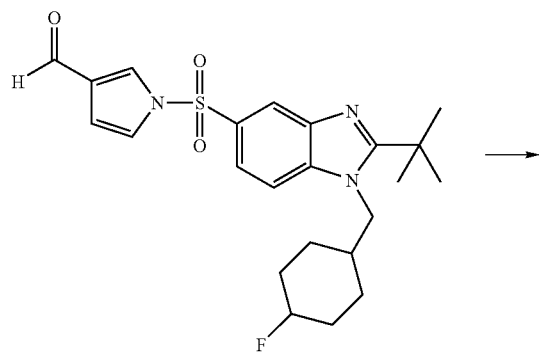

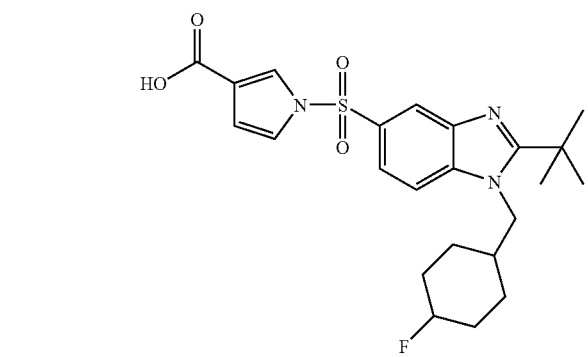

Oxone® (0.36 g, 0.53 mmol) was added to a solution of 1-({2-tert-butyl-1-[(4fluorocyclohexyl)methyl]-1H-benzimidazol-5-yl}sulfonyl)-1H-pyrrole-3-carbaldehyde (0.23 g, 0.53 mmol) in DMF (15 mL). The reaction mixture was stirred overnight at ambient temperature and the solvent was concentrated. The product was recovered in DCM, washed with 10% HCl solution, brine and dried over anhydrous Na$_2$SO$_4$. The solvent was concentrated to provide the pure title compound as white solid. Yield: 0.26 g (99%). MS (ESI) (M+H)$^+$=462.1.

Example 127

1-({2-tert-Butyl-1-[(4-fluorocyclohexyl)methyl]-1H-benzimidazol-5-yl}sulfonyl)-1H-pyrrole-3-carboxamide

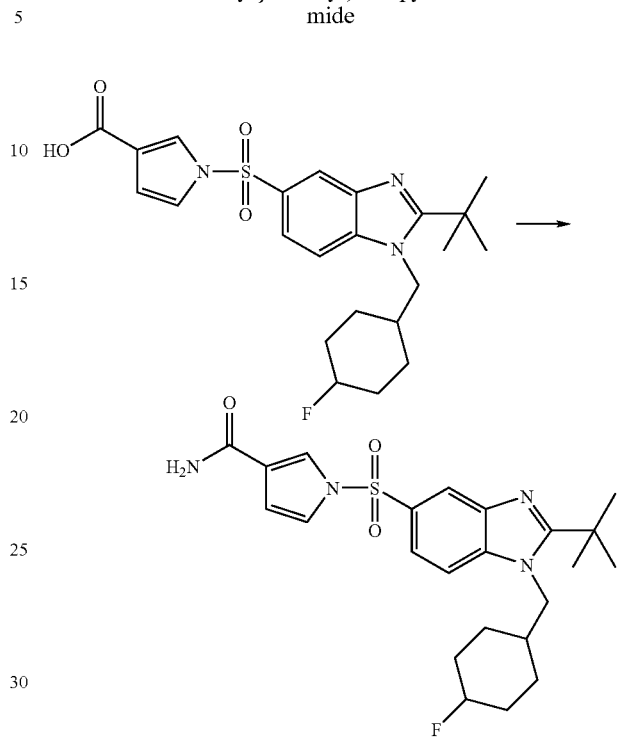

Following the same procedure in Example 126, step A, using gaseous ammonia, HATU (58 mg, 0.15 mmol), 1-({2-tert-butyl-1-[(4-fluorocyclohexyl)methyl]-1H-benzimidazol-5-yl}sulfonyl)-1H-pyrrole-3-carboxylic acid (64 mg, 0.14 mmol) and DIPEA (30 uL, 0.17 mmol) in DMF (5 mL). The crude product was purified by reverse-phase preparative HPLC using 10-90% MeCN/H$_2$O and lyophilized affording the title compound as the corresponding TFA salt. Yield: 29 mg (36%); $^1$H NMR (400 MHz, CDCl$_3$) δ 1.10-1.34 (m, 1 H), 1.34-1.53 (m, 4 H), 1.52-1.64 (m, 10 H), 1.64-1.79 (m, 1 H), 1.88-2.24 (m, 1 H), 4.15-4.28 (m, 2 H), 4.33-4.97 (m, 1 H), 6.63 (dd, J=3.32, 1.56 Hz, 1 H), 7.09-7.22 (m, 1 H), 7.40-7.53 (m, 1 H), 7.76 (dd, J=8.69, 1.86 Hz, 1 H), 7.81-7.91 (m, 1 H), 8.32 (s, 1 H); MS (ESI) (M+H)$^+$=461.2.

Example 128

1-({2-tert-Butyl-1-[(4-fluorocyclohexyl)methyl]-1H-benzimidazol-5-yl}sulfonyl)-N-cyclopropyl-1H-pyrrole-3-carboxamide

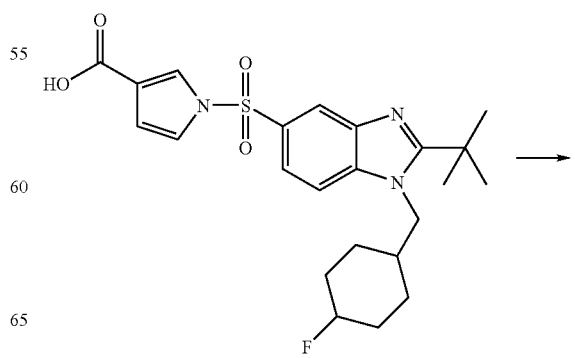

-continued

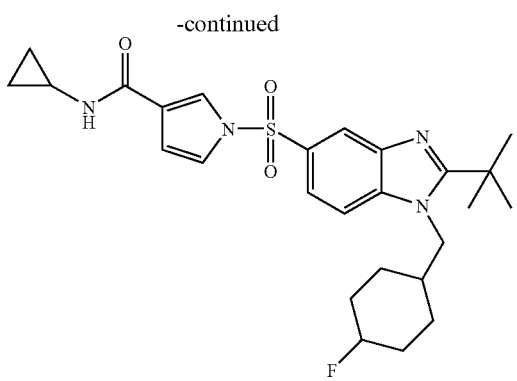

Following the same procedure in Example 126, step A, using cyclopropylamine (10 mg, 0.17 mmol), HATU (58 mg, 0.15 mmol), 1-({2-tert-butyl-1-[(4-fluorocyclohexyl)methyl]-1H-benzimidazol-5-yl}sulfonyl)-1H-pyrrole-3-carboxylic acid (64 mg, 0.14 mmol) and DIPEA (30 uL, 0.17 mmol) in DMF (5 mL). The crude product was purified by reverse-phase preparative HPLC using 10-90% MeCN/H$_2$O and lyophilized affording the title compound as the corresponding TFA salt. Yield: 36 mg (42%); $^1$H NMR (400 MHz, CDCl$_3$) δ 0.59 (m, 2 H), 0.69-0.88 (m, 2 H), 1.12-1.33 (m, 2 H), 1.33-1.55 (m, 2 H), 1.57-1.70 (m, 10 H), 1.73 (m, 3H), 1.89-2.31 (m, 1 H), 2.64-2.88 (m, 1 H), 4.24-4.38 (m, 2 H), 4.37-5.02 (m, 1 H), 6.45-6.62 (m, 1 H), 6.69-6.93 (m, 1 H), 7.08 (s, 1 H), 7.49-7.62 (m, 1 H), 7.65 (s, 1 H), 7.79-7.96 (m, 1 H), 8.40-8.57 (m, 1 H); MS (ESI) (M+H)$^+$=501.3.

Example 129

1-({2-tert-Butyl-1-[(4-fluorocyclohexyl)methyl]-1H-benzimidazol-5-yl}sulfonyl)-N-(2-hydroxyethyl)-1H-pyrrole-3-carboxamide

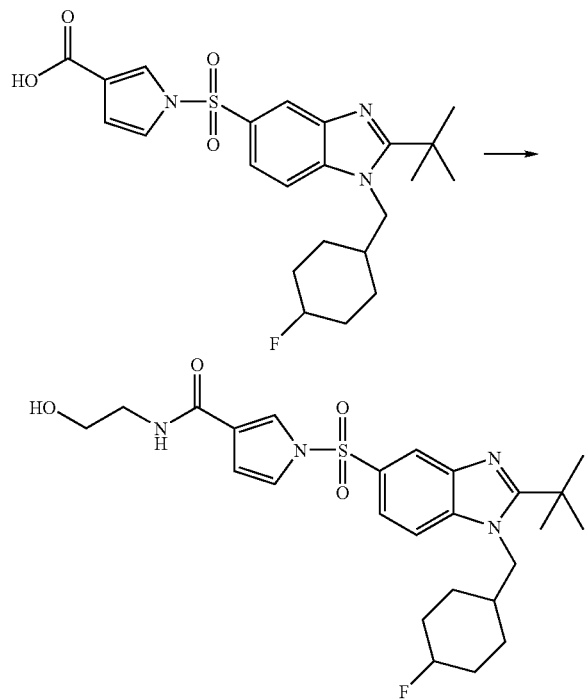

Following the same procedure in Example 126, step A, using 2-hydroxyethylamine (10 mg, 0.17 mmol), HATU (58 mg, 0.15 mmol), 1-({2-tert-butyl-1-[(4-fluorocyclohexyl)methyl]-1H-benzimidazol-5-yl}sulfonyl)-1H-pyrrole-3-carboxylic acid (64 mg, 0.14 mmol) and DIPEA (30 uL, 0.17 mmol) in DMF (5 mL The crude product was purified by reverse-phase preparative HPLC using 10-90% MeCN/H$_2$O and lyophilized affording the title compound as the corresponding TFA salt. Yield: 26 mg (30%); $^1$H NMR (400 MHz, CDCl$_3$) δ 1.14-1.30 (m, 1 H), 1.32-1.51 (m, 3 H), 1.51-1.64 (m, 10 H), 1.71 (d, J=12.50 Hz, 1 H), 1.89-2.24 (m, 3 H), 3.47 (q, J=5.08 Hz, 2 H), 3.60-3.78 (m, 2 H), 4.16-4.32 (m, 2 H), 4.35-4.97 (m, 1 H), 6.56-6.70 (m, 1 H), 7.08-7.21 (m, 1 H), 7.40-7.45 (m, 1 H), 7.46-7.62 (m, 1 H), 7.71-7.87 (m, 2 H), 8.30 (d, J=1.37 Hz, 1 H); MS (ESI) (M+H)$^+$=505.3.

Example 130

1-({2-tert-Butyl-1-[(4-fluorocyclohexyl)methyl]-1H-benzimidazol-5-yl}sulfonyl)-N-ethyl-1H-pyrrole-3-carboxamide

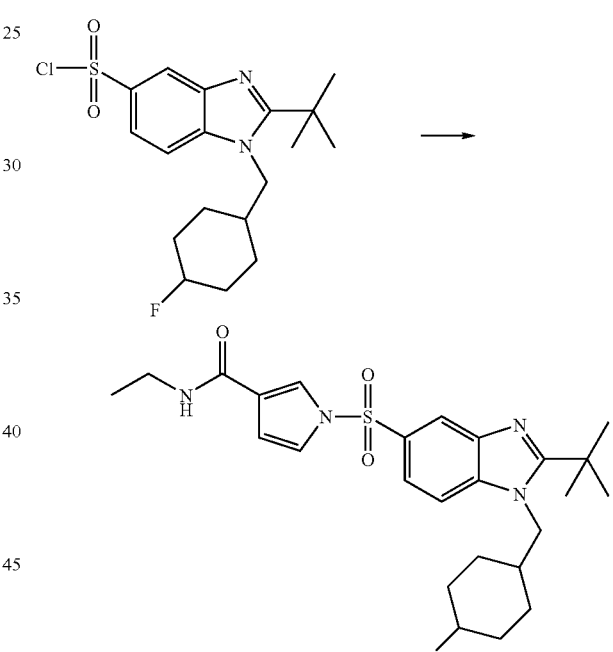

NaH (30 mg, 60%, 0.74 mmol) was added to a solution of N-ethyl-1H-pyrrole-3-carboxamide (50 mg, 0.36 mmol) in THF (5 mL) at 0° C. The reaction mixture was allowed to warm to ambient temperature, stirred for 1 h and cooled to 0° C. 2-tert-butyl-1-[(4-fluorocyclohexyl)methyl]-1H-benzimidazole-5-sulfonyl chloride (90 mg, 0.24 mmol) was added to the reaction mixture and stirred for 1 hr. The reaction mixture was quenched with saturated NaHCO$_3$ solution (5 mL) and the solvent was concentrated. Water (15 mL) was added to the residue and the product was extracted with DCM (workup). The product was purified by preparative reverse-phase HPLC to provide the TFA salt of the title compound as white solid. Yield: 46 mg (31%); $^1$H NMR (400 MHz, CDCl$_3$) δ 1.18 (t, J=7.23 Hz, 3 H), 1.25 (m, 2 H), 1.35-1.58 (m, 2 H), 1.58-1.68 (m, 9 H), 1.68-1.79 (m, 1 H), 1.95-2.23 (m, 2 H), 3.34-3.46 (m, 2 H), 4.27 (dd, J=15.14, 7.52 Hz, 2 H), 4.37-4.60 (m, 1 H), 4.77-4.98 (m, 1 H), 6.52-6.58 (m, 1 H), 7.08-7.16 (m, 1 H), 7.45-7.58 (m, 1 H), 7.65-7.71 (m, 1 H), 7.84-7.93 (m, 1 H), 8.54 (dd, J=18.85, 1.66 Hz, 1 H); MS (ESI) (M+H)⁺=437.7.

Example 131

1-({2-tert-Butyl-1-[(4,4-difluorocyclohexyl)methyl]-1H-benzimidazol-5-yl}sulfonyl)-N-(2-hydroxyethyl)-1H-pyrazole-4-carboxamide

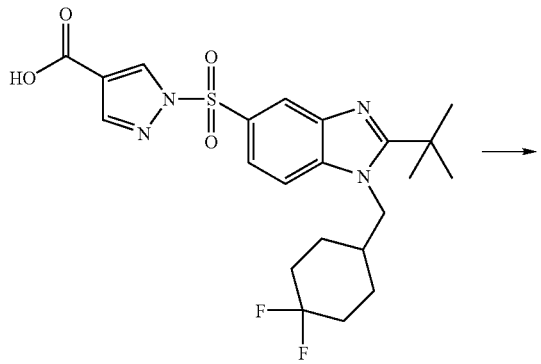

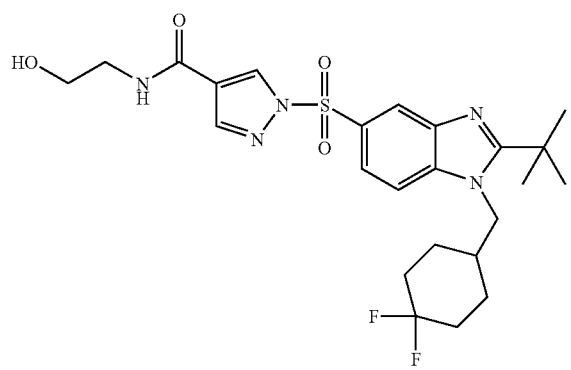

1-({2-tert-Butyl-1-[(4,4-difluorocyclohexyl)methyl]-1H-benzimidazol-5-yl}sulfonyl)-1H-pyrazole-4-carboxylic acid (56 mg, 0.116 mmol), HATU (53 mg, 0.139 mmol) and ethanolamine (8 uL, 0.139 mmol) were stirred in 5 mL of DMF containing DIPEA (30 uL, 0.174 mmol) at rt for 2 h. The solvent was evaporated. The product was dissolved in EtOAc and washed with saturated aqueous NaHCO₃ solution, brine and dried over MgSO₄. The solvent was evaporated and the product was purified by reversed-phase HPLC using 10-50% CH₃CN/H₂O and lyophilized affording the title compound as the corresponding TFA salt. Yield: 36 mg (49%). ¹H NMR (400 MHz, METHANOL-D₄) δ 1.45-1.57 (m, 2 H), 1.60 (s, 9H), 1.61-1.70 (m, 2 H), 1.71-1.79 (m, 1 H), 1.81-1.88 (m, 1 H), 1.98-2.09 (m, 3 H), 2.14-2.23 (m, 1 H), 2.84 (d, J=7.03 Hz, 1 H), 3.40 (t, J=5.66 Hz, 2 H), 3.63 (t, J=5.66 Hz, 2 H), 4.45 (d, J=7.42 Hz, 2 H), 7.92-7.97 (m, 1 H), 8.00-8.04 (m, 1 H), 8.06 (s, 1 H), 8.37 (d, J=1.56 Hz, 1 H), 8.78 (s, 1 H); MS (ESI) (M+H)⁺=524.3.

Example 132

2-tert-Butyl-1-[(4,4-difluorocyclohexyl)methyl]-5-[(3-fluoroazetidin-1-yl)sulfonyl]-1H-benzimidazole

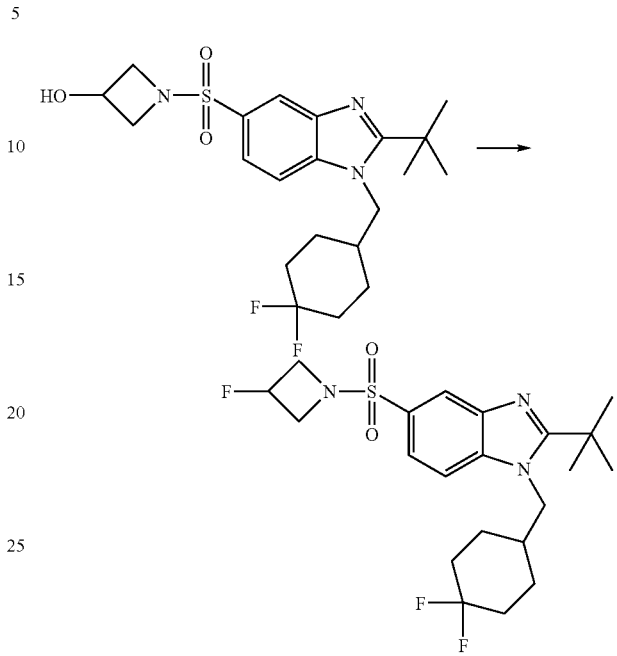

1-({2-tert-Butyl-1-[(4,4-difluorocyclohexyl)methyl]-1H-benzimidazol-5-yl}sulfonyl)azetidin-3-ol (78 mg, 0.177 mmol) was dissolved in 5 mL of DCM at 0° C. under nitrogen. DAST (0.035 mL, 0.266 mmol) was added dropwise and the solution was stirred at rt for 2 h. Another 0.035 mL of DAST was added and the solution was stirred at rt for another 2 h. The solution washed with saturated aqueous NaHCO₃ solution, brine and dried over anhydrous MgSO₄. The solvent was evaporated and the product was purified by reversed-phase HPLC using 10-50% CH₃CN/H₂O and lyophilized affording the title compound as the corresponding TFA salt. Yield: 37 mg (37%). ¹H NMR (400 MHz, METHANOL-D₄) δ 1.55 (t, 2 H), 1.64 (s, 9 H), 1.67-1.75 (m, 3 H), 1.75-1.82 (m, 1 H), 2.00-2.10 (m, 2 H), 2.20-2.29 (m, 1 H), 3.73-3.85 (m, 2 H), 4.05-4.16 (m, 2 H), 4.51 (d, J=7.42 Hz, 2 H), 5.00-5.21 (m, 1 H), 7.89 (dd, J=8.69, 1.66 Hz, 1 H) 8.01 (d, J=8.20 Hz, 1 H), 8.16 (d, J=1.17 Hz, 1 H); MS (ESI) (M+H)⁺=443.95.

Example 133

1-({2-tert-Butyl-1-[(trans-4-fluorocyclohexyl)methyl]-1H-benzimidazol-5-yl}sulfonyl)-N-cyclopropyl-1H-pyrazole-4-carboxamide

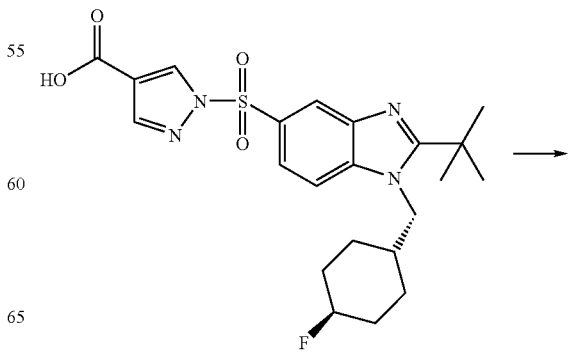

-continued

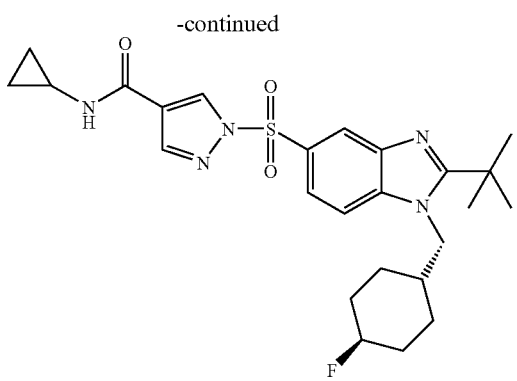

1-({2-tert-Butyl-1-[(trans-4-fluorocyclohexyl)methyl]-1H-benzimidazol-5-yl}sulfonyl)-1H-pyrazole-4-carboxylic acid (30 mg, 0.0649 mmol) (see following steps B and C for preparation), HATU (30 mg, 0.0779 mmol) and cyclopropylamine (6 uL, 0.0779 mmol) were stirred in 1 mL of DMF containing DIPEA (17 uL, 0.0974 mmol) at rt for 1 h. The solvent was evaporated. The product was dissolved in EtOAc and washed with saturated aqueous NaHCO₃ solution, brine and dried over anhydrous MgSO₄. The solvent was evaporated and the product was purified by reversed-phase HPLC using 10-50% CH₃CN/H₂O and lyophilized affording the title compound as the corresponding TFA salt. Yield: 25 mg (63%). ¹H NMR (400 MHz, METHANOL-D4) δ 0.52-0.58 (m, 2 H), 0.72-0.78 (m, 2 H), 1.24-1.41 (m, 4 H), 1.58 (s, 9 H), 1.60-1.67 (m, 2 H), 2.00-2.10 (m, 3 H), 2.71-2.79 (m, 1 H), 4.34-4.55 (m, 3 H), 7.85-7.89 (m, 1 H), 7.95-7.99 (m, 1 H), 8.03 (s, 1 H), 8.33 (d, J=1.56 Hz, 1 H), 8.74 (s, 1 H); MS (ESI) (M+H)⁺=501.94.

Step B: 1-({2-tert-Butyl-1-[(trans-4-fluorocyclohexyl)methyl]-1H-benzimidazol-5-yl}sulfonyl)-1H-pyrazole-4-carbaldehyde

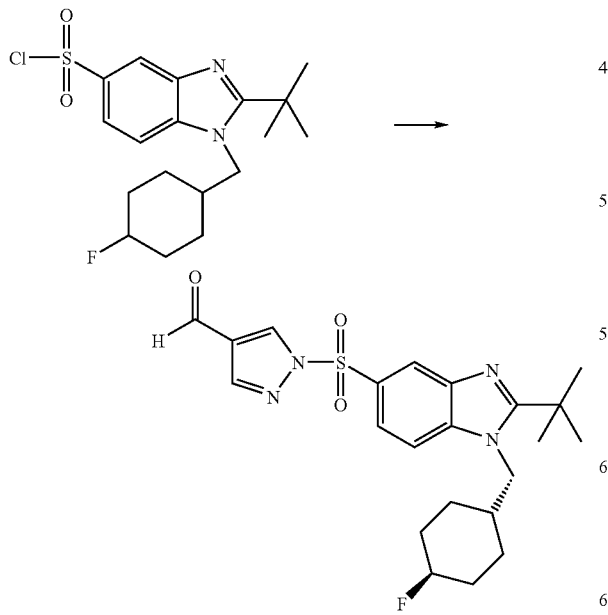

2-tert-Butyl-1-[(4-fluorocyclohexyl)methyl]-1H-benzimidazole-5-sulfonyl chloride (400 mg, 1.03 mmol), pyrazole-4-carboxaldehyde (300 mg, 3.09 mmol) (see Example 126, step H for preparation) and DMAP (catalytic) were stirred in 10 mL of DCM containing DIPEA (0.90 mL, 5.15 mmol) at rt for 3 h. The solution washed with saturated aqueous NaHCO₃ solution, brine and dried over anhydrous MgSO₄. The crude product was purified by flash chromatography on silica gel using hexanes/EtOAc (1:1) as eluent. Yield: 131 mg (28%). ¹H NMR (400 MHz, CHLOROFORM-D) δ 1.16-1.26 (m, 2 H), 1.35-1.48 (m, 2 H), 1.54-1.56 (m, 9 H), 1.72 (dd, J=8.69, 3.03 Hz, 2 H), 1.95-2.04 (m, 1 H), 2.11-2.19 (m, 2 H), 4.17-4.21 (m, 2 H), 4.37-4.46 (m, 1 H), 4.50-4.59 (m, 1 H), 7.44 (d, J=8.59 Hz, 1 H), 7.96 (dd, J=8.69, 1.86 Hz, 1 H), 8.08 (s, 1 H), 8.44 (d, J=1.37 Hz, 1 H), 8.64 (s, 1 H), 9.91 (s, 1 H).

Step C: 1-({2-tert-Butyl-1-[(trans-4-fluorocyclohexyl)methyl]-1H-benzimidazol-5-yl}sulfonyl)-1H-pyrazole-4-carboxylic acid

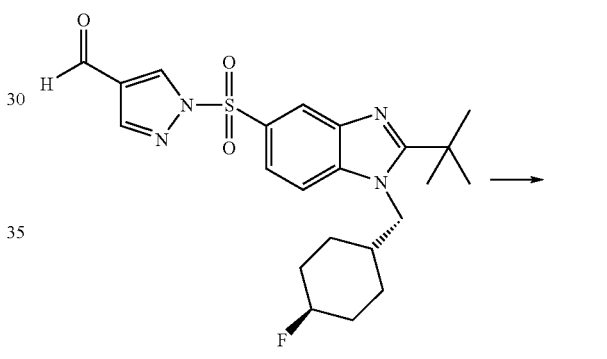

1-({2-tert-Butyl-1-[(trans-4-fluorocyclohexyl)methyl]-1H-benzimidazol-5-yl}sulfonyl)-1H-pyrazole-4-carbaldehyde (130 mg, 0.291 mmol) and oxone (215 mg, 0.349 mmol) were stirred in 10 mL of DMF at rt overnight. The solvent was evaporated. The residue was dissolved in DCM and washed with water, brine and dried over anhydrous MgSO₄. Yield: 135 mg (99%). MS (ESI) (M+H)⁺=463.06.

Example 134

1-({2-tert-Butyl-1-[(trans-4-fluorocyclohexyl)methyl]-1H-benzimidazol-5-yl}sulfonyl)-N-ethyl-1H-pyrazole-4-carboxamide

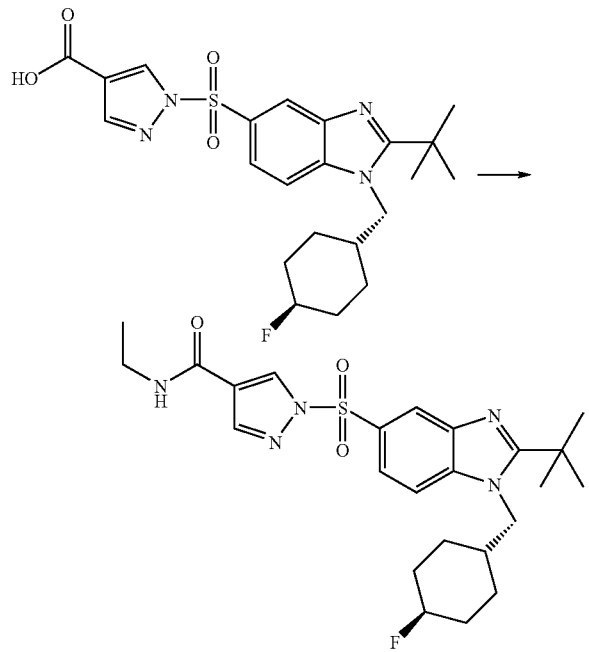

Following the same procedure in Example 133, step A, using 1-({2-tert-butyl-1-[(trans-4-fluorocyclohexyl)methyl]-1H-benzimidazol-5-yl}sulfonyl)-1H-pyrazole-4-carboxylic acid (30 mg, 0.0649 mmol), HATU (30 mg, 0.0779 mmol), DIPEA (0.017 mL, 0.0974 mmol) and ethylamine (40 uL, 2M in THF, 0.0779 mmol) in DMF (1 mL). The product was purified by reversed-phase HPLC using 10-50% CH$_3$CN/H$_2$O and lyophilized affording the title compound as the corresponding TFA salt. Yield: 28 mg (71%). $^1$H NMR (400 MHz, METHANOL-D4) δ 1.15 (t, J=7.23 Hz, 3 H), 1.25-1.40 (m, 4 H), 1.59 (s, 9 H), 1.61-1.68 (m, 2 H), 2.01-2.09 (m, 3 H), 3.30-3.34 (m, 2 H) 4.35-4.53 (m, 3 H), 7.88-7.92 (m, 1 H), 7.97-8.02 (m, 1 H), 8.04 (s, 1 H), 8.35 (d, J=1.37 Hz, 1 H), 8.75 (s, 1 H); MS (ESI) (M+H)$^+$=489.98.

Example 135

1-({2-tert-Butyl-1-[(trans-4-fluorocyclohexyl)methyl]-1H-benzimidazol-5-yl}sulfonyl)-N-(2-hydroxyethyl)-1H-pyrazole-4-carboxamide

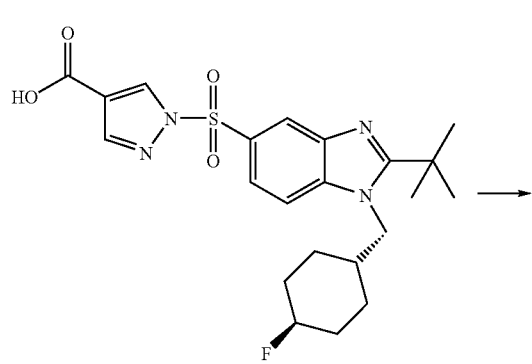

-continued

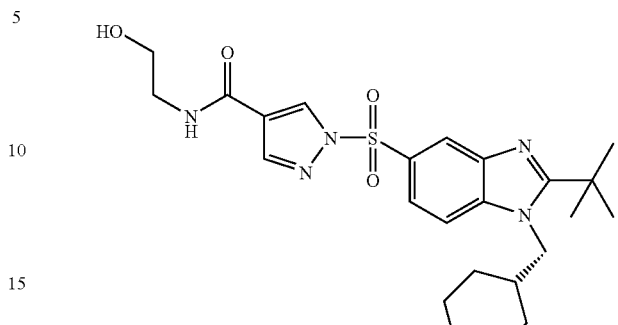

Following the same procedure in Example 133, step A, using 1-({2-tert-Butyl-1-[(trans-4-fluorocyclohexyl)methyl]-1H-benzimidazol-5-yl}sulfonyl)-1H-pyrazole-4-carboxylic acid (30 mg, 0.0649 mmol), HATU (30 mg, 0.0779 mmol), DIPEA (0.017 mL, 0.0974 mmol) and ethanolamine (0.005 mL, 0.0779 mmol) in DMF (1 mL). The product was purified by reversed-phase HPLC using 10-50% CH$_3$CN/H$_2$O and lyophilized affording the title compound as the corresponding TFA salt. Yield: 28 mg (70%). $^1$H NMR (400 MHz, METHANOL-D$_4$) δ 1.24-1.43 (m, 4 H), 1.58 (s, 9 H), 1.60-1.68 (m, 2 H), 2.01-2.09 (m, 3 H), 3.40 (t, J=5.76 Hz, 2 H), 3.63 (t, J=5.76 Hz, 2 H), 4.33-4.54 (m, 3 H), 7.86-7.90 (m, 1 H), 7.96-8.01 (m, 1 H), 8.05 (d, J=0.78 Hz, 1 H), 8.34 (d, J=1.37 Hz, 1 H), 8.77 (s, 1 H); MS (ESI) (M+H)$^+$=505.90.

Example 136

1-({2-tert-Butyl-1-[(trans-4-fluorocyclohexyl)methyl]-1H-benzimidazol-5-yl}sulfonyl)-N-methyl-1H-pyrazole-4-carboxamide

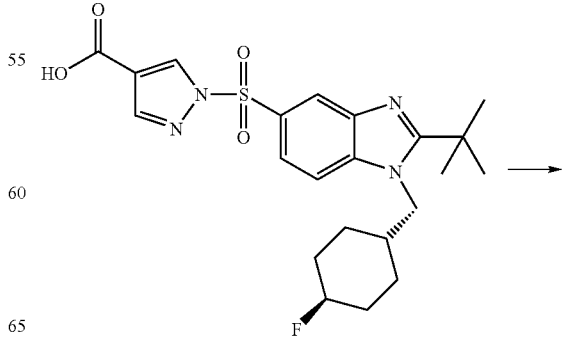

-continued

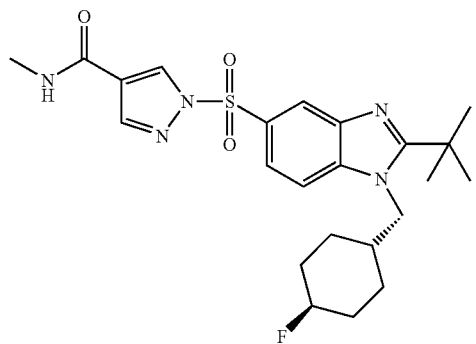

Following the same procedure in Example 133, step A, using 1-({2-tert-butyl-1-[(trans-4-fluorocyclohexyl)methyl]-1H-benzimidazol-5-yl}sulfonyl)-1H-pyrazole-4-carboxylic acid (40 mg, 0.0849 mmol), HATU (40 mg, 0.102 mmol), DIPEA (0.023 mL, 0.127 mmol) and methylamine (52 uL, 2 M in THF, 0.102 mmol) in DMF (1 mL). The product was purified by reversed-phase HPLC using 10-50% $CH_3CN/H_2O$ and lyophilized affording the title compound as the corresponding TFA salt. Yield: 20 mg (39%). $^1$H NMR (400 MHz, METHANOL-$D_4$) δ 1.26-1.40 (m, 4 H), 1.58 (s, 9 H), 1.60-1.67 (m, 2 H), 2.01-2.09 (m, 3 H), 2.82 (s, 3 H), 4.33-4.55 (m, 3 H), 7.86 (d, J=8.79 Hz, 1 H), 7.95-7.99 (m, 1 H), 8.02 (d, J=0.59 Hz, 1 H), 8.33 (d, J=1.76 Hz, 1 H), 8.72 (d, J=0.78 Hz, 1 H); MS (ESI) (M+H)$^+$=476.3.

Example 137

2-(1-{[2-tert-Butyl-1-(tetrahydro-2H-pyran-4-ylmethyl)-1H-benzimidazol-5-yl]sulfonyl}azetidin-3-yl)-N-ethylacetamide

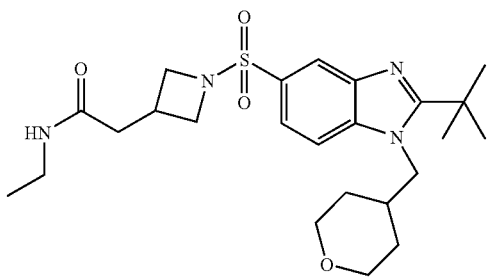

Step A: 2-(1-{[2-tert-Butyl-1-(tetrahydro-2H-pyran-4-ylmethyl)-1H-benzimidazol-5-yl]sulfonyl}azetidin-3-yl)-N-ethylacetamide

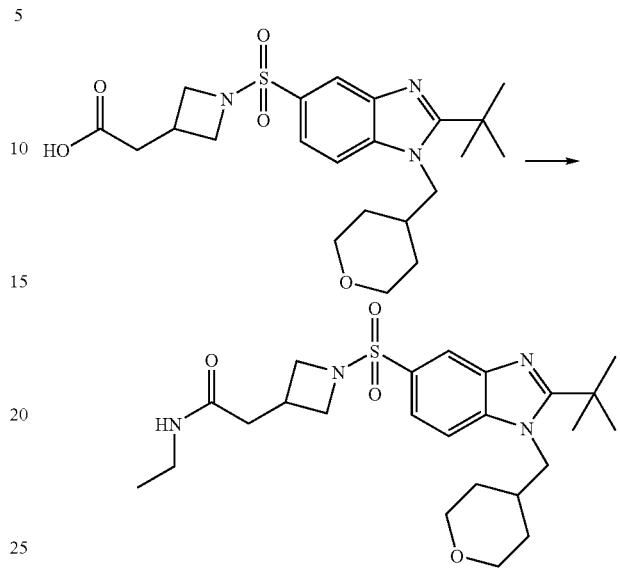

Following the same procedure in Example 24, Step A, using ethylamine hydrochloride (36 mg, 0.44 mmol), DIPEA (1 mL), (1-{[2-tert-butyl-1-(tetrahydro-2H-pyran-4-ylmethyl)-1H-benzimidazol-5-yl]sulfonyl}azetidin-3-yl)acetic acid (100 mg, 0.22 mmol) (see following step B for preparation) and HATU (161 mg, 0.44 mmol) in DMF (2.5 mL), provided the title compound as its TFA salt (32 mg, 23%). $^1$H NMR (400 MHz, CDCl$_3$) δ 1.06 (t, J=7.4 Hz, 3 H), 1.66 (m, 4 H), 1.73 (s, 9 H), 2.28 (d, J=7.8 Hz, 2 H), 2.32 (m, 1 H), 2.88 (m, 1 H), 3.17 (m, 2 H), 3.35 (m, 4 H), 3.88 (t, J=8.0 Hz, 2 H), 4.02 (d, J=8.2 Hz, 2 H), 4.43 (d, J=7.3 Hz, 2 H), 6.31 (m, 1 H), 7.75 (s, 2 H), 8.05 (s, 1 H); MS (ESI) (M+H)$^+$=477.2.

Step B: (1-{[2-tert-Butyl-1-(tetrahydro-2H-pyran-4-ylmethyl)-1H-benzimidazol-5-yl]sulfonyl}azetidin-3-yl)acetic acid

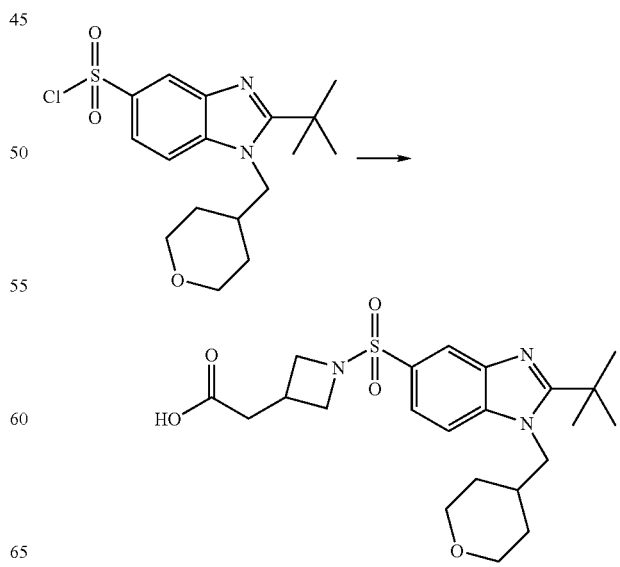

Following the same procedure in Example 1, Step A, using 2-tert-butyl-1-(tetrahydro-2H-pyran-4-ylmethyl)-1H-benzimidazole-5-sulfonyl chloride (700 mg, 1.9 mmol), azetidin-3-ylacetic acid hydrochloride (495 mg, 3.3 mmol) and DIPEA (4 mL) in DMF (20 mL), provided the title compound as a crude product (600 mg, 70%), which was used directly in Step A.

Example 138

2-(1-{[2-tert-Butyl-1-(tetrahydro-2H-pyran-4-ylmethyl)-1H-benzimidazol-5-yl]sulfonyl}azetidin-3-yl)-N-(2-fluoroethyl)acetamide

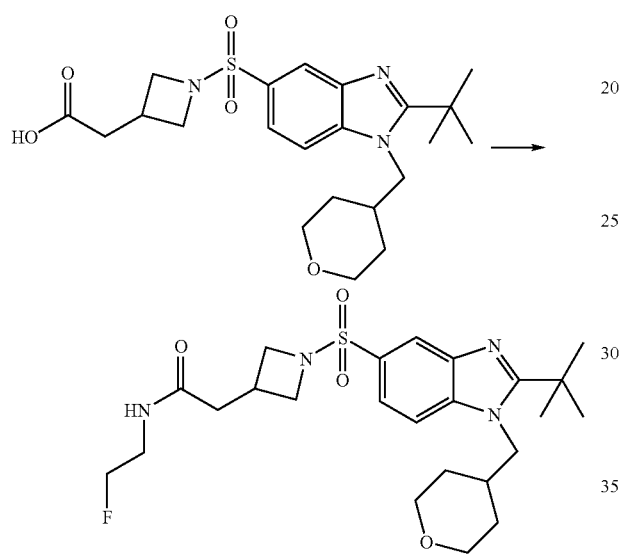

Following the same procedure in Example 24, Step A, using (2-fluoroethyl)amine hydrochloride (44 mg, 0.44 mmol), DIPEA (1 mL), (1-{[2-tert-butyl-1-(tetrahydro-2H-pyran-4-ylmethyl)-1H-benzimidazol-5-yl]sulfonyl}azetidin-3-yl)acetic acid (100 mg, 0.22 mmol) and HATU (161 mg, 0.44 mmol) in DMF (2.5 mL), provided the title compound as its TFA salt (16 mg, 12%). MS (ESI) (M+H)+ 495.3.

Example 139

1-{[2-tert-Butyl-1-(tetrahydro-2H-pyran-4-ylmethyl)-1H-benzimidazol-5-yl]sulfonyl}-N-(2-fluoroethyl)-1H-pyrrole-3-carboxamide

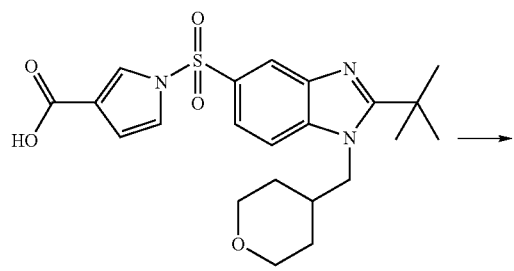

-continued

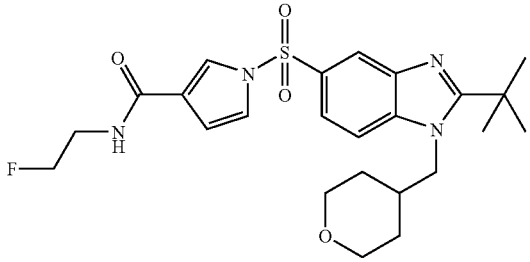

Following the same procedure in Example 31, method B, using 2-fluoroethylamine hydrochloride (0.70 g, 6.98 mmol), N,N-diisopropylethylamine (2.13 ml, 12.3 mmol), HATU (1.46 g, 3.83 mmol) and 1-{[2-tert-butyl-1-(tetrahydro-2H-pyran-4-ylmethyl)-1H-benzimidazol-5-yl]sulfonyl}-1H-pyrrole-3-carboxylic acid (3.49 mmol) in DMF (90 mL). The crude product was purified by MPLC on silica gel using EtOAc to provide the title compound as white solid. Yield: 0.74 g (35%). $^1$H NMR (400 MHz, METHANOL-D$_4$) δ 1.40-1.46 (m, 5 H), 1.51 (dd, J=13.28, 3.71 Hz, 2 H), 1.57 (s, 9 H), 3.52 (td, J=26.02, 5.15 Hz, 2 H), 3.86 (dd, J=11.52, 3.52 Hz, 2 H), 4.39 (d, J=7.81 Hz, 2 H), 4.43 (m, 2 H), 6.64 (dd, J=3.32, 1.56 Hz, 1 H), 7.26-7.28 (m, 1 H), 7.80-7.83 (m, 1 H), 7.87-7.93 (m, 2 H), 8.24 (d, J=1.17 Hz, 1 H); MS (APPI) (M+H)+=491.3.

Example 140

1-{[2-tert-Butyl-1-(tetrahydro-2H-pyran-4-ylmethyl)-1H-benzimidazol-5-yl]sulfonyl}-N-(2,2-difluoroethyl)-1H-pyrrole-3-carboxamide

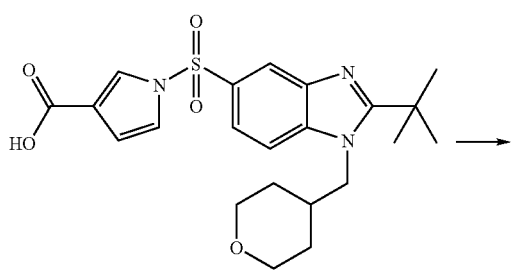

Following the same procedure in Example 31, method B, using 2,2-difluoroethylamine (138 mg, 1.7 mmol), N,N-diisopropylethylamine (0.8 ml, 4.4 mmol), HATU (646 mg, 1.7 mmol) and 1-{[2-tert-butyl-1-(tetrahydro-2H-pyran-4-ylmethyl)-1H-benzimidazol-5-yl]sulfonyl}-1H-pyrrole-3-carboxylic acid (1.1 mmol) in DMF (15 mL). The crude product was purified on LCMS using high pH column 40-70% acetonitrile gradient to afford 9 mg (2% yield) of the title compound. $^1$H NMR (400 MHz, METHANOL-D$_4$) δ 1.43-1.51

(m, 3 H), 1.51-1.58 (m, 2 H), 1.60 (s, 9 H), 3.22 (q, J=7.36 Hz, 1 H), 3.33 (d, J=2.93 Hz, 1 H), 3.62 (m, 1 H), 3.68-3.76 (m, 1 H), 3.90 (dd, J=10.64, 3.42 Hz, 2 H), 4.43 (d, J=7.42 Hz, 2 H), 5.90 (m, 1 H), 6.68 (dd, J=3.03, 1.46 Hz, 1 H), 7.30-7.34 (m, 1 H), 7.87 (s, 1 H), 7.90-7.99 (m, 2 H), 8.28 (s, 1 H); MS (APPI) (M+H)$^+$=509.3.

Example 141

N-{[1-({2-tert-Butyl-1-[(4,4-difluorocyclohexyl)methyl]-1H-benzimidazol-5-yl}sulfonyl)azetidin-3-yl]methyl}propanamide Step A: N-{[1-({2-tert-Butyl-1-[(4,4-difluorocyclohexyl)methyl]-1H-benzimidazol-5-yl}sulfonyl)azetidin-3-yl]methyl}propanamide

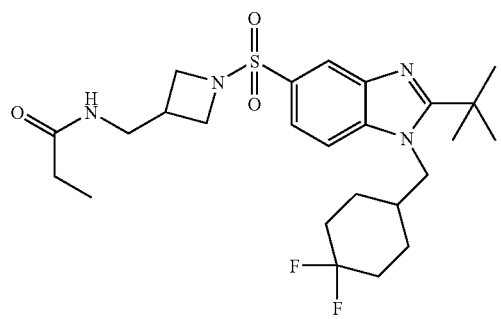

Following the same procedure in Example 1, Step A, using 2-tert-butyl-1-[(4,4-difluorocyclohexyl)methyl]-1H-benzimidazole-5-sulfonyl chloride (81 mg, 0.2 mmol), N-(azetidin-3-ylmethyl)propanamide (TFA salt, 102 mg, 0.4 mmol) (see following step B for preparation) and DIPEA (1 mL) in CH$_2$Cl$_2$ (10 mL), provided the title compound as its TFA salt (64 mg, 51% yield). $^1$H NMR (400 MHz, CD$_3$OD) δ 0.99 (t, J=7.7 Hz, 3 H), 1.58 (m, 2 H), 1.68 (s, 9 H), 1.73 (m, 4H), 2.00 (d, J=7.7 Hz, 2 H), 2.04 (m, 2 H), 2.26 (m, 1H), 2.54 (m, 1 H), 3.00 (d, J=6.8 Hz, 2H), 3.46 (t, J=8.2 Hz, 2 H), 3.80 (t, J=8.2 Hz, 2 H), 4.57 (d, J=7.5 Hz, 2H), 7.86 (d, J=8.8 Hz, 1 H), 8.08 (s, 1 H), 8.09 (d, J=8.8 Hz, 1H); MS (ESI) (M+H)$^+$=511.3.

Step B: N-(Azetidin-3-ylmethyl)propanamide

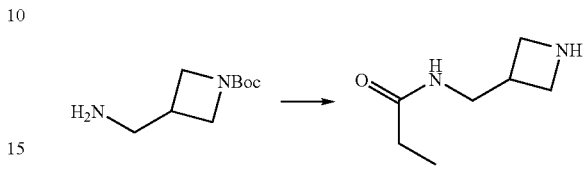

Propanoic anhydride (286 mg, 2.2 mmol) was added into a solution of tert-butyl 3-(aminomethyl)azetidine-1-carboxylate (200 mg, 1.08 mmol) and triethylamine (1 mL) in CH$_2$Cl$_2$ (20 mL) at r.t. After 2 hr, the reaction mixture was condensed. The residue was dissolved in CH$_2$Cl$_2$ (10 mL) and treated with TFA (10 mL) at r.t. for 1 h. Evaporation of solvents provided the desired product as its TFA salt, which was used in Step A directly.

Example 142

N-{[1-({2-tert-Butyl-1-[(4,4-difluorocyclohexyl)methyl]-1H-benzimidazol-5-yl}sulfonyl)azetidin-3-yl]methyl}cyclopropanecarboxamide

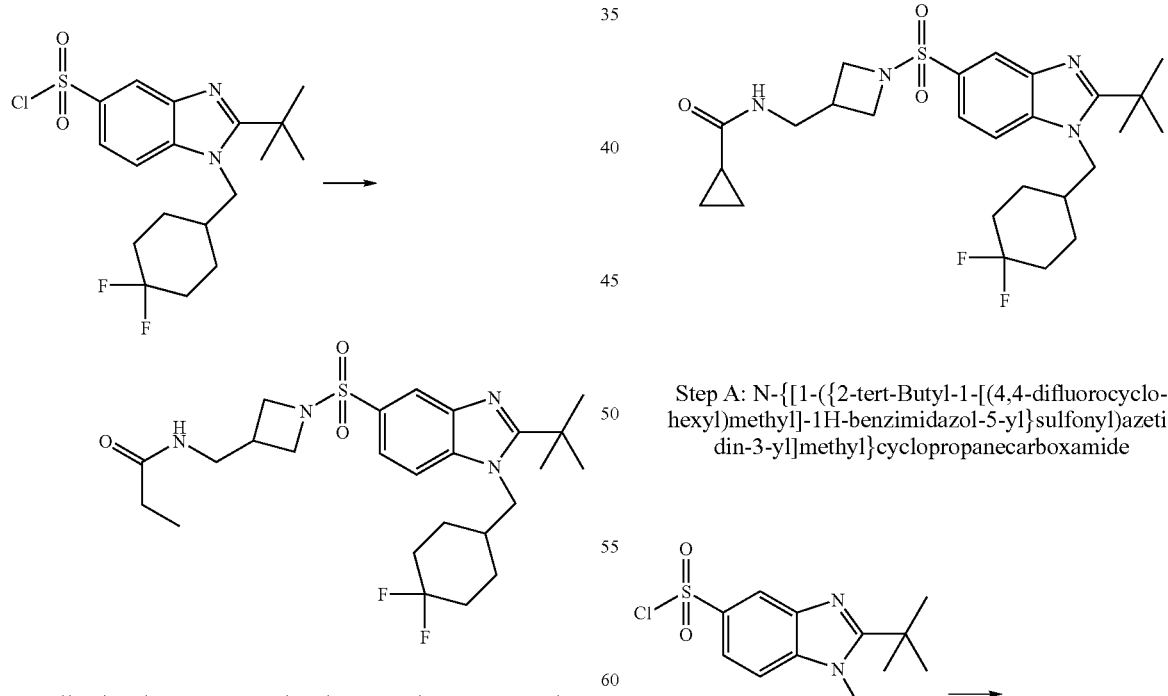

Step A: N-{[1-({2-tert-Butyl-1-[(4,4-difluorocyclohexyl)methyl]-1H-benzimidazol-5-yl}sulfonyl)azetidin-3-yl]methyl}cyclopropanecarboxamide

185

-continued

[Structure diagram]

Following the same procedure in Example 1, Step A, using 2-tert-butyl-1-[(4,4-difluorocyclohexyl)methyl]-1H-benzimidazole-5-sulfonyl chloride (81 mg, 0.2 mmol), N-(azetidin-3-ylmethyl)cyclopropanecarboxamide (TFA salt, 107 mg, 0.4 mmol) (see following step B for preparation) and DIPEA (1 mL) in $CH_2Cl_2$ (10 mL), provided the title compound as its TFA salt (39 mg, 31% yield). $^1$H NMR (400 MHz, $CD_3OD$) δ 0.64 (m, 2H), 0.70 (m, 2H), 1.38 (m, 1H), 1.58 (m, 2 H), 1.67 (s, 9 H), 1.73 (m, 4H), 2.02 (m, 2H), 2.25 (m, 1H), 2.52 (m, 1 H), 3.00 (d, J=6.8 Hz, 2H), 3.48 (t, J=8.2 Hz, 2 H), 3.84 (t, J=8.2 Hz, 2 H), 4.55 (d, J=7.5 Hz, 2H), 7.89 (d, J=8.8 Hz, 1H), 8.07 (d, J=8.8 Hz, 1H), 8.12 (s, 1 H); MS (ESI) (M+H)$^+$=523.3.

Step B:
N-(Azetidin-3-ylmethyl)cyclopropanecarboxamide

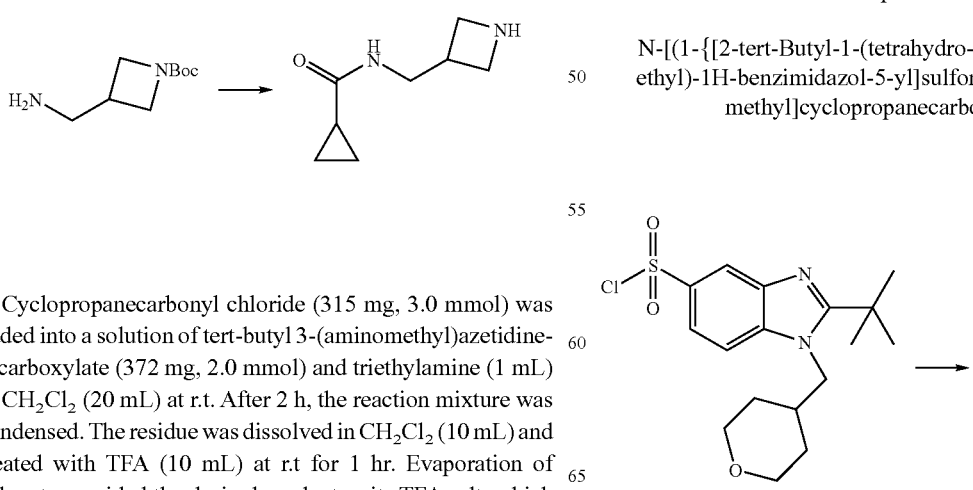

Cyclopropanecarbonyl chloride (315 mg, 3.0 mmol) was added into a solution of tert-butyl 3-(aminomethyl)azetidine-1-carboxylate (372 mg, 2.0 mmol) and triethylamine (1 mL) in $CH_2Cl_2$ (20 mL) at r.t. After 2 h, the reaction mixture was condensed. The residue was dissolved in $CH_2Cl_2$ (10 mL) and treated with TFA (10 mL) at r.t for 1 hr. Evaporation of solvents provided the desired product as its TFA salt, which was used in Step A directly.

186

Example 143

N-[(1-{[2-tert-Butyl-1-(tetrahydro-2H-pyran-4-ylmethyl)-1H-benzimidazol-5-yl]sulfonyl}azetidin-3-yl)methyl]propanamide

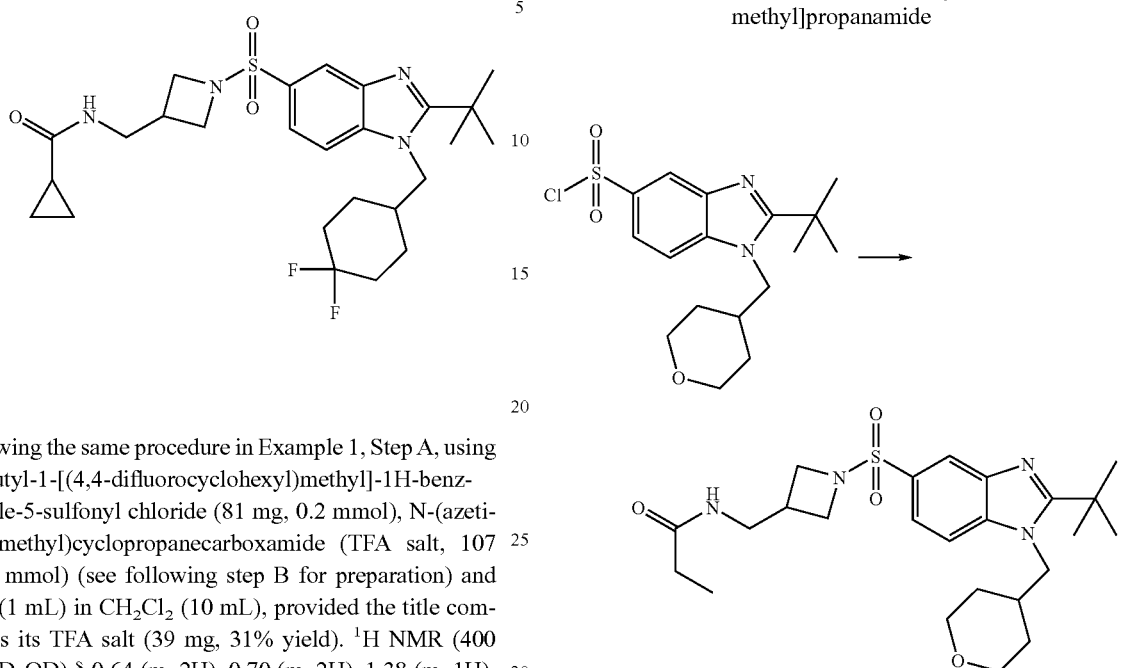

Following the same procedure in Example 1, Step A, using 2-tert-butyl-1-(tetrahydro-2H-pyran-4-ylmethyl)-1H-benzimidazole-5-sulfonyl chloride (74 mg, 0.2 mmol), N-(azetidin-3-ylmethyl)propanamide (TFA salt, 102 mg, 0.4 mmol) and DIPEA (1 mL) in $CH_2Cl_2$ (10 mL), provided the title compound as its TFA salt (58 mg, 49%). $^1$H NMR (400 MHz, $CDCl_3$) δ 0.99 (t, J=7.6 Hz, 3H), 1.58 (m, 4 H), 1.69 (s, 9 H), 2.01 (q, J=7.6 Hz, 2H), 2.38 (m, 1 H), 2.52 (m, 1 H), 2.99 (d, J=7.0 Hz, 2H), 3.33 (m, 2 H), 3.46 (m, 2 H), 3.80 (t, J=7.6 Hz, 2 H), 3.93 (m, 2 H), 4.56 (d, J=7.4 Hz, 2 H), 7.87 (d, J=8.8 Hz, 1H), 8.08 (s, 1H), 8.11 (d, J=8.8 Hz, 1H); MS (ESI) (M+H)$^+$= 477.2.

Example 144

N-[(1-{[2-tert-Butyl-1-(tetrahydro-2H-pyran-4-ylmethyl)-1H-benzimidazol-5-yl]sulfonyl}azetidin-3-yl)methyl]cyclopropanecarboxamide

[Structure diagram]

-continued

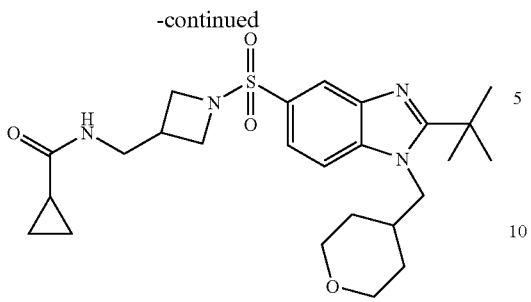

Following the same procedure in Example 1, Step A, using 2-tert-butyl-1-(tetrahydro-2H-pyran-4-ylmethyl)-1H-benzimidazole-5-sulfonyl chloride (74 mg, 0.2 mmol), N-(azetidin-3ylmethyl)cyclopropanecarboxamide (TFA salt, 107 mg, 0.4 mmol) and DIPEA (1 mL) in CH$_2$Cl$_2$ (10 mL), provided the title compound as its TFA salt (56 mg, 46% yield). $^1$H NMR (400 MHz, CDCl$_3$) δ 0.70 (m, 4H), 1.40 (m, 1H), 1.58 (m, 4 H), 1.71 (s, 9 H), 2.38 (m, 1 H), 2.52 (m, 1 H), 3.00 (d, J=8.0 Hz, 2 H), 3.35 (m, 2 H), 3.47 (m, 2 H), 3.83 (t, J=7.6 Hz, 2 H), 3.93 (m, 2 H), 4.58 (d, J=7.4 Hz, 2 H), 7.91 (d, J=8.8 Hz, 1H), 8.11 (s, 1H), 8.16 (d, J=8.8 Hz, 1H); MS (ESI) (M+H)$^+$= 489.3.

Example 145

1-{[2-tert-Butyl-1-(tetrahydro-2H-pyran-4-ylmethyl)-1H-benzimidazol-5-yl]sulfonyl}-N-cyclopropyl-3-methyl-1H-pyrazole-4-carboxamide

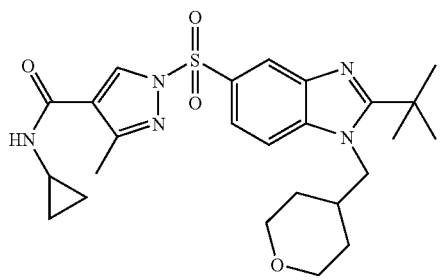

Step A: 1-{[2-tert-Butyl-1-(tetrahydro-2H-pyran-4-ylmethyl)-1H-benzimidazol-5-yl]sulfonyl}-N-cyclopropyl-3-methyl-1H-pyrazole-4-carboxamide

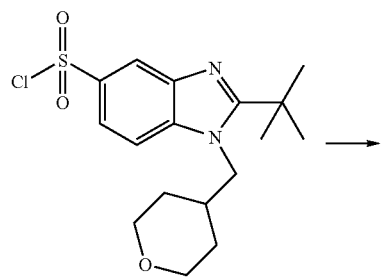

-continued

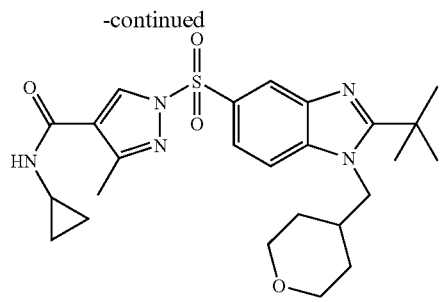

Sodium hydride (120 mg, 60%, 3.0 mmol) was added to a solution of N-cyclopropyl-3-methyl-1H-pyrazole-4-carboxamide (150 mg, 0.91 mmol) (see following step B for preparation) in 8 mL of DMF at −10° C. After 20 min, 2-tert-butyl-1-(tetrahydro-2H-pyran-4-ylmethyl)-1H-benzimidazole-5-sulfonyl chloride (150 mg, 0.41 mmol) was added. The reaction mixture was stirred for 10 min at 0° C., quenched with NH$_4$Cl (20 mL) and EtOAc (100 mL). The organic phases were washed with NaCl and dried over Na$_2$SO$_4$. The crude product was purified by HPLC to give the title compound as its TFA salt (82 mg, 33% yield). $^1$H NMR (400 MHz, CD$_3$OD) δ 0.55 (m, 2 H), 0.73 (m, 2H), 1.53 (m, 4 H), 1.59 (s, 9 H), 2.30 (m, 1H), 2.32 (s, 3H), 2.71 (m, 1H), 3.29 (m, 2 H), 3.89 (m, 2 H), 4.41 (d, J=7.3 Hz, 2 H), 7.88 (d, J=8.88 Hz, 1H), 7.91 (d, J=8.88 Hz, 1H), 8.29 (s, 1 H), 8.65 (s, 1H); MS (ESI) (M+H)$^+$=500.3.

Step B: N-Cyclopropyl-3-methyl-1H-pyrazole-4-carboxamide

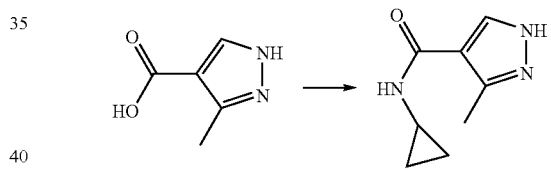

Following the same procedure in Example 29 (Step B and C in Method B), using 3-methyl-1H-pyrazole-4-carboxylic acid (252 mg, 2.0 mmol) and cyclopropylamine (285 mg, 5.0 mmol), provided the desired crude compound (310 mg, 94%), which was used in Step A directly.

Example 146

1-{[2-tert-Butyl-1-(tetrahydro-2H-pyran-4-ylmethyl)-1H-benzimidazol-5-yl]sulfonyl}-N-ethyl-3-methyl-1H-pyrazole-4-carboxamide

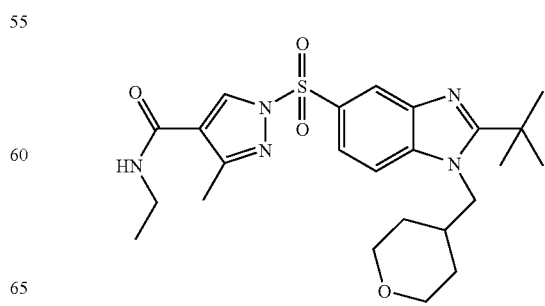

Step A: 1-{[2-tert-Butyl-1-(tetrahydro-2H-pyran-4-ylmethyl)-1H-benzimidazol-5-yl]sulfonyl}-N-ethyl-3-methyl-1H-pyrazole-4-carboxamide

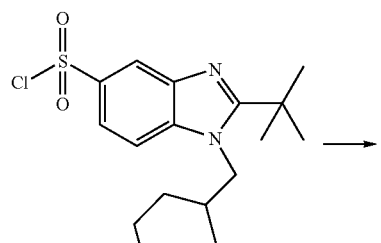

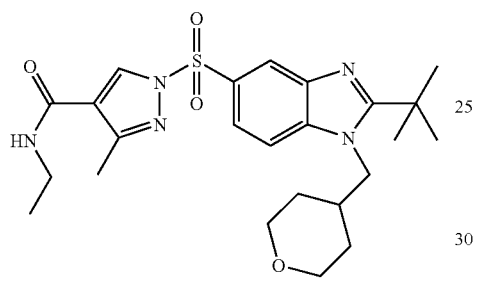

Following the same procedure in Example 145, using 2-tert-butyl-1-(tetrahydro-2H-pyran-4-ylmethyl)-1H-benzimidazole-5-sulfonyl chloride (100 mg, 0.27 mmol) and N-ethyl-3-methyl-1H-pyrazole-4-carboxamide (150 mg, 1.0 mmol) (see following step B for preparation), provided the title compound as its TFA salt (25 mg, 15% yield). $^1$H NMR (400 MHz, CD$_3$OD) δ 1.15 (d, J=7.2 Hz, 3 H), 1.53 (m, 4 H), 1.63 (s, 9 H), 2.31 (s, 4 H), 3.29 (m, 2 H), 3.88 (m, 2 H), 4.05 (m, 1 H), 4.48 (d, J=7.3 Hz, 2 H), 8.04 (s, 2 H), 8.37 (s, 1 H), 8.68 (s, 1 H); MS (ESI) (M+H)$^+$=488.3.

Step B: N-Ethyl-3-methyl-1H-pyrazole-4-carboxamide

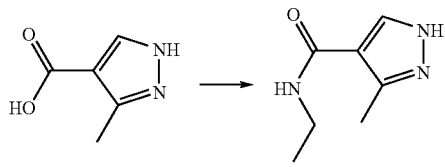

Following the same procedure in Example 29 (Steps B and C in Method B), using 3-methyl-1H-pyrazole-4-carboxylic acid (252 mg, 2.0 mmol) and ethylamine (225 mg, 5.0 mmol), provided the desired crude compound (306 mg, 100%), which was used in Step A directly.

Example 147

2-[1-({2-tert-Butyl-1-[(4,4-difluorocyclohexyl)methyl]-1H-benzimidazol-5-yl}sulfonyl)azetidin-3-yl]-N-ethylacetamide

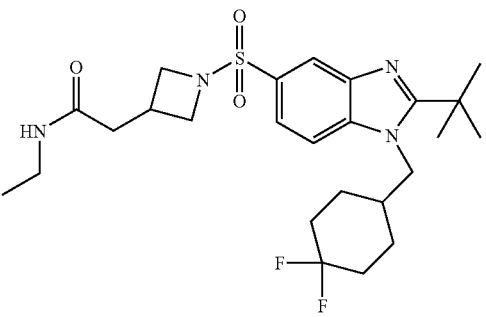

Step A: 2-[1-({2-tert-Butyl-1-[(4,4-difluorocyclohexyl)methyl]-1H-benzimidazol-5-yl}sulfonyl)azetidin-3-yl]-N-ethylacetamide

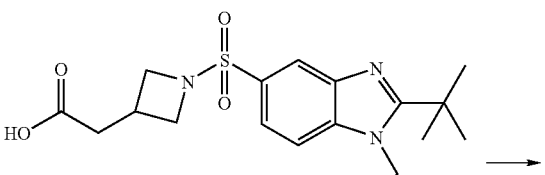

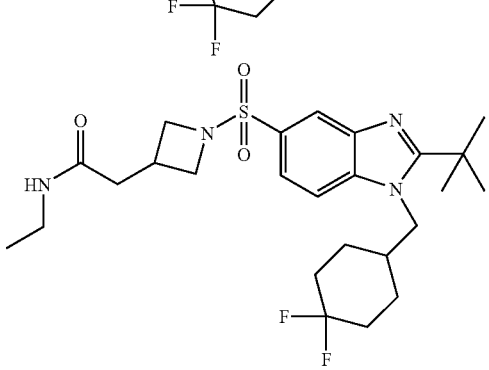

Following the same procedure in Example 24, Step A, using ethylamine hydrochloride (164 mg, 2.0 mmol) (see following steps B and C for preparation), DIPEA (1 mL), [1-({2-tert-Butyl-1-[(4,4-difluorocyclohexyl)methyl]-1H-benzimidazol-5-yl}sulfonyl)azetidin-3-yl]acetic acid (310 mg, 0.64 mmol) (see following step C for preparation) and HATU (230 mg, 0.64 mmol) in DMF (6.0 mL), provided the title compound as its TFA salt (49 mg, 12% yield). $^1$H NMR (400 MHz, CD$_3$OD) δ 1.01 (t, J=7.4 Hz, 3H), 1.59 (m, 2 H), 1.70 (s, 9 H), 1.75 (m, 4H), 2.01 (m, 2 H), 2.23 (d, J=7.8 Hz, 2 H), 2.25 (m, 1H), 2.68 (m, 1 H), 3.05 (q, J=7.4 Hz, 2H), 3.47 (t, J=8.2 Hz, 2 H), 3.85 (t, J=8.2 Hz, 2 H), 4.58 (d, J=7.5 Hz, 2 H), 7.88 (d, J=8.8 Hz, 1H), 8.07 (s, 1H), 8.12 (d, J=8.8 Hz, 1 H); MS (ESI) (M+H)⁺=511.0.

Step B: Azetidin-3-ylacetic acid hydrochloride

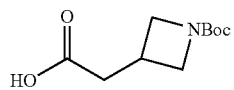 → 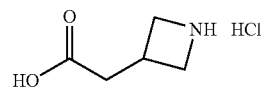

[1-(tert-Butoxycarbonyl)azetidin-3-yl]acetic acid (2.15 g, 10 mmol) was treated with 4 N HCl in dioxane (40 mL) for 4 h at r.t. The reaction mixture was condensed to provide the desire compound as its HCl salt, which was used directly in Step A.

Step C: [1-({2-tert-Butyl-1-[(4,4-difluorocyclohexyl) methyl]-1H-benzimidazol-5-yl}sulfonyl)azetidin-3-yl]acetic acid

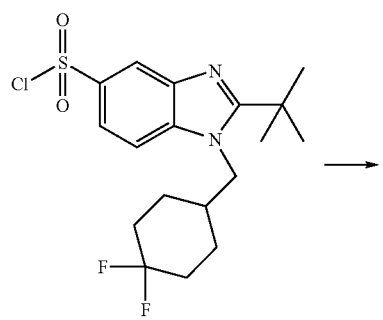

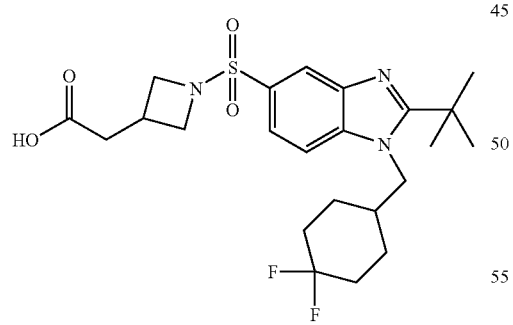

Following the same procedure in Example 1, Step A, using 2-tert-butyl-1-[(4,4-difluorocyclohexyl)methyl]-1H-benzimidazole-5-sulfonyl chloride (1.06 g, 2.6 mmol), azetidin-3-ylacetic acid hydrochloride (1.17 g, 7.8 mmol) and DIPEA (4 mL) in CH₂Cl₂ (20 mL), provided the title compound as crude product (930 mg, 74% yield), which was used directly in Step A.

Example 148

2-[1-({2-tert-Butyl-1-[(4,4-difluorocyclohexyl)methyl]-1H-benzimidazol-5-yl}sulfonyl)azetidin-3-yl]-N-cyclopropylacetamide

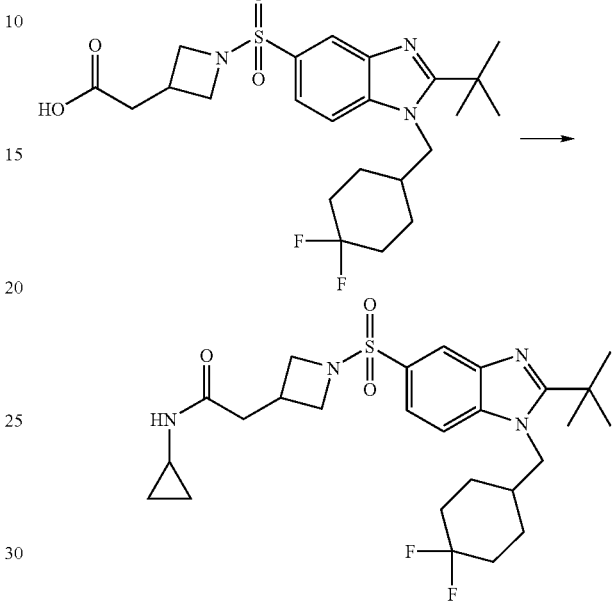

Following the same procedure in Example 24, Step A, using cyclopropylamine (114 mg, 2.0 mmol), DIPEA (1 mL), [1-({2-tert-Butyl-1-[(4,4-difluorocyclohexyl)methyl]-1H-benzimidazol-5-yl}sulfonyl)azetidin-3-yl]acetic acid (310 mg, 0.64 mmol) and HATU (230 mg, 0.64 mmol) in DMF (6.0 mL), provided the title compound as its TFA salt (54 mg, 12% yield). ¹H NMR (400 MHz, CD₃OD) δ 0.37 (m, 2 H), 0.59 (m, 2H), 1.54 (m, 2 H), 1.68 (s, 9 H), 1.77 (m, 4H), 2.02 (m, 2H), 2.19 (d, J=7.8 Hz, 2 H), 2.22 (m, 1 H), 2.49 (m, 1 H), 2.67 (m, 1 H), 3.45 (m, 2 H), 3.83 (t, J=8.2 Hz, 2 H), 4.57 (d, J=7.5 Hz, 2 H), 7.86 (d, J=8.8 Hz, 1 H), 8.05 (s, 1H), 8.11 (d, J=8.8 Hz, 1H); MS (ESI) (M+H)⁺ 523.3.

Example 149

2-[1-({2-tert-Butyl-1-[(4,4-difluorocyclohexyl)methyl]-1H-benzimidazol-5-yl}sulfonyl)azetidin-3-yl]-N-methylacetamide

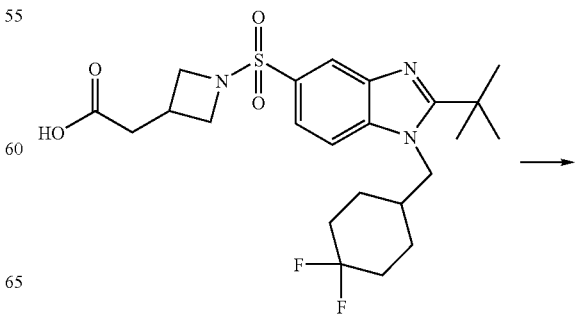

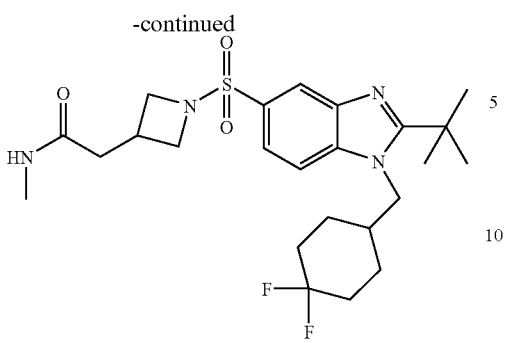

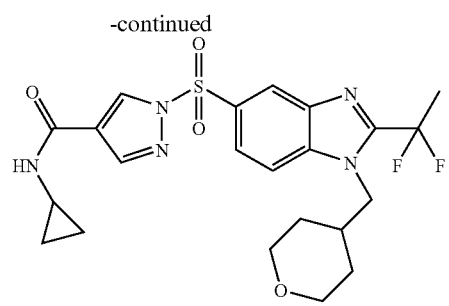

Following the same procedure in Example 24, Step A, using methylamine hydrochloride (136 mg, 2.0 mmol), DIPEA (1 mL), [1-({2-tert-Butyl-1-[(4,4-difluorocyclohexyl)methyl]-1H-benzimidazol-5-yl}sulfonyl)azetidin-3-yl]acetic acid (310 mg, 0.64 mmol) and HATU (230 mg, 0.64 mmol) in DMF (6.0 mL), provided the title compound as its TFA salt (41 mg, 10% yield). $^1$H NMR (400 MHz, CD$_3$OD) δ 1.59 (m, 2 H), 1.67 (s, 9 H), 1.72 (m, 4H), 2.05 (m, 2H), 2.25 (d, J=7.8 Hz, 3 H), 2.57 (s, 3H), 2.68 (m, 1 H), 3.50 (t, J=8.2 Hz, 2 H), 3.86 (t, J=8.2 Hz, 2 H), 4.56 (d, J=7.5 Hz, 2 H), 7.90 (d, J=8.8 Hz, 1H), 8.08 (d, J=8.8 Hz, 1H), 8.13 (s, 1H); MS (ESI) (M+H)$^+$=497.0.

Example 150

N-Cyclopropyl-1-{[2-(1,1-difluoroethyl)-1-(tetrahydro-2H-pyran-4-ylmethyl)-1H-benzimidazol-5-yl]sulfonyl}-1H-pyrazole-4-carboxamide Sodium hydride (80 mg, 60%, 2.0 mmol) was added to a solution of N-cyclopropyl-1H-pyrazole-4-carboxamide (70 mg, 0.5 mmol) in 4 mL of DMF at −10° C. After 10 min, 2-(1,1-difluoroethyl)-1-(tetrahydro-2H-pyran-4-ylmethyl)-1H-benzimidazole-5-sulfonyl chloride (100 mg, 0.23 mmol) (see following steps B, C and D for preparation) was added. The reaction mixture was stirred for 10 min at 0° C., quenched with NH$_4$Cl (10 mL) and EtOAc (50 mL). The organic phases were washed with NaCl and dried over Na$_2$SO$_4$. The crude product was purified by HPLC to give the title compound as its TFA salt (12 mg, 11% yield). $^1$H NMR (400 MHz, METHANOL-D$_4$) δ 0.56 (m, 2H), 0.75 (m, 2H), 1.44 (m, 4 H), 2.24 (t, J=19.5 Hz, 3H), 2.26 (m, 1H), 2.75 (m, 1H), 3.88 (m, 2H), 4.37 (d, J=7.6 Hz, 2H), 7.92 (d, J=8.8 Hz, 1H), 7.99 (d, J=8.8 Hz, 1H), 8.03 (s, 1H), 8.44 (s, 1H), 8.74 (s, 1H); MS (APPI) (M+H)$^+$=494.0.

Step B: N-[2-(1,1-Difluoroethyl)-1-(tetrahydro-2H-pyran-4-ylmethyl)-1H-benzimidazol-5-yl]acetamide Step A N-Cyclopropyl-1-{[2-(1,1-difluoroethyl)-1-(tetrahydro-2H-pyran-4-ylmethyl)-1H-benzimidazol-5-yl]sulfonyl}-1H-pyrazole-4-carboxamide

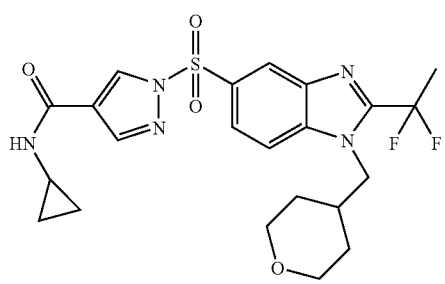

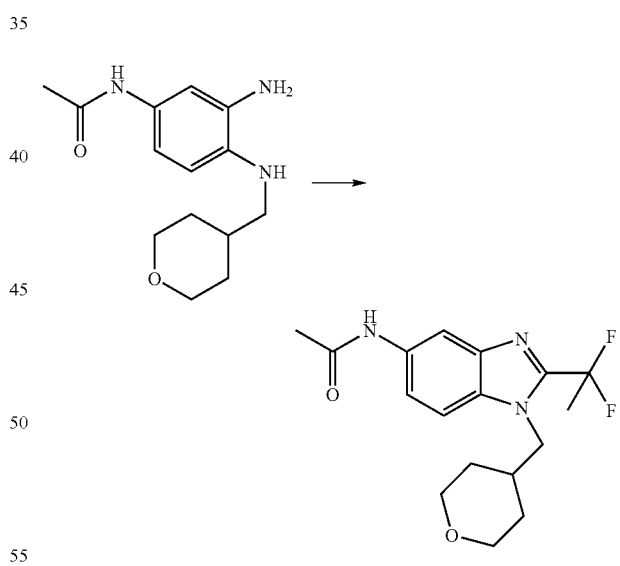

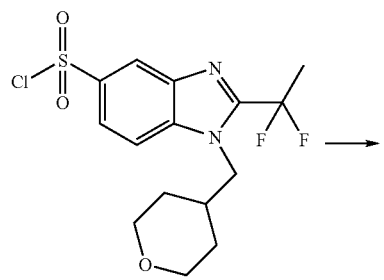

HATU (1.58 g, 4.17 mmol) and N-{3-amino-4-[(tetrahydro-2H-pyran-4-ylmethyl)amino]phenyl}acetamide (1.00 g, 3.79 mmol) were added to a solution of 2,2-difluoropropanoic acid (0.43 g, 3.98 mmol) and DIPEA (0.80 mL, 4.55 mmol) in DMF (100 mL) at ambient temperature. The reaction mixture was stirred overnight and the solvent was concentrated. The intermediate was heated to 80° C. for 3 h in glacial AcOH (100 mL), and the solvent was concentrated. The crude product was recovered in DCM (300 mL), washed with saturated NaHCO$_3$ solution (3×100 mL), brine and dried over anhydrous MgSO$_4$. The solvent was concentrated and the product was purified by normal-phase MPLC using MeOH 5% and Acetone 10% in DCM to provide the title compound as a white solid. Yield: 1.07 g (83%); MS (ESI) (M+H)⁺=338.2.

Step C: 2-(1,1-Difluoroethyl)-1-(tetrahydro-2H-pyran-4-ylmethyl)-1H-benzimidazol-5-amine

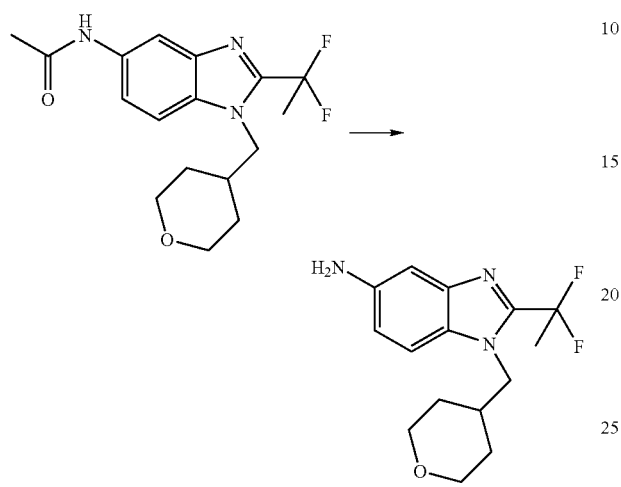

A mixture of N-[2-(1,1-difluoroethyl)-1-(tetrahydro-2H-pyran-4-ylmethyl)-1H-benzimidazol-5-yl]acetamide (1.07 g, 3.17 mmol), 6 M aqueous solution of NaOH (5 mL) and MeOH (5 mL) was heated to 70° C. for 24 h. The reaction mixture was diluted with water (200 mL) and the product was extracted with EtOAc (4×100 mL). The combined organic layers were dried over anhydrous Na₂SO₄ and the solvent was concentrated to provide the title compound as white solid. Yield: 0.90 g (96%); MS (ESI) (M+H)⁺=296.2.

Step D: 2-(1,1-Difluoroethyl)-1-(tetrahydro-2H-pyran-4-ylmethyl)-1H-benzimidazole-5-sulfonyl chloride

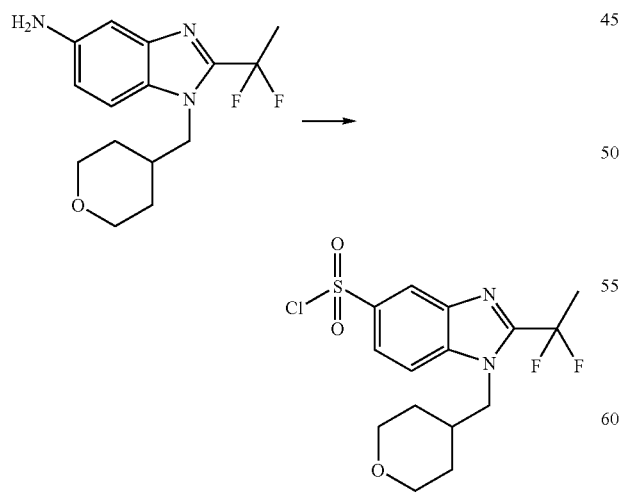

A solution of NaNO₂ (2.5 g, 36.23 mmol) in 9 mL of water was added to a solution of 2-(1,1-difluoroethyl)-1-(tetrahydro-2H-pyran-4-ylmethyl)-1H-benzimidazol-5-amine (11.9 g, 33.28 mmol) in 80 mL of AcOH/HCl (1:2 v/v) at 0° C. The resulting mixture was stirred for 1 h at 0° C., which was then poured portion-wise to a mixture of SO₂ (80 mL) and CuCl₂·2H₂O (2.3 g, 13.49 mmol) in AcOH (46 mL) at −30° C. The mixture was stirred at 0° C. for 2 h and then warmed gradually to rt and stirred for 5 h. The mixture was poured over ice (500 mL) while shaken vigorously. The mixture was extracted with cold CH₂Cl₂ (2×500 mL). The combined organic phases were dried over anhydrous Na₂SO₄. Removal of solvent in vacuo gave the desired product (HCl salt) as a beign solid (14.5 g, yield 98.7%). MS (ESI) (M+H)⁺=405.01.

Example 151

1-{[2-(1,1-Difluoroethyl)-1-(tetrahydro-2H-pyran-4-ylmethyl)-1H-benzimidazol-5-yl]sulfonyl}-N-ethyl-1H-pyrazole-4-carboxamide

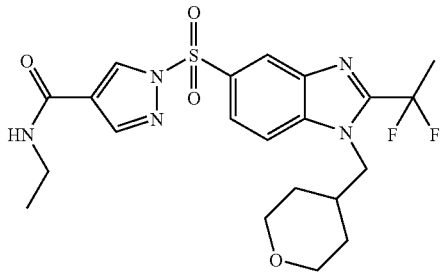

Step A: 1-{[2-(1,1-Difluoroethyl)-1-(tetrahydro-2H-pyran-4-ylmethyl)-1H-benzimidazol-5-yl]sulfonyl}-N-ethyl-1H-pyrazole-4-carboxamide

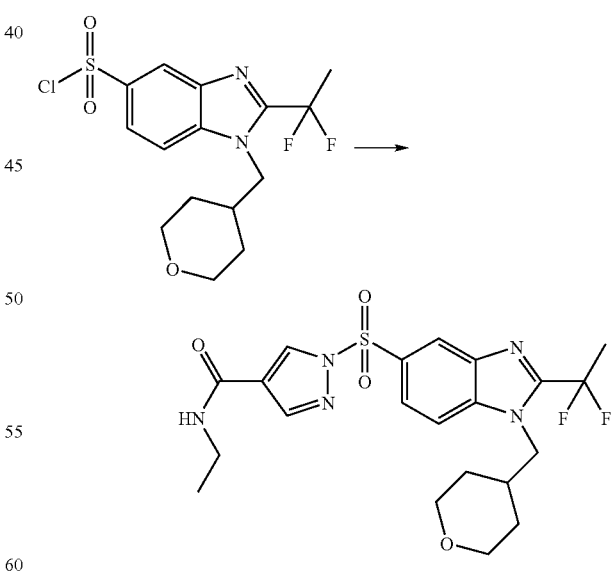

Following the same procedure in Example 150, using 2-(1,1-difluoroethyl)-1-(tetrahydro-2H-pyran-4-ylmethyl)-1H-benzimidazole-5-sulfonyl chloride (100 mg, 0.23 mmol) and N-ethyl-1H-pyrazole-4-carboxamide (60 mg, 0.47 mmol), provided the title compound as its TFA salt (10 mg, 9%). ¹H NMR (400 MHz, METHANOL-D₄) δ 1.15 (t, J=7.3 Hz, 3H), 1.44 (m, 4 H), 2.24 (t, J=19.5 Hz, 3H), 2.26 (m, 1H), 3.26 (m, 2H), 3.88 (m, 2H), 4.37 (d, J=7.6 Hz, 2H), 7.92 (d, J=8.8 Hz, 1H), 7.99 (d, J=8.8 Hz, 1H), 8.03 (s, 1H), 8.44 (s, 1H), 8.74 (s, 1H); MS (APPI) (M+H)+=481.85.

Step B: N-Ethyl-1H-pyrazole-4-carboxamide

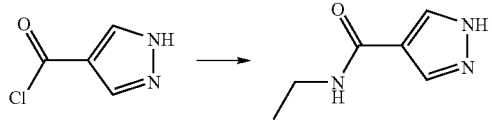

Following the same procedure in Example 28 (Step C of Method B), using 1H-pyrazole-4-carbonyl chloride (0.47 g, 3.6 mmol), ethylamine (3.0 mL, 2.0 M in THF, 6.0 mmol) and triethylamine (1.01 g, 1.39 mL, 10 mmol) in CH₂Cl₂ (15 mL), provided the title compound as a white solid. Yield: 0.49 g (97% yield). ¹H NMR (400 MHz, METHANOL-D₄) δ 1.18 (t, J=7.23 Hz, 3 H) 3.34 (q, J=7.23 Hz, 2 H) 7.92 (s, 1 H) 8.09 (s, 1 H)

Example 152

1-{[2-(1,1-Difluoroethyl)-1-(tetrahydro-2H-pyran-4-ylmethyl)-1H-benzimidazol-5-yl]sulfonyl}-N-ethyl-1H-pyrrole-3-carboxamide

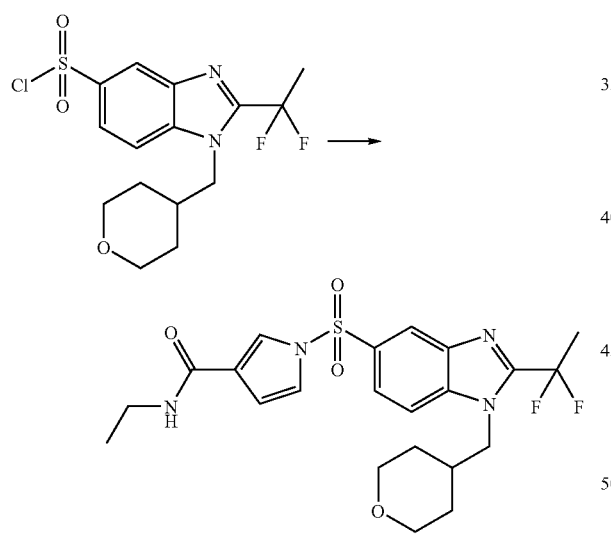

N-Ethyl-1H-pyrrole-3-carboxamide (50 mg, 0.36 mmol) was dissolved in THF (3 mL) and the solution was cooled down to 0° C. NaH (72 mg, 60%, 1.8 mmol) was then added and the reaction mixture was allowed to warm to room temperature and stirred for 1 hour at room temperature. The reaction mixture was cooled down to 0° C. again and 2-(1,1-difluoroethyl)-1-(tetrahydro-2H-pyran-4-ylmethyl)-1H-benzimidazole-5-sulfonyl chloride (114 mg, 0.30 mmol) was added slowly, allowing the reaction to warm to room temperature and stirred for 3 hours. The reaction mixture was slowly added to a stirring mixture of EtOAc and NH₄Cl at −20° C., which was extracted with EtOAc, washed with NH₄Cl, water then brine. Concentrated under vacuum and purified by LCMS using high pH column 40-70% acetonitrile gradient to afford the title compound as a white solid. Yield: 25 mg (17%). ¹H NMR (400 MHz, METHANOL-D₄) δ 1.14 (t, J=7.23 Hz, 3 H), 1.32-1.41 (m, 2 H), 1.40-1.43 (m, 3 H), 1.43-1.53 (m, 2 H), 2.25 (t, J=19.53 Hz, 5H), 3.89 (dd, J=11.52, 2.54 Hz, 2 H), 4.37 (d, J=7.62 Hz, 2 H), 6.65 (s, 1 H), 7.31 (t, J=2.34 Hz, 1 H), 7.82 (s, 1 H), 7.88-7.94 (m, 1 H), 7.95-8.01 (m, 1 H), 8.40 (s, 1 H); MS (APPI) (M+H)+=481.2; Anal. Calc. for C₂₂H₂₆F₂N₄O₄S+0.4 TFA: C, 52.05; H, 5.06; N, 10.65. Found: C, 52.41; H, 3.78; N, 10.41.

Example 153

N-Cyclopropyl-1-{[2-(1,1-difluoroethyl)-1-(tetrahydro-2H-pyran-4-ylmethyl)-1H-benzimidazol-5-yl]sulfonyl}-1H-pyrrole-3-carboxamide

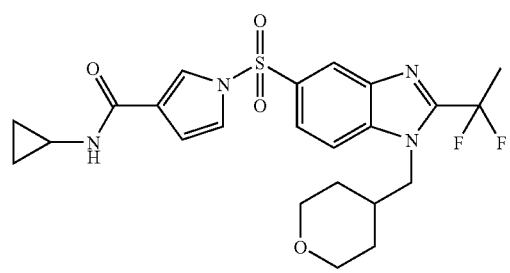

Step A: N-Cyclopropyl-1-{[2-(1,1-difluoroethyl)-1-(tetrahydro-2H-pyran-4-ylmethyl)-1H-benzimidazol-5-yl]sulfonyl}-1H-pyrrole-3-carboxamide

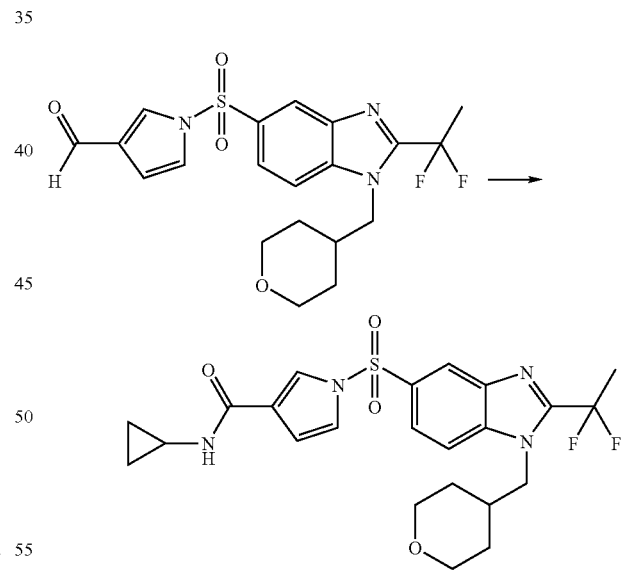

Oxone (1.33 g, 2.17 mmol) was added to a solution of 1-{[2-(1,1-difluoroethyl)-1-(tetrahydro-2H-pyran-4-ylmethyl)-1H-benzimidazol-5-yl]sulfonyl}-1H-pyrrole-3-carbaldehyde (0.86 g, 11.97 mmol) (see following step B for preparation) in DMF (15 mL). The reaction mixture was stirred overnight at room temperature and then cooled down to 0° C. Cyclopropylamine (0.23 g, 0.27 ml, 3.94 mmol) and N,N-diisopropylethylamine (1.02 g, 1.37 ml, 7.88 mmol) were added. Stirring for 20 min, HATU (1.35 g, 3.55 mmol) was added portionwise and the reaction was allowed to warm to room temperature. The reaction mixture was diluted with water (200 mL), and extracted with EtOAc (3×100 mL). The combined organic phases washed with NaCl (2×20 mL) and dried over $Na_2SO_4$. The crude product was purified by normal-phase MPLC using EtOAc to provide the title compound as a light brown solid. Yield: 0.70 g (72%). $^1$H NMR (400 MHz, METHANOL-$D_4$) δ 0.51-0.59 (m, 2 H), 0.68-0.78 (m, 2 H), 1.37-1.54 (m, 5 H), 2.25 (t, J=19.43 Hz, 3 H), 2.68-2.77 (m, 1 H), 3.27 (d, J=2.54 Hz, 1 H), 3.33 (d, J=2.93 Hz, 1 H), 3.84-3.94 (m, 2 H), 4.38 (d, J=7.62 Hz, 2 H), 6.65 (dd, J=3.32, 1.56 Hz, 1 H), 7.30 (dd, J=3.32, 2.34 Hz, 1 H), 7.81-7.84 (m, 1 H), 7.88-7.94 (m, 1 H), 7.94-8.00 (m, 1 H), 8.39 (d, J=1.56 Hz, 1 H); MS (APPI) (M+H)$^+$=493.3; Anal. Calc. for $C_{23}H_{26}F_2N_4O_4S$+0.8 TFA: C, 50.61; H, 4.63; N, 9.60. Found: C, 50.84; H, 3.87; N, 9.39.

Step B: 1-{[2-(1,1-difluoroethyl)-1-(tetrahydro-2H-pyran-4-ylmethyl)-1H-benzimidazol-5-yl]sulfonyl}-1H-pyrrole-3-carbaldehyde

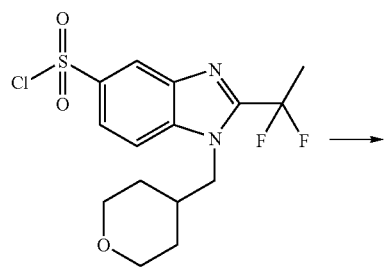

Sodium hydride (0.55 mg, 60%, 13.8 mmol) was added to a solution of 1H-Pyrrole-3-carbaldehyde (0.26 g, 2.7 mmol) in 30 mL of THF at 0° C. After stirring for 1 h, 2-(1,1-difluoroethyl)-1-(tetrahydro-2H-pyran-4-ylmethyl)-1H-benzimidazole-5-sulfonyl chloride (0.95 g, 2.5 mmol) was added. The reaction mixture was stirred for 3 h at 0° C., quenched with $NaHCO_3$ (10 mL) and diluted with EtOAc (150 mL). The organic phases were washed with NaCl (2×20 mL) and dried over $Na_2SO_4$. The product was purified by normal-phase MPLC using Hex/EtOAc (1:1) to provide the title compound as a white solid. Yield: 0.86 g (79%); MS (ESI) (M+H)$^+$=437.88.

Example 154

2-(1-{[2-tert-Butyl-1-(tetrahydro-2H-pyran-4-ylmethyl)-1H-benzimidazol-5-yl]sulfonyl}azetidin-3-yl)-N-(2,2-difluoroethyl)acetamide

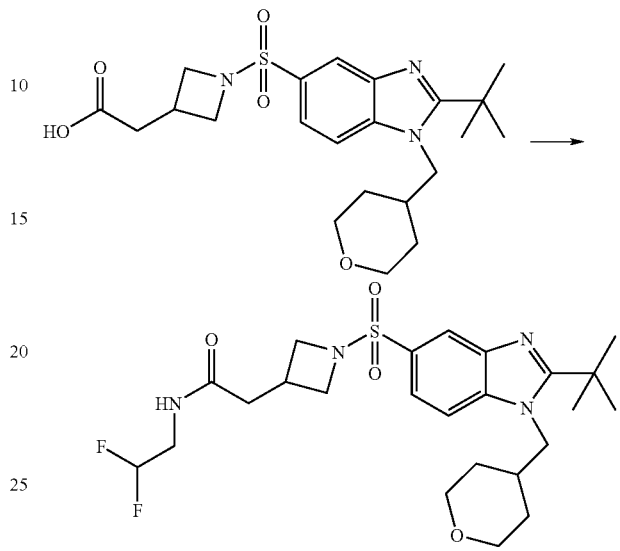

Following the same procedure in Example 24, Step A, using (2,2-difluoroethyl)amine (36 mg, 0.44 mmol), DIPEA (1 mL), (1-{[2-tert-butyl-1-(tetrahydro-2H-pyran-4-ylmethyl)-1H-benzimidazol-5-yl]sulfonyl}azetidin-3-yl)acetic acid (100 mg, 0.22 mmol) and HATU (161 mg, 0.44 mmol) in DMF (2.5 mL), provided the title compound as its TFA salt (58 mg, 41% yield). $^1$H NMR (400 MHz, $CDCl_3$) δ 1.60 (m, 4 H), 1.75 (s, 9 H), 2.36 (d, J=7.6 Hz, 2 H), 2.89 (m, 1 H), 3.43 (m, 7H), 4.02 (m, 4 H), 4.44 (t, J=7.4 Hz, 2 H), 5.62-5.90 (m, 1H), 7.08 (s, 1H), 7.71 (d, J=8.8 Hz, 1H), 7.86 (d, J=8.8 Hz, 1H), 8.28 (s, 1 H); MS (ESI) (M+H)$^+$=513.3.

Example 155

2-(1-{[2-tert-Butyl-1-(tetrahydro-2H-pyran-4-ylmethyl)-1H-benzimidazol-5-yl]sulfonyl}azetidin-3-yl)-N-cyclopropylacetamide

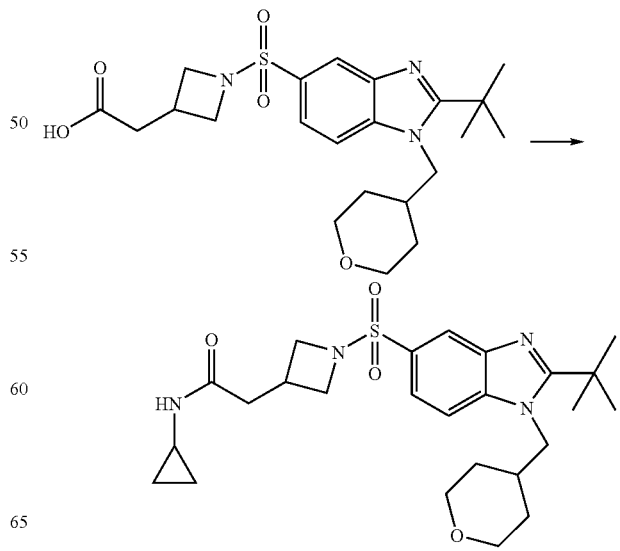

Following the same procedure in Example 24, Step A, using cyclopropylamine (24 mg, 0.44 mmol), DIPEA (1 mL), (1-{[2-tert-butyl-1-(tetrahydro-2H-pyran-4-ylmethyl)-1H-benzimidazol-5-yl]sulfonyl}azetidin-3-yl)acetic acid (100 mg, 0.22 mmol) and HATU (161 mg, 0.44 mmol) in DMF (2.5 mL), provided the title compound as its TFA salt (34 mg, 25% yield). $^1$H NMR (400 MHz, CDCl$_3$) δ 0.45 (m, 2 H), 0.65 (m, 2H), 1.66 (m, 4 H), 1.73 (s, 9 H), 2.25 (d, J=7.8 Hz, 2 H), 2.58 (m, 1 H), 2.60 (m, 1 H), 2.86 (m, 1 H), 3.31 (m, 2 H), 3.38 (m, 2H), 3.86 (t, J=7.6 Hz, 2 H), 4.00 (m, 2 H), 4.44 (d, J=7.3 Hz, 2 H), 6.52 (m, 1H), 7.72 (d, J=8.8 Hz, 1H), 7.77 (d, J=8.8 Hz, 1 H), 8.00 (s, 1 H); MS (ESI) (M+H)$^+$=489.3.

What is claimed is:

1. N-Cyclopropyl-1-{[2-(1,1-difluoroethyl)-1-(tetrahydro-2H-pyran-4-ylmethyl)-1H-benzimidazol-5-yl]sulfonyl}-1H-pyrrole-3-carboxamide or a pharmaceutically acceptable salt thereof.

2. A pharmaceutical composition comprising a compound according to claim 1 and a pharmaceutically acceptable carrier.

* * * * *